(12) United States Patent
Shchegolikhin et al.

(10) Patent No.: US 6,610,351 B2
(45) Date of Patent: Aug. 26, 2003

(54) RAMAN-ACTIVE TAGGANTS AND THEIR RECOGNITION

(75) Inventors: Alexander Nikitovich Shchegolikhin, Moscow (RU); Olga Leonidovna Lazareva, Moscow (RU); Valery Pavlovich Mel'nikov, Moscow (RU); Vassili Yu Ozeretski, Moscow (RU); Lyle David Small, Peyton, CO (US)

(73) Assignee: Quantag Systems, Inc., Colorado Springs, CO (US)

( * ) Notice: Subject to any disclaimer, the term of this patent is extended or adjusted under 35 U.S.C. 154(b) by 0 days.

(21) Appl. No.: 09/833,218

(22) Filed: Apr. 11, 2001

(65) Prior Publication Data

US 2002/0025490 A1 Feb. 28, 2002

Related U.S. Application Data

(60) Provisional application No. 60/196,876, filed on Apr. 12, 2000.

(51) Int. Cl.$^7$ ................................................. B41M 3/14
(52) U.S. Cl. ............................... 427/7; 427/8; 427/553; 427/554; 427/555; 106/31.14; 106/31.15; 283/85; 283/91; 283/92; 283/901
(58) Field of Search .............................. 427/7, 8, 553, 427/554, 555; 106/31.14, 31.15; 283/85, 91, 92, 901, 902; 428/916

(56) References Cited

U.S. PATENT DOCUMENTS

| | | | |
|---|---|---|---|
| 5,324,567 A | 6/1994 | Bratchley et al. | 428/195 |
| 5,718,754 A | 2/1998 | Macpherson et al. | 106/413 |
| 5,818,047 A | 10/1998 | Chaney et al. | 250/341.8 |
| 5,853,464 A | 12/1998 | Macpherson et al. | 106/316 |
| 5,935,755 A | 8/1999 | Kazmaier et al. | 430/120 |
| 6,030,657 A | 2/2000 | Butland et al. | 427/7 |
| 6,039,894 A | 3/2000 | Sanjurjo et al. | 252/301.4 R |
| 6,155,605 A | 12/2000 | Bratchley et al. | 283/72 |
| 6,203,069 B1 | 3/2001 | Outwater et al. | 283/88 |

*Primary Examiner*—Bret Chen
*Assistant Examiner*—Kirsten Crockford Jolley
(74) *Attorney, Agent, or Firm*—Law Office of Dale B. Halling, LLC

(57) ABSTRACT

An organic or organoelement, linear or branched, monomeric or polymeric composition of matter having a Raman-active component in the form of particles. The particles having a maximum dimension of 50 μm. The Raman-active compound is applied to a substrate. When the Raman-active compound is exposed to a laser light wavelength which is batochromically well beyond a spectral region of maximum absorbance of said Raman-active compound, Raman scattering can be detected.

21 Claims, 36 Drawing Sheets

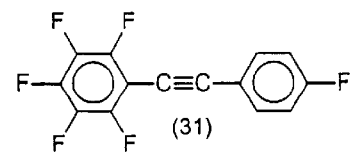 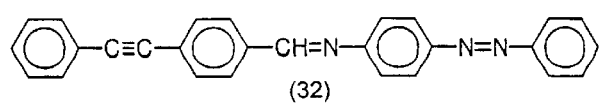
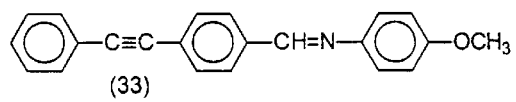 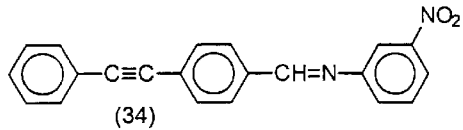
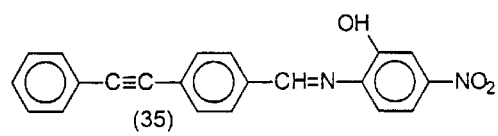 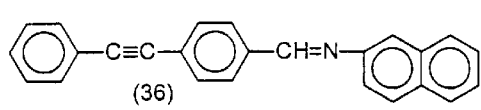
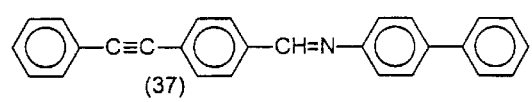 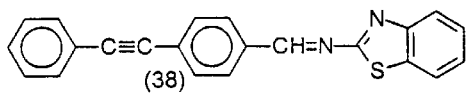
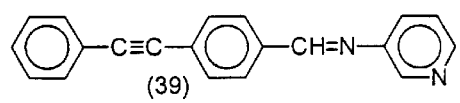 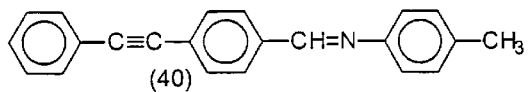
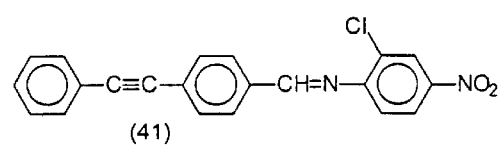 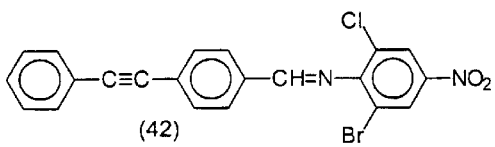
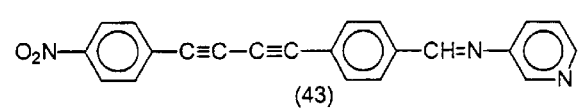 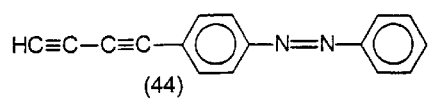
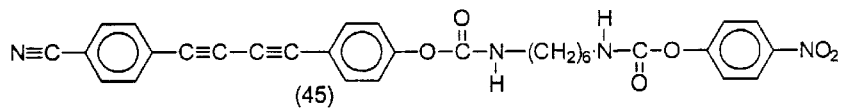

(46)

(47)

(48)

(49)

(50)

(51)

(52)

(53)

(54)

(55)

(56)

(57)

(58)

(59)

(60)

(61)

(62)

(63)

(64)

(65)

(66)

(120)
(121)
(122)
(123)
(124)
(125)
(126)
(127)
(128)
(129)

Fullerene C60

Fullerene C76

Fullerene C60Cl$_6$

Fullerene C82

Tubulene

Wherein n = 1, 2, 3, 4, 5, 7, 9  (145)

Wherein n = 1, 2, 3, 4, 5, 7, 9  (146)

Wherein n = any integer > 1  (147)

Wherein n = 1, 2, 3  (148)
$R^{18} = R^{19}$ or
$R^{18} \neq R^{19}$ and, independently of each other, is: an Alkyl, an Aryl, a Heteroaryl, or a substituted Alkyl, a substituted Aryl, a substituted Heteroaryl, etc.

Wherein n = any integer > 1  (149)

(150)

Wherein n = an integer from 0 up to 20

(151)

Wherein n and m, independently of each other, are any integer from 1 up to 20

(152)

(153)

(154)

(155)

Wherein n = any integer from 1 to 20; m = 2 - 100,000

(156)

Wherein n = an integer from 1 to 20;
m = 10 - 100,000;
p = 1 - 10; q = 500 - 100,000; r = 1 - 10;

X = alkylene or arylene, e.g.: hexamethylene, —⌬—, —⌬—CH₂—⌬—, etc.

Z = —CH₂-CH₂-CH₂-CH₂—, —CH(CH₃)-CH₂—, —CH₂—CH₂—, —⌬—, etc.

Note: Exciting Nd:YAG laser having 1064 nm (or 9394 cm$^{-1}$) wavelength has been used

RAMAN-ACTIVE TAGGANTS AND THEIR RECOGNITION

This application claims the benefit of provisional application No. 60/196,876, filed Apr. 12, 2000.

FIELD OF THE INVENTION

The present invention pertains to the field of processes for prefatory anti-forgery protection and consecutive machine-assisted authentication of genuine documents and other values. More particularly, the invention pertains to the use of processes for authenticating security items with Raman spectroscopy. In particular, the present invention relates to improved Raman-active compounds and compositions thereof. In some embodiments the present invention relates to use of improved Raman-active compounds on documents and other security items in the form of visible, camouflaged or completely concealed prints and markings for the purposes of authentication. Further, the present invention relates to techniques of composing and placing security markings on the items which need to be protected against forgery or counterfeiting.

Being directed, in some embodiments at least, to more reliable, facilitated, rapid and cost-effective mass authentication of genuine items "in the field" by virtue of machine-assisted recognition of the corresponding Raman-active molecular codes, tags and markings, the present invention relates also to employment of rugged, portable and affordable Raman spectrometers comprising: (a) corresponding types of radiation sources (such as lasers, light emitting diodes, etc.); (b) solid state radiation detectors of the corresponding type (such as CCDs, photo-diodes, detector arrays, etc.); (c) dispersive, electrooptic or interferometric means and filters for processing electromagnetic radiation (light) in the corresponding region of electromagnetic spectrum within the spectrometer; (d) optionally corresponding fiber optic conduits and probes for transporting the probing and/or the gathered (selectively transmitted, absorbed, reflected, scattered or emitted) light from or to the spectrometer; (e) corresponding computer and hardware responsible for analog to digital conversion of the signals; and (f) corresponding software responsible for processing, optimization, search and comparison of the spectral data as well as for presenting final results of the molecular code identification to an operator in an unambiguous and convenient form.

Other embodiments of the present invention are directed to a process which comprises (a) applying to a genuine item to be protected against duplicating, forgery or counterfeiting a marking material comprising an efficient Raman-active compound (or a composition of several such compounds) which, when irradiated with monochromatic radiation from the near infrared region of electromagnetic spectrum, is capable of emitting a detectable Raman spectrum, thereby forming a molecular code or security mark on the genuine item; (b) irradiating the security mark on the such protected genuine item with monochromatic radiation from the near infrared region of electromagnetic spectrum; (c) measuring the Raman spectrum of radiation scattered from the security mark when the mark is irradiated with monochromatic radiation belonging to the near infrared region of electromagnetic spectrum; and (d) processing the spectral data so obtained with the aid of corresponding dedicated software and presenting the results of the molecular code recognition to an operator in an unambiguous and convenient form.

BACKGROUND OF THE INVENTION

Valuable and genuine items such as checks, passports, tickets, banknotes, licenses, identification cards and branded articles need to be produced in a manner which allows the genuine item to be reliably authenticated. For instance, in printing of paper values, highly diversified measures have been adopted to provide this, ranging from printing of easily recognizable visible features through printing discrete camouflaged visible features up to applying completely hidden from the human eye features which are only identifiable and may be verified by a machine.

The use of the human eye recognizable or camouflaged security features has been described, for example, in U.S. Pat. Nos. 5,630,869 and 5,807,625 disclosing reversibly photochromic printing inks; in U.S. Pat. Nos. 5,591,255 and 5,997,849 disclosing thermochromic printing inks; in U.S. Pat. Nos. 5,826,916, 5,772,248, 5,636,874, 5,873,604, 5,704, 5,449,200, 5,465,301, etc. Currently, a security printer is able to select from a variety of measures to prevent counterfeiting or forgery and to allow authentication. Any one document can include a range of such measures, and the choice of those that are actually included in a specific document already presents a formidable task to a wrongdoer. Nonetheless, there is a constant need to add, diversify and improve the measures that are employed, particularly those which lend themselves to present day security printing manufacturing, identification and sorting equipment.

Although the human visual system is highly capable of the perception of spectral energy within the visible region of electromagnetic spectrum, manifesting itself as brightness and color, it is less capable when used for quantification and recall. To perform these functions with much higher confidence, reproducibility, precision and speed than the human eye can do, spectral radiometers and/or spectrophotometers (spectrometers) can be used. Since an advanced machine-readable security feature can reveal its specific physical characteristics or attributes in different regions of electromagnetic spectrum (e.g., in the so called ultra-violet (UV), near-infrared (NIR) and middle-infrared (MIR) regions of the spectrum), the identification process should be performed with the aid of an appropriate spectroscopy method. Currently, it is possible to select, e.g., from the so called UV-, VIS-, Fluorescence, NIR-, MIR- and Raman spectroscopies which have been successfully used for many years for identification of chemical compounds in research, analytical and forensic laboratories. UV-, VIS-, NIR- and MIR-absorption spectra arise when respectively the ultra-violet (0.1–0.35 $\mu$m), visible (0.35–0.75 $\mu$m), near infrared (0.75–2.0 $\mu$m) or middle-infrared (2.0–30.0 $\mu$m) light incident upon a sample of the material is absorbed. Normal fluorescence can be detected by illuminating a material with light of an appropriate excitation wavelength (usually 200–600 nm) and by subsequent detection of the resultant spectral emissions with the aid of an electro-optical sensor. Raman spectra arise as a result of inelastic scattering of a laser light (which may have any wavelength from 0.25–2.0 $\mu$m region) incident upon a sample of a material. The Raman effect occurs when small portions of photons in a laser light beam gain or loose some discrete amounts of energy upon colliding with vibrating molecules of a substance. This energy exchange alters the wavelength of the incident (exciting) light and the new wavelengths that are emitted constitute the Raman spectrum.

In any case, needed for such analyses spectrophotometers and/or radiometers perform the same type of physical measurement. Actually they calculate a series of weighted integrations of electromagnetic energy over wavelength. Spectrophotometers and spectral radiometers are generally capable of reporting tens to thousands of weighted integrations. The weighting functions for these instruments each usually have a common shape which is ideally a narrow triangle. For radiometers the sample is a radiant source, and the weighting function is the product of the spectral intensity of the source, a filter parameters, and the spectral sensitivity of the detector. Spectrophotometers generally use broadband light sources and detectors, and the weighting function is provided by multiple filters, by monochromators, by spectrographs, or by interference techniques. Both spectral radiometers and spectrophotometers are intended to allow measuring transmittance (absorbance), reflectance or intensity spectrum of the sample with reference to wavelengths to be represented as a set of points, or a curve, or a spectrum.

More specifically, instrumentally measured UV- and, VIS-absorption (which, depending upon the sampling and the optical experiment geometry, may be measured in transmittance, absorbance or reflectance units) occurs when the wavelength of the incident probing beam of light turns out to be equal (that is in resonance with) to that of an optical absorption band in the material. The electrons responsible for the absorption are located on a number of molecular orbitals on subset of atoms in the compound, known as the chromophore. By absorbing an appropriate photon of the probing light, electrons temporarily transit from orbitals with lower energies to those having higher energies giving rise to the so called electron absorption bands. Usually, these phenomena involve a large number of different molecular orbitals in a compound and, as a consequence, UV- and VIS-absorption spectra of complex compounds are represented by a number of overlapping broad bands. While these absorption bands frequently have very high intensity (which is the measure of probability of a given electron transition) facilitating detectability of a compound, broadness of the absorption bands puts some restrictions on the analytical value of the method because very strict machine readability criteria (high optical resolution, high signal to noise ratio, narrow acceptability interval, high photometric accuracy, etc.) should be applied, especially when exploiting complex mixtures of several compounds as security features.

Conventional Middle-Infrared (MIR) absorption spectroscopy, in principle, has much higher analytical value compared to UV-VIS-absorption spectroscopy. Very roughly, MIR region is commonly defined as electromagnetic radiation with frequencies between 5,000 and 500 cm−1 (2.0–20.0 $\mu$m). When a normal molecular motion such as a vibration, rotation or lattice mode (as well as combination, difference, or overtone of these normal vibrations) results in a change in the molecule's dipole moment, a molecule can absorb infrared radiation in this region of the electromagnetic spectrum. In other words, very selective resonant absorptions of monochromatic constituents of the infrared light from a broadband source by those molecular fragments of a compound which oscillate with the frequencies corresponding to the frequencies of the incident light are responsible for arising the infrared absorption bands. The corresponding frequencies and intensities of these infrared bands, the infrared spectrum, are then used to characterize the material. In terms of developing new anti-counterfeiting measures, the prime importance is the fact that infrared spectral information may be used to identify the presence and amount of a particular compound in a mixture. Modem instrumentation allows the collection of infrared spectra of materials at low-picogram levels. The ability of infrared spectroscopy to examine and identify materials under a wide variety of conditions has earned this technique the premier position as the "workhorse" of analytical science. However, the main problem that always exists during analytical work in the infrared (and which always must be circumvented when applying IR-spectroscopy for security purposes also) is the so called "transparency window problem". Though the problem exists during absorption spectroscopy measurements in different spectral regions, it is especially severe in the infrared. Actually, despite the attractiveness of infrared spectroscopy for authentication purposes, this method yet did not find wide use "in the field" security measurements. The main obstacles for this are comparative sophistication and fragility of the instrumentation as well as the costs of the latter. "Transparency window problem" and labor costs for usually tedious and time consuming sample preparation of a sample before the analysis may be the additional reasons. Of importance, however, is the fact that MIR absorption spectroscopy, in principle, provides information which is similar to that obtainable by normal Raman scattering spectroscopy. Both infrared light absorption and Raman light scattering phenomena result in obtaining vibrational spectra of a compound. Both these spectra are mutually superimposable, but do not constitute replicas of each other. Rather, they are luckily complement each other giving a complete vibrational spectrum of a compound. While any one (MIR or Raman) vibrational spectrum of the two is a fingerprint of a compound and may be used for identification of the latter, the sum of the two spectra gives a much more detailed fingerprint of a compound and permits considerably more confident identification to be made. Moreover, as a rule of thumb, those normal vibrations which are Raman-active are considerably less active in the infrared absorption spectroscopy. And vice versa. It means that to facilitate identification of an unknown (or authentication of a searched, but known beforehand) compound, a judicious choice of a method is desirable.

NIR-absorption spectroscopy is very similar to the conventional infrared (MIR) analogue. Among advantages of this method are comparative simplicity of the necessary instrumentation and a possibility to run NIR-absorption spectra without any sample preparation. An essential drawback of the method, however, is that in NIR region of electromagnetic spectrum one has to exploit either overtones and/or combinations of the fundamental vibrations taking place in the MIR-region. In principle, the spectral bands corresponding to overtones and combinations have much lower intensity and are characteristically broadened—the circumstances which worsen the analytical value of the NIR-absorption spectroscopy in terms of reliable identification of fakes and forgery.

In contrast to the above methods, Fluorescence spectroscopy (or fluorometry) is an emission technique. Normally it is based on use of fluorescent compounds (fluorophores) which typically are organic dye molecules. These molecules are capable of absorbing electromagnetic energy in a particular absorption wavelength spectrum and subsequently to emit light at more longer wavelengths. Usually, the sensitivity and reliability of detection of a fluorophore is related to both the type of the compound employed and the quality and type of equipment available to detect it. A wide variety of fluorescent dyes are available and offer a selection of excitation and emission spectra. And, in principle, it is possible to select fluorophores having emission spectra that are sufficiently different so as to permit their multitarget detection and discrimination. Unfortunately, detection methods which employ fluorescent labels are of limited sensitivity and reliability for a variety of reasons. Most importantly, with conventional fluorophores it is difficult to discriminate specific fluorescent signals from nonspecific background signals. Very often, the general characteristics of organic dye fluorescence are also applicable to background signals which are attributed to other compounds (e.g., vehicles, ink pigments, paper whiteners, etc). An extra problem with organic dye fluorophores is their photolytic decomposition (i.e., photobleaching). Due to this, even in situations where background noise is relatively low, it is often not possible to integrate a weak fluorescent signal over a needed detection time, since the dye molecules decompose as a function of incident irradiation dose absorbed in the UV, near-UV or even VIS bands.

Recently, a variety of inorganic phosphors with excitation in the infrared region have been introduced in to the market. These materials have seemingly greater potential in security applications, especially in areas where high-speed machine readability is required. Materials which can be excited with infrared radiation to emit radiation of a higher energy in the near infrared or visible region of the spectrum are known as "anti-Stokes" or "up-converting" phosphors. The "normal" fluorescence is a quantum phenomenon in which energy is resonantly absorbed by the phosphor in the form of single photons of ultra-violet or visible radiation and, after energy losses for non-radiative phenomena, is emitted as photons of a longer wavelength light. In all normal fluorescence it follows that the exciting radiation must have a shorter wavelength than the emitted light. This observation is referred to as Stoke's Law. In difference to this, the class of anti-Stokes phosphors has the ability to absorb two or three photons of longer wavelength infrared light and combine their energies to emit a single photon of, e.g. visible light. Phosphors of this class have characteristic excitation spectra in the infrared and near infrared, often coinciding with the wavelengths produced by NIR and IR light emitting diodes (LEDs) or lasers. An essential advantage of such anti-Stokes phosphors is that they are not susceptible to photobleaching and, due to the fact that excitation is performed in far red, NIR or IR region, they do not induce unwanted autofluorescence of substrates and impurities.

However, despite the great amount of efforts spent up to date to improve reliability of fluorescence spectroscopy, this method still possess a number of intrinsic drawbacks. Thus, for instance, when trying a "blanking" or "zeroing" instrument, one usually expects to obtain a result where whatever residual signal of the blank material it will be eliminated or canceled out. Unfortunately, with fluorescence instruments this is never the case. The very name "fluorescence blank" is misleading, because even non-fluorescent materials can give rise to artifactual peaks. The problem arises from several sources. Artifactual peaks are generated in non-fluorescent blanks from (1) Rayleigh-Tyndall scatter, (2) Raman scatter, and (3) complex, but predictable, harmonic order reflections of these same scatter peaks caused by the diffraction grating employed in the monochromator or spectrograph of the instrument. Scatter emissions are generated by any material containing small particles: i.e., solids, liquids and gases. Because of the ubiquitous nature of the scattering phenomenon, artifactual peaks are generated by virtually any sample or material. Thus, there exist a significant need in the art for detection methods which permit sensitive optical and/or spectroscopic identification of specific label signal(s) with essentially total rejection of non-specific background noise and which are nondestructive for different kinds of substrates carrying the labels.

In Raman spectroscopy, the scattered light includes light of the laser wavelength plus, at much lower intensity, light of additional wavelengths which are characteristic of the compound. Raman scattering effect is extremely weak; typically a few Raman (inelastically) scattered photons exist among millions of elastically scattered photons. The additional light appears at frequencies which are shifted from that of the laser beam by amounts equal to the frequencies of normal vibrations of the atoms in the compound. These frequencies are determined by the masses of the atoms comprising the material and the forces which hold them together. All molecules vibrate and do so in multitudinous fundamental modes, giving rise to changes in dipole moment (if nonsymmetrical) and/or polarizability (the ease with which electrons can be induced to respond to a potential gradient). The dipole change enables one to measure the frequency of molecular vibrations by infrared absorption; the polarizability change provides the driving force for Raman scattering. As fundamental vibrational modes are almost always unique for every chemical compound, the MIR- and Raman spectra are often used as its fingerprint. Raman spectroscopy has experimental advantages over infrared absorption. Firstly, window problems hardly exist, if visible or near infrared lasers are used as excitation sources. Secondly, since transmission through the sample is not a necessary prerequisite, hardly any sample preparation is required in Raman spectroscopy. Since Raman spectra reveal unique features that are specific to the materials under examination, this method provides an ideal way of detecting compositional variations in substances. In this way, the compound may be identified in various conditions, for example as a crystal, in solution, as a powder and in mixtures with other compounds. Thus, Raman spectroscopy might be rendered as, perhaps, the most promising candidate for providing highest degrees of protection against forgery and counterfeiting.

In the prior art, several examples of employing Raman spectroscopy for security purposes have been disclosed. Thus, for instance, use of polydiacetylenes as Raman-active components of an ink for printing security documents which then could be identified by Resonance Raman Spectroscopy (RRS) has been described in U.S. Pat. No. 5,324,567 (Ink compositions and components thereof, 1994, Bratchley et al., Thomas de la Rue and Company). In accordance with the teachings of this document, fourteen polydiacetylenes are suggested to be used in the form of particles having a maximum dimension of 40 $\mu$m. The authors rely upon Resonance Raman Scattering which occurs when the wavelength of the incident laser beam is equal to, i.e. in resonance with, that of an optical absorption band of the material. They primarily rely on the circumstance that, under resonance conditions, the Raman scattered light should be greatly enhanced in intensity. According to their evaluations, the intensity of Raman lines due to collective vibrations of the backbone atoms of a polydiacetylene under resonance conditions can be at least 104 times greater than those arising from atomic vibrations in the side groups. Although the authors note that, in principle, the exciting laser light may be in the ultraviolet, visible or near infra-red regions of the spectrum, in their examples they used only a HeNe laser, emitting at a wavelength of 632.8 nm, and deliberately chosen so that the laser wavelength would fall within the optical absorption band of the material. Further, they exposed their samples to laser light and then measured with a photomultiplier a resonance Raman scattering intensity above the background fluorescence. Not providing factual Raman spectra of inks obtainable in accordance with their invention, the authors suggest to use only the five most prominent resonantly enhanced lines typical for RRS spectra of polydiacetylenes: one line at about 2100 cm−1, two near 1500 cm−1 and two between 1300 and 900 cm−1, displaced to lower energy from the incident laser source wavenumber. The authors suggest that positive identification of a polydiacetylene can be made with reasonable certainty by detecting the triple bond vibration alone near 2100 cm−1. They state also that positive identification can be made virtually certain by adding an additional criterion, viz., that the intensity of the Raman scattered light be nearly the same as that from a reference polydiacetylene sample. In the two examples of practical identification of the polydiacetylenes provided in the Patent, however, one can only find indication that " . . . The scattered Raman light . . . was detected by a photomultiplier at the wavelength of maximum emission for the particular Raman scattering being tested." And, further: "In all the test prints containing the polymer, peaks due to the polydiacetylene backbone were readily observed. The vehicle, paper and colored pigments gave some overall general scattering, but of sufficiently low intensity not to obscure the polydiacetylene peaks." In another example the authors disclose that: "Signal strength was measured at the point of maximum response. Non-Raman background scattering including fluorescence was subtracted from the total signal, to give that solely due to Raman, thus providing a unique document authentication system."

In the U.S. Pat. No. 5,718,754 (Pigment compositions, 1998, Macpherson et al., Ciba Specialty Chemicals) the use of coding compounds containing an azo, azomethine or polycyclic chromophore as Raman-detectable additives to pigments for security printing inks has been disclosed. These coding compounds are adsorbed on a printing pigment surface, or are used as a physical mixture with the pigment, in an amount sufficient to be detected by Raman or Resonance Raman Scattering (RRS) spectroscopy. Excitation with Argon Ion Lasers at wavelength of 514.5 nm or with different wavelengths in the red region obtainable with the aid of dye laser sources has been used for detection. As a pigment the authors suggest to employ any pigment commonly used in printing inks, such as arylamide, diarylide, azo metal salt, or phthalocyanine pigment. The coding compound adsorbed on the surface of the pigment is preferably a compound which is not normally used in printing inks, such as a copper phthalocyanine derivative. The coding compound which is physically mixed with the pigment is preferably an isoindolinone, diketopyrrolopyrrole, Schiff base metal complex, ferricyanide or a metal phtalocyanine derivatives. The authors note that the coding compound should preferably have an absorption frequency maximum at or near an absorption minimum of the pigment or even be outside the spectral range of the pigment. This separation gives the maximum sensitivity for detection by RRS. It is noted also that if the wavelength of the illuminating light is matched with the absorption maximum of the coding compound then the Raman spectrum recovered is significantly enhanced allowing much greater sensitivities to be obtained. It is further suggested that the matching of the wavelengths of the illuminating radiation and the absorption maximum of the coding compound can be achieved in two ways. Firstly, the laser wavelength may be selected to any devised wavelength and can therefore be used to detect the Raman spectrum of the coding compound in the presence of many different substances. Alternatively the coding compound can be selected so that it possesses an absorption maximum at or close to the available laser frequency. This latter option allows the lower cost system without loss of efficiency since tunable lasers are expensive. Although the authors note that the laser frequency can be visible, ultraviolet or infra-red when matched with suitably absorbing coding compounds, it is obvious that they rely on traditional RRS approach for detection. Not presenting factual exemplary spectra obtainable in accordance with their invention, Macpherson et al. provide only several Raman shift values for some of the peaks seen in the spectra they obtained. It is worth noting also that all the spectral information mentioned in the text of the patent has been acquired with the aid of expensive and non-portable Raman (Renishaw 2000 or an Anaspec modified Cary 81) spectrometers, rather fragile Argon Ion or expensive Dye lasers, and, deliberately, by using Resonance Raman Spectroscopy.

In another patent of Macpherson et al. (U.S. Pat. No. 5,853,464, Pigment compositions, 1998, Ciba Specialty Chemicals) use of Raman-detectable coding compounds that are adsorbed onto colloids or other nano scale metal particles is disclosed, and their use in printing inks for security applications such as banknotes and other security items is suggested. These coding compounds are detected by Surface Enhanced Resonance Raman Scattering (SERRS) spectroscopy to increase the intensity and detectability of the scattered light. According to the patent, the coding compounds may be a dye or a pigment and may be for example a phthalocyanine, a perinone, a quinacridone, an indanthrone, a flavanthrone, a pyranthrone, a perylene, a thioindigo, a dioxazine, an isoindoline, a diketopyrrolopyrrole, a basic dye complex, a metal complex, a monoazo, an azo metal salt, a disazo or a ferricyanide. Preferably coding compounds are used which have similar electronic absorption frequencies to the SERS plasmon resonance frequency. The authors recognize that Normal Raman scattering (NRS) is a very weak effect and gives with their materials low intensity signals, which can make detection difficult. So, in lines with traditional approach, they suggest to exploit tuning of the laser frequency to match an absorption maximum of the Raman-detectable compound, since scattering can be increased in efficiency by a factor of 103 to 104 due to resonance with the molecular electronic transitions. That is, they again rely on Resonance Raman scattering (RRS). To additionally increase the Raman signal intensity, it is suggested to exploit another known effect, the so called Surface Enhanced Raman Scattering (SERS). Surface enhancement arises from molecules which have been adsorbed onto a roughened surface, for example, roughened electrodes or aggregated colloids of nano-scale particles of SERS-active metals, such as silver, gold, copper, and lithium. Expectedly, surface enhancement can increase the intensity of the Raman scattering by up to 106. The size of the effect is dependent, however, on (i) the nature of the surface roughness, (ii) the distance of the Raman active molecules from the surface, (iii) the orientation of the molecules on the surface and (iv) the metal. Thus sensitivity varies widely depending on the exact nature of preparation of the surface or aggregated colloid and the method of addition of the Raman active molecules. Expecting that the scattering from a Raman active molecule on or near the surface of a SERS-active metal can be further enhanced when the laser light frequency is in resonance with an electronic transition of the Raman active molecule, the authors suggest to use the so called Surface Enhanced Resonance Raman Scattering (SERRS). They suggest that sensitivity of SERRS is much greater than the sum of SERS and RRS, and the identification of the Raman active molecule present is also extremely specific. Indeed, very low amounts of the Raman-detectable coding compound (between 0.1 and 100 ppm, preferably between 0.5 and 10 ppm) added of the SERS-active metal colloid are claimed in the patent. The authors further claim the following advantages of their SERRS system for use in security ink systems: (i) the sensitivity is much higher and there is a greater degree of selectivity with only vibrations from the coding compound being detected; (ii) in principle, photodecomposition could be minimized by SERRS since the energy transfer process between the coding compound and the surface reduces the lifetime of excited states and low powered lasers can be employed; (iii) SERRS can be used with both fluorescing and non-fluorescing compounds since fluorescence is quenched at the surface. It is further claimed that such an ink may be doped with extremely small quantities of the SERS-active metal aggregates of colloids known as the SERRS active sol. Then the ink can be printed by normal lithographic printing processes. It is claimed that the sensitivity is so great that unique, easily distinguished signals may be obtained from inks which contain so little of the specially prepared SERRS active sol that these inks are otherwise indistinguishable from clear varnish. The areas of surface required for examination can be as low as 1 $\mu m^2$, if a suitable microscope attachment is used. Nonetheless, although it is claimed that the coding compound which is adsorbed on the surface of the SERS active metal colloid may be selected from any compound which exhibits a characteristic Raman spectrum, those familiar with the art will appreciate that, up to date, only a very limited number of molecules giving useful SERRS spectra has been reported. The authors note that SERRS is preferred over SERS, where coding compounds are used which have a suitable electronic transition. But this condition in fact even further limits the choice of coding molecules. Another limitation is connected with the fact that, as the authors note, preferably the laser frequency is chosen to be close to that of the electronic transition and/or the frequency of the SERS plasmon resonance of the SERS-active metal colloid. It means the necessity to use expensive tunable lasers as excitation sources for the SERRS. Provided by the authors teaching that the coding compound should preferably be such that it gives a strong interaction with the SERS active metal colloid surface in fact additionally narrows the choice of molecules suitable for the role. It should be noted also that the known procedures of SERRS active sol preparation are rather tedious and plagued by poor reproducibility. Again, not presenting factual spectra permitting to evaluate, e.g., signal to noise ratio, resolution, and/or reproducibility of the obtainable spectra, the authors cite frequencies for several spectral bands without any assignments of the latter. Also, quoted spectra were acquired with the aid of expensive equipment. All this makes problematic a mass use of this system as a machine-readable security feature—especially in view of highly desirable adoption of Raman detection for computerized spectral search and control by unskilled operator "in the field".

Concerning the Resonance Raman Spectroscopy approach deliberately used by the inventors in the above cited U.S. Pat. Nos. 5,324,567, 5,718,754 and 5,853,464, the disclosures of each of which are totally incorporated herein by reference, it is necessary to note the following. Indeed, until now in scientific circles as well as in patent literature the RRS, permitting to obtain a several orders of magnitude (ca. $10^4$–$10^6$ times) enhancement of the Raman signal, sometimes is considered to be an advantageous technique compared to normal Raman scattering. However, this traditional approach, being based on use of laser excitation wavelengths falling in clear resonance with electronic or excitonic transitions characteristic for a compound to be detected, has serious drawbacks and limitations. For instance (and this is of prime importance in terms of the aims and spirit of our invention which will be disclosed later), the RRS (or SERRS) can hardly be rated as truly quantitative spectroscopic tools. The main reasons for this are: (i) the resonance Raman spectra are often contaminated or distorted by considerable thermal or fluorescent backgrounds caused by absorption of the laser frequency, the latter additionally being the cause for severe sample heating and/or degradation; (ii) intensity of the RR scattered light is not governed by the fundamental 4 law and is hardly predictable; (iii) shapes and intensities of the bands constituting the resonantly enhanced Raman spectra vary with the excitation wavelength used; (iv) when short-wave visible excitation is used, the generated Raman photons often have frequencies coinciding with spectral region of strong optical opacity of the sample, and hence reabsorption of the Raman photons by the sample unavoidably, and in an unpredictable manner, distorts the true intensity of the Raman bands. These and other less obvious shortcomings of the RRS approach will be discussed and illustrated in more details later (cf. DETAILED DESCRIPTION OF THE INVENTION section below), during discussion of essentials of the preferred by us "normal" Raman approach.

There is also a patent in the prior art disclosing employment of non-resonance Raman spectroscopy for security purposes "in the field" (U.S. Pat. No. 5,818,047, Detector for explosive substances, 1998, Chaney et al., Renishaw P L C). According to the patent, Raman-active ingredients of some plastic explosives can be detected even in microquantities by virtue of analyzing traces of explosives in samples such as fingerprints left on a paper card. In this case the Raman-active ingredients of a plastic explosive Semtex (such as cyclotrimethylene-trinitramine, or RDX, and pentaerythritotetranitrate, or PETN) were detected by using an expensive research-grade Renishaw X20 Raman microscope (objective NA=0.45) and excitation with 25 mW HeNe laser emitting at 632.8 nm. The authors indicate that amount of power reaching the sample was about 5 mW, which corresponds to an energy density of $2\times10^9$ W/m2. Acquisition times of 5 s were sufficient for obtaining high quality spectra of RDX and PETN. The authors note, however, that both RDX and PETN appear to have large Raman scattering cross sections, making the Raman spectra easy to acquire. They have also tested a 514.5 nm line $Ar^+$ laser with the same single crystalline samples and obtained essentially identical results. Moreover, the spectra were similar in appearance to those acquired using the FT Raman technique with 1064 nm Nd:YAG laser excitation. The tests of Chaney et al. have shown that their Raman apparatus and non-resonant approach can be successful in detecting extremely small particles of Semtex, e.g. about 1 $\mu$m3, weighing about 1 picogram, in a few seconds. Their tests simulated real life conditions in which they made "impure" samples with fingerprints which were cross contaminated by both Semtex and other greasy substances. The authors note that, in order to improve reliability of the detection, it may (among other possibilities) also be desirable to ensure that the boarding cards for taking fingerprints are made of a non-fluorescent (under 632.8 mn excitation) card material. An alternative to using non-fluorescent card they see in using a laser which produces light in the far red or in the infra-red region of the spectrum.

Of importance for comprehending aims, scope and advantages of the present invention is the fact that (as the patent of Chaney et al. Also surmises) there is no necessity always to provide Resonance Raman conditions to obtain good and useful Raman spectra of an analyte. Rather, Raman spectra of very high quality can be easily obtained also by using non-resonant or far from resonance excitations. In this case, however, the nature of a sample (i.e., whether this is an efficient Raman scatterer or not) is primarily responsible for whether intense or poor Raman spectrum will be produced. Hence, taking into account all the shortcomings of Resonance Raman spectroscopy noted above, it would be highly desirable to exploit an alternative approach based on normal Raman effect. The latter, however, although in principle being capable of providing more reliable, quantitative, practicable, simple and cost-effective means for detection of security features, automatically necessitates employment of intrinsically efficient Raman scatterers. Therefore, in accordance with the aims and scope of the present invention, there arises a substantial need for materials, coding compounds or taggants that would be intrinsically highly Raman-active, i.e. would have large Raman scattering cross sections and would be capable of producing intense Raman spectra under effect of characteristically non-resonant or far from resonance laser excitations.

For the sake of better understanding aims, scope, novelty and advantages of the present invention it seems necessary to analyze in more details teachings of the U.S. Pat. No. 5,935,755 (Method for document marking and recognition, 1999, Kazmaier et al., Xerox Corporation) the disclosure of which is totally incorporated herein by reference. This document discloses numerous marking materials comprising the so called Raman-detectable compounds suitable for employment in printing inks and xerography toners for security applications such as authentication of documents. Particularly preferred Raman-detectable components are considered to be those that exhibit a distinct Raman spectrum at a wavelength where most paper and dye or pigment colorants are transparent. More particularly, it is stated that, when exposed to a Nd:YAG laser at 1064 nm, many squaraine compounds emit a strong, unique signal in the Raman spectrum at about 1600 cm−1 off the excitation laser line. Squaraine compounds preferred in the patent are of the general formula

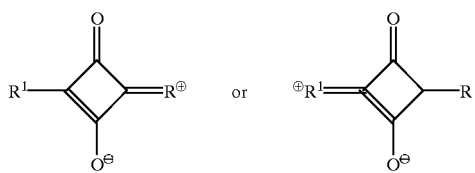

(1)

wherein R and R1 each, independently of the other, can be

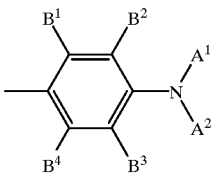

(2)

wherein A1 and A2 can each, independently of the other, be hydrogen atoms, alkyl groups, preferably with from 1 to about 18 carbon atoms, substituted alkyl groups, preferably with from 1 to about 18 carbon atoms, aryl groups, preferably with from about 6 to about 20 carbon atoms, substituted aryl groups, preferably with from about 6 to about 20 carbon atoms, arylalkyl groups, preferably with from about 6 to about 38 carbon atoms, substituted arylalkyl groups, preferably with from about 6 to about 38 carbon atoms, heterocyclic rings, preferably of from about 5 to about 7 members wherein the hetero atom is nitrogen, oxygen, sulfur, phosphorus, boron, or the like, such as pyrrolidine, pyridine, piperidine, piperazine, quinoline, isoquinoline, quinuclidine, pyrazole, triazole, tetrazole, triazine, imidazole, pyrimidine, pyradizine, pyrazine, oxazole, isoxazole, morpholine, and the like, halogen atoms, cyano groups, mercapto groups, hydroxy groups, amine groups, imine groups, ammonium groups, pyridine groups, pyridinium groups, ether groups, aldehyde groups, ketone groups, ester groups, amide groups, carboxylic acid groups, carbonyl groups, thiocarbonyl groups, sulfate groups, sulfonate groups, sulfide groups, sulfoxide groups, phosphine groups, phosphonium groups, phosphate groups, cyano groups, nitrile groups, mercapto groups, nitroso groups, nitro groups, sulfone groups, acyl groups, acid anhydride groups, azide groups, and the like, and wherein A1 and A2 can be joined together to form a ring containing the nitrogen atom to which A1 and A2 are attached, such as a pyrrole ring, an indole ring, an indolizine ring, a pyrrolidine ring, a pyridine ring, a piperidine ring, a piperazine ring, a quinoline ring, an isoquinoline ring, a quinuclidine ring, an indazole ring, a pyrazole ring, a triazole ring, a tetrazole ring, a triazine ring, a urazole ring, an imidazole ring, a pyrimidine ring, a pyradizine ring, a pyrazine ring, an oxazole ring, an isoxazole ring, a morpholine ring, or the like, and wherein B1, B2, B3, and B4 can each, independently of the other, be hydrogen atoms, alkyl groups, preferably with from 1 to about 18 carbon atoms, substituted alkyl groups, preferably with from 1 to about 18 carbon atoms, aryl groups, preferably with from about 6 to about 20 carbon atoms, substituted aryl groups, preferably with from about 6 to about 20 carbon atoms, arylalkyl groups, preferably with from about 6 to about 38 carbon atoms, substituted arylalkyl groups, preferably with from about 6 to about 38 carbon atoms, heterocyclic rings, preferably of from about 5 to about 7 members wherein the hetero atom is nitrogen, oxygen, sulfur, phosphorus, boron, or the like, such as pyrrolidine, pyridine, piperidine, piperazine, quinoline, isoquinoline, quinuclidine, pyrazole, triazole, tetrazole, triazine, imidazole, pyrimidine, pyradizine, pyrazine, oxazole, isoxazole, morpholine, and the like, halogen atoms, cyano groups, mercapto groups, hydroxy groups, amine groups, imine groups, ammonium groups, pyridine groups, pyridinium groups, ether groups, aldehyde groups, ketone groups, ester groups, amide groups, carboxylic acid groups, carbonyl groups, thiocarbonyl groups, sulfate groups, sulfonate groups, sulfide groups, sulfoxide groups, phosphine groups, phosphonium groups, phosphate groups, cyano groups, nitrile groups, mercapto groups, nitroso groups, nitro groups, sulfone groups, acyl groups, acid anhydride groups, azide groups, and the like, wherein the B groups can be joined together to form one or more rings,

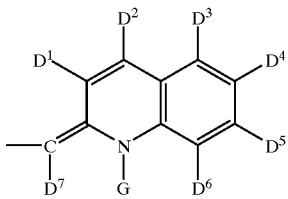

(3)

wherein G is selected from the group consisting of hydrogen atoms, alkyl groups, preferably with from 1 to about 18 carbon atoms, substituted alkyl groups, preferably with from 1 to about 18 carbon atoms, aryl groups, preferably with from about 6 to about 20 carbon atoms, substituted aryl groups, preferably with from about 6 to about 20 carbon atoms, arylalkyl groups, preferably with from about 6 to about 38 carbon atoms, substituted arylalkyl groups, preferably with from about 6 to about 38 carbon atoms, heterocyclic rings, preferably of from about 5 to about 7 members wherein the hetero atom is nitrogen, oxygen, sulfur, phosphorus, boron, or the like, such as pyrrolidine, pyridine, piperidine, piperazine, quinoline, isoquinoline, quinuclidine, pyrazole, triazole, tetrazole, triazine, imidazole, pyrimidine, pyradizine, pyrazine, oxazole, isoxazole, morpholine, and the like, halogen atoms, cyano groups, mercapto groups, hydroxy groups, amine groups, imine groups, ammonium groups, pyridine groups, pyridinium groups, ether groups, aldehyde groups, ketone groups, ester groups, amide groups, carboxylic acid groups, carbonyl groups, thiocarbonyl groups, sulfate groups, sulfonate groups, sulfide groups, sulfoxide groups, phosphine groups, phosphonium groups, phosphate groups, cyano groups, nitrile groups, mercapto groups, nitroso groups, nitro groups, sulfone groups, acyl groups, acid anhydride groups, azide groups, and the like, and D1, D2, D3, D4, D5, D6, and D7 each, independently of the others, can be hydrogen atoms, alkyl groups, preferably with from 1 to about 18 carbon atoms, substituted alkyl groups, preferably with from 1 to about 18 carbon atoms, aryl groups, preferably with from about 6 to about 20 carbon atoms, substituted aryl groups, preferably with from about 6 to about 20 carbon atoms, arylalkyl groups, preferably with from about 6 to about 38 carbon atoms, substituted arylalkyl groups, preferably with from about 6 to about 38 carbon atoms, heterocyclic rings, preferably of from about 5 to about 7 members wherein the hetero atom is nitrogen, oxygen, sulfur, phosphorus, boron, or the like, such as pyrrolidine, pyridine, piperidine, piperazine, quinoline, isoquinoline, quinuclidine, pyrazole, triazole, tetrazole, triazine, imidazole, pyrimidine, pyradizine, pyrazine, oxazole, isoxazole, morpholine, and the like, halogen atoms, cyano groups, mercapto groups, hydroxy groups, amine groups, imine groups, ammonium groups, pyridine groups, pyridinium groups, ether groups, aldehyde groups, ketone groups, ester groups, amide groups, carboxylic acid groups, carbonyl groups, thiocarbonyl groups, sulfate groups, sulfonate groups, sulfide groups, sulfoxide groups, phosphine groups, phosphonium groups, phosphate groups, cyano groups, nitrile groups, mercapto groups, nitroso groups, nitro groups, sulfone groups, acyl groups, acid anhydride groups, azide groups, and the like, and wherein two or more of the G and D groups can be joined together to form one or more rings,

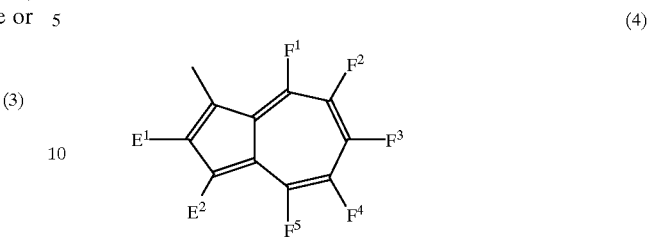

(4)

wherein E1 and E2 each, independently of the other, can be hydrogen atoms, alkyl groups, preferably with from 1 to about 18 carbon atoms, substituted alkyl groups, preferably with from 1 to about 18 carbon atoms, aryl groups, preferably with from about 6 to about 20 carbon atoms, substituted aryl groups, preferably with from about 6 to about 20 carbon atoms, arylalkyl groups, preferably with from about 6 to about 38 carbon atoms, substituted arylalkyl groups, preferably with from about 6 to about 38 carbon atoms, heterocyclic rings, preferably of from about 5 to about 7 members wherein the hetero atom is nitrogen, oxygen, sulfur, phosphorus, boron, or the like, such as pyrrolidine, pyridine, piperidine, piperazine, quinoline, isoquinoline, quinuclidine, pyrazole, triazole, tetrazole, triazine, imidazole, pyrimidine, pyradizine, pyrazine, oxazole, isoxazole, morpholine, and the like, halogen atoms, cyano groups, mercapto groups, hydroxy groups, amine groups, imine groups, ammonium groups, pyridine groups, pyridinium groups, ether groups, aldehyde groups, ketone groups, ester groups, amide groups, carboxylic acid groups, carbonyl groups, thiocarbonyl groups, sulfate groups, sulfonate groups, sulfide groups, sulfoxide groups, phosphine groups, phosphonium groups, phosphate groups, cyano groups, nitrile groups, mercapto groups, nitroso groups, nitro groups, sulfone groups, acyl groups, acid anhydride groups, azide groups, and the like, and F1, F2, F3, F4, and F5 each, independently of the others, can be hydrogen atoms, alkyl groups, preferably with from 1 to about 18 carbon atoms, substituted alkyl groups, preferably with from 1 to about 18 carbon atoms, aryl groups, preferably with from about 6 to about 20 carbon atoms, substituted aryl groups, preferably with from about 6 to about 20 carbon atoms, arylalkyl groups, preferably with from about 6 to about 38 carbon atoms, substituted arylalkyl groups, preferably with from about 6 to about 38 carbon atoms, heterocyclic rings, preferably of from about 5 to about 7 members wherein the hetero atom is nitrogen, oxygen, sulfur, phosphorus, boron, or the like, such as pyrrolidine, pyridine, piperidine, piperazine, quinoline, isoquinoline, quinuclidine, pyrazole, triazole, tetrazole, triazine, imidazole, pyrimidine, pyradizine, pyrazine, oxazole, isoxazole, morpholine, and the like, halogen atoms, cyano groups, mercapto groups, hydroxy groups, amine groups, imine groups, ammonium groups, pyridine groups, pyridinium groups, ether groups, aldehyde groups, ketone groups, ester groups, amide groups, carboxylic acid groups, carbonyl groups, thiocarbonyl groups, sulfate groups, sulfonate groups, sulfide groups, sulfoxide groups, sulfonate groups, phosphine groups, phosphonium groups, phosphate groups, cyano groups, nitrile groups, mercapto groups, nitroso groups, nitro groups, sulfone groups, acyl groups, acid anhydride groups, azide groups, and the like, wherein two or more of the E and F groups can be joined together to form one or more rings, and the like.

Also preferred as Raman-detectable components in frames of the U.S. Pat. No. 5,935,755 are named phtalocyanines of the general formula

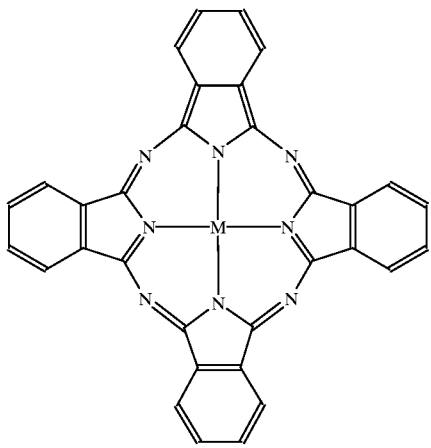

(5)

wherein M represents a metal atom, such as copper or the like, a functionalized metal, that is, any metal bearing additional substituents or ligands beyond the phthalocyanine moiety, such as oxovanadium, hydroxygallium, or the like, wherein bonding can be either predominantly ionic or covalent in nature, or two hydrogen atoms (metal-free phthalocyanine). Also preferred as Raman-detectable components are considered to be metal dithiolates, of the general formula

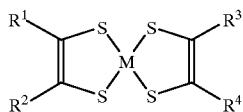

(6)

wherein M represents a transition metal atom, with nickel being preferred, and wherein R1, R2, R3, and R4 each, independently of the others, can be an alkyl group, preferably with from about 1 to about 18 carbon atoms, a substituted alkyl group, preferably with from about 1 to about 18 carbon atoms, an aromatic group, preferably with from about 6 to about 20 carbon atoms, a substituted aromatic group, preferably with from about 6 to about 20 carbon atoms, an arylalkyl group, preferably with from about 6 to about 38 carbon atoms, a substituted arylalkyl group, preferably with from about 6 to about 38 carbon atoms, or a heterocyclic ring, preferably with from about 5 to about 7 members, with the hetero atom being nitrogen, oxygen, sulfur, phosphorus, boron, or the like, with examples of suitable substituents including but not limited to mercapto groups, hydroxy groups, amine groups, imine groups, ammonium groups, pyridine groups, pyridinium groups, ether groups, aldehyde groups, ketone groups, ester groups, amide groups, carboxylic acid groups, carbonyl groups, thiocarbonyl groups, sulfate groups, sulfonate groups, sulfide groups, sulfoxide groups, sulfate groups, sulfonate groups, phosphine groups, phosphonium groups, phosphate groups, cyano groups, nitrile groups, mercapto groups, nitroso groups, nitro groups, sulfone groups, acyl groups, acid anhydride groups, azide groups, and the like, with examples of preferred groups including (but not limited to) phenyl, indole, furan, pyrrole, and the like, and wherein two or more of the R groups can be joined to form a ring.

Thus, according to the U.S. Pat. No. 5,935,755, the numerous disclosed Raman-detectable compounds, when irradiated with monochromatic radiation in the near infrared region of the spectrum, exhibit a detectable Raman spectrum which can be measured using standard FT-Raman instruments. Preferably, the Raman-detectable component is one that gives a Raman spectrum when irradiated with light in the near-infrared region, more particularly in the wavelength range of from about 680 to about 1400 nm. The authors recognize that Raman-detectable components which emit a Raman signal at excitation wavelengths lower than about 680 nm are also suitable, but may be less preferred because papers, toner pigments, ink colorants, and other similar materials which may also be present on or in the recording sheet may also absorb energy at these lower wavelengths, which might mask the Raman signal of the Raman-detectable component. Raman-detectable components which emit a Raman signal at wavelengths higher than about 1400 nanometers are also suitable, but may be difficult to obtain.

In a typical example, a squaraine compound [bis(4-dimethylamino-2-phenyl)-squaraine] (9) in powdered form was applied to a sheet of a plain paper as a small dot by pressing the material into the paper with a spatula and removing loose material by gently blowing the area with a stream of nitrogen. The paper thus treated was placed into the sample compartment of a Perkin-Elmer 1760 NIR-FT Raman spectrometer. To obtain the spectrum, the paper was aligned so that the Nd:YAG laser impinged on the treated spot. The Raman signal obtained from the treated spot was compared to the signal obtained from an untreated spot on the same paper, and a signal characteristic of the squaraine compound was recorded. In other examples the same approach has been used for marking a polyester film, a glass surface and an aluminium plate. However, despite the numerous compounds are quoted in the disclosure, in fact the authors give examples of preparing toners and inks for ink-jet printers comprising only the squaraine compounds of the few specific formulae below:

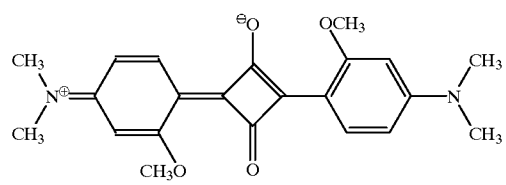

(7)

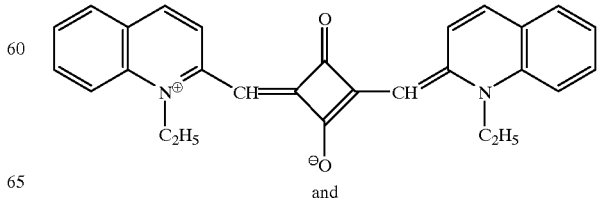

(8)

and

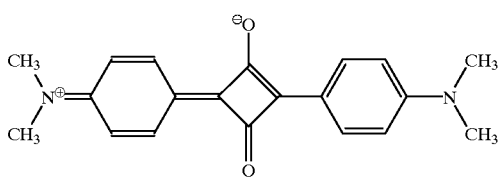

(9)

In additional examples, dry toner compositions suitable for developing electrostatic images, inks suitable for ink-jet printers, a UV-curable liquid developer suitable for polarizable liquid development processes and an electrophoretic developer were prepared comprising bis(4-dimethylamino-2-hydroxy-6-methylphenyl)squaraine or bis(4-dimethylamino-3-methoxy-phenyl)-squaraine (7) compounds as the Raman-detectable component in different proportions to other ingredients of the toner, ink or developer compositions. In all given examples, however, the developed images were rendered by the authors to be Raman-detectable without providing either factual NIR-FT Raman spectra or any indication for the Raman bands frequencies, not saying of the laser powers used or of intensity characteristics for different Raman bands if any. Instead, in all these instances the authors state that: "The Raman signal obtained from the treated spot is compared to the signal obtained from an untreated spot on the same substrate, and it is believed that a strong signal characteristic of the squaraine compound will be recorded."

Not questioning here the disclosed in the U.S. Pat. No. 5,935,755 facts of observing Raman spectra for several squaraine compounds with the aid of a research-grade NIR-FT Raman instrument, it is necessary to note the following.

(a) Yet 10 years ago, Raman spectroscopy has been used exclusively in research labs, almost never in analytical ones and positively never "in the field". The reasons are color and fluorescence problems that frequently arise when conventional shorter wavelength (visible) excitation is used. Colored samples absorb the source radiation and prevent one from seeing the Raman scatter, while even very weak fluorescence is much stronger than Raman scatter and effectively drowns it out. According to estimates of those familiar with the art, less than 20% of the vast range of samples studied up to date with conventional (visible) excitations have given observable Raman spectra; industrial analytical labs that used blue, green and red lasers reported similar success rates with consequently high costs per spectrum. At the beginning of 90 several main manufacturers of Fourier transform (FT) infrared spectrometers announced marketing of their near infrared (NIR) FT Raman spectrometers. The idea in NIR-FT Raman spectroscopy is to excite the spectrum with a near infrared laser, pass the scattered light through filters to remove the reflected and Rayleigh scattered excitation radiation, and then to process the Raman scatter on a Fourier transform infrared (FTIR) instrument. The pioneers used a range of research grade FTIRs and have developed filter and detector technologies allowing excellent spectra to be recorded in the near infrared. Being infrared excited, the spectra were virtually clear of fluorescence, while color (due to absorption of laser wavelength) was far less of a problem in near infrared than with conventional techniques. Thus, the following major advances have been achieved: (i) almost all tried samples give some sort of Raman spectrum; (ii) fluorescence and color present minimal problems; (iii) the quality of spectra previously difficult to study is frequently exceptional. Turning now to the preferred embodiments of the U.S. Pat. No. 5,935,755, it should be emphasized that all experiments described therein have been performed with the aid of research-grade (and hence of high-quality, but expensive) Perkin-Elmer 1760 or BOMEM Corporation (Maarssen, Netherlands) NIR-FT Raman spectrometers. However, as practitioners in the art will probably appreciate (and as it has been indicated above), almost all tried samples give some sort of Raman spectrum with the aid of such high-end instruments. Those familiar with the art will recognize also that, in order for provide a reliable Raman spectroscopic detection (authentication) of molecular security labels or markings, the tagging compounds are highly desirable which not only would be Raman-detectable, but would be strong Raman scatterers. Being devoid a possibility to evaluate the Raman-scattering ability (intensity of the corresponding Raman spectra) of the compounds disclosed in the U.S. Pat. No. 5,935,755 from the text, one is free to believe that the squaraine compounds of the patent may be only moderately Raman-active by their nature. This suggestion was supported by the results of comparative experiments constituting an integral part of the present invention (cf. DETAILED DESCRIPTION OF THE INVENTION section below) in which superior Raman-active compounds are disclosed and counterposed to those ones suggested in frames of the U.S. Pat. No. 5,935,755.

(b) Until now NIR-FT Raman spectrometers have not find considerable employment in so called "field" measurements of samples from real life. The main reasons are (i) comparative fragility of the interferometer and hence its disaligment problems, leading to worsening the signal to noise ratio (SNR) of collected spectra; and (ii) rather high cost of the desktop instruments based mainly on research-grade FTIRs. Hence, being acquired with the aid of expensive and fragile laboratory instruments, teachings of the U.S. Pat. No. 5,935,755 are hardly directly transferable for measurements "in the field" which would be made with the aid of less expensive dispersive Raman spectrometers.

(c) Those familiar with the art will recognize that, in order to perform spectroscopic detection (authentication) of security labels or markings "in the field" and in mass application, a Raman spectrometer would need to be rugged, sensitive, stable and inexpensive. One would need a reasonable optical resolution and a wide spectral range. Remote sampling through fiber optics would be a great advantage, allowing access to parts, articles and to environments which could not be reached by a conventional desktop or laboratory instrument. The ideal instrument would need only electricity to operate, with no requirements for cooling water, cryogens or other services. From a spectropists point of view, it would be desirable to work with strong fundamental vibrational bands rather than overtones and combinations. In principle, NIR-Raman spectroscopy can answer all of the needs on the above list, but until now the technique has been restricted to the laboratory because instrumentation was not sufficiently rugged. The renaissance in Raman spectroscopy, begun by the development of FT-Raman instruments, is now being further boosted by significant advances in dispersive Raman technology. Recent and continuing improvements in solid state lasers, filters and detectors have made dramatic improvements in both the ruggedness and sensitivity of dispersive Raman spectrometers. As a result, truly portable, rugged, sufficiently sensitive, and rather economic dispersive Raman spectrometers are feasible now which can find mass employment in the field for security authentication purposes. Nonetheless, those skilled in the art would appreciate that, for exploiting machine-readable technologies for security authentication purposes, it would be advantageous (in the same fashion as humans for long devised, optimized and used more bright, more contrast and hence more clearly visible labels, marks and signs for different self-needs and convenience) to deliberately devise, produce and use machine-readable tags, marks and labels which, while sometimes being rather dull or even completely invisible for unaided human eye, would be highly bright, highly contrast, more easy and "convenient" for the machine to detect and to identify. We recognized (and this notion has been laid down in the grounds of the present invention) that, on this way, it is imperative to try to provide as easy tasks for a detecting machine as possible. It is supposed also that these efforts will be compensated later by thus achievable higher reliability and convenience of the authentication process as well as by costs savings for the instrumentation, since the easier the task the more simple the detecting machine can be. As it will be illustrated later (cf. DETAILED DESCRIPTION OF THE INVENTION section below) by way of comparative experiments, besides those NIR-FT Raman-detectable compounds which has been disclosed in the U.S. Pat. No. 5,935,755, and which should be rendered in fact as moderately Raman-active ones, there exists a plenty of superior Raman-active compounds which has been deliberately devised in lines with the just mentioned philosophy and which are Raman-active in such extent that can be easily detected and authenticated "in the field" even with the aid of simplest dispersive Raman spectrometers using a low-power NIR laser as the excitation source.

(d) Practitioners in the art will probably recognize that the Raman-detectable compounds of the U.S. Pat. No. 5,935,755 have another, less obvious but essential in the long run, drawback. More close analysis of chemical formulas of the compounds preferred in the patent shows that aromatic or heteroaromatic cycles along with the squaraine cycle and a short chain of conjugated double bonds are the main structural blocks for the most of the compounds suggested for the role of a Raman-detectable marking. These will reveal their most prominent characteristic Raman bands in the region of 1650–1300 cm−1. At the same time, despite the apparent multiformity of the numerous disclosed in the patent substituents and groupings bearing different chemical names, most of them will also exhibit their most prominent characteristic Raman bands in the same Raman shifts region. In other words, it is expected that, frequently, the spectral region of 1650–1300 cm−1 will be overcrowded with spectral features. The latter circumstance will tend to result in an ensemble of poorly resolved and/or superimposed bands with broad shoulders instead of a clear sequence of well resolved spectral features, thus worsening reliability of the authentication process or calling for necessity to work at higher resolutions or using longer scanning times or both. This drawback could be especially troublesome during attempts to employ mixtures of different compounds from the lot disclosed in the U.S. Pat. No. 5,935,755—e.g., in order to increase the number of available authenticating markings and codes.

(e) Another potential drawback of the Raman-detectable compounds disclosed in the U.S. Pat. No. 5,935,755 is connected with the fact that these compounds are rather "photo-active". Those familiar with the art will recognize that squaraines, also called Squarylium dyes, for some time are being marketed as near infrared photoreceptors for laser printers. For instance, according to an article entitled "Near-Infrared Absorbing Dyes," Chemical Reviews, 1992, No. 6, 1197–1226 (July 1992) by Fabian et al., a symmetrical Squarylium exhibits photoconductivity under irradiation with light at a wavelength of 830 nm. Although this article is silent on the subject of fluorescence for Squarylium dyes, their fluorescence characteristics are mentioned and exploited in U.S. Pat. No. 5,928,954 (Tagging hydrocarbons for subsequent identification, Jul. 27, 1999, Rutledge, et al., BP Amoco Corporation), the disclosure of which is totally incorporated herein by reference. In particular, this patent states that Squarylium dyes (or squaraines) constitute a preferred group of fluorescent dyes (along with naphthalocyanine, phthalocyanine, cyanine, methine and croconium dyes) due to the ability of these effectively absorb and fluoresce at wavelength in the range of about 600 to 2500 mn. Hence, although there is no mentioning about fluorescence of squaraines under Nd:YAG laser in the U.S. Pat. No. 5,935,755, there are strong chances to induce fluorescence for squaraines by using other NIR laser frequencies. For instance, probability to produce fluorescence instead of Raman signal with squaraines will be especially high during attempts to employ many popular diode lasers (such as those lasing at 780 nm, 808 nm, 830 nm and, perhaps, 960 nm). Practitioners will recognize that the latter possibility is able to further limit applicability of the squaraine derivatives as Raman-detectable security markings. Alternatively, the same circumstance may lead to necessity of using more expensive InGaAs matrix or array detectors instead of more affordable silicon CCD's in corresponding dispersive Raman instrumentation suitable for identification of squaraines security markings.

(f) Finally, those familiar with the art will probably recognize that the Raman-detectable compounds of the U.S. Pat. No. 5,935,755 has another principal drawback. As is well known, in order for a molecular vibration to be Raman active, the vibration must be accompanied by a change in the polarizability of the molecule. The polarizability can be looked on as the deformability of the electron cloud of the molecule by the electric field (or the ease with which electrons can be induced to respond to a potential gradient). Roughly, probability of polarizability changes increases with symmetry and electron density between the oscillating masses. Raman scattering intensity depends upon the degree of modulation of the polarizability of the scattering species during a vibrational cycle, i.e., Raman frequencies arise from changes in the electronic polarizability associated with nuclear vibrational displacements. Thus symmetric vibrational modes of symmetric species and groups which contain polarizable bonds such as, e.g., I2, H2, —S—S—, >C=C<, —CN tend to scatter strongly (have relatively large Raman scattering cross-section). At the same time, since polar species have larger dipole moments than more symmetric molecular fragments, strong IR-absorption spectral features arise from vibrations of the asymmetric groups. And vice versa. Thus, as a rule of thumb, those normal vibrations which are highly active in the infrared absorption spectroscopy are usually less Raman-active, and vice versa. Turning again to the compounds disclosed in the U.S. Pat. No. 5,935,755, it may be seen that most of them, e.g. molecules (1)–(4) and (7)–(9) are asymmetrical. Also, an aromatic or phenyl ring is the most symmetrical element in these molecular structures, while ethene or aromatic double C=C bond is the most polarizable individual chromophore. Although the disclosed molecules posses some degree of conjugation (comprise a system of conjugated unsaturated chromophores within the molecule), and the latter is known to increase the Raman cross-section of a compound, the conjugation length, at best, is limited to 3–5 double bonds in these cases. And the so called effective conjugation length, in fact responsible for the Raman signal enhancement, should be much shorter in these systems because of geometrical factors. Further, according to the list of the side substituents to the main structures (1)–(4), the most of the groupings disclosed therein are either highly asymmetrical or polar by nature. More specifically, only few groups such as, e.g., piperazine (10), pyrazine (11), cyano group (12), imine group (13), nitro group (14), and sulfone group (15)

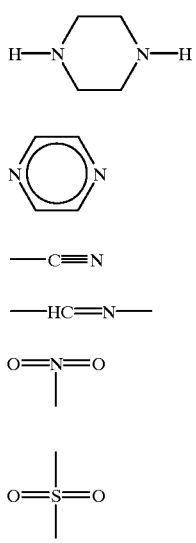

can expectedly exhibit more or less prominent Raman signals, while the rest, being active in infrared absorption spectroscopy, should be relatively Raman-inactive due to their asymmetry or polarity or both. Certainly, some of these molecules have some necessary attributes capable to impart them moderate Raman activity, but they hardly can have very high Raman scattering cross-section. Rather, those familiar with the art will probably appreciate that, in terms of their Raman activity, these disclosed compounds should be very close to ordinary aromatic, heteroaromatic or condensed aromatic molecular structures. Being devoid a possibility to assess the Raman-activity of the disclosed compounds due to the absence of factual spectra in the patent text, one is free to believe that the squaraine compounds of the U.S. Pat. No. 5,935,755 are only moderately Raman-active. This suggestion has been supported by the results of comparative experiments (cf. DETAILED DESCRIPTION OF THE INVENTION section below) in which superior Raman-active compounds of the present invention are disclosed and counterposed to those ones suggested in frames of the U.S. Pat. No. 5,935,755.

Thus, the analysis undertaken above suggests that, in the increasingly complex world of machine-assisted handling of paper and other values protected with special anti-forgery machine-readable marks and tags there is still a need for improved marking/recognition systems based on Raman spectroscopy.

It is apparent that a need exists for a Raman-spectroscopy-based methodology which would provide a reliable detection and authentication of different taggants without extensive sample preparation by means of truly quantitative, normal Raman scattering spectra excited far from electronic or excitonic resonances.

It is apparent also that it would be advantageous to provide a small, hand-held or portable Raman spectrometer having sufficient resolution and accuracy for use in a wide variety of applications relevant to verification or authentication of different security marks.

It is obvious further that a need remains for a low-cost miniaturized spectrometric sensor/transducer with a spectral resolution comparable to that of conventional Raman spectrometers, and capable of quantitative determining the Raman spectral signatures of a wide variety of substances "in the field".

It is apparent also that, although known Raman-detectable compounds and corresponding processes exist in the art which are suitable for their intended purposes, a need still remains for more reliable, simplified, expressive and economic methods of detecting and authenticating the security marks and tags by means of Raman spectroscopy.

It is apparent also that a need remains for marking materials capable, under non-resonant or far from resonance laser excitation, of generating intense and well resolved Raman spectra which could be easily detected, identified and/or authenticated by simple, rugged and affordable instruments directly "in the field".

It is apparent further that there is a substantial need for materials, coding compounds or taggants that are intrinsically highly Raman-active, i.e. have large Raman scattering cross sections, and are capable of producing intense Raman spectra under effect of characteristically non-resonant or far from resonance laser excitations.

Further, there is a need for producing a multiplicity of widely diversified Raman-active marking materials that would permit to generate an unlimited number of truly unique authenticating codes for fail-safe authentication of the items protected therewith.

Even further, it is apparent that there exist a significant need in the art for both tagging materials and detection methods that permit sensitive optical and/or spectroscopic detection of specific taggant signal(s) with essentially total rejection of nonspecific background noise and which are nondestructive for different kinds of substrates carrying the labels.

Finally, it is apparent that there is a need for new and diversified methods for marking documents that would be very difficult to duplicate or forge.

SUMMARY OF THE INVENTION

It is the main object of the present invention to provide an improved methodology of prefatory authenticity protection and consecutive machine-assisted authentication of genuine documents and other values which need to be protected against forgery and/or counterfeiting and which may be represented by: (1) traditional substrates used for printing of documents, such as different types of paper, (2) different types of plastics used for producing financial instruments, such as bankcard-grade PVC and the like, (3) multitudinous other articles bearing security printing which can include banknotes, banknote thread, currency, traveler's' checks, bonds, certificates, stamps, lottery tickets, ownership documents, passports, identity cards, credit cards, charge cards, access cards, smart cards, brand authentication labels and tags, tamperproof labels and the like. Instrumentally, this methodology relies upon Raman spectrometry in the near infrared region of the electromagnetic spectrum.

In brief, the essence of the invention may be reduced to the principle: "Before trying to perform authentication of a genuine item among fakes by means of Raman spectroscopy, equip the genuine item with a molecular tag, marking or label incorporating special chemicals capable of giving intense Raman spectra under NIR laser excitation. Then the authentication of the tagged genuine values among fakes can be reliably performed by using even extremely simple and economical spectrometers."

It is another object of the present invention to provide highly reliable processes for machine-assisted authentication of values and documents.

It is yet another object of the present invention to provide simple, rugged and affordable spectrometric means for authenticating genuine items marked with such materials "in the field".

It is still another object of the present invention to provide the processes for placing the efficient Raman-active materials of the invention on genuine items.

It is another object of the present invention to provide methods for covert marking of values and documents that would be very difficult to duplicate or forge.

It is another object of the present invention to provide multiplicity of highly diversified chemical compounds capable of emitting strong Raman spectra under effect of near infrared laser irradiation.

It is another object of the present invention to provide thermochromic marking materials capable of generating chromatic images that are visible and which can be identified and distinguished from other visible marking materials by means of both visual inspection and spectrometric techniques.

These and other objects of the present invention are achieved by providing a process which comprises (a) applying to a genuine item to be protected against duplicating, forgery or counterfeiting a marking material comprising an efficient Raman-active compound (or a mixture of several such compounds) which, when irradiated with monochromatic radiation from the near infrared region of electromagnetic spectrum, exhibits a detectable Raman spectrum, thereby forming a molecular code or security mark on the genuine item; (b) irradiating the security mark on the such protected genuine item with monochromatic radiation from the near infrared region of electromagnetic spectrum; (c) measuring the Raman spectrum of radiation scattered from the security mark when the mark is irradiated with monochromatic radiation belonging to the near infrared region of electromagnetic spectrum; and (d) processing the spectral data so obtained with the aid of corresponding dedicated software and presenting the results of the molecular code recognition to an operator in an unambiguous and convenient form.

In terms of materials science, the present invention is based on the discovery that several specific classes of chemical compounds comprising:
(i) essentially monomeric linear, quasi-linear or branched organic and organoelement compounds containing in terminal or internal positions within a molecule essentially symmetrical molecular moieties (or chromophores) having intrinsically high polarizabilities such as, e.g., HC≡C—, HC≡C—C≡C—, —C≡C—, >C=N—, —N=N—, >C=C<, —C≡C— C≡C—, —C≡C— Ph—C≡C—, —Ph—C≡C—Ph—, —C≡C—C≡C— C≡C—, —C≡C—C≡C—C≡C—C≡C—, —C≡C— C≡C—Pd—C≡C≡C—, >C=C—C=C<, etc.;
(ii) essentially polymeric linear or quasi-one-dimensional, ladder-like or comb-like, highly branched or dendritic macromolecular compounds containing long sequences of essentially symmetrical unsaturated chromophores in their backbones exhibiting intrinsically high polarizabilities and/or characterized by extensive delocalization of electron density along the conjugated backbone such as, for example, polyenes, polyenes, polysilylenes, polyenynes, poly(arylenevinylenes), poly(arylenevinyleneethynylenes), etc., along with new allotropic forms of carbon or quasi-zero-dimensional spheroidal large carbon molecules such as, for example, fullerness C60, C70, nanotubes and the like—all readily produce strong Raman spectra essentially devoid of autofluorescence or other interfering backgrounds.
(iii) lanthanide-ions-based inorganic up-converting phosphors, being used as such, as mixtures of one with another or as mixtures with organic Raman-active compounds, can constitute an unusual class of improved machine-readable taggants. Although the use of such compounds here is based on exploitation of Laser Induced Fluorescence (LIF) phenomenon rather than of normal Raman scattering, in frames of the invention the inorganic upconverting phosphors are tentatively qualified as efficient Raman-detectable taggants in view of the fact that they can be conveniently detected and identified with the aid of the very same equipment which normally is used for detecting the organic Raman-active compounds of the above classes (i) and (ii) in accordance with the invention.

As it has been discovered by the inventors in the course of extensive studies, materials of these three classes are amenable to be used as highly efficient Raman-active or Raman-detectable components of security codes, markings and tags that can be conveniently detected, identified and authenticated by their normal Raman and/or LIF/Raman spectra excited with the aid of near-infrared lasers.

In some embodiments, at least, the invention is based on the discovery that the above chemical compounds, being subjected to excitation by near-infrared lasers, reveal unusually high Raman scattering activity, making them outstanding or unique among many other classes of chemicals offered for producing Raman-detectable security marks in the prior art.

The effective Raman-active taggants and corresponding detection methods of the invention provide essentially total rejection of non-specific background emissions such as autofluorescence and/or thermal backgrounds. Of prime importance for practicing the invention is the fact that (contrary to teachings of the prior art that often rely on using visible lasers for inducing the RRS or SERRS phenomena) employment of NIR-laser excitations with compounds of the types disclosed in the present invention results in a number of essential advantages. Being based on employment of the pre-resonant, non-resonant or far-from-resonance laser excitations, the methods of the invention avoid the adverse effects of visible lasers upon the tagging materials. Also, due to preventing undesirable processes of molecular structure transformations or degradation of the taggants in the course of the detection procedure, grounds for true quantitative measurements are provided. Owing to this, for instance, detection of multiple Raman-active compounds of the invention in complex mixtures thereof becomes possible.

In contrast to Raman-detectable compounds of the types described in the previous art, those of the present invention are found to be equally useful as efficient and reliable Raman-detectable taggants when used incorporated in both either clearly visible or completely hidden from the eye markings, patterns and images. The detection of the hidden security markings becomes feasible in accordance with the invention due to the possibility to employ covering layers which, despite opaque in the visible range, can be fairly transparent to both NIR laser excitation wavelength and to the corresponding Raman photons.

Being based on the discovered ability of the disclosed chemicals to effectively generate Raman photons under NIR excitation, the present invention provides materials and detection methods which permit ultrasensitive detection and identification of the corresponding molecular tags, codes and markings and, thus, provides improved reliability of authentication of genuine items protected therewith.

In one embodiment, at least, the present invention is based on the discovery that containing lanthanide ions compounds exhibiting two-photon upconverting ability are of value as components of highly covert molecular labels and codes amenable to simple and reliable identification with the aid of the same instruments which are used for measuring normal Raman spectra of the other compounds of the invention, but with the aid of diversified light sources.

In several embodiments, inks, paints and other compositions of the invention incorporating the disclosed efficient Raman-active compounds can normally be used in addition to/beside security-printed areas in a variety of colors and can be applied by offset lithographic, screen or flexographic processes.

The Raman-active compositions of the invention may also be included in electro-photographic toners, matrix or daisy-wheel printer inks, and may be used in non-impact printing methods such as ink-jet printing or drafting and drawing with different writing tools such as pens, fountain-pens, flow-masters, permanent markers, plotter pens, roller pens, capillary pens, gel pens, etc.

The Raman-active compounds of the invention may also be included, not necessarily as inks, in paper including rag papers and plastic papers, banknote threads, plastic cards and other security documents or items which need to be authenticated, if necessary blended with a polymer and bonded other than in an ink. The Raman-active compounds of the invention may be deposited in a single area or a series of areas, if necessary or desired in a coded pattern. Moreover, the Raman-active compounds and compositions of the invention may be incorporated into other items which need to be authenticated, e.g. by incorporating it in a label such as a holographic label bearing printing in an ink containing a Raman-active compound, or in a hot-stamping foil construction.

The nature of the invention provides considerable flexibility in the apparatus for carrying out the methods of the taggants identification. As a general matter, the excitation source may be any inexpensive near-infrared laser diode and the detector may be any convenient CCD array or matrix. The laser light is preferably delivered with the aid of a fiber optic probe to a small area covered with a mark incorporating a Raman-active compound (or a mixture thereof) of the invention, and the Raman light emanating from that area is collected and directed by a fiber optic conduit of the probe to the detector. An electrical signal representing the intensity of light in the Raman emission bands provides a molecular fingerprint of the Raman-active compound(s) present. In a preferred embodiment, the process as set forth above is carried out by a miniature or portable Raman spectrometer directly "in the field".

BRIEF DESCRIPTION OF THE DRAWINGS

The numerous objects and advantages of the present invention can be better understood by those skilled in the art by reference to the accompanying figures, in which:

FIG. 9($b$)—Shows exemplary formulas of preferable diacetylene-block-copolymers suitable for preparing the sub-class J materials of the present invention;

DESCRIPTION OF THE PREFERRED EMBODIMENT

Figure 1A:
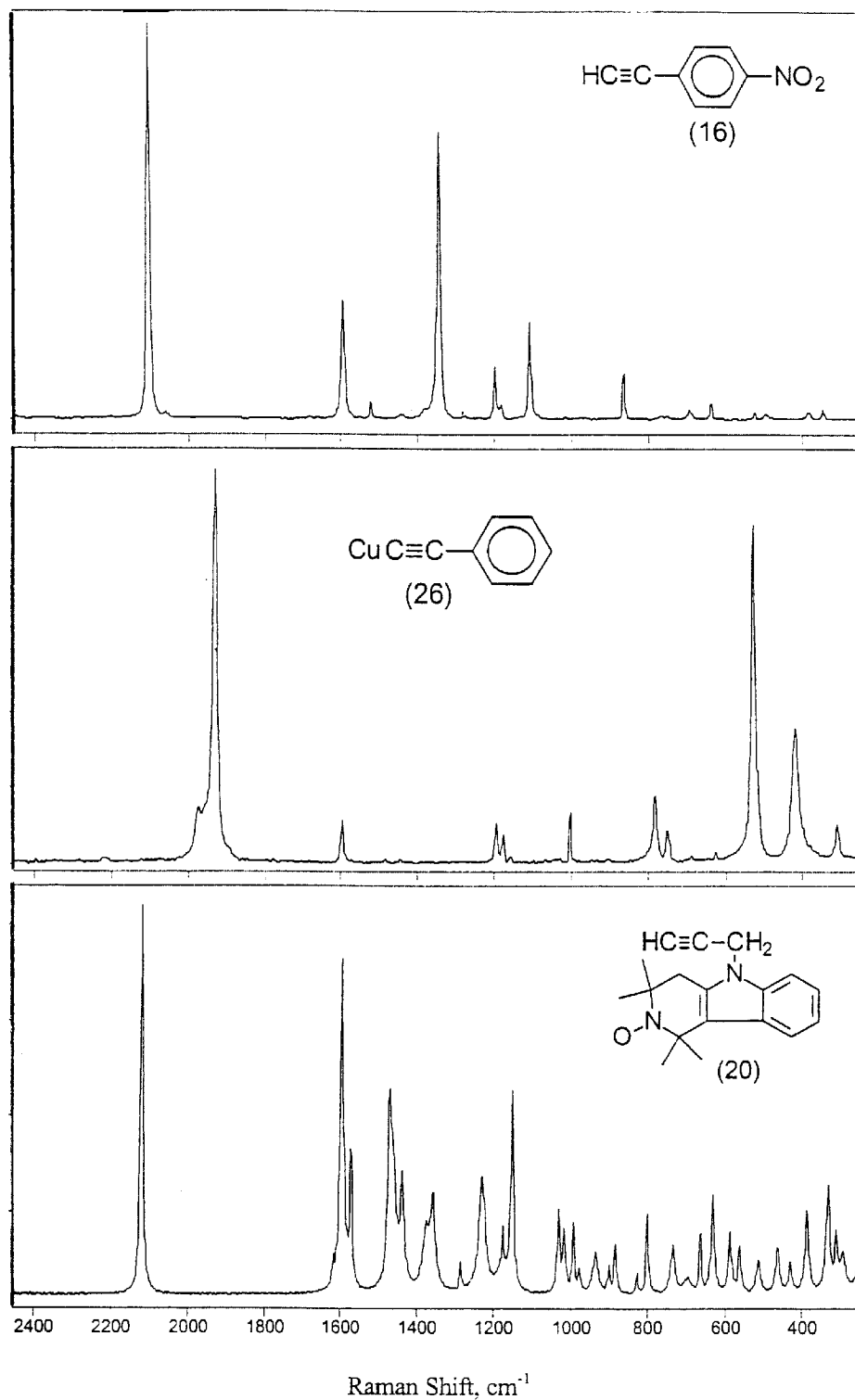
FIGS. 1(A–J)—Represent an exemplary selection of NIR-excited Raman spectra out of the multiplicity of those obtainable in accordance with the present invention for sub-classes A–J of the materials useful as efficient Raman-active taggants in frames of the present invention.
Figure 1B:
Figure 1C:
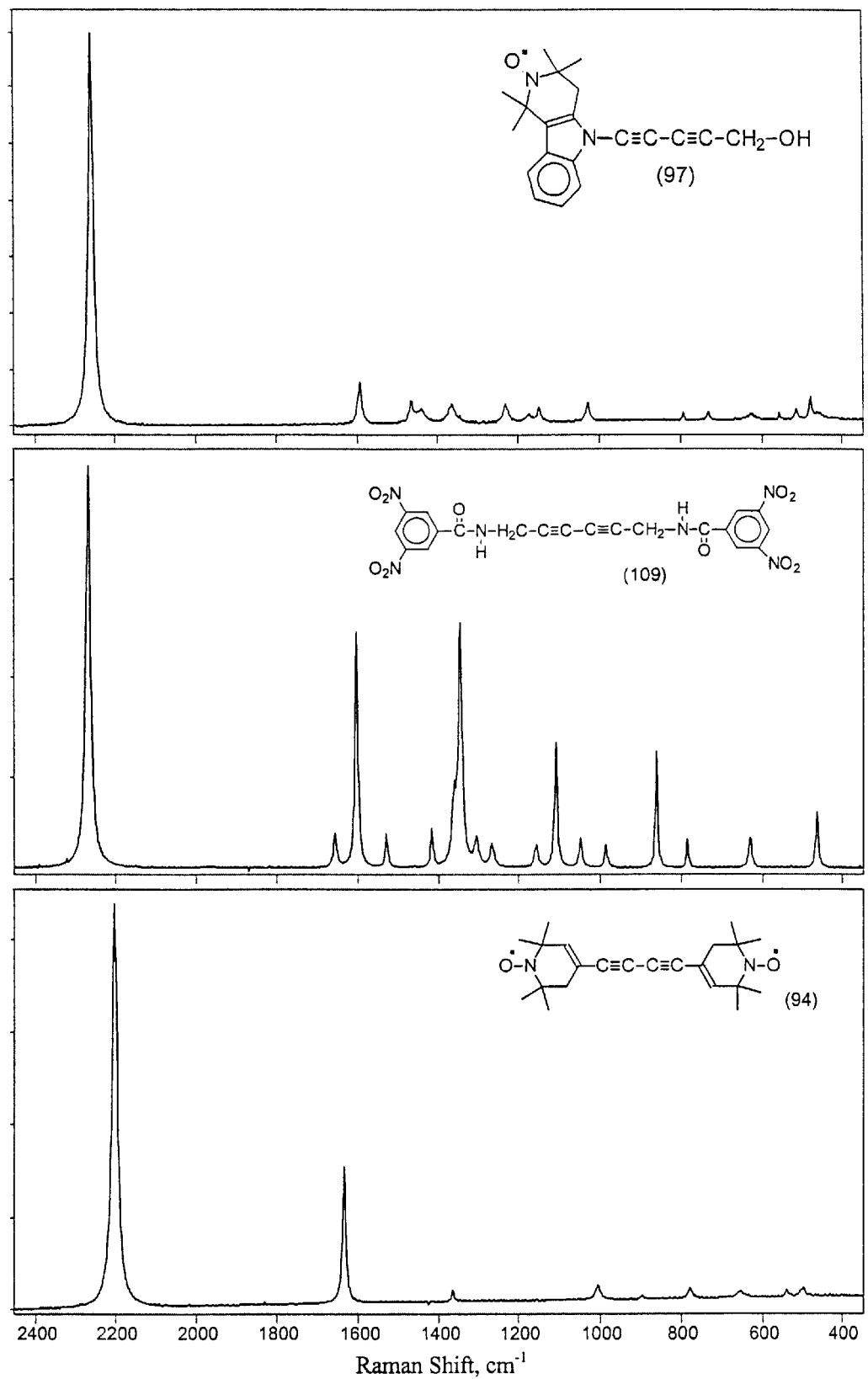
Figure 1D:
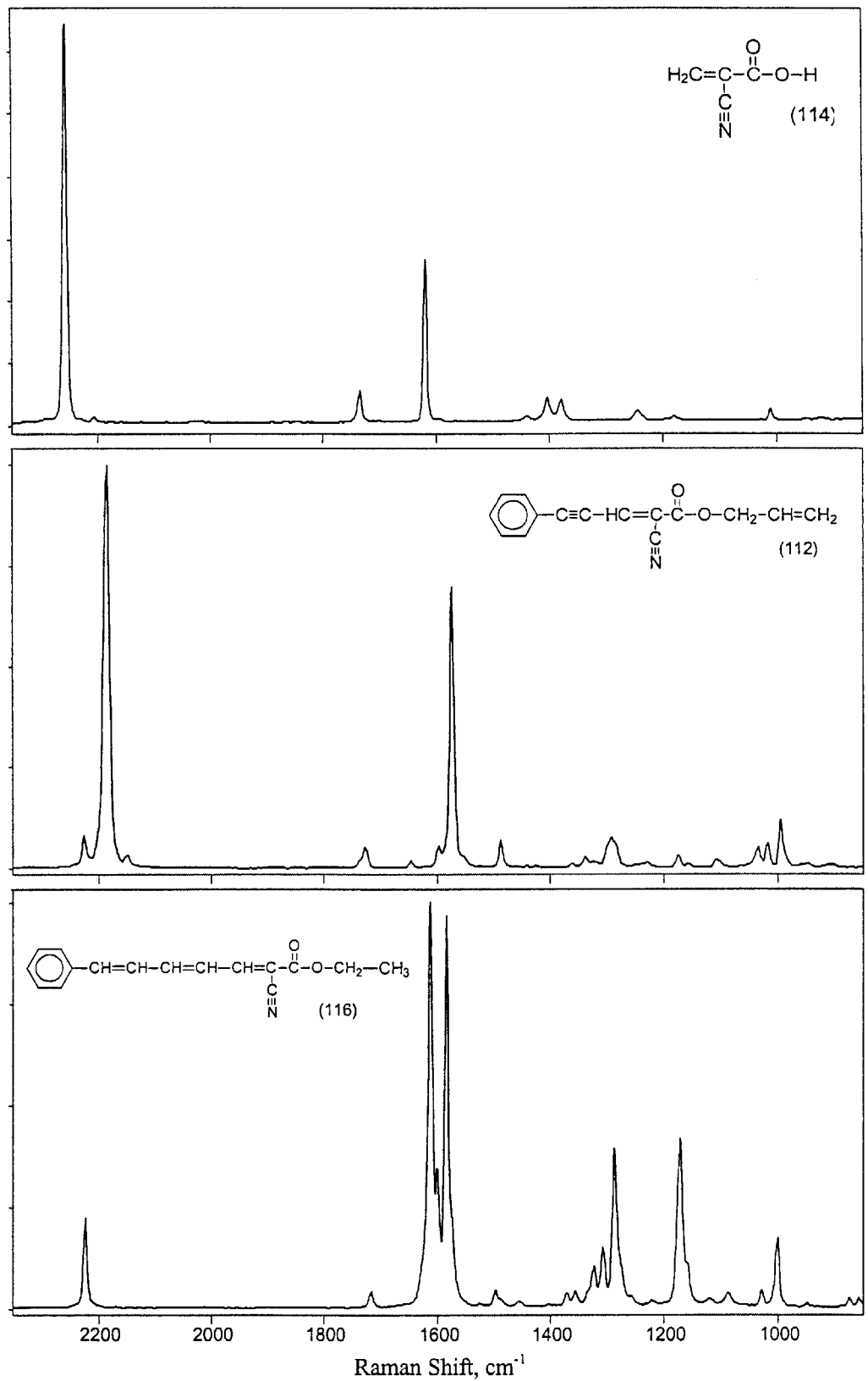
Figure 1E:
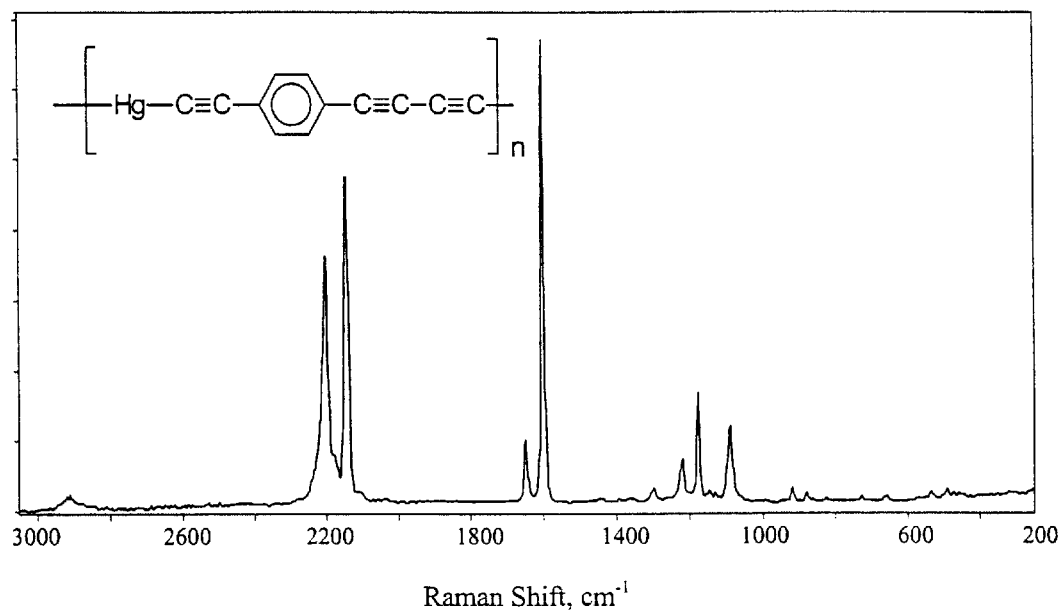
Figure 1F:
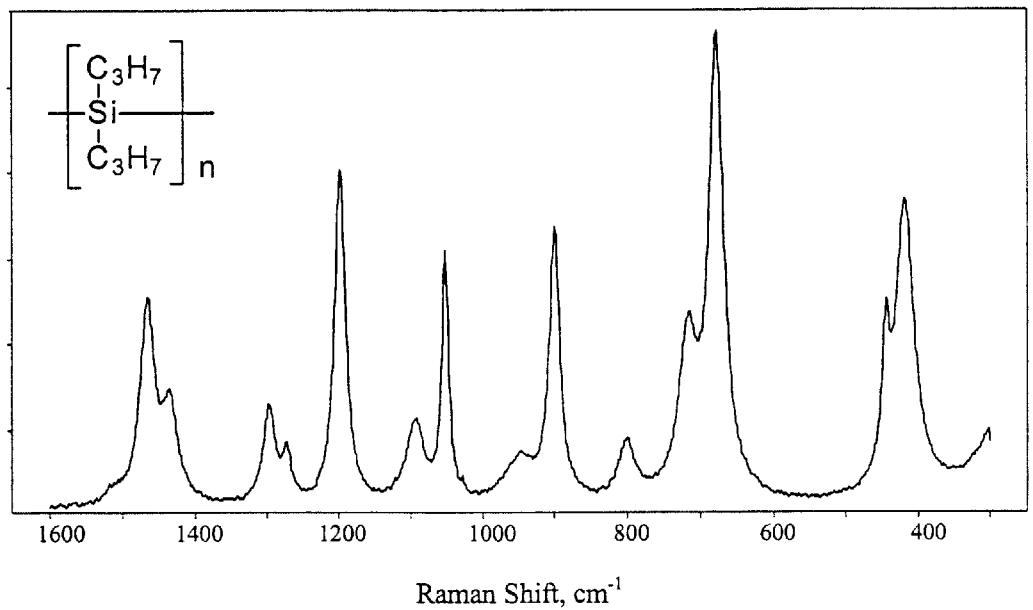
Figure 1G:
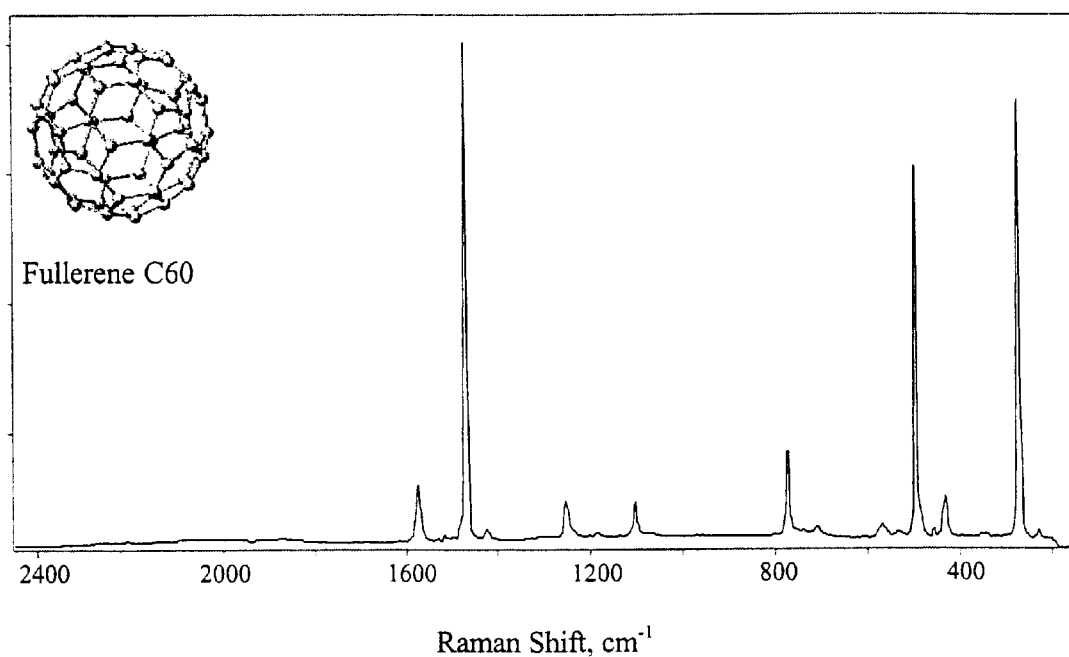
Figure 1H:
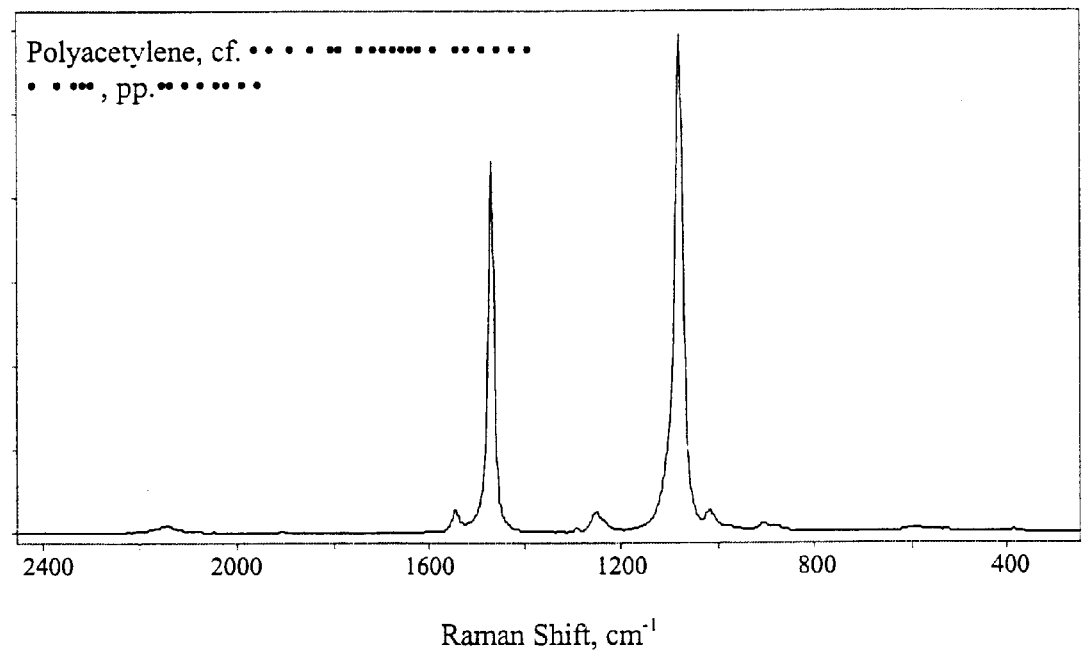
Figure 1I:
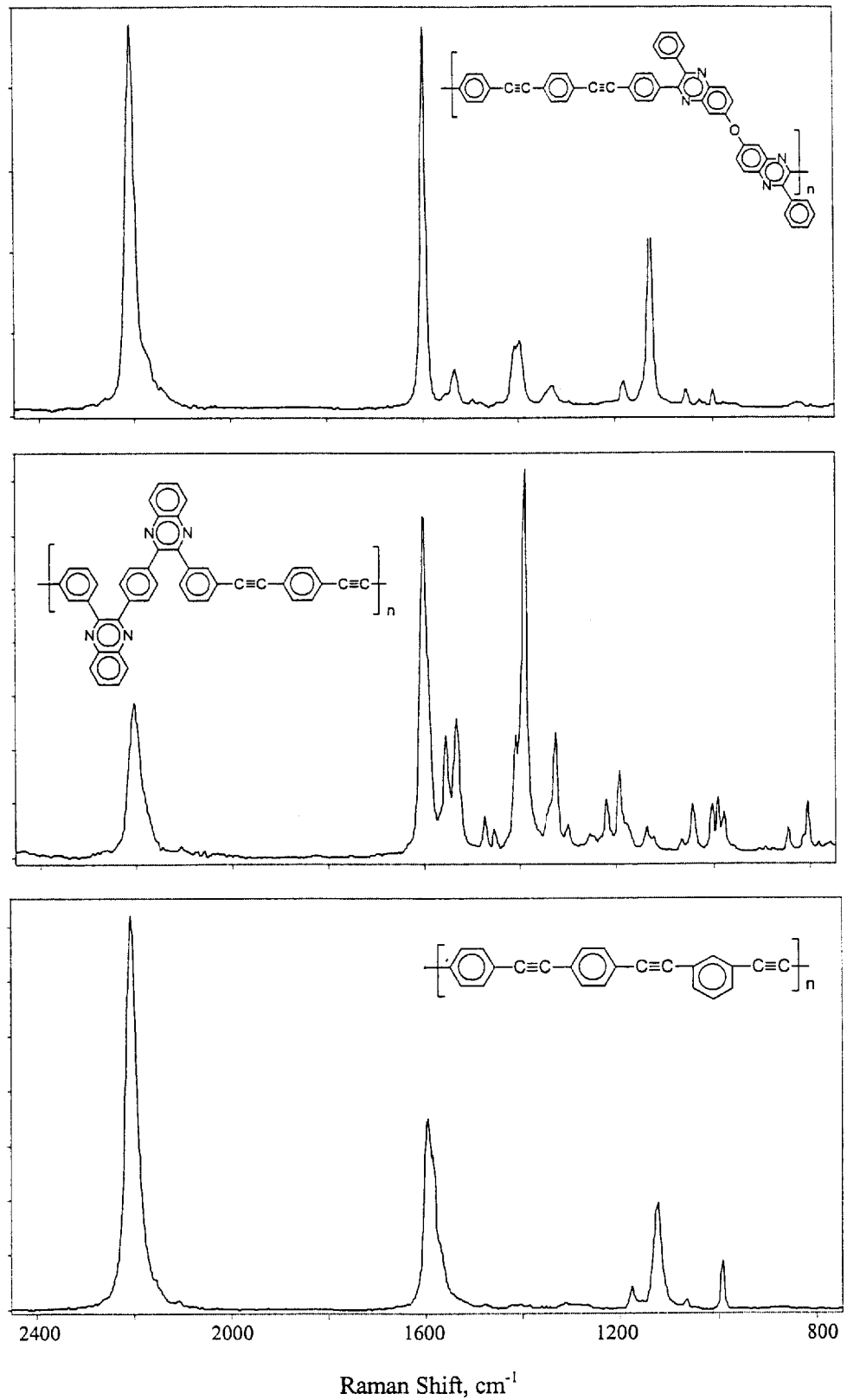
Figure 1J:
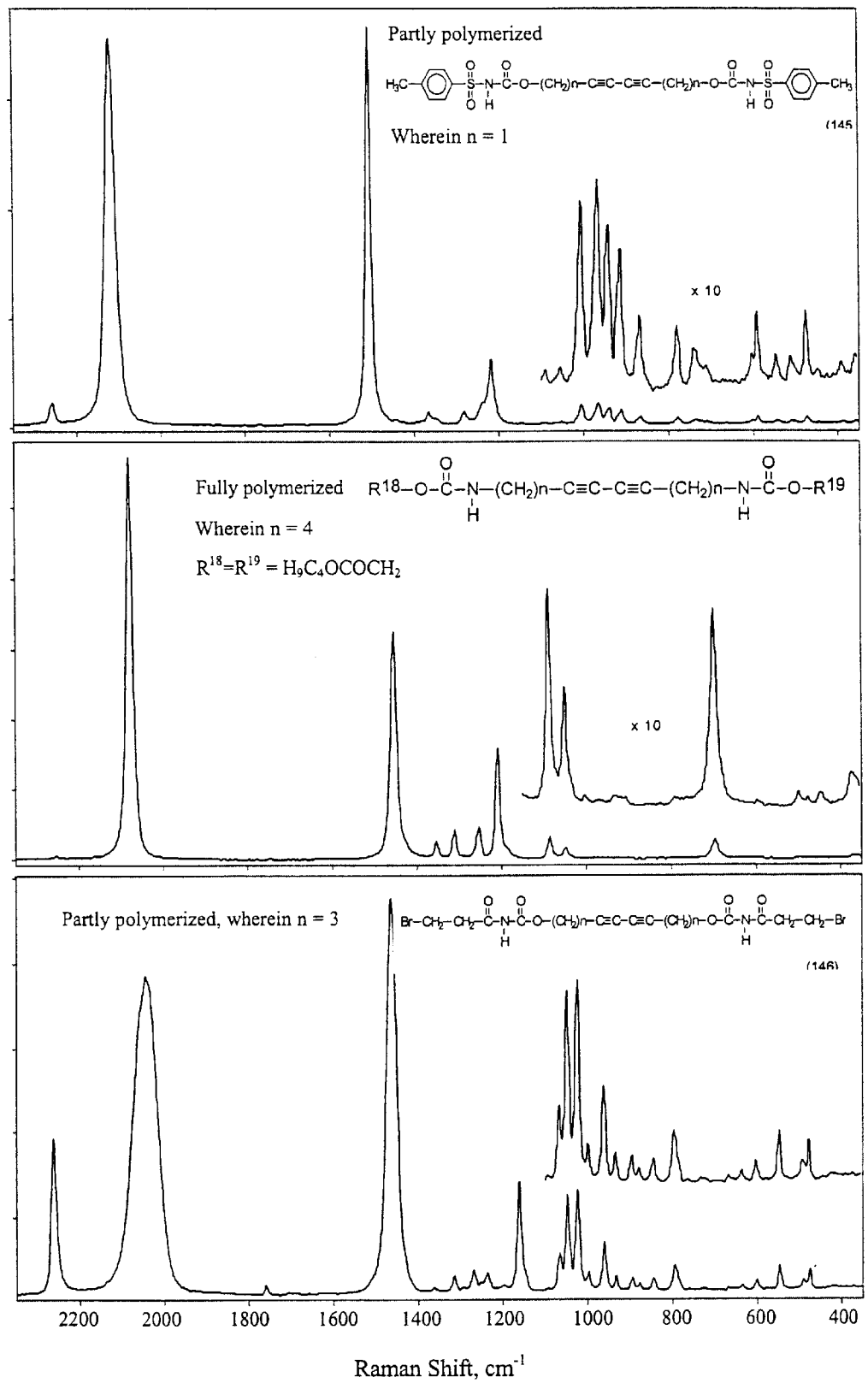
Figure 2A:
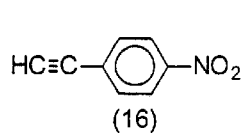
FIGS. 2($a$–$b$)—Show exemplary structural formulas of essentially monomeric asymmetrical molecules having acetylenic or diacetylenic moiety and constituting the sub-class A of the compounds useful as efficient Raman-active taggants in accordance with the present invention.
Figure 2A:
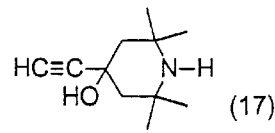
Figure 2A:
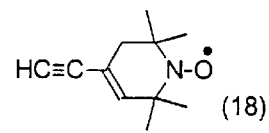
Figure 2A:
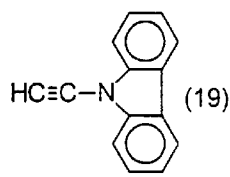
Figure 2A:
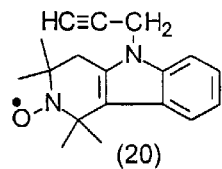
Figure 2A:
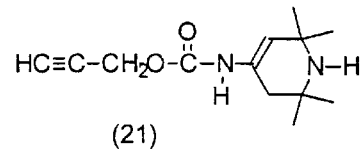
Figure 2A:
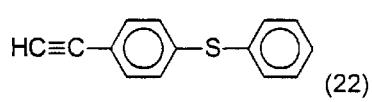
Figure 2A:
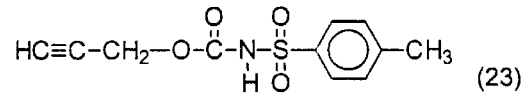
Figure 2A:
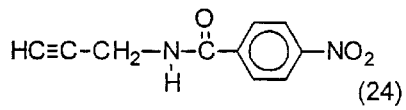
Figure 2A:
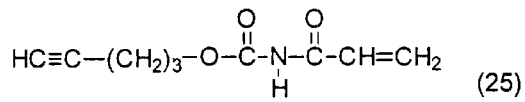
Figure 2A:
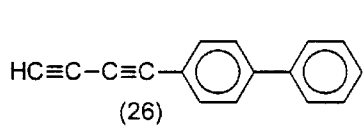
Figure 2A:
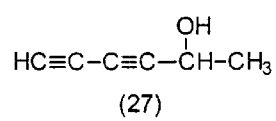
Figure 2A:
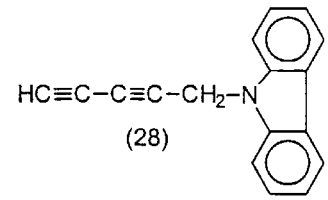
Figure 2A:
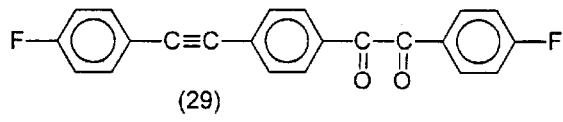
Figure 2A:
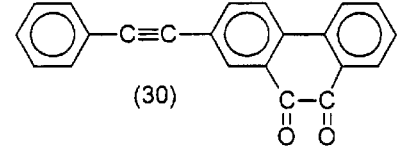

The processes of the present invention entail the steps of: (a) applying to a genuine item to be protected against duplicating, forgery or counterfeiting a marking material comprising an efficient Raman-active compound (or a mixture thereof) which, when irradiated with monochromatic radiation from the near infrared region of electromagnetic spectrum, is capable of emitting a detectable Raman spectrum, thereby forming a security mark on the genuine item; (b) illuminating the security mark on the such protected genuine item with monochromatic radiation from the near infrared region of electromagnetic spectrum; (c) measuring the Raman spectrum of radiation scattered from the security mark when the mark is illuminated with monochromatic radiation belonging to the near infrared region of electromagnetic spectrum; and (d) processing the spectral data so obtained with the aid of corresponding dedicated software and presenting the results of the molecular code recognition to an operator in an unambiguous and convenient form.

Any of a wide variety of suitable marking methods can be employed. Normally, to a marking material, whether solid or liquid, is added an efficient Raman-active compound, and the marking composition thus prepared is then used in any suitable patterning method. In some instances, the marking composition may consist of 100 percent of the Raman-active compound (taggant). The Raman-active compound is present in the marking composition in any amount effective for enabling detection and/or identification of a Raman spectrum of the Raman-active compound when the marking material on the protected item is irradiated with near-infrared monochromatic radiation. Typically, the Raman-active component is present in the marking composition in amounts of from about 0.1 to about 100 percent by weight, preferably from about 5 to about 100 percent by weight, and most preferably from about 50 to about 100 percent by weight, although the amount can be outside these ranges.

Preferably, the Raman-active compound of the invention is one that efficiently emits Raman photons when irradiated with a light chosen from the near-infrared region, more particularly, with a monochromatic light chosen within the wavelength range of from about 700 to about 1500 nanometers. Particularly preferred Raman-active compounds are those that exhibit a strong, distinct Raman spectrum consisting of several well resolved bands having Full Width at Half Maximum (FWHM) from about 2 to about 100 $cm^{-1}$, and preferably from about 5 to about 50 $cm^{-1}$, when amount of a laser light power reaching the sample is from about 1 mW to about 2000 mW, and preferably from 5 mW to 500 mW, the cross-section of the laser beam being ca. 1 $mm^2$, which corresponds to an energy density at the sample of 0.5–50 $W/cm^2$.

Specifically, when exposed, for example, to a neodymium-doped ittrium-aluminium-garnet-based (Nd:YAG) solid-state laser emitting at 1064 nm, to a gallium-aluminum-arsenic-based (GaAlAs) diode laser emitting at 785 nm or to an indium-gallium-arsenic-phosphorus-based (InGaAsP) diode laser emitting at 980 nm the compounds such as:

(i) essentially monomeric linear or branched organic and organoelement compounds containing, in internal or terminal positions within the molecule, essentially symmetrical molecular moieties (or chromophores) having intrinsically high polarizabilities such as, e.g., HC≡C—, HC≡C—C≡C—, —C≡C—, >C=N—, —N=N—, >C=C<, —C≡C—C≡C—, —C≡C—Ph—C≡C—, —Ph—C≡C—Ph—, —C≡C—C≡C—C≡C—, —C≡C—C≡C—C≡C—C≡C—, —C≡C— C≡C— Pd—C≡C≡C—, >C=C—C=C<, etc.;

(ii) essentially polymeric linear or quasi-one-dimensional, ladder-like or comb-like, highly branched or dendritic macromolecular compounds containing long sequences of essentially symmetrical unsaturated chromophores in their backbones exhibiting intrinsically high polarizabilities and/or characterized by extensive delocalization of electron density along the conjugated backbone such as, for example, polymes, polyenes, polysilylenes, polyenynes, poly(arylenevinylenes), poly(arylenevinylene)ethynylenes, etc., along with new allotropic forms of carbon or quasi-zero-dimensional spheroidal large carbon molecules such as, for example, fullerenes C60, C70, nanotubes and the like—all readily produce strong Raman spectra essentially devoid of autofluorescence or other interfering backgrounds.

(iii) in a specific embodiment of the invention, lanthanide-ions-based inorganic phosphors, being used as such, as mixtures of one with another or as mixtures with organic Raman-active compounds, constitute the third class of improved machine-readable taggants of the invention. Although the use of such compounds is based on exploitation of Laser Induced Fluorescence (LIF) phenomenon rather than normal Raman scattering, the inorganic materials of the class (iii) are nonetheless rendered as efficient Raman-detectable taggants in frames of the invention, owing to the fact that they can be conveniently detected and identified with the aid of the very same equipment which normally is used for detecting the organic Raman-active taggants of the above classes (i) and (ii) in accordance with the invention.

Figure 10:
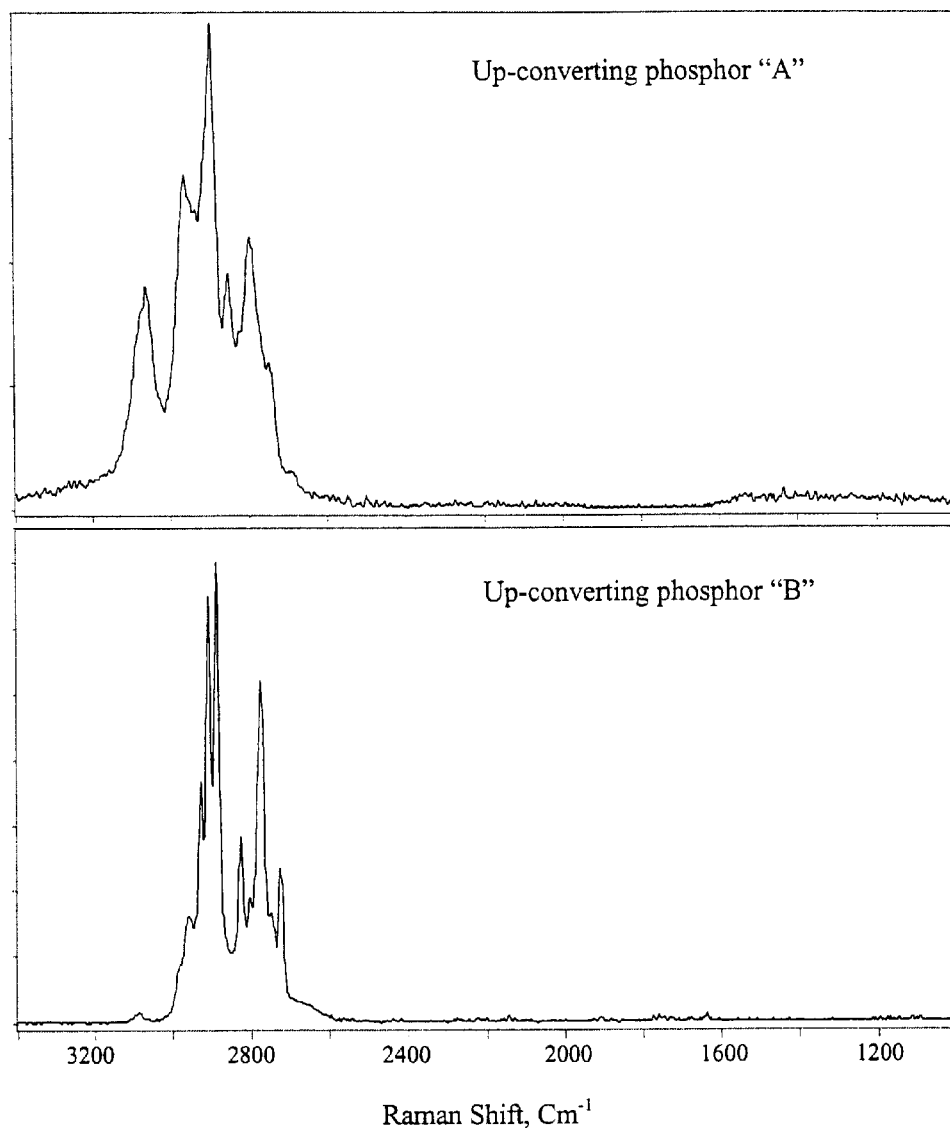
FIG. 10—Shows exemplary NIR-excited LIF/Raman spectra of inorganic up-converting phosphors constituting the class (iii) of the materials useful as efficient LIF/Raman-detectable taggants in frames of the present invention.

A small selection of NIR-excited Raman spectra out of the multiplicity of those obtainable in accordance with the present invention is presented in FIGS. 1(A–J) and FIG. 10. These spectra are provided here in order to, at least roughly, typify and/or exemplify different sub-classes of Raman-active compounds disclosed in the invention. It should be noted, however, that every single spectrum of those presented in FIGS. 1(A–J) and in FIG. 10 is factually unique and, strictly speaking, can not be used to generalize simultaneously even a pair of the closest relatives within a common sub-class of the above outlined classes (i), (ii) and (iii) of the materials, which will be disclosed and specified in more details below.

More specifically, preferred materials of the first class (i) of the present invention embrace monomeric linear or branched organic and organoelement molecules differing from those of the prior art in that they include at least one essentially symmetrical acetylenic molecular moiety (or chromophore) with intrinsically high polarizability. Such molecules, being excited with NIR lasers, readily produce strong Raman spectra actually devoid of autofluorescence or other interfering backgrounds. For clarity, these monomeric compounds are subdivided below into the following sub-classes A–D:

(A) Essentially monomeric asymmetrical molecules having acetylenic or diacetylenic moiety and represented by the general formula (I):

$$R^1—(C\equiv C)_n—X^1—Y^1—R^2 \qquad (I)$$

wherein n is an integer of 1 or 2; $R^1$ can be H, a transition metal atom such as copper or silver, n-alkyl or substituted alkyl, preferably with from about 3 to about 18 carbon atoms, aryl or substituted aryl preferably with from about 6 to about 18 carbon atoms, with examples of substituents residing on the said alkyls or aryls including but not limited to halogen atoms, cyano group, vinyl group, mercapto group, hydroxy group, amine group, aldehyde group, carboxylic acid group, nitrile group, diazo group, nitro group, or azide group; $X^1$ can be absent or represents a molecular bridge such as n-alkylene, substituted alkylene, preferably with from about 1 to about 12 carbon atoms, cycloalkylene, alkenylene, arylene and substituted arylene, preferably with from about 6 to about 18 carbon atoms, with examples of substituents residing on the said molecular bridge including but not limited to halogen atoms, cyano group, vinyl group, mercapto group, hydroxy group, amine group, aldehyde group, carboxylic acid group, nitrile group, diazo group, nitro group, or azide group; $Y^1$ can be absent or represents a moiety such as —H, —O—, —S—, —CO—, —CO—CO—, —OCO—, —NH—, —NHCO—, —NHCOO—, —CONHCOO—, —NHCONH—, sulfonyl group, —HC=N—, —N=N—, >C=C<, >C=C—C=C<, —Ph—C≡C—Ph—, —C≡C—Ph—C≡C—, —C≡C—M—C≡C—, wherein M is Hg, Pt, Ni, Pd, Si, Ge; and $R^2$ represents —H or a residue such as n-alkyl, substituted alkyl, preferably with from about 1 to about 12 carbon atoms, cycloalkyl, alkenyl, alkynyl, aryl, substituted aryl, preferably with from about 6 to about 18 carbon atoms, arylalkyl, substituted arylalkyl, preferably with from about 7 to about 30 carbon atoms, a substituted or unsubstituted heterocyclic structure, preferably of from about 5 to about 15 members wherein the hetero atom is nitrogen, oxygen or sulfur, such as piperidinoxyl, carbazole, dehydropiperidinoxyl, carbolinoxyl, pyrrolidine, pyridine, piperidine, piperazine, quinoline, isoquinoline, quinuclidine, pyrazole, triazole, tetrazole, triazine, imidazole, pyrimidine, pyradizine, pyrazine, oxazole, isoxazole, morpholine, or the like, with examples of substituents residing on the said structures including but not limited to halogen atoms, cyano group, vinyl group, mercapto group, hydroxy group, amine group, aldehyde group, carboxylic acid group, nitrile group, diazo group, nitro group, or azide group.

These asymmetrical compounds containing acetylenic or diacetylenic functionalities are exemplified (but not limited) by the molecular structure formulas (16)–(45) shown in FIG. 2. The synthesis of these compounds is rather straightforward and several methods are known in the art. Many such compounds can be prepared with good yields by following teachings of, for example, "Preparative Acetylenic Chemistry", L. Brandsma, 2nd ed., Elsevier, Amsterdam, 1988. Compounds useful in the invention can be synthesized also as is described, for example, in articles by Sarkar et al., Ind. J. Chem., 1991, 30B, 360 and by Chodkiewicz et al., Compt. Rend., 248 (1959) 116, 259. Many particular compounds preferable in the invention can be synthesized as has been described, for example, in articles entitled "Synthesis of new diacetylenic monomers containing nitroxyl radicals", Izvestiya Akademii Nauk USSR, Ser. Chim., 1991, No. 6, 226–230 by Lazareva et al. and "Reactions of copper and silver acetylenides", Uspekhi Khimii, 48 (1979) No. 9, 1625–1683 by Sladkov et al., the disclosures of each of which are totally incorporated herein by reference. The compounds of the sub-class A disclosed in the invention are environmentally stable, harmless solids. Preferable in terms of the invention are those which are soluble and crystallizable. The compounds of this sub-class can be colored, but the most preferred of them are actually transparent in the NIR region of the spectrum and do not produce interfering luminescence or autofluorescence when irradiated with NIR lasers. Typical illustrative NIR-excited Raman spectra for some representatives of this sub-class A of the materials preferred in the invention are disclosed in FIG. 1(A). Most preferable within the sub-class A are those compounds which, besides acetylenic or diacetylenic moieties, additionally contain highly polarizable substituents such as —C≡N, —CH=CH₂, —NO₂ and the like residing on alkyl, aryl or heterocyclic groupings present in the molecule.

(B) Essentially monomeric compounds containing symmetrically bridged acetylenic or diacetylenic moieties and represented by the general formula (II):

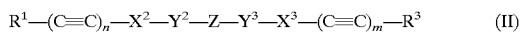

$$R^1-(C\equiv C)_n-X^2-Y^2-Z-Y^3-X^3-(C\equiv C)_m-R^3 \qquad (II)$$

wherein integer n can be equal to or different from m and each, independently of the other, is 1 or 2; $R^1$ can be equal to or different from $R^3$ and each, independently of the other, can be H, a transition metal atom such as copper or silver, n-alkyl or substituted alkyl, preferably with from about 3 to about 18 carbon atoms, aryl or substituted aryl preferably with from about 6 to about 18 carbon atoms, with examples of substituents residing on the said alkyls or aryls including but not limited to halogen atoms, cyano group, vinyl group, mercapto group, hydroxy group, amine group, aldehyde group, carboxylic acid group, nitrile group, diazo group, nitro group, or azide group; $X^2$ is equal to $X^3$ and both simultaneously can be absent or represent a molecular bridge such as n-alkylene, substituted alkylene, preferably with from about 1 to about 12 carbon atoms, cycloalkylene, arylene, substituted arylene, preferably with from about 6 to about 18 carbon atoms, a substituted or unsubstituted heterocyclic structure, preferably of from about 5 to about 15 members, wherein the hetero atom is nitrogen, oxygen or sulfur, such as pyrrolidine, pyridine, piperidine, piperazine, quinoline, isoquinoline, quinuclidine, pyrazole, triazole, tetrazole, triazine, imidazole, pyrimidine, pyradizine, pyrazine, oxazole, isoxazole, morpholine, piperidinoxyl, dehydropiperidinoxyl, carbolinoxyl, carbazole, and the like, with examples of suitable substituents residing on the said molecular bridge including but not limited to halogen atoms, cyano group, vinyl group, mercapto group, hydroxy group, amine group, aldehyde group, carboxylic acid group, nitrile group, diazo group, nitro group, or azide group; $Y^2$ is equal to $Y^3$ and both simultaneously can be absent or represent a moiety such as —S—, —O—, —CO—, —OCO—, —CO—CO—, —NH—, —NHCO—, —NHCOO—, —CONHCOO—, —NHCONH—, sulfonyl group, —C≡C—, >C=N—, —N=N—, >C=C<, >C=C—C=C<, —C≡C—Ph—C≡C—, —C≡C—C≡C—, —Ph—C≡C—Ph—, and the like; Z may be nil or represents a molecular bridge such as n-alkylene, substituted alkylene, preferably with from about 1 to about 12 carbon atoms, cycloalkylene, arylene, substituted arylene, preferably with from about 6 to about 18 carbon atoms, a substituted or unsubstituted heterocyclic structure, preferably of from about 5 to about 15 members, wherein the hetero atom is nitrogen, oxygen, sulfur, or the like, such as pyrrolidine, pyridine, piperidine, piperazine, quinoline, isoquinoline, quinuclidine, pyrazole, triazole, tetrazole, triazine, imidazole, pyrimidine, pyradizine, pyrazine, oxazole, isoxazole, morpholine, piperidinoxyl, dehydropiperidinoxyl, carbolinoxyl, carbazole, and the like, a covalently bound element such as Hg, Pd, Pt, Ni, Si, Ge, or a moiety such as —S—, —O—, —CO—, —OCO—, —CO—CO—, —C≡C—, >C=N—, —N=N—, >C=C<, >C=C—C=C<, —C≡C—Ph—C≡C—, —Ph—C≡C—Ph—, and the like, with examples of substituents residing on the said molecular bridge including but not limited to halogen atoms, cyano group, vinyl group, mercapto group, hydroxy group, amine group, aldehyde group, carboxylic acid group, nitrile group, diazo group, nitro group, or azide group.

Figure 3A:
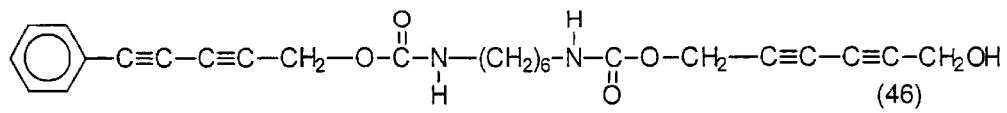
FIGS. 3($a$–$d$)—Show exemplary structural formulas of essentially monomeric compounds containing symmetrically bridged acetylenic or diacetylenic moieties and constituting the sub-class B of the compounds useful as efficient Raman-active taggants in frames of the present invention.
Figure 3A:
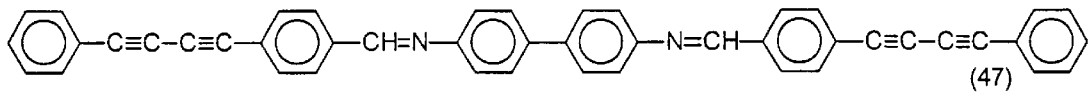
Figure 3A:
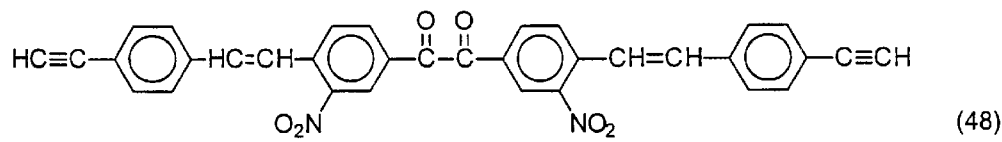
Figure 3A:
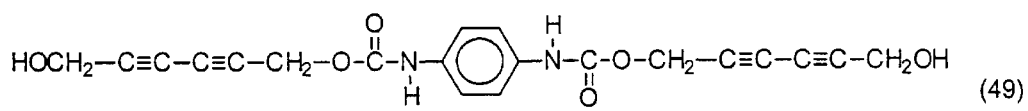
Figure 3A:
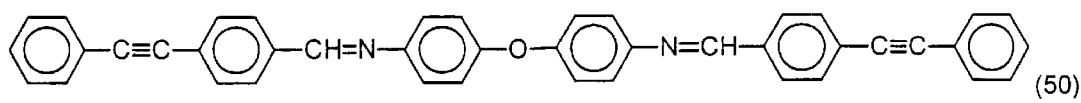
Figure 3A:
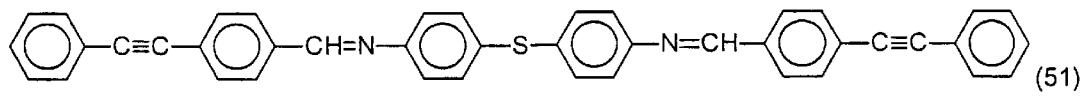
Figure 3A:
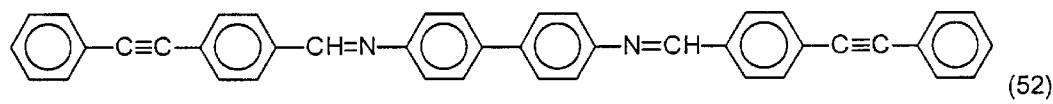
Figure 3A:
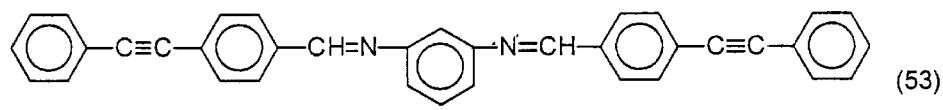
Figure 3A:
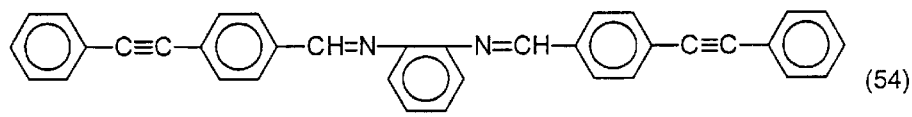
Figure 3A:
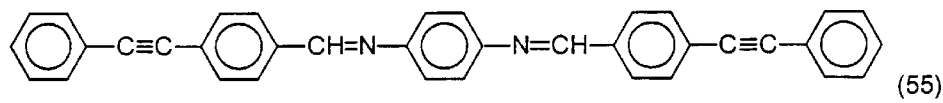
Figure 3A:
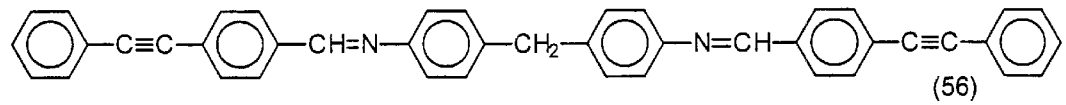
Figure 3B:
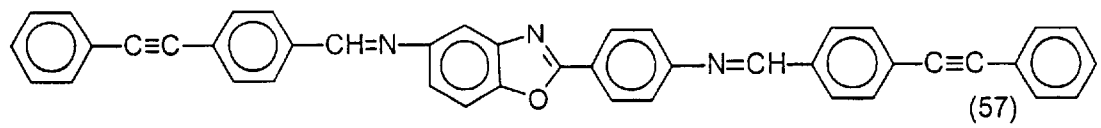
Figure 3B:
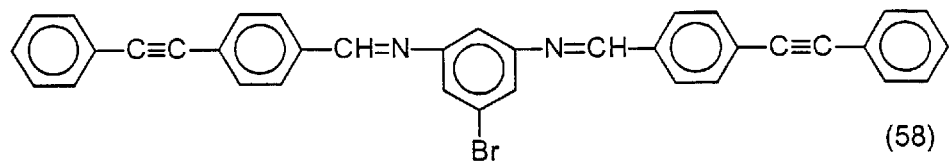
Figure 3B:
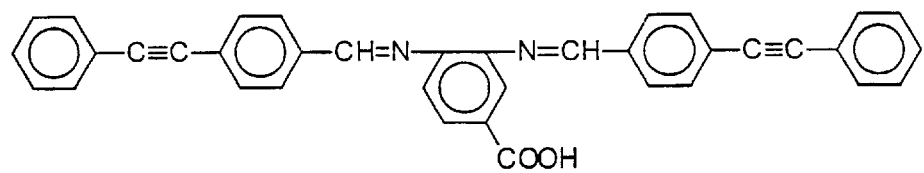
Figure 3B:
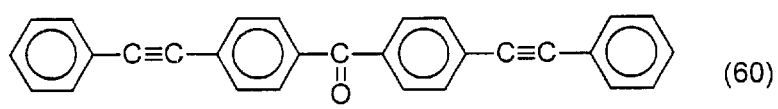
Figure 3B:
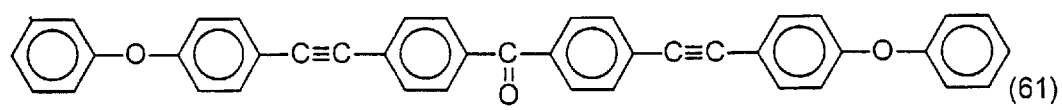
Figure 3B:
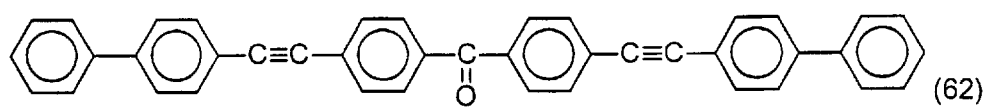
Figure 3B:
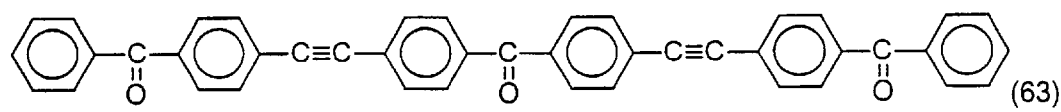
Figure 3B:
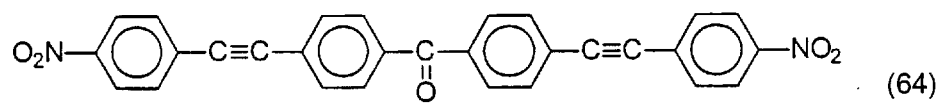
Figure 3B:
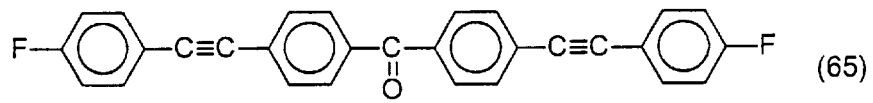
Figure 3B:
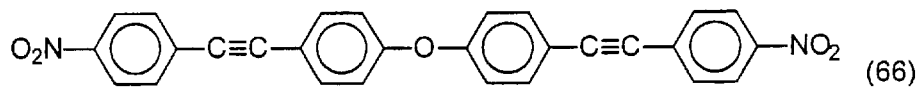
Figure 3:
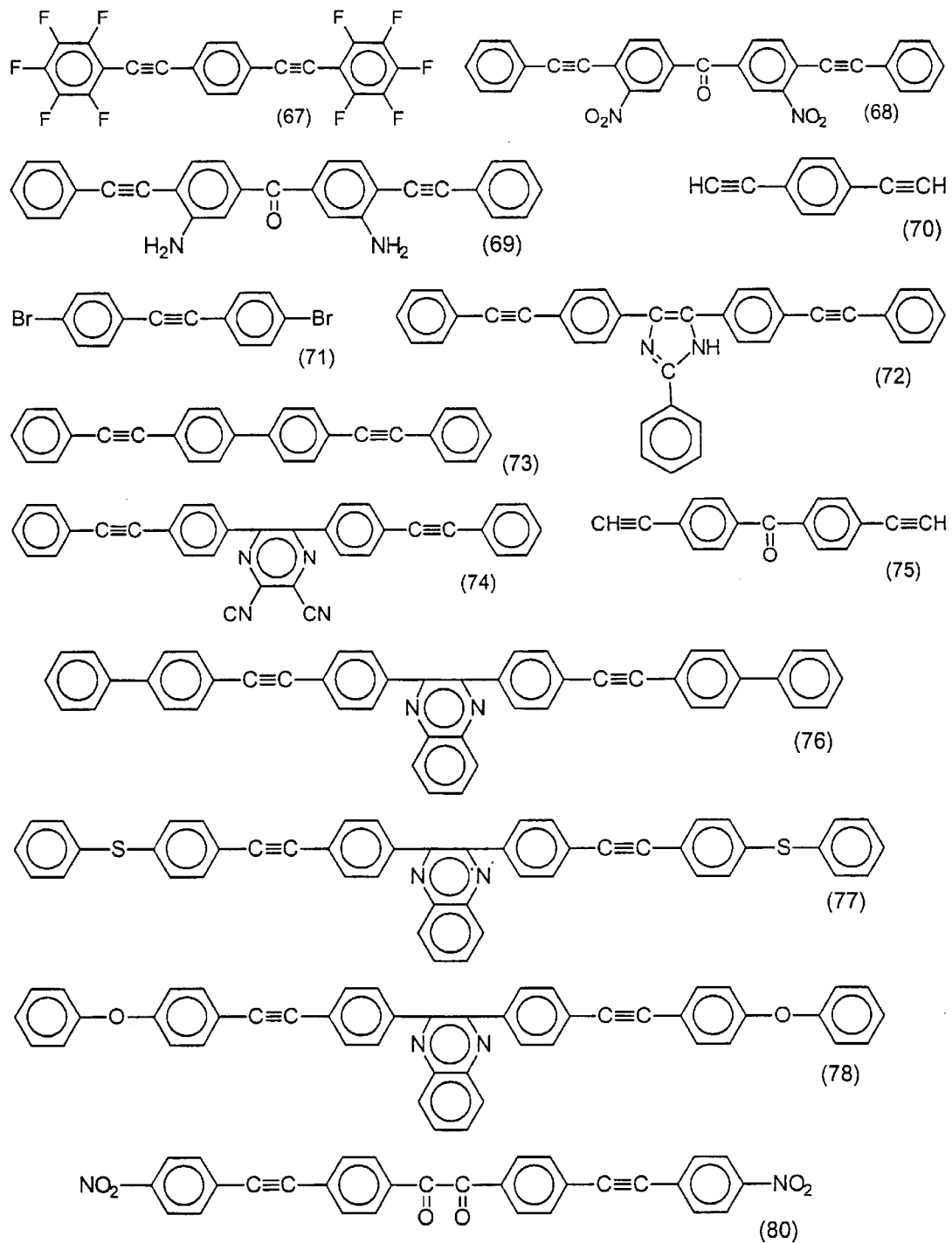
Figure 3D:
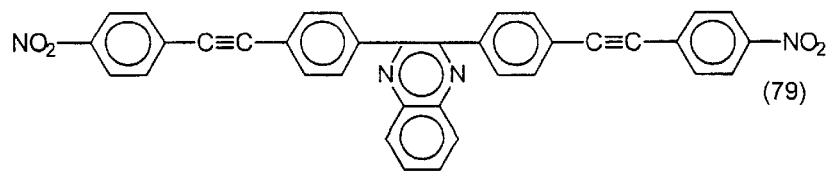
Figure 3D:
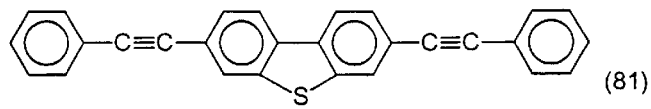
Figure 3D:
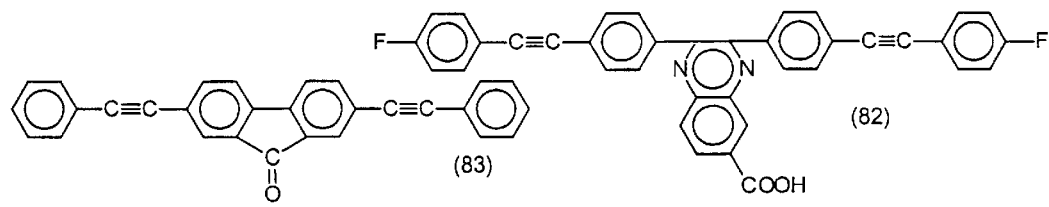
Figure 3D:
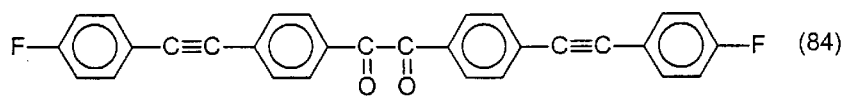
Figure 3D:
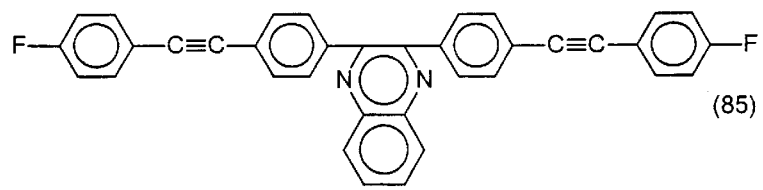
Figure 3D:
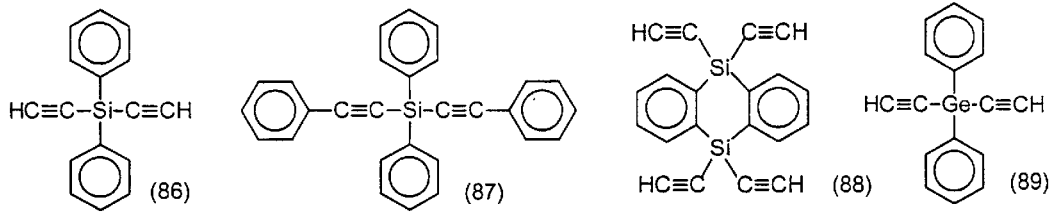
Figure 3D:
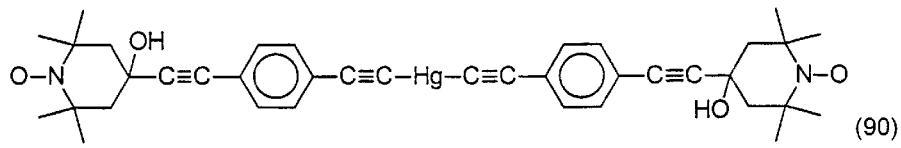
Figure 3D:
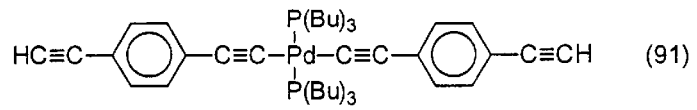
Figure 4A:
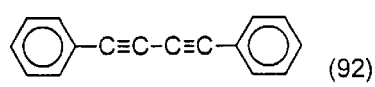
FIGS. 4($a$–$b$)—Show exemplary molecular formulas of the symmetrically and/or asymmetrically disubstituted essentially monomeric diacetylenic, triacetylenic and tetraacetylenic compounds constituting the sub-class C of the compounds useful as efficient Raman-active taggants in frames of the present invention.
Figure 4A:
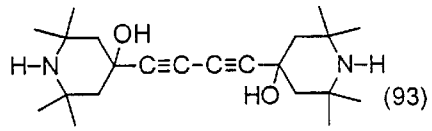
Figure 4A:
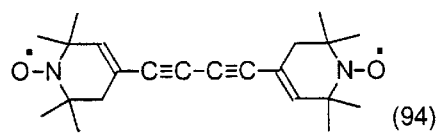
Figure 4A:
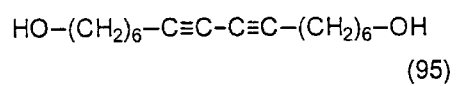
Figure 4A:
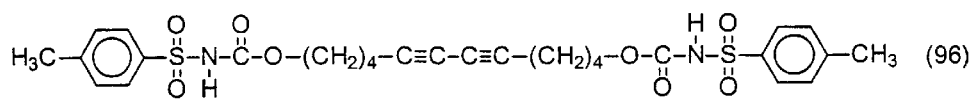
Figure 4A:
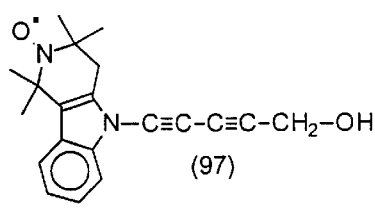
Figure 4A:
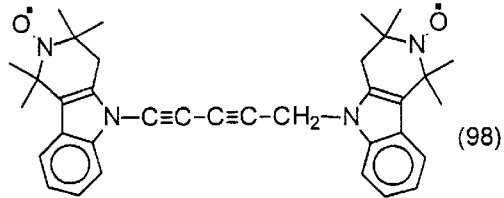
Figure 4A:
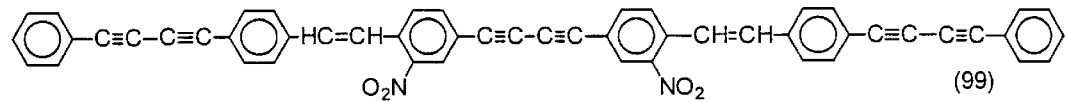
Figure 4A:
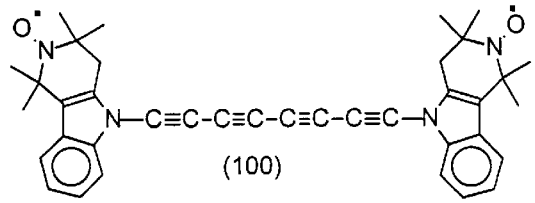
Figure 4A:
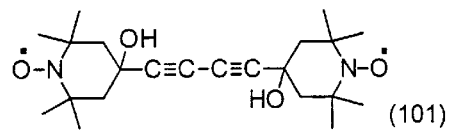
Figure 4B:
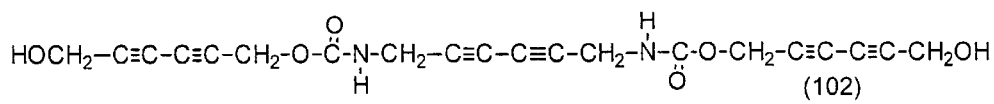
Figure 4B:
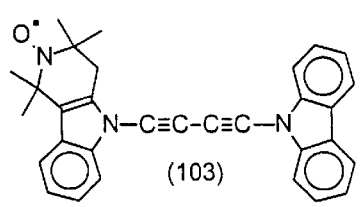
Figure 4B:
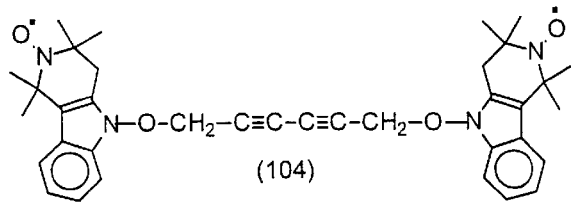
Figure 4B:
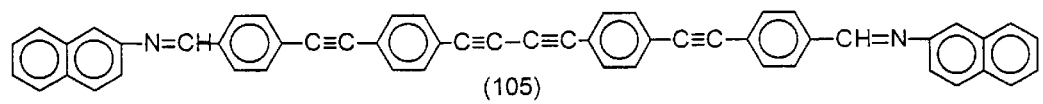
Figure 4B:
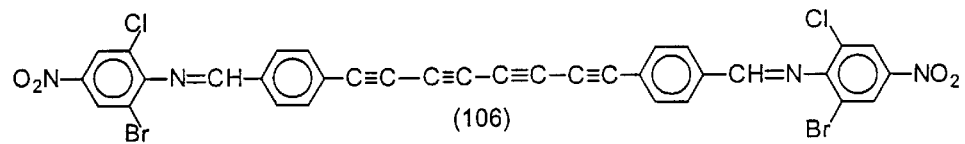
Figure 4B:
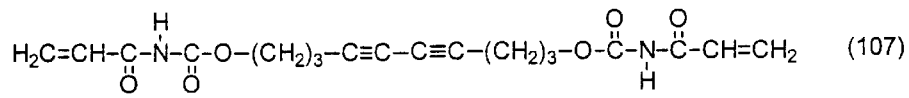
Figure 4B:
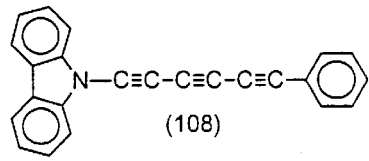
Figure 4B:
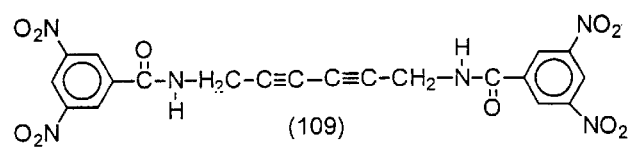

These essentially monomeric compounds containing symmetrically bridged acetylenic or diacetylenic moieties are exemplified (but not limited) by the molecular structure formulas (46)–(91) shown in FIGS. 3(a–d). The synthesis of such compounds of the sub-class B may be accomplished as described, for example, in articles entitled "Synthesis of new aryl- and heteroaryl-dibromides and diiodides—monomers for obtaining poly(arylene)ethynylenes", *Izvestiya Akademii Nauk, Ser. Chim.*, 1996, *No.* 5, 1229–1234 by Rusanov et al; "New bis-tetraaryl-cyclopentadienones", *Izvestiya Akademii Nauk, Ser. Chim.*, 1998, *No.* 2, 325–327 by Rusanov et al. [*Russ. Chem. Bulletin* 47 (1998), No. 2, 318–320 (*English translation*)]; and "New aromatic tetracarboxylic dianhydrides", *Izvestiya Akademii Nauk, Ser. Chim.*, 1999, No. 10, 1966–1969 by Keshtov et al., the disclosures of each of which are totally incorporated herein by reference. The compounds of the sub-class B disclosed herein are environmentally stable and harmless solids. Preferable in frames of the invention are those which are soluble and crystallizable. Despite the fact that some compounds of this sub-class are intensely colored, most of them are actually transparent in the NIR region of the spectrum and do not produce interfering luminescence or autofluorescence when irradiated with NIR lasers. Typical NIR-excited Raman spectra for some representatives of this sub-class B of the invention are exemplified by those disclosed in FIG. 1(B). Most preferable within the sub-class B are those compounds which besides acetylenic or diacetylenic moieties additionally contain highly polarizable substituents such as —C≡N, —CH=CH$_2$, —NO$_2$ and the like residing on alkyl, aryl or heterocyclic groupings present in the molecule.

(C) Essentially monomeric symmetrically and asymmetrically bis-substituted diacetylenic, triyne and tetrayne compounds of the general formula (III):

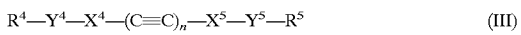

$$R^4-Y^4-X^4-(C\equiv C)_n-X^5-Y^5-R^5 \qquad (III)$$

wherein n is an integer from 1 to 4; $X^4$ may be equal to or different from $X^5$ and each, independently of the other, can be absent or represents a molecular bridge such as n-alkylene, substituted alkylene, preferably with from about 1 to about 12 carbon atoms, cycloalkylene, arylene, substituted arylene, preferably with from about 6 to about 18 carbon atoms, with examples of suitable substituents residing on the said molecular bridge including but not limited to halogen atoms, cyano group, vinyl group, mercapto group, hydroxy group, amine group, aldehyde group, carboxylic acid group, nitrile group, diazo group, nitro group, or azide group; $Y^4$ may be equal to or different from $Y^5$ and each, independently of the other, can be absent or represents a moiety such as H, —OH, —COH, —COOH, —NH$_2$, —NO$_2$, —C≡N, —CH=CH$_2$, phenyl, sulfonyl group, —S—, —O—, —CO—, —OCO—, —NH—, —NHCO—, —NHCOO—, —CONHCOO—, —NHCONH—, —C≡C—, >C=N—, —N=N—, >C=C<, >C=C—C=C<, —C≡C—C≡C—, —C≡C—Ph—C≡C—, —Ph—C≡C—Ph—, —C≡C—C≡C—C≡C—, —C≡C—C≡C—C≡C—C≡C—, and —C≡C—C≡C—M—C≡C≡C— moiety wherein M is an element such as Hg, Ni, Pd, Pt, Si, Ge or the like; and $R^4$ may be equal to or different from $R^5$ and each, independently of the other, can be absent or represents a functional group such as —H, —OH, —COH, —COOH, —NH$_2$, —NO$_2$, —C≡N, —CH=CH$_2$, —C≡CH, —C≡C—C≡CH, —C≡C—Ph—C≡CH, —Ph—C≡C—Ph, or an organic residue such as n-alkyl, substituted alkyl, preferably with from about 1 to about 12 carbon atoms, cycloalkyl, aryl, substituted aryl, preferably with from about 6 to about 18 carbon atoms, arylalkyl, substituted arylalkyl, preferably with from about 7 to about 30 carbon atoms, a substituted or unsubstituted heterocyclic structure, preferably of from about 5 to about 15 members wherein the hetero atom is nitrogen, oxygen or sulfur, such as pyrrolidine, pyridine, piperidine, piperazine, quinoline, isoquinoline, quinuclidine, pyrazole, triazole, tetrazole, triazine, imidazole, pyrimidine, pyradizine, pyrazine, oxazole, isoxazole, morpholine, carbazole, piperidinoxyl, dehydropiperidinoxyl, carbolinoxyl and the like, with examples of suitable substituents residing on the said structures including but not limited to halogen atoms, cyano group, vinyl group, mercapto group, hydroxy group, amine group, aldehyde group, carboxylic acid group, nitrile group, diazo group, nitro group, or azide group.

The symmetrically and/or asymmetrically bis-substituted essentially monomeric diacetylenic, triacetylenic and tetraacetylenic compounds constituting the sub-class C of the invention are exemplified (but not limited) by the particular molecular structure formulas (92)–(109) shown in FIGS. 4(a–b). The synthesis of these compounds is rather straightforward and several methods are known in the art. For instance, many such compounds can be prepared with good yields as has been described, for example, in *J. Org. Chem.*, 25 (1960) 1275; *J. Org. Chem.*, 25 (1960) 2928 and in *J. Org. Chem.*, 27 (1962) 3320 by A. S. Hay. Those familiar with the art will probably appreciate that a vast majority of diversified compounds belonging to the sub-class C can be prepared starting from corresponding compounds embraced by the disclosed above sub-classes A and B of the invention with the aid of synthetic procedures described, for example, in *J. Chem. Soc.*, 1951, 44 by Armitage et al., in *J. Chem. Soc.*, 1959, 889 by Eglinton et al., and in *Bull. Soc. Chim. France*, 1958, 298 by Chodkiewicz et al. Many compounds preferable in the invention can be synthesized as has been described, for example, in articles entitled "Nitroxyl radicals substituted diacetylene monomers: molecular design, synthesis, solid-state polymerizability", *Synth. Met.* 85 (1997) No. 1–3, 1685–1686 by Lazareva et al. and in "Octatetraynes with directly linked aromatic sidegroups: preparation and polymerization", *Macromolecules*, 1998, 31, 5624–5630 by Sarkar et al. Preparation of many disubstituted diacetylene, triyne and tetrayne compounds as monomers for subsequent solid-state polymerization has been disclosed, for example, in U.S. Pat. No. 3,999,946, U.S. Pat. No. 4,195,056, U.S. Pat. No. 4,215,208, U.S. Pat. No. 4,339,951, U.S. Pat. No. 4,788,151, U.S. Pat. No. 5,085,801, U.S. Pat. No. 5,420,000, the disclosures of each of which are totally incorporated herein by reference. The compounds of the sub-class C disclosed in the present invention are environmentally stable and harmless solids. Preferable in terms of the invention are those which are soluble, crystallizable and are "spontaneous polymerization inactive", that is, do not reveal any ability to the thermally- or radiation-induced solid-state polymerization. Some of the compounds of this sub-class are colored, but all of them are actually transparent in the NIR region of the spectrum and do not produce interfering luminescence or autofluorescence when irradiated with NIR lasers. Typical NIR-excited Raman spectra for some representatives of this sub-class C of the invention are exemplified by those disclosed in FIG. 1(C). Most preferable within the sub-class C are those compounds which, besides a diacetylenic, triacetylenic or tetraacetylenic moiety, additionally contain other highly polarizable substituents such as —C≡N, —CH=CH$_2$, —C≡CH, —NO$_2$ and the like residing on alkyl, aryl or heterocyclic groupings present in the molecule.

(D) Cyanoacrylic acid derivatives of the general formula (IV):

$$R^6\text{---CH}\text{=}C(CN)\text{---COO---}R^7 \quad\quad (IV)$$

wherein $R^6$ can be equal to or different from $R^7$ and each, independently of the other, represents —H or a residue such as n-alkyl, substituted alkyl, preferably with from about 1 to about 12 carbon atoms, cycloalkyl, aryl, substituted aryl, preferably with from about 6 to about 18 carbon atoms, arylalkyl, substituted arylalkyl, preferably with from about 7 to about 30 carbon atoms, a substituted or unsubstituted heterocyclic ring, preferably of from about 5 to about 7 members wherein the hetero atom is nitrogen, oxygen or sulfur, such as pyrrolidine, pyridine, piperidine, piperazine, quinoline, isoquinoline, quinuclidine, pyrazole, triazole, tetrazole, triazine, imidazole, pyrimidine, pyradizine, pyrazine, oxazole, isoxazole, morpholine, carbazole, piperidinoxyl, carbolinoxyl and the like, or terminal functional groupings such as —CH=CH$_2$, —HC=CH—HC=CH$_2$, —C≡CH, —C≡C—C≡CH, —Ph—C≡CH, and —Ph—C≡C—Ph.

Figure 5:
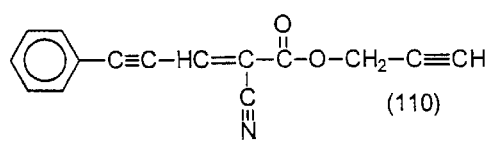
FIG. 5—Shows exemplary molecular formulas of cyanoacrylic acid based compounds constituting the sub-class D of the materials useful as efficient Raman-active taggants in frames of the present invention.
Figure 5:
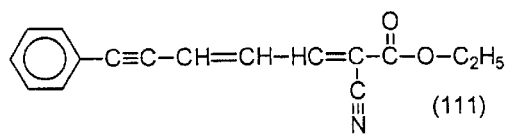
Figure 5:
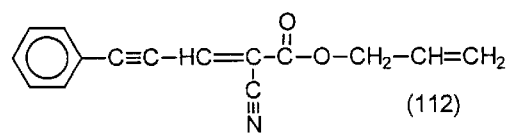
Figure 5:
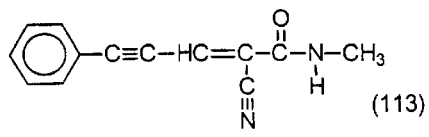
Figure 5:
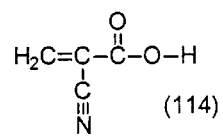
Figure 5:
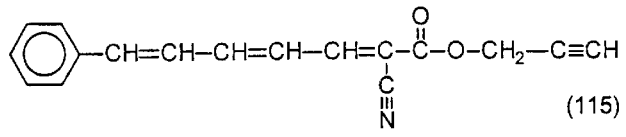
Figure 5:
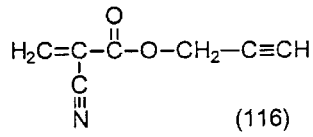
Figure 5:
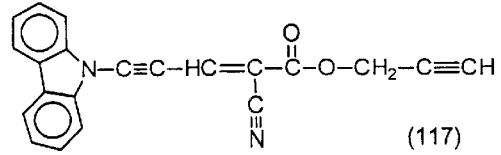
Figure 5:
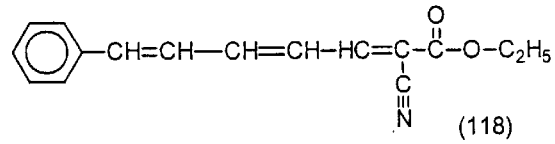
Figure 5:
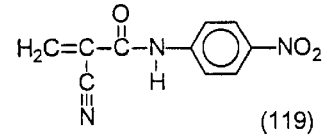

Such cyanoacrylic acid based compounds constituting the sub-class D of the invention are exemplified (but not limited) by the molecular structure formulas (110)–(119) shown in FIG. 5. Preparation of many cyanoacrylics useful in the invention can be accomplished as has been described, for example, in *Russ. Chem. Bull.*, 1994, 43, No. 4, 595 by Guseva et al., and in papers entitled "Investigation of thermal destruction of polycyanoacrylates", *Russ. Polym. News*, 1999, 4, No. 2, 6–13 by Guseva et al., and "N-Substituted amides of 2-cyanopenta-2E,4-dienoic acid", *Izvestiya Akademii Nauk, Ser, Chim.*, 1999, No. 5, 933–937 by Gol'ding et al., the disclosures of each of which are totally incorporated herein by reference. It should be noted that, besides the monomeric compounds of the sub-class D such as, for example, methylamide-, anylide-, p-methylanylide-, m-methylanylide-, p-chloroanylide-, cyclohexylamide- and ethylamide of 2-cyanopenta-2E,4-dienoic acid, ethyl-2-cyanoacrylate, propyl-2-cyanoacrylate, allyl-2-cyanoacrylate, allyloxyethyl-2-cyanoacrylate, (3-allyloxy)-propyl-2-cyanoacrylate, allylcarboxymethyl-2-cyanoacrylate, (2-methyl-2-allyloxy)-ethyl-2-cyanoacrylate, propargyl-2-cyanoacrylate, phenylpropargyl-2-cyanoacrylate and the like, corresponding poly (cyanoacrylates) can be advantageously used in frames of the invention. Preferable in frames of the invention are those cyanoacrylic derivatives which are soluble in conventional organic solvents and contain in the molecule additional highly polarizable moieties or substituents such as —CH=CH$_2$, —HC=CH—HC=CH$_2$, —C≡CH, —C≡C—C≡CH, —Ph—C≡CH, —Ph—C≡C—Ph, —C≡N, —CH=N—, —NO$_2$ and the like. Despite the fact that some compounds of this sub-class are colored, all of them are actually transparent in the NIR region of the spectrum and do not produce interfering luminescence or autofluorescence when irradiated with NIR lasers. Typical NIR-excited Raman spectra for some representatives of this sub-class D of the invention are exemplified by those disclosed in FIG. 1(D).

(ii) The second important class of highly Raman-active materials especially preferred in frames of the invention embraces a number of more or less specific families of macromolecular compounds and/or polymers including high molecular weight quasi-one-dimensional polymers, linear rigid-rod polymers, ladder-like polymers, comb-like polymers, highly branched polymers, hyper-branched polymers and quasi-zero-dimensional spheroidal large carbon molecules or new allotropic forms of carbon such as, for example, fullerenes C60, C70, tubulenes and the like.

More specifically, preferred in frames of the invention materials of the second class (ii) embrace macromolecular compounds and/or polymers including high molecular weight quasi-one-dimensional, linear rigid-rod, ladder-like, comb-like, highly branched and hyper-branched polymers such as, for example, polymes, polysilylenes, polyenes, polyenynes, poly(arylenevinylenes), poly(arylenevinyleneethynylenes) or the like, along with the so called quasi-zero-dimensional spheroidal large carbon molecules or new allotropic forms of carbon such as, for example, fullerenes C60, C70, tubulenes or nanotubes and the like. Preferred materials of this class contain extended sequences of essentially symmetrical unsaturated moieties having intrinsically high polarizabilities, are characterized by extensive delocalization of electron density along the conjugated backbones and/or spheroidal shells, and, being excited with NIR lasers, readily produce strong Raman spectra actually devoid of autofluorescence or other interfering backgrounds. For clarity, these macromolecular compounds are subdivided below into the following sub-classes (E)–(J):

(E) Linear organoelement polymes, polyimines and polyazines represented by the following general formulae (V)–(VII), respectively:

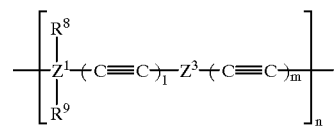

(V)

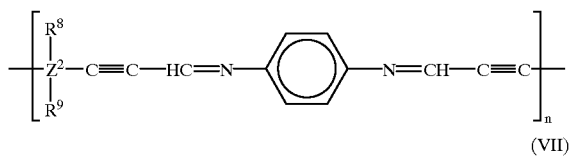

(VI)

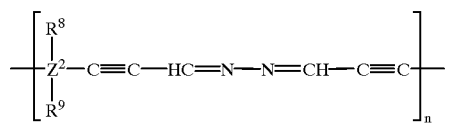

(VII)

wherein l and m are integers which can be equal to or different from each other, and each, independently of the other, can be 0, 1, 2 or 4; n is an integer preferably with from about 5 to about 10,000; $Z^1$ represents an atom such as mercury, nickel, platinum, palladium, silicon, germanium or the like; $Z^2$ represents an atom such as silicon or germanium; $Z^3$ can be absent or represents arylene, substituted arylene, preferably with from about 6 to about 30 carbon atoms, or a substituted or unsubstituted heteroarylene structure, preferably of from about 5 to about 17 members wherein the hetero atom is nitrogen, oxygen or sulfur; $R^8$ can be equal to or different from $R^9$ and each, independently of the other, can be absent or represents an organic residue such as n-alkyl, substituted alkyl, preferably with from about 3 to about 16 carbon atoms, cycloalkyl, aryl, substituted aryl, preferably with from about 6 to about 30 carbon atoms, arylalkyl, substituted arylalkyl, preferably with from about 7 to about 30 carbon atoms, a substituted or unsubstituted heterocyclic ring, preferably of from about 5 to about 7 members wherein the hetero atom is nitrogen, oxygen or sulfur, or a complexation ligand such as, e.g. trans-trialkylphosphine, and the like.

Figure 6:
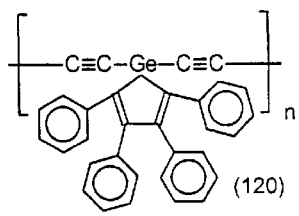
FIG. 6—Shows exemplary molecular formulas of linear organoelement polyynes, polyimines and polyazines constituting the sub-class E of materials useful as efficient Raman-active taggants in frames of this invention.
Figure 6:
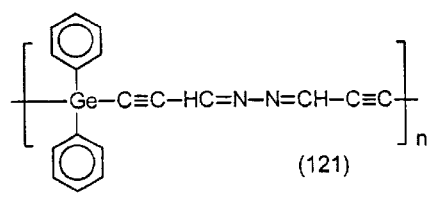
Figure 6:
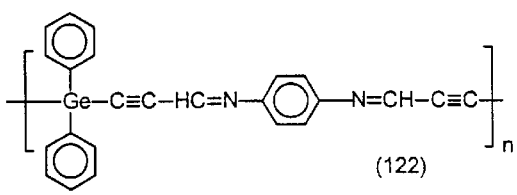
Figure 6:
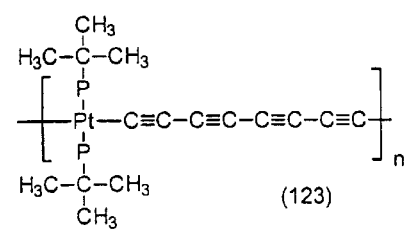
Figure 6:
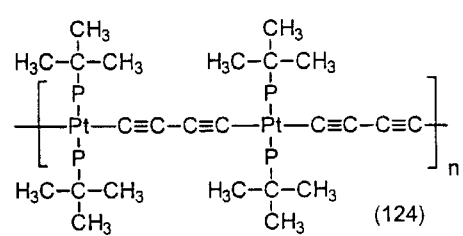
Figure 6:
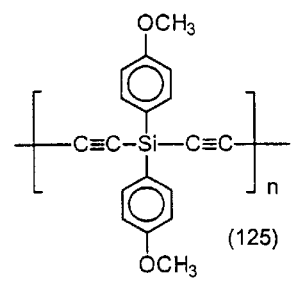
Figure 6:
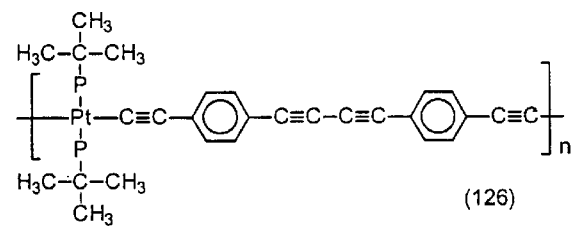
Figure 6:
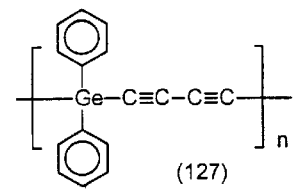
Figure 6:
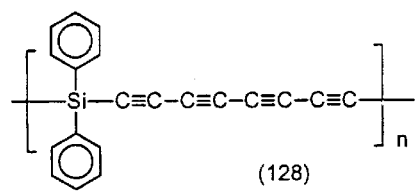
Figure 6:
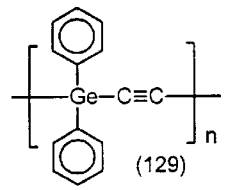

The polymers constituting the sub-class E of the invention can be exemplified (but are not limited) by the particular structure formulas (120)–(129) shown in FIG. 6. Several preparative methods leading to obtaining such polymers are known in the art and are described, for example, in "*The Chemistry of Functional Groups, Supplement C: The Chemistry of Triple-Bonded Functional Groups*", S. Patai and Z. Rappoport Eds., John Willey & Sons Ltd, 1983, p. 917; and in "*Polyconjugated Polymers: Collection of articles*"—*A. M. Sladkov, Moscow, Nauka,* 1989. Many polymers corresponding to the sub-class E of the invention can be synthesized as has been described, for example, in Macromolecules 10 (1977) 879 by Sonogashira et al.; *J. polym. Sci., Polymer Chem. Ed.* 18 (1980) 661 by Takahashi et al.; *Vysokomolekulyarnye Soedineniya,* 1967, 9, N4, 910–914 by Luneva et al.; *Doklady Akademii Nauk USSR,* 1961, 136, N6, 1342–1344 by Sladkov et al.; *Vysokomolekulyarnye Soedineniya,* 1959, 1, No.12, 1817–1820 by Berlin et al.; *Izvestiya Akademii Nauk, Ser. Chim.,* 1968, No.1, 170–174 by Luneva et al.; *Izvestiya Akademii Nauk, Ser. Chim.,* 1978, No.9, 2149–2151 by Vasneva et al.; *Izvestiya Akademii Nauk, Ser. Chim.,* 1975, No.8, 1890–1892 by Luneva et al.; and in *Synth. Met.* 1993, 57, 390 by Nalwa et al., the disclosures of which are totally incorporated herein by reference. The compounds of the sub-class E disclosed herein are environmentally stable solids. Preferable in terms of the invention are those which are soluble in conventional organic solvents. Despite the fact that some compounds of this sub-class are intensely colored, most of them are actually transparent in the NIR region of the spectrum and do not produce interfering luminescence or autofluorescence when irradiated with NIR lasers. Most preferable materials within the sub-class E are those which, besides acetylenic, diacetylenic, or tetraacetylenic moieties, additionally contain other highly polarizable substituents, such as —C≡N, —CH═CH$_2$, —C≡CH, —NO$_2$ and the like, residing on alkyl, aryl or heterocyclic groupings present in the macromolecule. An illustrative NIR-excited Raman spectrum for this sub-class of the Raman-active materials of the invention is disclosed in FIG. 1(E).

(F) Polysilylenes or poly(silanes) of the general formula VIII:

(VIII)

wherein n is an integer preferably from about 5 to about 100,000; $R^{10}$ and $R^{11}$ may be the same or different and each, independently of the other, represents n-alkyl, preferably with from about 1 to about 18 carbon atoms, substituted alkyl, preferably with from about 3 to about 30 carbon atoms, unsubstituted and substituted phenyl preferably with from about 6 to about 30 carbon atoms, aryl, substituted aryl, preferably with from about 12 to about 30 carbon atoms, arylalkyl, or substituted arylalkyl, preferably with from about 13 to about 30 carbon atoms.

The poly(silylenes) useful in frames of the invention can be exemplified (but are not limited) by such particular polymers as, for instance, poly(di-methylsilylene), poly(diethylsilylene), poly(di-n-propylsilylene), poly(di-iso-propylsilylene), poly(di-n-butylsilylene), poly(di-iso-butylsilylene), poly(di-tert-butylsilylene), poly(di-phenylsilylene) and the like. In general, both poly(dialkylsilylenes) and poly(diarylsilylenes) preferable in the invention are macromolecules containing only silicon atoms in the backbone and only σ-bonds between all Si atoms. These compounds exhibit some properties analogous to those of conjugated polyenes; for this reason polysilylenes are considered to be σ—σ conjugated systems with delocalization of the σ-electrons belonging to the Si—Si bond. The synthesis of these polymers is rather straightforward and several methods are known in the art. Poly (dialkylsilylenes), for instance, can be prepared with good yield by sodium coupling of the corresponding dialkyldichlorosilanes in toluene at temperatures close to the boiling point of toluene. Preparative synthesis of polysilanes has been reviewed in, for example, *Chem. Rev.,* 1989, 89, 1353 by Miller et al., in *"The Chemistry of Organosilicon Compounds"*, S. Patai and Z. Rappoport Eds., John Wiley & Sons, NY, 1989, p. 1207–1240 by R. West and is described in *Synth. Met.,* 1989, 28, C581 by Zeigler, the disclosures of each of which are totally incorporated herein by reference. In the present invention we advantageously exploited the discovery that the σ—σ conjugation in polysilanes affects the Raman scattering qualitatively in the same way as σ—σ conjugation in polyenes, both phenomena leading to an increase in intensity of the lines corresponding to the symmetrical stretching vibrations of conjugated moieties. In particular, the characteristic symmetric skeleton stretching vibrations of Si—Si bond in the vicinity of 450 $cm^{-1}$ and symmetric Si—C vibrations in the vicinity of 650–700 $cm^{-1}$ are greatly enhanced in the spectra of the polymers and are of clear analytical value in accordance with aims and scope of the invention. The polysilylenes having an all-trans planar structure favoring the maximum σ—σ conjugation along the backbone are preferred in frames of the invention. Typical exemplary NIR-excited Raman spectrum for materials of this sub-class F of the invention is disclosed in FIG. 1(F).

Figure 7:
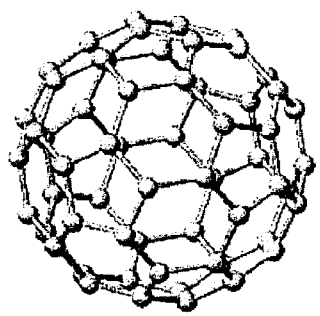
FIG. 7—Shows exemplary structural formulas of large spheroidal carbon molecules and new allotropic forms of carbon such as, for example, fullerness and tubulenes constituting the sub-class G of materials useful as efficient Raman-active taggants in frames of the invention.
Figure 7:
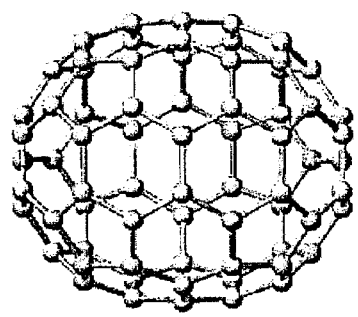
Figure 7:
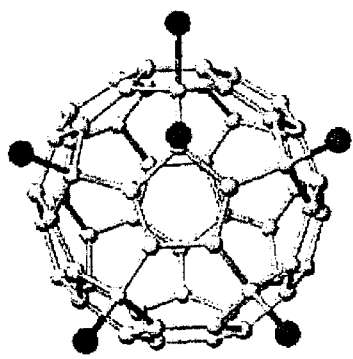
Figure 7:
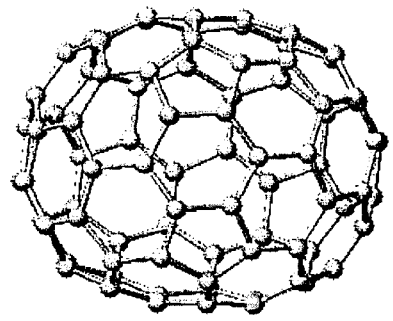
Figure 7:
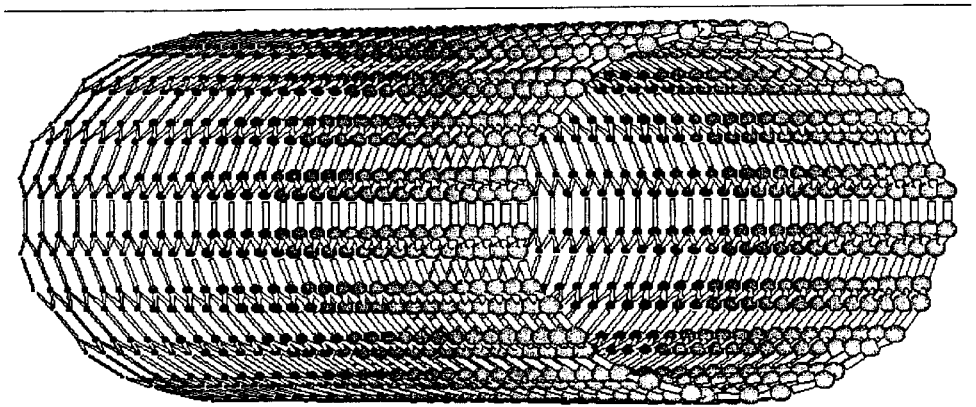

(G)—Large spheroidal carbon molecules and new allotropic forms of carbon such as, for example, fullerenes and tubulenes exemplary molecular structures of which are represented (but not limited) by those shown in FIG. 7.

More specifically, molecular fullerenes have been described as entirely closed, hollow spheroidal shells of carbon atoms containing 32 to 1,000 or more carbon atoms in each sphere. The preparation of fullerenes from the contact arc vaporization of graphite and a number of the fullerene characteristics such as solubility, crystallinity, color and the like have been described in *Nature,* 1990, Vol. 347, pp. 354–358 by Kratschmer et al. and in *Chemical and Engineering News*, Oct. 29, 1990, pp. 22–25 by Baum, the disclosures of which are totally incorporated herein by reference. There are many patents issued in the art related to synthesis/production of buckyballs, nanotubes, and other fullerenes, for example, the U.S. Pat. No. : 5,132,105—Materials with diamond-like properties and method and means for manufacturing them; U.S. Pat. No. 5,177,248—Process of forming polysubstituted fullerenes; U.S. Pat. No. 5,227,038—Electric arc process for making fullerenes; U.S. Pat. No. 5,271,890—Method for producing carbon allotrope; U.S. Pat. No. 5,275,705—Process for making fullerenes; U.S. Pat. No. 5,300,203—Process for making fullerenes by the laser evaporation of carbon; U.S. Pat. No. 5,304,366—Process and apparatus for producing and separating fullerenes; U.S. Pat. No. 5,316,636—Production of fullerenes by electron beam evaporation; U.S. Pat. No. 5,346,683—Uncapped and thinned carbon nanotubes and process; U.S. Pat. No. 5,395,496—Process for the synthesis of fullerenes; U.S. Pat. No. 5,393,955—Preparation of fullerenes and apparatus therefor; U.S. Pat. No. 5,416,188—Polysubstituted fullerenes and their preparation (C-2608); U.S. Pat. No. 5,493,094—Preparation of fullerenes and apparatus therefor; U.S. Pat. No. 5,547,748—Carbon nanoencapsulates; as well as many patents for purification of these compounds, for example, the U.S. Pat. No. 5,281,406—Recovery of C60 and C70 buckiminsterfullerenes from carbon soot by supercritical fluid; U.S. Pat. No. 5,458,742—Isolation of fullerenes; etc., the disclosures of each of which are totally incorporated herein by reference.

Although among many cage-like structures of carbon atoms already found by scientists the most abundant form produced is buckmininsterfullerene (C60), with 60 carbon atoms arranged in a spherical structure, there are a great number of larger fullerenes containing from 70 to 1000 or more carbon atoms (see for example K. Kobayashi et al., "Endohedral Metallofullerenes. Are the Isolated Pentagon Rule and Fullerene Structures Always Satisfied?", *J. Am. Chem. Soc.,* 1997, 119, 12693–12694). The novel properties of these polycarbon supercages are receiving intense interest from the scientific and industrial world. This interest has created a demand for supplies of the pure fullerene materials and, as a result, many of them are now commercially available. Thus, for instance, many different fullerenes and tubulenes are available from Texas Fullerenes Corporation, 2415 Shakespeare Suite 5, Houston, Tex. 77030–1038; Materials & Electrochemical Research (MER) Corporation, 7960 South Kolb Road, Tucson, Ariz. 85706; Research Materials, Inc., 1667 Cole Boulevard, Golden, Colo. 80401; an UK-based company such as Dynamic Enterprises Ltd (DEL); ICP, Moscow, Russia and/or from many R&D laboratories around the World. Alternatively, special generators have been already devised in the art which can be installed in an ordinary research laboratory, in order to produce fullerenes as required. Roughly, the procedure of obtaining fullerenes usually comprises: (a) generation of the carbon soot (for example, the generator with moveable graphite rod based on the Kratschmer-Huffman design apparatus can be used, which is run in a laboratory at 80–100 amps, 25V AC, 100–120 torr He); (b) the second necessary stage is extracting of fullerenes from the soot produced by the generator; (c) after extraction, the solvent (usually toluene or benzene) is removed using a rotary evaporator, leaving behind a solid mixture of mostly C60 with small amounts of larger fullerenes. Pure fullerenes, e.g. C60, is obtained by liquid chromatography. The mixture is dissolved in toluene and pumped through a column of activated charcoal mixed with silica gel. The magenta C60 comes off first, followed by the red C70. The different color solutions are collected separately and the toluene removed using the rotary evaporator. The color of the allotrope can depend on the number of carbon atoms n in the cage. For example, when n is equal to 70 the color is red-orange, when n is equal to 60 the color is purple magenta, and when n is equal to 62 the color is yellow.

It has been recognized by specialists in the art that these new forms of carbon could possess a number of advantages as pigments for liquid thermal ink jet and toner applications. Among these advantages are, for example, their solubility in organic solvents and, with appropriate chemical modification, solubility in water. The other known carbon forms, diamond and graphite and derivatives thereof, are not considered to be soluble in such solvents. Potential advantages of C60 and the like fullerenes as pigments over those known in the art include their unusual stability against chemical and physical degradation, together with other unique characteristics. These and other advantages offered by fullerenes have been exploited, for example, in the U.S. Pat. No. 5,114,477, Liquid ink compositions; U.S. Pat. No. 5,232,810, Toner composition comprising fullerene; U.S. Pat. No. 5,234,475, Hydrocarbon fuels having one or more fullerenes therein as identification media; U.S. Pat. No. 5,248,498, Fullerene compositions for magnetic resonance spectroscopy and imaging; disclosures of each of which are totally incorporated herein by reference. Raman spectra of fullerenes have received considerable attention in scientific circles in terms of investigating molecular structure of the new carbon allotropes. Good Raman spectra of fullerenes can be found, for example, in papers entitled "The vibrational Raman spectra of C60 and C70", Spectrochim. Acta, 47A (1991) No. 9/10, pp.1289–1292, by T. J. Dennis et al., and "Raman Scattering from Single—Crystal KC60", J. Raman Spectroscopy 27 (1996) 373, by J. Winter et al.

To our best knowledge, however, there are no publications either in periodical or patent literature suggesting to employ fullerenes and other allotropic forms of carbon as NIR-excited Raman-active taggants for security applications. Thus, hereinbelow we disclose that the fullerenes (or "buckyballs") along with many tubular carbon structures which are a molecular form of pure carbon, or the so called third allotropes of carbon, constitute an important sub-class of the materials useful in frames of the present invention as effective Raman-active taggants in accordance with aims and scope of the invention. Accordingly to the invention, the fullerenes and tubulenes which are characterized by extensive delocalization of electron density along their conjugated cage-like carbon shells, being excited with NIR lasers, readily produce strong Raman spectra actually devoid of autofluorescence or other interfering backgrounds. Preferable in frames of the present invention are stable fullerenes and isomers thereof such as the so called fullerenes C60, C70, C72, C80, C140, C180, C240, C260, C320, C420, C432, C500, C504, C540, C560, C576, C620, C720, C740, C780, C860, C980, C1040, C1260, and the like; the so called Goldberg polyhedra or small isomers C20–C60; the so called carbon nanotubes and helical nanotubes; the so called carbon nanotoruses; the so called non-classical fullerenes, e.g. C62; the so called graphitic triply periodic minimal surfaces, graphitic sponges, etc. Although miscellaneous derivatives such as the so called polymerized fullerenes, dimerized heterofullerenes, metal-doped fullerenes, endohedral metallofullerenes and the like can also be used in accordance with the invention in order to achieve its aims, the stable undoped fullerenes in minimally "deformed" state are the most preferred in frames of the invention. Typical exemplary NIR-excited Raman spectrum for materials of this sub-class G of the invention is disclosed in FIG. 1(G).

(H) Polyenes or polyacetylenes represented by the general formula:

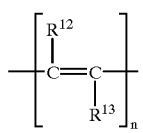

(IX)

wherein n is an integer preferably from about 3 to about 100,000; $R^{12}$ and $R^{13}$ may be the same or different and, independently of each other, can be H, n-alkyl preferably with from about 1 to about 8 carbon atoms or substituted alkyl, preferably with from about 3 to about 12 carbon atoms, or phenyl. Normally, these polymers are prepared by polymerization of corresponding monomers in the gas or liquid phase and in presence of stereospecific catalysts. Various such compounds are described, for example, in "Handbook of Conducting Polymers", T. A. Skotheim ed., Marcel Dekker: New York, 1986, vol 1 and 2; and in J. C. W. Chien, "Polyacetylenes: Chemistry, Physics, and Material Science", Academic Press, Orlando, 1984. Polyacetylenes can be synthesized as described, for example, in Synth. Metals, 1, 101 (1979/1980) by MacDiarmid et al.; and in Polym. J, 2, 231 (1971) by Shirakawa et al., the disclosures of each of which are totally incorporated herein by reference. Carotenoids such as trans-β-carotene, lycopene, astaxanthin, allo-ocimene, trans-retinole, trans-retinale, dodecapreno-β-carotene and the like containing from 3 up to 19 conjugated double bonds in their backbone and described, for example, in J. Chem. Phys., 71, 3561 (1979) by Siebrand et al., also may be used in frames of the invention. However, polyacetylenes prepared by traditional synthetic routes are rather unstable materials, and their conjugation system readily degrades because of oxidation destruction under effect of atmospheric oxygen. Accordingly, the most preferred in frames of the present invention are the so called polymer-matrix-stabilized polyacetylenes having the simplest formula wherein $R^{12}=R^{13}=H$. Such polyacetylenes are prepared by means of acetylene gas polymerization on a catalytic system composed of binuclear Rhenium complexes and a reducing agent as is described, for example, in Vysokomolekulyarnye Soedineniya, Ser. B, 1994, 36, No. 5, pp. 881–894 by Kobryanskii et al., the disclosures of which are totally incorporated herein by reference. The polymerization process is performed in solutions of appropriate conventional polymers such as poly(vinylchloride), poly(vinylbutyral), poly(vinylacetate), and the like, resulting in obtainment of soluble compositions comprising nanoparticles of highly-ordered polyacetylene in a polyolefin matrix. Of importance is the fact that by this route a stabilized composition of polyacetylene having very low content of conformational and chemical defects is obtained. Properties of such polyacetylenes are described, for example, in Phys. Rev. B: Condens. Matter, 1994, 50, No. 2, pp. 907–913, by Paraschuk et al.; in a paper entitled "Temperature evolution of electronic and lattice configurations in highly ordered trans-polyacetylene" JETP Lett., 64 (1996) No. 9, pp. 658–663 by Paraschuk et al., and in an article entitled "Thermochromism, Raman activity and electroabsorption in highly-ordered trans- and cis-polyacetylene"

*Synth. Met.* 85 (1997) No. 1–3, by Paraschuk et al., the disclosures of which are totally incorporated herein by reference. The preferred in the present invention stable polyacetylenes are differing from the polyenes and polyacetylenes known from the prior art in that they readily give intense Raman spectra and do not produce interfering luminescence or autofluorescence when irradiated with NIR lasers. Typical exemplary NIR-excited Raman spectrum for materials of this sub-class H of the invention is disclosed in FIG. 1(H).

(I) Poly(ethynylene)arylenes and poly(ethynylene) heteroarylenes of the general formula X:

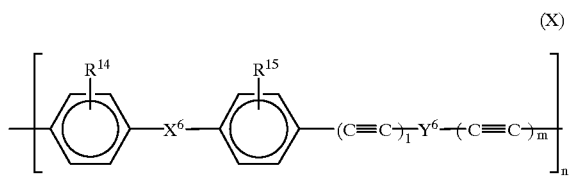

(X)

wherein integer l can be equal to or different from m and each, independently of the other, is 0, 1, 2, 3 or 4; n is an integer preferably from about 5 to about 100,000; $X^6$ can be equal to or different from $Y^6$ and each, independently of the other, can be absent or represents a moiety such as >C=C<, —CO—, —CO—CO—, —CH$_2$—, —O—, —S—, —SO$_2$—, —NH—, —NHCO—, —NHCOO—, —CONHCOO—, —NHCONH—, sulfonyl group, >C=N—, —N=N—, >C=C—C=C<, —Ph—C≡C—Ph—, p- or m-phenylene, diphenyleneoxide, tetraaryl substituted phenylene, cycloalkylene, arylene, substituted arylene, preferably with from about 6 to about 30 carbon atoms, a substituted or unsubstituted heterocyclic structure, preferably of from about 5 to about 15 members, wherein the hetero atom is nitrogen, oxygen or sulfur, such as pyrrolidine, pyridine, piperidine, piperazine, quinoline, isoquinoline, quinuclidine, pyrazole, triazole, tetrazole, triazine, imidazole, pyrimidine, pyradizine, pyrazine, oxazole, isoxazole, morpholine, piperidinoxyl, dehydropiperidinoxyl, carbolinoxyl, carbazole, and the like, with examples of suitable substituents residing on the said structures including but not limited to halogen atoms, cyano group, vinyl group, mercapto group, hydroxy group, amine group, aldehyde group, carboxylic acid group, nitrile group, diazo group, nitro group, or azide group; $R^{14}$ can be equal to or different from $R^{15}$ and each, independently of the other, can be absent or represents from one up to four substituents such as phenyl, alkyl preferably with from about 1 to about 12 carbon atoms, halogen atoms, cyano group, vinyl group, mercapto group, hydroxy group, amine group, carboxylic acid group, nitrile group, diazo group, nitro group, or azide group.

Figure 8A:
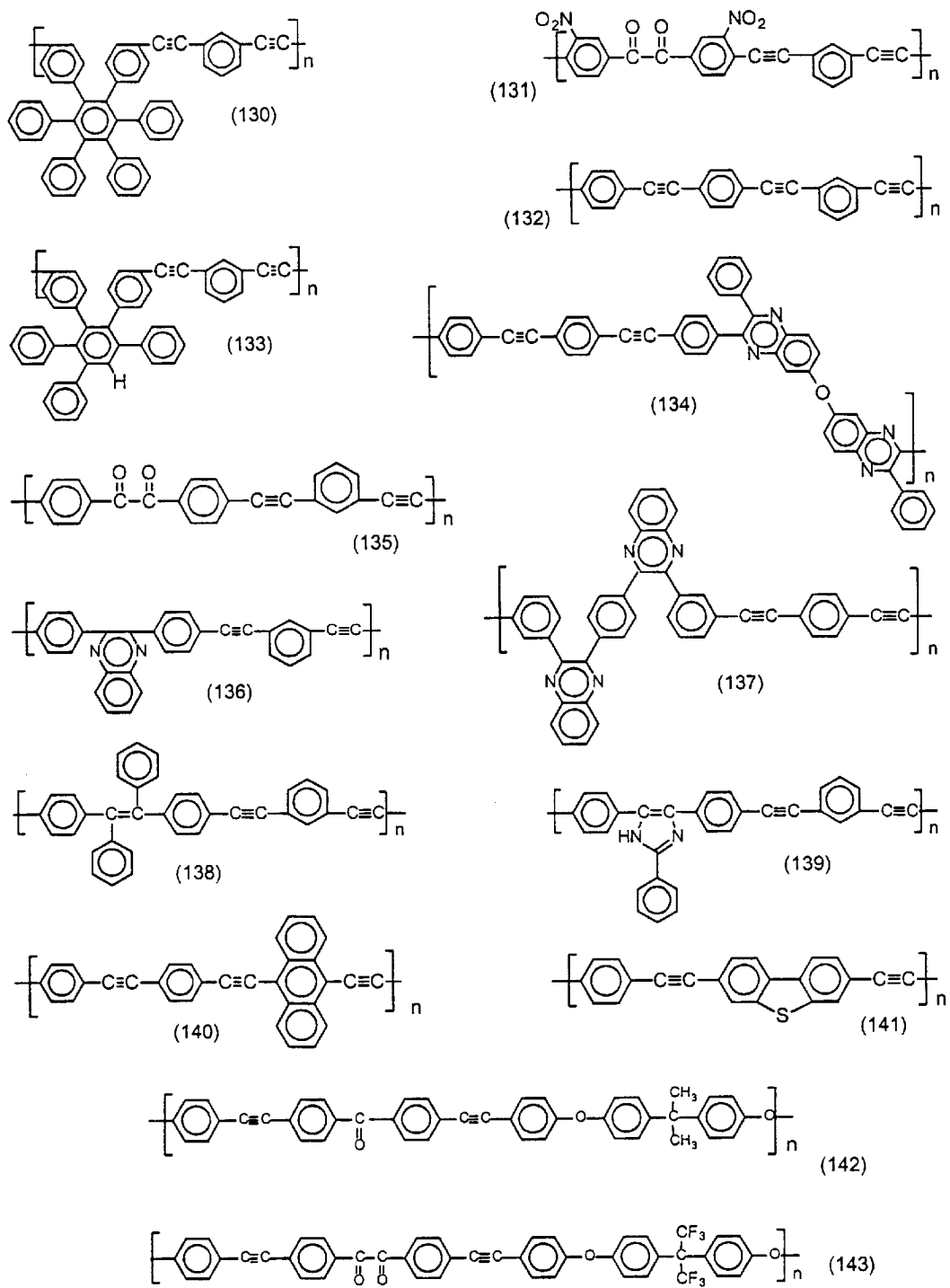
FIGS. 8($a$–$b$)—Show exemplary structural formulas of poly(ethynylene)arylenes and poly-(ethynylene)heteroarylenes constituting the sub-class I of materials useful as efficient Raman-active taggants in frames of this invention.
Figure 8B:
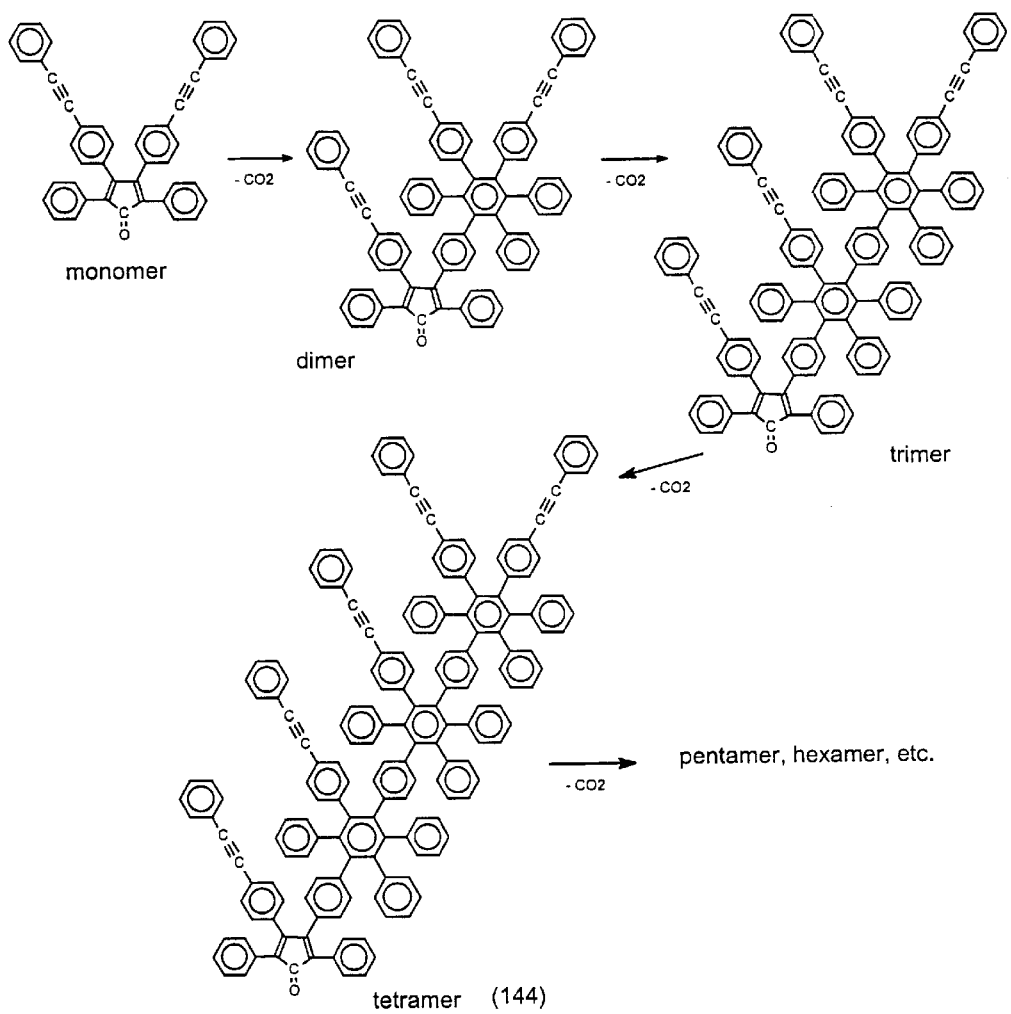

The polymers constituting the sub-class I of the invention are exemplified (but are not limited) by the several particular structures (130)–(144) shown in FIG. 8(*a*) and FIG. 8(*b*). Many macromolecular compounds corresponding to the sub-class I of the invention can be prepared as is described, for example, in a text-book "*Palladium Reagents in Organic Synthesis*", Academic Press, New York, 1985 by R. F. Heck; in articles entitled "Synthesis and investigation of aromatic polyethers bearing acetylenic groups in the backbone", *Vysokomolekulyarnye Soedineniya, Ser. A,* 1998, 40, N 3, 397–402 by Rusanov et al.; "Chloral-based phenylated polyphenylenes", *Vysokomolekulyarnye Soedineniya, Ser. A,* 40 (1998) No. 6, 902–908 by Rusanov et al.; "Poly (phenylquinoxalines) bearing acetylenic groups in the backbone", *Polymer Science, Ser. A,* 1999, 41, 9, 877–882 by Rusanov et al.; "Phenylated polyphenylenes containing hexafluoroisopropylidene groups", *ACS Polymer Prepr.,* 1999, 40(1), 794–795 by Rusanov et al.; "Rapid solid-phase synthesis of oligo(1,4-phenyleneethynylene)s", *ACS Polymer Prepr.,* 1999, 40(1), 525–526 by Huang et al., "Comparative evaluation of conjugated polymers as optical frequency converters", *ICSM-98 Book of Abstr., Jul.* 12–18, 1998, Montpellier, France, WEP127, p. 159 by Shchegolikhin et al.; "Optical properties of soluble poly(arylene) ethynylenevinylenes, poly(phenylene-quinoxalines) and poly(phenylene)ethynylenes", *ICSM-98 Book of Abstr., Jul.* 12–18, 1998, Montpellier, France, THP194, p. 213 by Shchegolikhin et al.; "Synthesis and properties of organosoluble poly(arylene)ethynylenes", *ICSM-98 Book of Abstr., Jul.* 12–18, 1998, Montpellier, France, WEP83, p. 151 by Keshtov et al.; as well as in the papers *Bull. Chem. Soc. Jpn.,* 1984, 57, 752 by Sanechika et al.; *J. Polym. Sci., Polym. Chem. Ed.,* 1986, 24, 2311 by Trumbo et al.; *ACS Polym. Prepr.,* 1994, 35(1), 369 by Wright et al., the disclosures of each of which are totally incorporated herein by reference. The synthesis of other polyarylene polymers with unsaturated groupings in the backbone which are also useful in frames of the invention is well known, and is described in, for example, U.S. Pat. No. 4,837,096, U.S. Pat. No. 5,011,907, U.S. Pat. No. 5,496,503, U.S. Pat. No. 5,783,306, U.S. Pat. No. 5,804,101, U.S. Pat. No. 5,881,083, the disclosures of each of which are totally incorporated herein by reference. The compounds of the sub-class I disclosed herein are environmentally stable solids. Preferable in frames of the invention are those which are soluble in conventional organic solvents. Despite the fact that some compounds of this sub-class are intensely colored, most of them do not produce interfering luminescence or autofluorescence when irradiated with NIR lasers. Most preferable materials within the sub-class I are those which, besides acetylenic or diacetylenic moieties in the backbone, additionally contain highly polarizable substituents such as —C≡N, —CH=CH$_2$, —C≡—CH, —NO$_2$ and the like residing on alkyl, aryl or heterocyclic groupings present in the macromolecule. Those familiar with the art will probably recognize that many useful polymers belonging to the sub-class I of the invention can be readily prepared starting from the corresponding essentially monomeric compounds disclosed hereinabove in the sub-classes A, B and C of the invention. Some exemplary NIR-excited Raman spectra for materials of this sub-class I are disclosed in FIG. 1(I).

(J) Poly(enynes) or polydiacetylenes of the general formula:

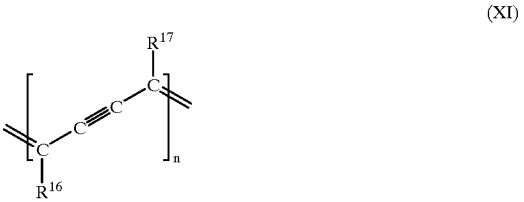

(XI)

where $R^{16}$ and $R^{17}$ are typically independently selected from alkyl and substituted alkyl groups, preferably monosubstituted alkyl groups, including urethane-modified alkyl, arylsulfonyl-modified alkyl, heterocyclic-substituted alkyl, ether-substituted alkyl, ester-substituted alkyl, amide-substituted alkyl, urea-substituted alkyl, carboxy-substituted alkyl, hydroxy-substituted alkyl, and the like.

Polymers of this sub-class J of the invention are obtainable starting from corresponding monomeric diacetylenes by topochemical polymerization reaction which is initiated thermally or with energetic radiation (UV-, γ- or electron beam) and proceeds in the solid state according to the general Scheme (XII) below:

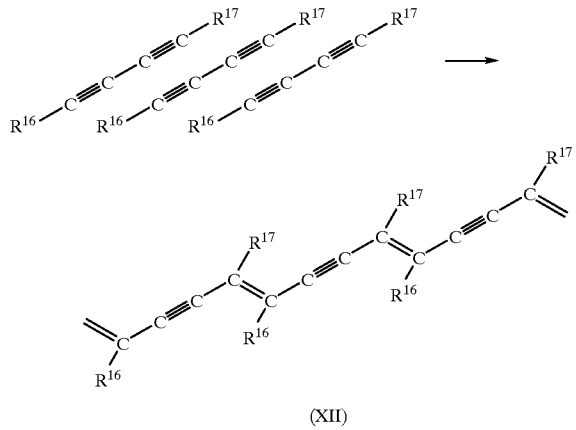

(XII)

Figure 9A:
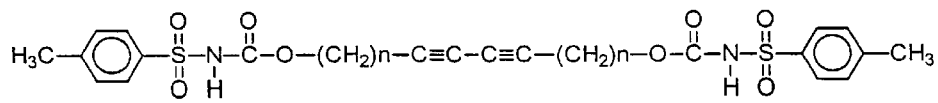
FIG. 9($a$)—Shows exemplary formulas of diacetylenic monomers preferable for preparing polydiacetylenes to be used as the sub-class J of the materials of the present invention.
Figure 9A:
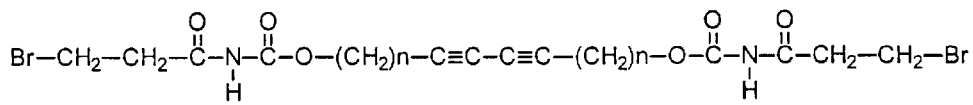
Figure 9A:
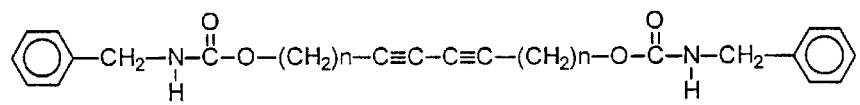
Figure 9A:
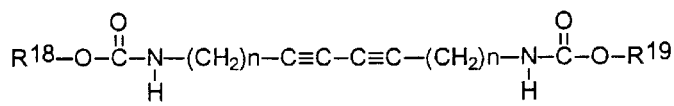
Figure 9A:
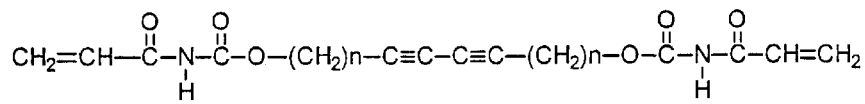
Figure 9A:
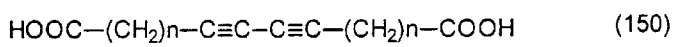
Figure 9A:
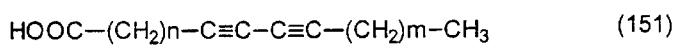

The reaction mechanism is now well understood. The existence of a crystalline or, at least, "para-crystalline" phase packing for the diacetylene moieties of the monomer molecules, meeting specific crystallographic criteria, has been shown to be a necessary prerequisite for the polymerization to proceed. Many monomeric diacetylenes suitable for obtaining polydiacetylenes can be prepared with good yields by procedures described, for example, in *J. Org. Chem.*, 25 (1960) 1275; *J. Org. Chem.*, 25 (1960) 2928 and *J. Org. Chem.*, 27 (1962) 3320 by A. S. Hay; in *J. Chem. Soc.*, 1951, 44 by Armitage et al., in *J. Chem. Soc.*, 1959, 889 by Eglinton et al., and in *Bull. Soc. Chim. France*, 1958, 298 by Chodkiewicz et al., the disclosures of each of which are totally incorporated herein by reference. Many particular monomeric diacetylenes preferable in the invention can be synthesized as has been described, for example, in articles entitled "Nitroxyl radicals substituted diacetylene monomers: molecular design, synthesis, solid-state polymerizability", *Synth. Met.* 85 (1997) No. 1–3, 1685–1686 by Lazareva et al.; and "FTIR and NIR-FT Raman study of potential molecular ferromagnetics—poly (diacetylenes) substituted with nitroxyl radicals", by Shchegolikhin et al., *Synthetic Metals*, 1995, 71, 1825–1826. Preparation of many disubstituted diacetylene compounds as monomers for subsequent solid-state polymerization has been described in, for example, U.S. Pat. Nos. 3,999,946, 4,125,534, 4,195,056, 4,215,208, 4,220,747, 4,339,951, 4,788,151, 5,085,801, 5,420,000, the disclosures of each of which are totally incorporated herein by reference. It should be noted that precursors of the materials constituting the sub-class J of the invention, i.e., the monomers containing diacetylenic moiety in the molecule, can be represented in fact by the same general formula (III) which has been used above for representing materials of the sub-class C of the invention. However, while within the sub-class C of the invention the most preferred are those monomeric compounds which lack ability to polymerize in the solid-state, for the sub-class J, on the contrary, the most preferred are those diacetylenic monomers which are readily react in the solid state by the topochemical polymerization mechanism leading to the crystalline, highly ordered conjugated polymer. Because of the polymerizability requirement, certain limitations emerge for chemical structure of the substituents in the latter case. Due to these, some types of the substituents proper for obtainment of stable diacetylenes, which are preferred within the sub-class C, turn out to be totally inappropriate in terms of synthesis of the polymerizable monomers suitable for subsequent preparation (by the route depicted in Scheme XII) of corresponding polydiacetylenes, which are preferred materials within the sub-class J. As a general rule, following preparation of a polymerizable diacetylene of the invention, it should be recrystallized from an appropriate solvent, from the melt, or from the vapor so as to provide a solid material in a substantially crystalline phase, which is polymerizable. Suitable solvents employed in a solution crystallization include alkyl esters of monocarboxylic acids, alkyl alcohols, paraffins, olefins, benzenes, alkylated benzenes, ethers, ketones, petroleum ethers, halogenated hydrocarbons and water. Representative examples include ethyl acetate, methyl propionate, methanol, ethanol, butanol, isopropanol, hexane, heptane, 1,4-dimethylheptane, benzene, toluene, xylene, diethylether, isopropylether, 1,2-dimethoxyethane, tetrahydrofuran, dioxane, acetone, acetonitrile, methylethyl ketone, chloroform, dichloromethane and trichloromethane and mixtures thereof. Especially preferred as crystallizing solvents for diacetylenic Raman-active compounds of the invention are diethyl ether, 1,2-dimethoxyethane, dioxane, tetrahydrofuran, petroleum ether, acetone, chloroform, benzene, methanol, ethanol, xylene, ethylacetate, formic acid, acetic acid and water. Some exemplary molecular structure formulas representing (but not limiting) preferable diacetylenic monomers suitable for preparing polydiacetylenes to be used as the sub-class J materials in frames of the present invention are disclosed in FIG. 9(a).

Figure 9B:
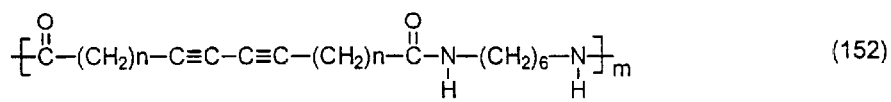
Figure 9B:
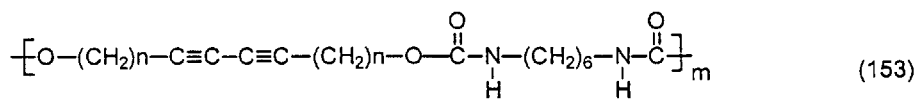
Figure 9B:
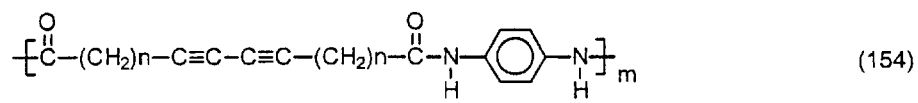
Figure 9B:
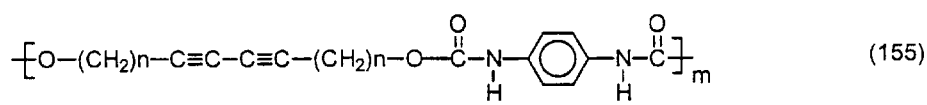
Figure 9B:
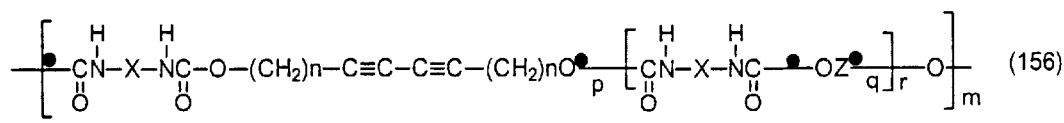

In another preferred embodiment of the present invention, the substituents $R^{16}$ and $R^{17}$ (cf. General formula XI or Scheme XII) are independently selected from macromolecular residues having average degree of polymerization from 5 up to 100,000 and represented by polyalkylenes, polyoxymethylenes, polyoxypropylenes, polyethers, polyesters, polyurethanes, polyamides and polyetheramides. Many polydiacetylene-block-copolymers of such type can be synthesized as has been described, for example, in an article entitled "Optical properties of poly(diacetylene) block-copoly(ether-urethanes), containing covalently bound nitroxyl spin labels in the main chain" by Shchegolikhin et al., *Synthetic Metals*, 1995, 71, 2091–2092. Some exemplary chemical structures representing (but not limiting) polydiacetylene-block-copolymers suitable for use as the sub-class J materials in frames of the present invention are disclosed in FIG. 9(b).

In practice, many polydiacetylenes can be prepared from corresponding diacetylenes by heating the monomer, e.g. in an oven, at temperatures not exceeding the melting point of the monomer. Alternatively, other diacetylenes may be polymerized in thin polycrystalline layers or as a fine suspension of microcrystalls in an inert solvent by irradiating them with a short-wave (e.g., 254 nm) UV-light or γ-radiation (e.g., from $^{60}$Co-source). It is supposed that there is an anti-correlation of thermal and radiation polymerizability, i.e., the materials with rapid radiation-induced polymerization generally polymerize slowly when heated, and vice versa. In any case, the products of diacetylenic solid state polymerization are intensely colored, have unusually high molar extinction coefficients and frequently reveal a metallic luster when viewed under reflected light. As has been already noted above (cf. BACKGROUND OF THE INVENTION Section), the use of polydiacetylenes as components of an ink for printing security documents which can be identified by RRS has been suggested in the U.S. Pat. No. 5,324,567, the disclosure of which is totally incorporated herein by reference. However, the RRS approach (and this is of prime importance in terms of the aims and spirit of the present invention) can hardly provide truly quantitative spectroscopic data during identification of many polydiacetylenes. Besides those undesirable issues that the resonance Raman spectra of polydiacetylenes: (a) often are contaminated or distorted by considerable thermal or fluorescent backgrounds; (b) often absorption of the laser energy causes severe sample heating and/or degradation; (c) intensity of the RR scattered light is not governed by the fundamental $v^4$ law and is hardly predictable; (d) shapes and intensities of the bands constituting the resonantly enhanced Raman spectra vary with the excitation wavelength chosen; (e) Raman photons thus generated often have frequencies coinciding with spectral region of strong optical opacity of the sample, and hence reabsorption of the Raman photons by the sample distorts the true intensity of the Raman bands; the RRS is actually inappropriate for reliable identification of the so called thermochromic polydiacetylenes. [These and other less obvious shortcomings of the RRS approach will be discussed and illustrated in more details below in this Section.]

Here it should be emphasized that a great portion of all polydiacetylenes synthesized up to date turned out to be thermochromic by nature. It means that they revealed the ability to change their color depending on temperature. Visually, the thermochromicity phenomenon in polydiacetylenes is manifested as gradual (e.g., from red to red-orange, then to bright orange, then to yellow-orange and, finally, to lemon-yellow) or abrupt (e.g., from navy-blue to bright-red) change of color of a polydiacetylene under gradual heating of the material. Physically, these color changes reflect nothing but structural transformations of the conjugated backbones of the polydiacetylene macromolecules. This phenomenon has been exploited in a number of patents (see for example the U.S. Pat. Nos. 4,916,211 and 5,085,801) and was the subject of many scientific investigations (see, for example E. Morrow et al., *Chem. Phys. Lett.* 1989, 158, 499; L. X. Zheng et al., *Phys. Rev. B* 1990, 42, 3235; and papers entitled "DRAFT and NIR-FT Raman—new handy tools in conjugated polymer studies"—*Proc. 1st Korea-China-Russia Symp. Synt. Metals*, Jul. 20–24, 1994, Seoul, Korea, by Shchegolikhin et al.; "Structural transformations of diacetylenes during solid-state polymerization and chromatic transitions of poly(diacetylenes) as measured by a modified diffuse reflection-absorption FTIR technique", *ICSM-94*, Seoul, Korea, Jul. 24–29 1994, *Book of Abstr.* TUE P186, by Shchegolikhin et al.; "Is NIR-FT Raman a quantitative tool for polydiacetylenes studies?", *Synth. Met.* 85 (1997) No. 1–3, 991–992, by Lazareva et al.; "A NIR-FT Raman image of solid-state polymerization of PTS diacetylene", *Spectrochim. Acta Part A*, 1997, 53, No.1, 67–79 by Shchegolikhin et al.; "Raman study of structural transitions in polyacetylene (PA) and polydiacetylenes (PDA)", *ICSM-98 Book of Abstr.*, Jul. 12–18, 1998, Montpellier, France, WEP129, p. 159, by Shehegolikhin et al.), the disclosures of which are totally incorporated herein by reference. Of importance for the present invention is the fact that, as it has been discovered by the inventors, the normal Raman spectroscopy permits advantageously employ not only any one of non-thermochromic polydiacetylenes (those having comparatively thermally insensitive molecular and/or sub-molecular organization in the solid state), but many thermochromic polydiacetylenes as well. Thus, it will be disclosed hereinbelow that, despite all polydiacetylenes are intensely colored and/or many of them are thermochromic, these materials (for clarity segregated into the sub-class J of materials of the invention) can be advantageously and effectively used as convenient Raman-active taggants for achieving the purposes of the invention. Some exemplary NIR-excited Raman spectra for materials of this sub-class J are disclosed in FIG. 1(J). In one embodiment of the invention, the most preferable materials within the sub-class J are those which are not intrinsically thermochromic, that is, are not capable of changing their color under effect of temperature. In another embodiment of the invention, on the contrary, namely those materials of the sub-class J which exhibit obvious capability to change color depending on the temperature applied to them are considered to be most preferable. Yet in another embodiment of the invention, the most preferable are those materials of the sub-class J which can be produced in the form of micron- or even sub-micron-sized particles well suited for subsequent production of ink-jet printing inks, toners or offset printing inks based thereof.

(iii) Essentially inorganic the so called anti-Stokes up-converting phosphors comprising ions of rare earth and lanthanide elements constitute the third specific class of materials useful in frames of the invention as convenient and efficient "LIF/Raman-detectable" taggants.

A variety of such anti-Stokes phosphors with excitation in the infrared region have been introduced in to the market recently. These materials apparently have great potential in security applications, especially in areas where high-speed machine readability is required. In all normal fluorescence it follows that the exciting radiation must have a shorter wavelength than the emitted light. This observation is referred to as Stoke's Law. In difference to this, the class of anti-Stokes phosphors has the ability to absorb two or three photons of longer wavelength infrared light and combine their energies to emit a single photon of, e.g. visible light. An essential advantage of such anti-Stokes phosphors is that they are not susceptible to photobleaching and, due to the fact that excitation is performed in far red, NIR or IR region, they do not induce unwanted autofluorescence of substrates and impurities. It has been discovered by the present inventors that many such materials can be advantageously used as convenient and efficient "LIF/Raman-detectable" taggants in accordance with aims and spirit of the present invention.

There exist a large number of patents covering synthesis and applications of the up-converting phosphors in diversified spheres of life and technology (see, for example, the U.S. Pat. No. 5,166,948, Optically pumped up converting light source; U.S. Pat. No. 5,287,217, Optical amplification at the 1.31 mcm wavelength; U.S. Pat. No. 5,525,380, Method of making a device for converting infrared radiation; U.S. Pat. No. 5,736,410, Up-converting reporters for biological and other assays using laser excitation techniques; U.S. Pat. No. 5,684,815, Upconversion laser material; U.S. Pat. No. 5,541,012, Infrared-to-visible up-conversion material; U.S. Pat. No. 5,684,621, Method and system for three-dimensional display of information based on two-photon upconversion; U.S. Pat. No. 5,754,570, Co-doped optical material emitting visible light; U.S. Pat. No. 5,891,361, Method for preparing small particle size fluoride up-converting phosphors; the disclosures of each of which are totally incorporated herein by reference. In very general terms, an up-converting material may be thought of as a matter responsive to light emitted from a pump light for producing visible and/or ultraviolet light therefrom which is of a shorter wavelength than the pump light. This matter usually contains active ions of trivalent rare earth elements and a host material of either anhydrous rare earth halides or rare earth oxysulfides. Such usually crystalline structure can be represented by the atomic formula $M_{(1-x)} R_x Z_3$ or $M_{2(1-x)}R_{2x}O_2S$ wherein M comprises at least one rare earth element selected from the group comprising cerium, gadolinium, yttrium, lanthanum, and mixtures thereof; R is a dopant selected from the group comprising neodymium, thulium, erbium, holmium, samarium, and mixtures thereof; x is a value in the range from 0.005 to 1.0; and Z is a halogen selected from the group comprising chlorine, bromine, and iodine. When optically pumped, the crystalline structure produces visible and/or ultraviolet light by either a direct or indirect two step up-conversion process. Currently, these materials are commercially available from a number of manufacturers. Much more materials of the kind which are suitable for purposes of the present invention can be synthesized in laboratory. According to a specific embodiment of the invention, these lanthanide-ions-based inorganic phosphors comprising oxides and salts (chlorides, fluorides, sulfides, fluorosulfides, nitrates, acetates, carbonates, hydroxides, hydrates, etc.) of La, Nd, Ho, Sm, Ce, Eu, Er, Tb, Gd, Dy, Yb and Lu can be used as such, as mixtures of one with another or as mixtures with organic Raman-active compounds of the invention. Strictly speaking, the use of such compounds in frames of the present invention is based on exploitation of Laser Induced Fluorescence (LIF) phenomenon rather than of normal Raman scattering. Nonetheless, owing to the fact that they can be conveniently detected and identified with the aid of the very same equipment which normally is used for detecting the organic Raman-active taggants of the above classes (i) and (ii) in accordance with the invention, temporarily we offer to render the inorganic materials of the class (iii) in frames of the invention as unusual but efficient "LIF/Raman-detectable" taggants of the invention. Exemplary NIR-excited Laser-Induced Fluorescence spectra for materials of this class (iii) are disclosed in FIG. 10.

This and other specific embodiments of the invention as well as principles, novelty and advantages of the present invention compared to the achievements of the prior art will be explained in more details below with reference to the accompanying drawings and figures.

Thus, the present invention is based on the discovery that specific classes of chemical compounds such as conjugated polymers, molecules with extensive conjugation system, molecules containing acetylenic chromophores with high polarizability and some inorganic substances comprising lanthanide ions are of value as efficient Raman-active or fluorescent components of improved molecular labels and codes which can be reliably identified by their near infrared excited Raman spectra or by LIF/Raman spectroscopy.

The present invention is based also on the recognition that, despite the significant achievements of previous practitioners, a need still existed in the art for an improved system of tagging compounds, marking compositions and determining their presence. Preferably, the improved system should include taggants which, for example, are invisible to the naked eye, yet recognizable with a machine by a relatively quick and simple detection procedure. Preferably, the detection procedure requires minimal instrumentation. Desirably, the improved system should permit detection of the taggants at comparatively low concentrations in mixtures with other ingredients. In this context, the limitations of the methods suggested or existing in the art perhaps may be best illustrated by reference to teachings of the U.S. Pat. No. 5,935,755 (Method for document marking and recognition, 1999), the disclosure of which is totally incorporated herein by reference. As has been noted above (see BACKGROUND OF THE INVENTION Section): (a) all experiments described in the patent have been performed with the aid of research-grade and, hence, expensive and fragile NIR-FT Raman spectrometers; (b) most of the Raman-active compounds disclosed in the patent will exhibit their most prominent Raman bands in the same Raman shifts region, tending to give ensembles of poorly resolved and/or superimposed bands with broad shoulders instead of a clear sequence of well resolved spectral features, thus worsening reliability of the authentication process or calling for necessity to work at higher resolutions or using longer scanning times or both. This drawback should be especially troublesome during attempts to employ mixtures of different compounds from the lot disclosed in the patent—e.g., in order to increase the number of available authenticating markings and codes; (c) most of the Raman-active compounds and molecular groupings disclosed in the patent are either highly asymmetrical or polar by nature. Being highly active in infrared absorption spectroscopy, they should be relatively Raman-inactive due to their asymmetry or polarity or both. Although some of these molecules have a few necessary attributes capable to impart them moderate Raman activity, they hardly can have very high Raman scattering cross-section.

Figure 11A:
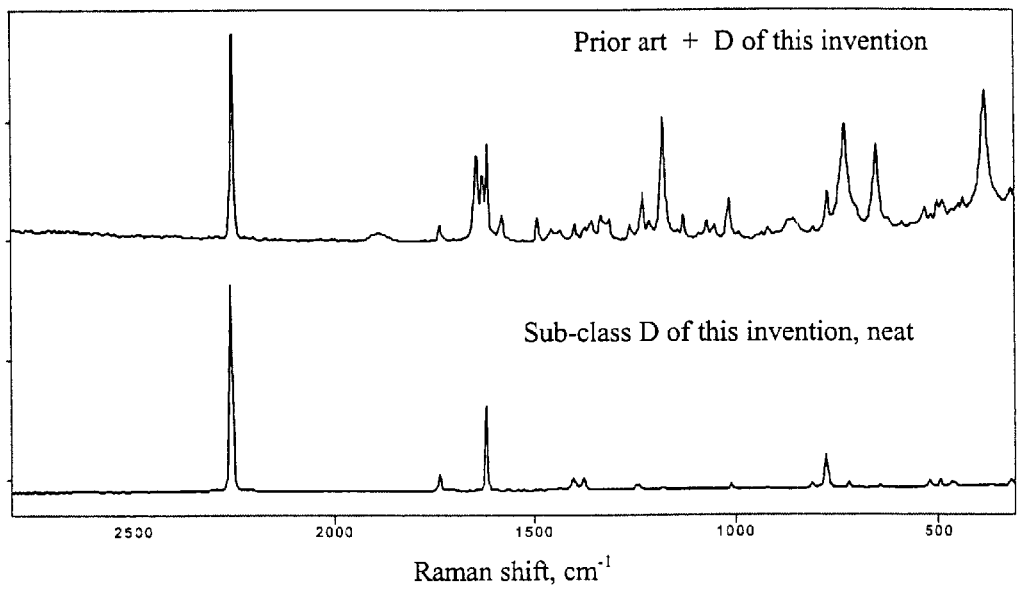
FIGS. 11($a$–$b$)—Is a comparison of Raman activities of a taggant of the prior art and the taggants of the present invention.
Figure 11B:
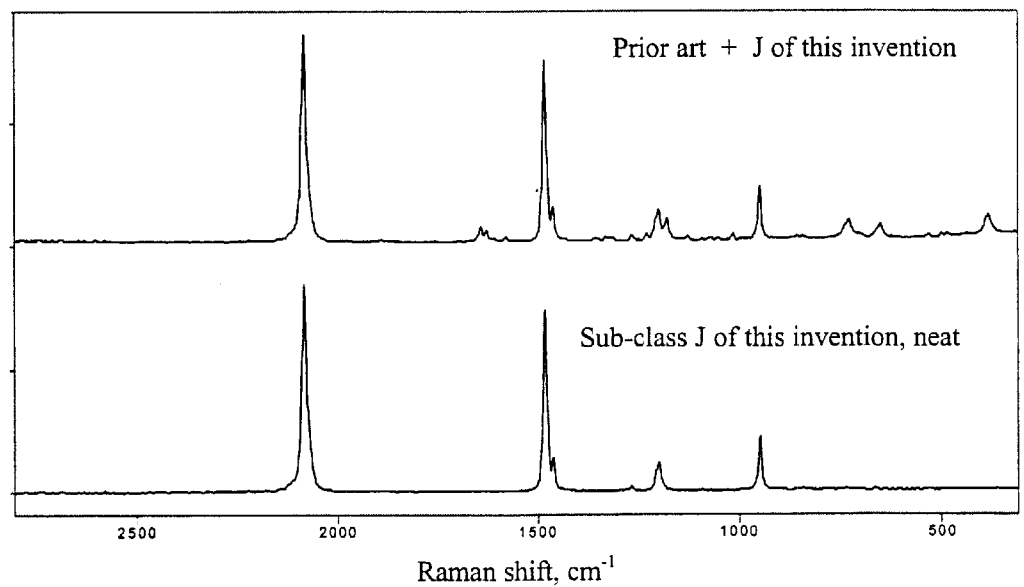

Indeed, as NIR-FT Raman spectra presented in FIG. 11 show, a squaraine compound, 1,2-bis-[p-(dimethylamino) phenyl]squaraine, structurally meeting the claims of the U.S. Pat. No. 5,935,755, turned out to be inferior to those of the present invention in terms of the Raman cross-section or Raman-activity. As FIG. 11(a) shows, the most prominent spectral features of the prior art compound, in a 50:50 by weight mixture with a compound #114 of the sub-class D of the present invention (see FIG. 5 and FIG. 1D), has lower or, at best, comparable intensity with the characteristic features of the other component of the mixture. The prior art compound reveals a number of moderate intensity bands which could be of analytical value, judging, however, by the spectra acquired with a research-grade NIR-FT Raman spectrometer. Further, as spectra in FIG. 11(b) show, the squaraines turn out to be much inferior to other compounds of the present invention in terms of their NIR Raman activity. For instance, a NIR-FT Raman spectrum of a 50:50 by weight mixture of the squaraine with bis-p-toluenesulfonate of 2,4-hexadiyne-1,6-diol (formally representing the sub-class J of the present invention) in fact clearly reveals only one component of the mixture. Due to considerably lower Raman cross-section, the squaraine compound manifests itself only as a minor component in the 50:50 mixture with a conjugated polymer. Again, owing to the fact that the spectra were acquired with the aid of a high-end spectrometer, the squaraine contribution into the spectrum of the mixture can have some analytical value, but, strictly speaking, adds little if any to the analytical value already provided by the compound of the present invention. It should be noted that NIR-excited Raman spectra, in principle, reveal spectral contributions from many vibrating moieties within a molecule giving usually rather complex spectrum consisting of many Raman bands of comparable intensity. This is the case with the prior art squaraines. Certainly, such spectra can be of clear analytical value, but only in a scientific research work with the aid of expensive research-grade spectrometers. The present invention, on the other hand, exploits primarily those highly characteristic and intrinsically strong Raman bands which would be still outstanding in any NIR-excited Raman spectrum. Moreover, some of these outstanding Raman bands are advantageously positioned out of intrinsically "crowded" regions of the vibrational spectrum of complex organic molecules. Thus, taking into account the results of numerous experiments which have been accomplished by the present inventors with using both the prior art compounds and the compounds disclosed in the present invention, and paying due regard to other knowledge, ideas or hypotheses in the field through extensive studies of the subject, the known to the present inventors materials competing for the role of NIR-Raman-detectable taggants in the security applications are suggested to be arranged, according to their NIR-Raman activity or in terms of their practical potential or both, in the following order: squaraines (prior art)≦cyanoacrylics (sub-class D this invention)<monomeric acetylenes and/or diacetylenes (sub-classes A, B, C of this invention)≅polysilanes (sub-class F of this invention)<linear organoelement polymes, polyimines and polyazines (sub-class E of this invention)≦poly (ethynylene)arylenes and poly(ethynylene)heteroarylenes (sub-class I of this invention)<trans-polyacetylene and poly-enes (sub-class H of this invention)≦polydiacetylenes (sub-class J of this invention)≦fullerenes and tubulenes (sub-class G of this invention).

It is believed that such rating is reasonably supported also by the following fundamental considerations. As is well known to those familiar with the art, if a molecule is placed in the electric field of electromagnetic radiation then the electrons and protons will experience oppositely directed forces exerted by the electric field. As a result, the electrons are displaced relative to the protons and the polarized molecule has an induced dipole moment caused by the external field. The induced dipole moment, $\mu$, divided by the strength of the electric field E causing the induced dipole moment, is the polarizability $\alpha$. All these fundamental characteristics are related by the formulas: $\mu=\alpha$ E and $\alpha=\mu/E$. The polarizability $\alpha$ (which is a tensor and in general may be represented by an ellipsoid) can be looked on as the deformability of the electron cloud of the molecule by the electric field. Also, it is well known that in order for a molecular vibration to be Raman active, the vibration must be accompanied by a change in the polarizability of the molecule. Further, it is known that, while the polarizability ellipsoid may have higher symmetry than the molecule, all the symmetry elements possessed by the molecule will also be possessed by the ellipsoid. If the polarizability ellipsoid is changed in size, shape, or orientation as a result of molecular vibration or rotation, a Raman spectrum will result. Then it may be expected that the higher the polarizability plus symmetry of a molecular fragment the more Raman active its molecular vibration will be. In this context, such molecular fragments as e.g. —C≡C—, —C≡N, >C=C<, >C=N—, which intrinsically have high electron density localized in between an oscillating pairs of the atoms and, hence, exhibiting high polarizability, may be expected to provide an increased Raman activity to a parent molecule in which they are embedded. Namely this idea has been deliberately taken into account by the inventors and was judiciously exploited in the course of molecular design and then during practical synthesis of the molecules and macromolecules (cf. FIGS. 2–9) offered here to the role of highly Raman-active materials.

Moreover, as those experienced in the art will probably appreciate, even higher values of polarizability, which are imperative and advantageous for efficient Raman scattering, might be expectedly attained by virtue of uniting a number of highly polarizable molecular fragments into a conjugated system. Within the latter, each individual molecular fragment would contribute its partial polarizability into a total polarizability value of the system. By this approach very high polarizability values could be achieved and, in practical terms, desirable molecules and/or macromolecules exhibiting unusually high ability to Raman scattering could be prepared. This idea also has been exploited by the present inventors during synthesis of the Raman-active molecules (cf. FIGS. 2–9) preferred in the invention. Another finding that has been used by the present inventors is that, in principle, there is no strict necessity to induce the traditional, purely electronic, resonance (i.e. to exploit RRS effect) in order for obtain considerable enhancement of intensity of Raman lines corresponding to vibrations of the molecular moieties embedded into the conjugated backbone. "Tender" excitation with NIR lasers falling into the region of relative transparency of highly conjugated systems does the enhancement job on the latter perfectly or, at least, quite adequately for reaching aims of the present invention. Although in scientific circles in the Raman spectroscopy field this effect is still a subject of debates, a plenty of results obtained by the present inventors when dealing with conjugated systems shows that this effect is widespread over many types of conjugated materials. It should be noted further that, in terms of molecular design, the present inventors has preferred to exploit acetylenic functionality as the one which could be responsible for efficiency of NIR-Raman scattering instead of the carbon—carbon double bond, also possessing necessary prerequisites for imparting increased Raman-activity to a molecule. One of the weak features of the >C=C< moiety in terms of reaching the aims of the invention is the fact that, in a conjugated chain comprising several double bonds, there always exists a possibility of the so called trans-cis isomerization of the chain around an ordinary carbon—carbon bond. Those familiar with the art know that only conjugated chain consisting of double bonds in trans-configuration reveals an enhanced Raman-activity. Conjugated double bonds in cis-configuration are markedly less Raman-active. At the same time, presence of double bonds in a molecule does not always lead to obtainment of stable or crystallizable solids which are preferable in terms of the invention. Exception is made for fullerenes and the stabilized trans-polyacetylene (sub-classes G and H of the invention) because these materials are unique in terms of their sub- or supra-molecular structure. Namely the latter is responsible for their unique Raman activity, and this notion has been advantageously exploited in the invention. Embedding of the carbon—carbon triple bonds, —C≡C—, into a molecule during its synthesis, on the other hand, often leads to obtainment of stable and crystallizable solid. Besides the acetylenic functionality always give strong Raman band in comparatively "deserted" region of vibrational frequencies, the type of the acetylenic moiety permits fine tuning of the band position in the Raman spectrum. Thus, depending on the position of an acetylenic functionality within a molecule (e.g., internal, terminal, conjugated, etc.), vibrational frequency of the functionality (and, hence, the position of the corresponding Raman band in the spectrum) can vary in the range of ca. 250–300 $cm^{-1}$. The latter circumstance has especial value in terms of the present invention, and has been deliberately exploited by the inventors during selection of the materials for the role of efficient Raman taggants. Also, a molecular chain built of several conjugated —C≡C— bonds or combinations thereof with arylenes and other multiple bonds frequently represents the so called "rigid rod" structure. Such structures often exhibit their own unusual and unique vibrational behavior which has been advantageously used by the present inventors. As to the materials of the sub-class F of the invention, comprising the so called poly(silanes) or polysilylenes, these are peculiar in that their conjugated chains are considered to be σ—σ conjugated systems with delocalization of the σ-electrons belonging to the Si—Si bond. In the present case the inventors have advantageously exploited the notion that the σ—σ conjugation in polysilanes affects the Raman scattering qualitatively in the same way as π—π conjugation in polyenes, both phenomena leading to an increase in intensity of the lines corresponding to the symmetrical stretching vibrations of conjugated moieties. The polysilylenes having an all-trans planar structure favoring the maximum σ—σ conjugation along the backbone are preferred in frames of the invention. The similar considerations are partly applicable to yet another sub-class E of the invention and, in particular, to the polymes containing a metal atom in the main chain. Here electrons of d-orbital of the atom can be suggestively involved into the conjugated chain formation and, thus, are responsible for the observed enhanced Raman activity of these materials. In any case, however, the results of numerous experiments which have been accomplished by the present inventors with using both the prior art compounds and the compounds of the present invention showed that in terms of their NIR-Raman activity the numerous compounds disclosed herein can be arranged in the following order: squaraines (prior art) $\leq D < A$, B, $C \cong F < E \leq I < H \leq J \leq G$ (sub-classes of this invention).

Thus the present inventors have experimentally found a fact that there exist several families of chemical compounds capable of producing strong Raman spectra of high quality when irradiated with a NIR laser. Further, it has been found that both the molecules containing highly polarizable symmetrical chromophores and macromolecules containing sequences of highly polarizable conjugated chromophores (or, in other words, having extensive systems of delocalized electron density spread along the molecular backbone or over the molecular shell), may be advantageously used as highly-efficient Raman-active molecular taggants for producing markings, tags and codes which are readily machine-identifiable by means of normal (excited far from resonance) Raman spectroscopy.

A small selection of NIR-excited Raman spectra out of the multiplicity of those obtainable in accordance with the ideas and spirit of the present invention is disclosed in FIGS. 1(A–J) and FIG. 10. Concerning the Raman spectra shown in FIGS. 1(A–J) in general, it should be noted that these have been acquired by using 1064 nm or 785 nm laser excitations, the laser light output power being in the range of 5–200 mW in different experiments. All the spectra are shown "as acquired", i.e. uncorrected for the instrumental response function and without recourse to any cosmetic operations such as baseline correction, smoothing, etc. Specialists in the art will probably appreciate the excellent quality of the spectra and factual absence of undesirable thermal and/or fluorescent backgrounds in the spectral data.

In all embodiments of the invention, the Raman-active taggants of the invention are: (1) exposed to radiation of a predetermined near infrared wavelength to produce Raman scattering spectral bands; (2) at least a portion of the Raman spectral bands are collected and processed by a Raman spectrometer to convert the same into an electrical signal; and (3) the electrical signal is processed to detect and identify, qualitatively and/or quantitatively, the taggant(s). The process as set forth above can be carried out by a Raman spectrometer selected from the group consisting of: dispersing spectrometers, multichannel spectrometers, Fourier transform spectrometers, Hadamard transform spectrometers, stationary transform spectrometers, acousto-optic tunable filter spectrometers, integrated optic acousto-optic tunable filter spectrometers, fiber optic spectrometers, fiber optic array spectrometers, microscope spectrometers, imaging spectrometers, and imaging microscope spectrometers.

Figure 12A:
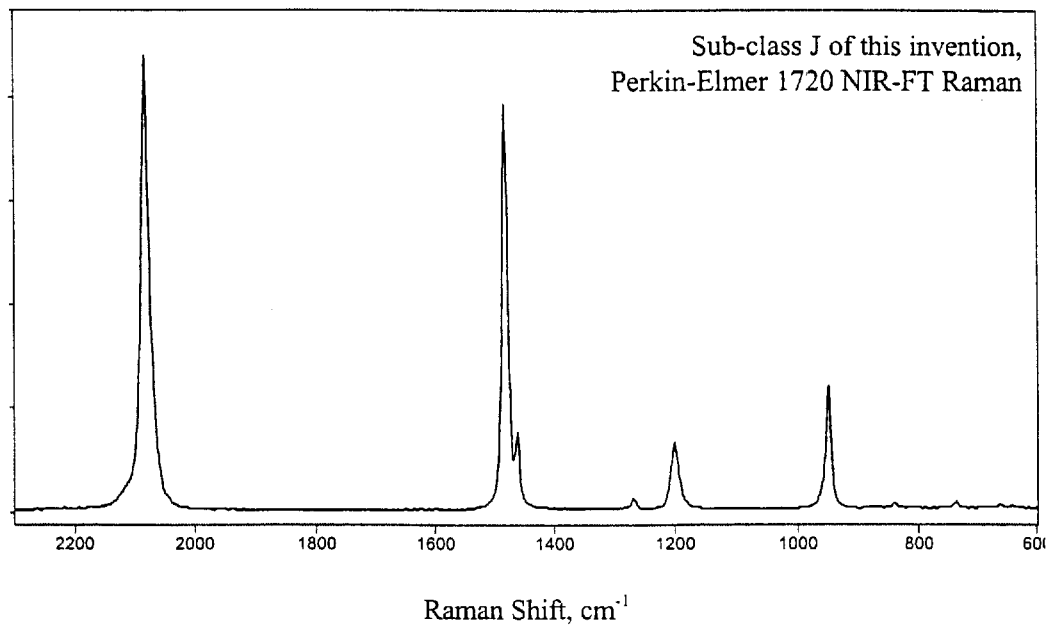
FIGS. 12($a$–$b$)—Is a comparison of NIR-excited Raman spectra of the taggants of the invention acquired with the aid of NIR-FT Raman and portable dispersive instruments.
Figure 12B:
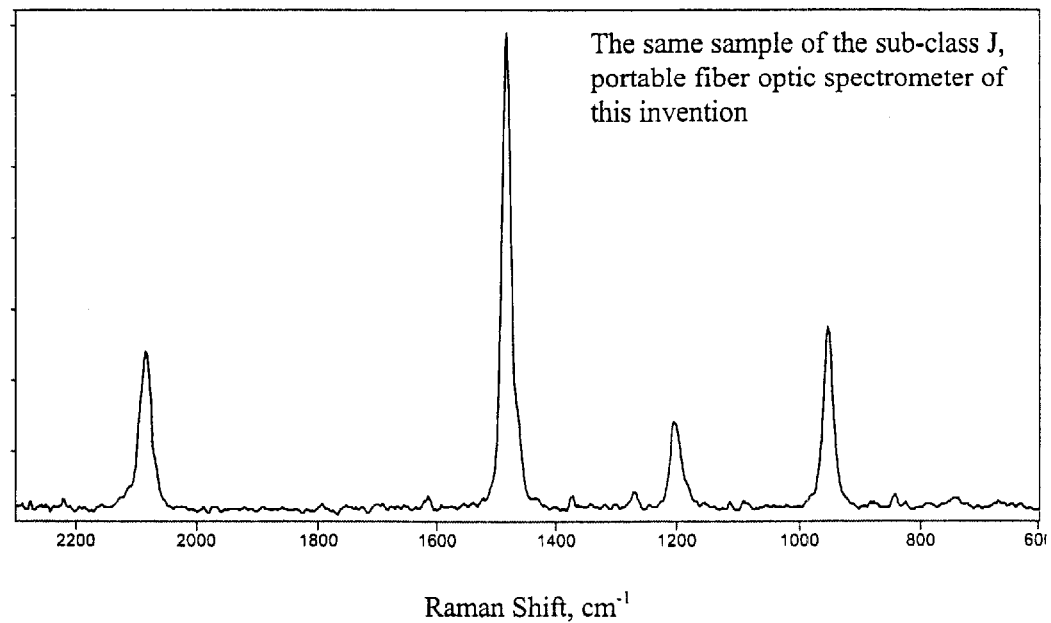

In a preferred embodiment, the process as set forth above is carried out by a miniature or portable Raman spectrometer directly "in the field". As the spectra in FIG. 12 show, the improved Raman-active taggants of the invention are amenable to detection not only by stationary research-grade NIR-FT Raman spectrometer, but, for example, by a miniature fiber optic array spectrometer also. Note that, deliberately, two marginal examples of detectability of the taggants of the invention, i.e. by one of the best in the market NIR-FT Raman instrument (top spectrum) and by the most miniature in the market dispersing one (bottom spectrum), are provided by the present inventors here. To the best knowledge of the inventors, the miniature Raman system we have built from the commercially available components of different manufacturers is, at the time, the most economical one also. The complete system (without a PC) consisting of purchased by retail prices the Ocean Optics Inc. S2000 spectrometer ($2,000), the Visionex Inc. Enviva fiber optic Raman probe ($1,200) and the World Star Tech Inc. INF-780 40 mW, single-mode AlGaAs diode laser pointer ($200) turned out to be capable of acquiring NIR-excited Raman spectra for most of the Raman-active compounds disclosed in the present invention. Turning once more to the prior art (teachings of the U.S. Pat. No. 5,935,755), it should be noted that all attempts of the present inventors to obtain a Raman spectrum of the squaraine compound (cf. FIG. 11 above) by means of the system based on the OOI spectrometer and the WST laser excitation failed. Perhaps the most discouraging was the fact that under 785-nm excitation the squaraine compound fluoresced strongly, thus preventing obtainment of any useful Raman spectrum of the squaraine. Thus, summing up the results documented in FIGS. 1–9, 11 and 12, specialists in the art will probably appreciate that, compared to the prior art, a considerable improvement has been attained by practicing the present invention—in terms of both providing highly efficient Raman-active taggants and providing portable and economical instrumentation for detection thereof in the field.

Figure 13:
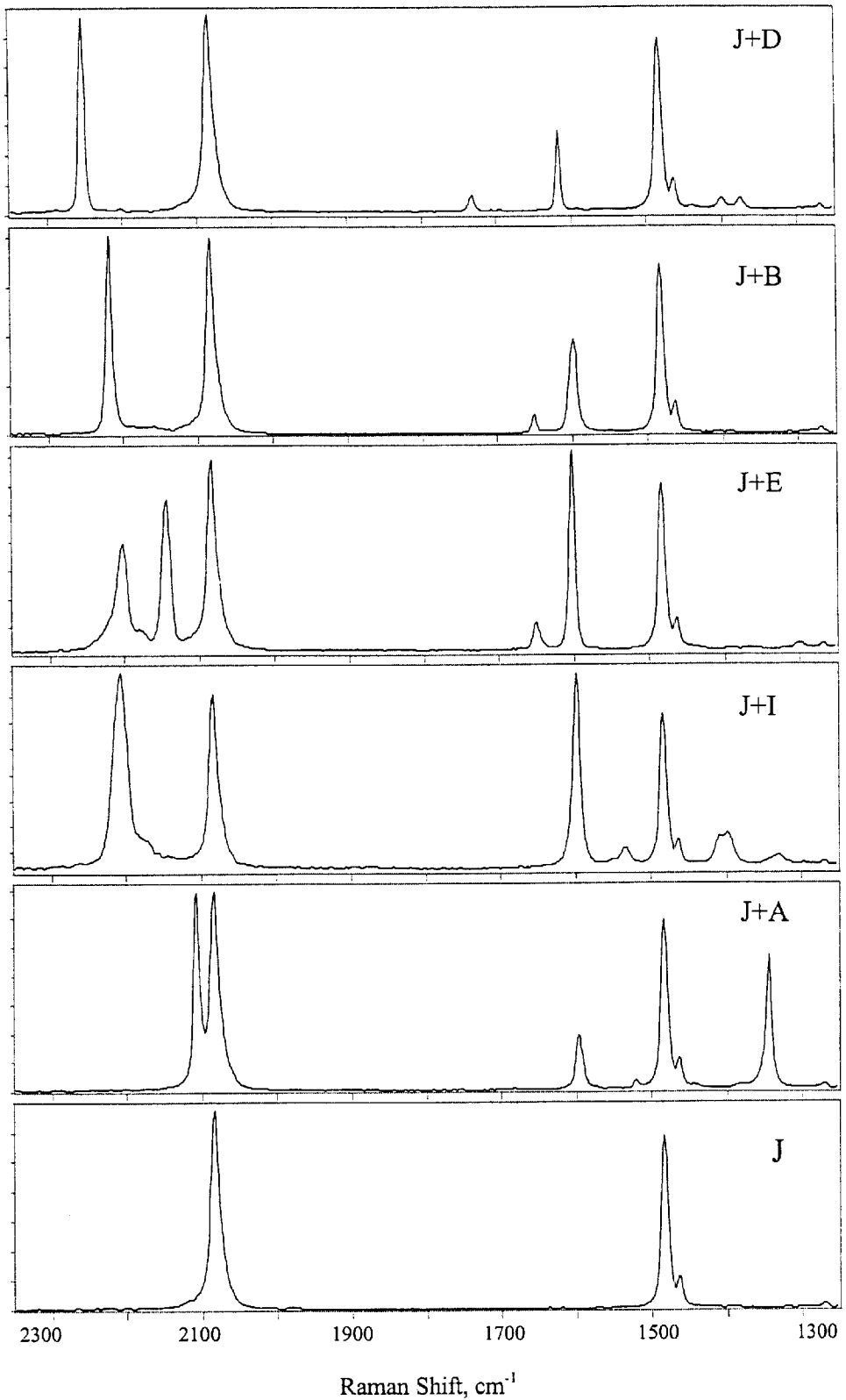
FIG. 13—Shows an exemplary selection of NIR-excited Raman spectra of six new and unique molecular labels prepared by physical pair-wise admixing of five individual taggants belonging to the sub-classes A, B, D, E and I of the invention with a sixth arbitrary chosen compound belonging to the sub-class J of the invention.

In another embodiment, mixtures containing more than one individual taggant of the invention are employed for producing improved Raman-detectable molecular codes or labels for protecting authenticity of different articles, products and documents. To illustrate practicing of this embodiment, FIG. 13 shows stacked NIR-FT Raman spectra of exemplary unique molecular tags or labels composed of materials belonging to different sub-classes of the invention. Only six traces and only 2300–1300 $cm^{-1}$ wavenumbers region are shown in this case for clarity. The letters at the upper right corner of each trace designate the sub-classes of the employed materials in accordance with the notation system adopted hereinabove. The bottom spectrum represents an individual compound of the invention belonging to the sub-class J, while the upper traces in the FIG. 13 are NIR Raman spectra of binary mixtures each comprising the same taggant J along with a second taggant taken, correspondingly, from the sub-classes A, B, D, E or I of the invention. Note that even visual comparison of these spectra permits one to state that "they all differ". In terms of the present invention it infers that a computer spectral library search program will unambiguously discriminate any particular spectrum in FIG. 13 from any one of the rest and, hence, an article protected against counterfeiting with any of such tags can be reliably authenticated. Spectra in FIG. 13 demonstrate also that, taking into account the large number of individual Raman-active taggants belonging to several sub-classes disclosed in the invention, great number of unique tags can be prepared by such approach, i.e. by simply mixing pair-wise each individual taggant with another. This approach constitutes one of the preferred embodiments of the invention. Note that it should be a difficult task for a wrongdoer to decipher or reproduce such molecular labels without knowledge of the components used in the mixtures.

Figure 14:
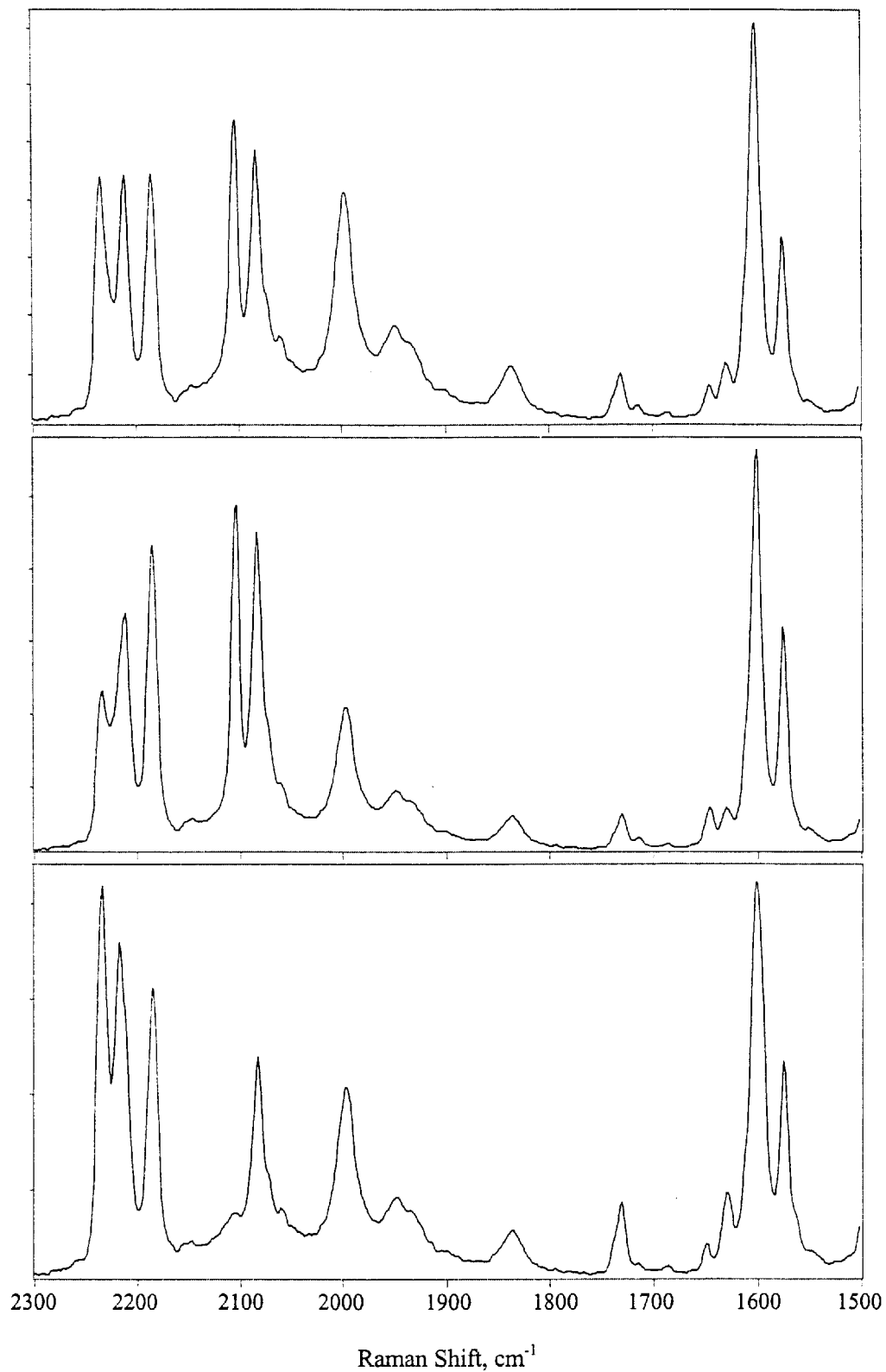
FIG. 14—Shows NIR-excited Raman spectra of exemplary molecular "super-tags" prepared by physical mixing seven different compounds of the invention altogether. Note that (i) the individual molecular constituents were deliberately chosen so that to minimize potentially possible overlapping of individual vibrational bands belonging to different individual compounds; and (ii) each of the three traces shown represents a physical mixture comprising the same seven components, but mixed in different proportions.

In yet another embodiment, the Raman-active taggants of the invention are used in the form of multicomponent mixtures comprising preferably more than two and less than ten or, most preferably, more than two and less than six individual Raman-active taggants of the invention simultaneously. Results of such approach to composing improved machine-readable security tags based on the Raman-active materials of the present invention are illustrated by the NIR-Raman spectra disclosed in FIG. 14. Each trace in this case represents a Raman spectrum obtainable for a physical mixture comprising seven (!) different judiciously chosen) individual compounds from all three classes of the Raman-detectable materials disclosed in the present invention. Note that, despite the large number of the bands present, all spectral features are still well resolved, and the "super-tag" thus produced is still readily amenable to error-proof computer search identification. At the same time, the three traces in FIG. 14, if taken altogether, should illustrate the cumulative potential of the Raman-active materials of the invention. As a matter of fact, each of the three traces shown in FIG. 14 represents a physical mixture comprising the same seven components, but mixed in different proportions. Again, since a dedicated computer search program capable of discriminating spectra in terms of both "critical peak frequencies" and "critical peaks relative intensities" can easily identify any one spectrum of the three in FIG. 14. (e.g., by the relative intensities of the peaks in this case), a large number of unique "super-tags" can be prepared from the same components by this approach. Notably, it should be actually improbable to decipher or reproduce such molecular label without knowledge at once of both the particular components and their proportions in the mixture. Thus, in accordance with this specific embodiment of the present invention, variation of the proportions of the improved Raman-active compounds in their multicomponent mixtures should impose a formidable task for a wrongdoer.

Figure 15A:
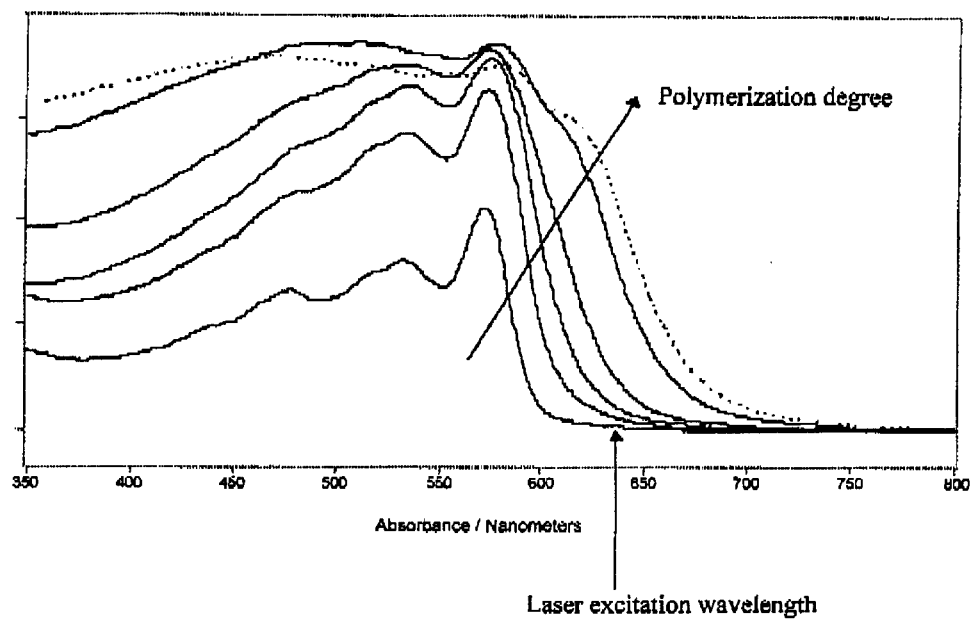
FIG. 15(a)—Shows evolution of the optical absorption spectra in the course of a diacetylene polymerization. Note both the absorption intensity increase and the batochromic shift of the absorption edge during polymerization.

In yet another embodiment, the improved Raman-active taggants of the invention are used as colored Raman-detectable pigments in paints, inks and toners suitable for security printing applications. Many of the highly polarizable and/or conjugated molecules and macromolecules of the invention are innately colored or very intensely colored materials having extremely high molar extinction coefficients. For example, FIG. 15(a) shows an evolution of optical (in the visible region) absorption spectra of a diacetylene during the solid state polymerization of the latter. The spectra were acquired with the aid of an integrating sphere by using a piece of paper impregnated with the monomer as the sample. The polymerization process was stimulated by using a short-wave UV-lamp (254 nm) irradiation. Several traces recorded at different UV doses are shown. The dashed line corresponds to a limiting (100%) polymerization degree for this particular monomer. It may be seen that, in parallel with the polymerization degree, the overall optical absorption of the material markedly increased during polymerization reaction. It is of importance that not only the intensity of the optical absorption increases as a result of polymerization, but a considerable batochromic (to longer wavelengths) shift of the absorption edge is also observed.

Figure 15B:
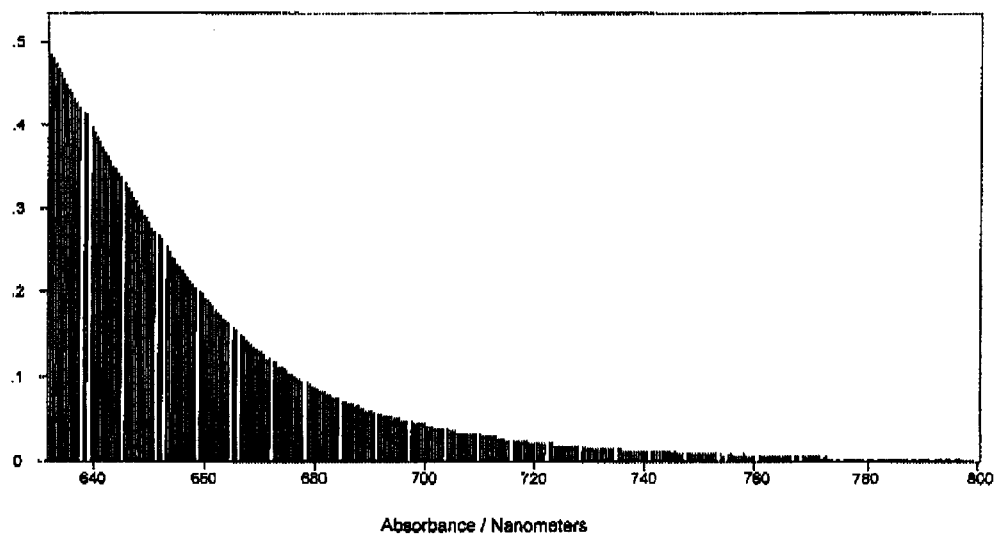
FIG. 15(b)—Is an expanded view of the absorption edge of a polydiacetylene illustrating undesirable absorption of Stokes Raman photons by the parent material when excitation with a visible laser (HeNe, 632.8 nm) is employed in accordance with teaching of the prior art.
Figure 16:
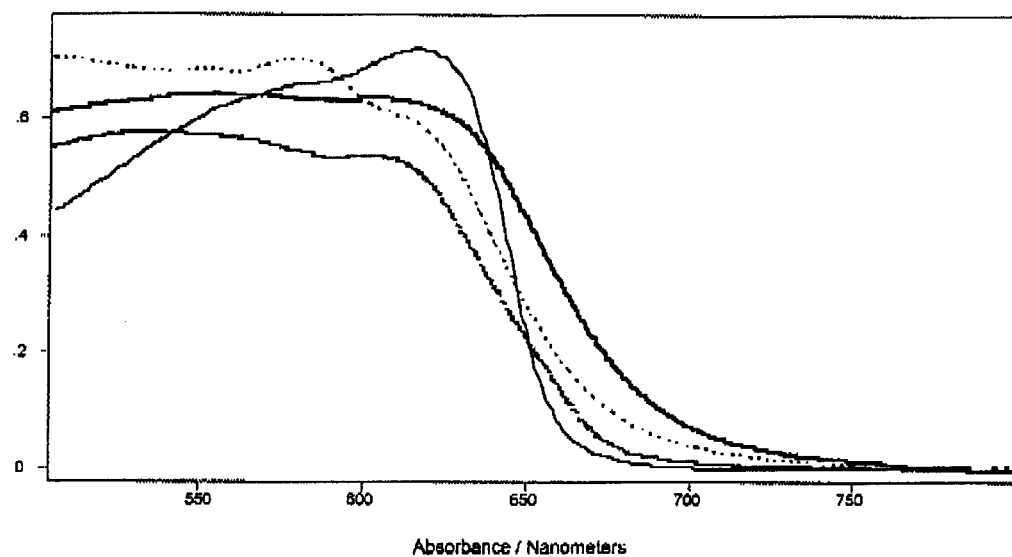
FIG. 16—Shows exemplary optical absorption spectra for different polydiacetylenes.

In fact, the fully polymerized material exhibits a measurable absorption even beyond 700 nm, but is actually transparent to any wavelengths from 750 nm to 2000 nm. Phenomenologically, excitation of electronic transitions with energies of approximately 2.0–4.0 eV by electromagnetic radiation (visible light) results in strong absorption bands in the visible region of the spectrum and, hence, is responsible for the colored appearance of conjugated polymers. It is well known that the energy of the excitations and, hence, the color of conjugated polymers is dependent on a number of factors. Among these, the length of the conjugated chain of the polymer, the polymer backbone conformation and the environment in which it is located are the most general. Irrelevantly to these factors and to the type of conjugated polymer, however, of prime practical importance in terms of the present invention is the following: When, in order to induce the RRS phenomenon, a laser excitation wavelength falling in the region of intense optical absorption of the material is employed (for example, 632.8 nm of a HeNe laser—a very popular excitation source in the prior art), then the Raman photons unavoidably have to travel to the spectrometer detector through a layer of intensely absorbing material. Note that only the so called Stokes Raman photons are of value in analytical experiments. However, almost all Stokes Raman photons in the above case would have frequencies within a spectral region of from 632.8 nm to ca. 750 nm. In the absolute scale, the wavelength region of 632.8–750 nm corresponds to 15,800–13,300 $cm^{-1}$ region of wave numbers, or to 2500 $cm^{-1}$ of Stokes Raman shifts in total. Such interval of Raman shifts comprises almost all most informative vibrational bands in Raman spectra (see, for example, the spectra in FIGS. 1A–J). In other words, when visible lasers are employed to excite Raman scattering in conjugated polymers, the polymer itself can act as a filter intercepting some part of the valuable Stokes Raman photons on their way to the instrument detector. For example, FIG. 15(b) which is an enlarged view of the absorption edge of the polydiacetylene presented by the dashed line in FIG. 15(a) can be looked on as a working characteristic of such an "anti-Raman filter". The blackened area under the curve depicts variation of the optical density of such a filter vs. wavelength for Stokes Raman photons which would be generated by a HeNe laser emitting at 632.8 nm. Thus, although preferred in the prior art use of laser excitations falling in the region of strong absorption of the sample provides chances to induce a resonance enhancement of the Raman process, leading to generation of more Raman photons, it is accompanied by inevitable loss of unpredictable quantities of those same Raman photons of interest. The situation depicted by the FIG. 15, in principle, is typical for many conjugated polymers such as polyacetylene and polyenes, polydiacetylenes, polymes, polysilanes, poly(ethynylene)arylenes and even fullerenes and tubulenes disclosed herein as Raman-active taggants. Further, FIG. 16 shows optical absorption spectra for several other polydiacetylenes along with the spectrum depicted earlier in FIG. 15 (dashed line in both cases). It is seen that the adverse situation with loss of valuable Raman photons may be slightly better (the lowest curve) or even considerably worse (both the full thin line with very steep absorption edge and the thick full line depicting even higher batochromic shift of the absorption edge). In any case, the situation becomes much worse when shorter excitation wavelengths, e.g. of lasers emitting at 547 nm, 532 nm, 514 nm, 488 nm, etc., are used. At the same time, considerable improvement can be gained by virtue of using far-red and near-infrared lasers emitting at wavelengths of, e.g., 750 nm, 782 nm, 980 nm, 1064 nm, etc. Therefore, the present invention, being actually based on employment of NIR lasers instead of preferred in the prior art visible ones, provides a considerable improvement compared to the prior art teachings concerning Raman detection of conjugated polymers.

In order to better communicate the principles, novelty and advantages of the present invention in comparison with the achievements of the prior art, it would be useful to highlight here the following. Indeed, until recently the traditional RRS, permitting to obtain a prominent (ca. $10^4$–$10^6$ times) enhancement of the Raman signal of some chromophores present in a sample in small concentration, considered to be an advantageous technique for analysis of conjugated polymers in the solid state also. It should be noted that, in lines with such tradition, the use of polydiacetylenes as components of an ink for printing security documents which can be identified by Resonance Raman Spectroscopy (RRS) has been suggested in the prior art (cf. BACKGROUND OF THE INVENTION Section, comments concerning the U.S. Pat. No. 5,324,567). As it follows from the teachings of the U.S. Pat. No. 5,324,567, the authors deliberately rely upon RRS which occurs when the wavelength of the incident laser beam is equal to, i.e. in resonance with, that of an optical absorption band in the material. They further rely on the circumstance that, under resonance conditions, the Raman scattered light should be greatly enhanced in intensity. Accordingly, in their examples they used only a HeNe laser (632.8 nm), deliberately chosen so that the laser wavelength would fall within the optical absorption maximum of the material. Further, they exposed their samples to laser light with an incident intensity of 1.5 to 3.2 mW and then measured with a photomultiplier a RRS intensity above the background fluorescence. Not providing factual Raman spectra of inks obtainable in accordance with their invention, Bratcheley et al. suggested to use only the five most prominent resonantly enhanced lines typical for RRS spectra of polydiacetylenes: one line at about 2100 $cm^{-1}$, two near 1500 $cm^{-1}$ and two between 1300 and 900 $cm^{-1}$ Raman shifts. In the Examples section, however, the following comments can be found: "Signal strength was measured at the point of maximum response. Non-Raman background scattering including fluorescence was subtracted from the total signal, to give that solely due to Raman . . . ", evidencing that even with polydiacetylenes (which are the most fluorescence-silent among all known conjugated polymers) RRS detection can be plagued by fluorescence.

Not questioning the very feasibility of acquiring Raman spectra of polydiacetylenes by RRS in principle and fully acknowledging the achievements of the prior art inventors, we would like to emphasize here the following. Perhaps the most important aspect of the present invention is the discovery that, being based on use of laser excitations falling in clear resonance with electronic or excitonic transitions inherent for the conjugated π-electron systems, the traditional approach has serious drawbacks and limitations. And especially so in terms of full realization of aims and function of the present invention. More specifically, it is of prime importance in terms of the present invention that RRS, in principle, can hardly be rated as a truly quantitative spectroscopic tool. The main reasons for this are: (i) the resonance Raman spectra are often contaminated or distorted by large thermal or fluorescent backgrounds caused by absorption of the laser frequency, the latter additionally being the cause for severe sample heating and/or degradation; (ii) intensity of the RR scattered light is not governed by the fundamental $v^4$ law and is hardly predictable; (iii) shapes and intensities of the bands constituting the resonantly enhanced Raman spectra vary with the excitation wavelength used; (iv) when short-wave visible excitation is used, the generated Raman photons often have frequencies falling in spectral region of strong optical opacity of the sample, and hence reabsorption of the Raman photons by the sample unavoidably, and in unpredictable manner, distorts the true intensity of the Raman bands; (v) because the resonance-enhanced Raman spectrum does not look like the unenhanced one, the analytical value of the technique in case of quantitative or even semi-quantitative measurements on solids can be suspect. These and other drawbacks of the RRS approach will be discussed in more details below by means of comparison with merits of the NIR-excited Raman approach preferred by the present inventors when dealing with conjugated polymers detection.

Accordingly, in order to even better explain the principles, novelty and advantages of the present invention compared to the achievements of the prior art, it seems useful to highlight here additionally the following. In principle, Raman scattering process is rather ineffective one. It means that every $10^6$–$10^8$ of laser photons pumped into the sample give only 1 (one) inelastically scattered Raman photon! When using visible laser excitation, indeed, the so called Raman cross-section of a conjugated polymer can be increased due to involvement of true electronic transitions into the inelastic scattering process, and the yield of Raman photons can be considerably enhanced (up to $10^2$–$10^4$ times ideally). However, even in best instance, the overall yield of Raman photons can reach only a fraction of a percent from the total amount of optical energy incident on the sample. What is the fate of the remaining 99.9+% of laser photons (or of the same part of energy of the laser beam) directed to the sample? In principle, these photons could reflect from the material, come through the material or could elastically scatter by the molecules not leaving much of their energy to the sample. For RRS, however, the wavelength of a visible laser is deliberately chosen so as to coincide with the optical absorption band of the sample. In this instance the laser light can not simply come through and leave the sample, rather it has to be absorbed. Not entering into scientific debates concerning possible paths for relaxation of the energy absorbed by a conjugated polymer in such case, note that the "useless" absorbed photons will be reprocessed by the sample mainly into heat. Therefore, in order to avoid excessive heating of a colored material when it is analyzed by RRS, one have to use only laser beams with very limited optical energy outputs. Typically, organic conjugated polymers and other intensely colored organic materials more or less safely tolerate only fractions of a mW or a few mW of incident visible laser beam energy at best. Thus, the one who intends to obtain a Raman spectrum of a conjugated polymer by virtue of RRS finds himself in triply disadvantageous situation. Firstly, a considerable fraction of Raman photons unavoidably is lost due to their reabsorption by the sample itself (cf. FIGS. 15–16). Secondly, a hypothetical possibility to pump more laser power into the sample, in order to generate more Raman photons, is not affordable in this case since there is always the risk to burn or otherwise destroy the sample. And, thirdly, reasonable desire not to subject the sample to the risk for a long time too often means lowering the number of accumulated scans and, hence, a poorer SNR of the resulting spectrum. In terms of the present invention, however, the utmost importance has the fact that, in any event, during acquisition of a RRS spectrum of a conjugated polymer the laser inevitably heats the sample. The higher the incident laser beam energy or the longer action of a laser beam on the sample, the more "hot" the sample becomes. Those familiar with the art will recognize that, under RRS conditions, undesirable heating of the sample for several tens degrees of centigrade is not rare. The worst thing is that, when dealing with conjugated polymers or other intensely colored materials by RRS, the laser heating persistently changes the molecular structure of a sample during analysis. Obviously, such mode of identification can not give precise results, since one has to analyze actually a sequence of several different samples (or a series of samples with differing molecular structure) during a single analysis! That is why RRS of conjugated polymers is able to provide only approximate, averaged and frequently inadequate spectral information about the object under investigation.

The normal Raman scattering, on the other hand, being based on use of near-infrared lasers, exhibits several important advantages compared to RRS when dealing with conjugated polymers in the solid state. Among these advantages are, for example, the following: (i) NIR-excited Raman spectroscopy has the advantage of excitation in a spectral region that, for most intensely colored materials and/or conjugated polymers, is actually transparent and is much less susceptible to fluorescence interferences; (ii) of essential importance for quantitative interpretation of NIR-excited Raman spectra is also the circumstance that relative intensities of Raman signals from vibrations of different species excited far away from resonance should be proportional to concentrations of those species in the sample; (iii) the NIR excitation falling into the region of optical transparency of conjugated polymers does not produce significant heating even for deeply colored materials; and (iv) the method gets a real possibility to acquire Raman spectra of thermally sensitive conjugated polymers without undesirable changing their molecular and/or submolecular structure by the laser heating during the spectrum acquisition, and, thus, with quantitative precision.

Figure 17:
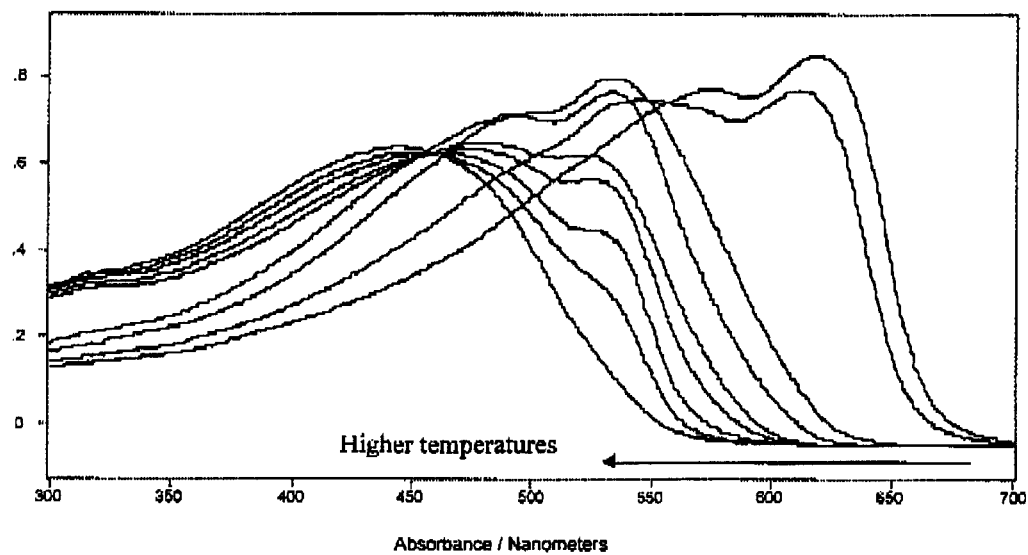
FIG. 17—Illustrates the thermochromic transitions for a polydiacetylene as measured with the aid of optical absorption spectroscopy in the visible range.

Accordingly, in one of its preferred embodiments, the present invention provides use of the so called thermochromic conjugated polymers as improved Raman-active taggants for producing covert molecular codes, tags and labels for protecting authenticity of different articles, products and documents. As has been noted above, excitation of electronic transitions by visible light in the visible region of the spectrum is responsible for the colored appearance of conjugated polymers. The energy of the excitations and, hence, the color of conjugated polymers is dependent on such factors as the length of the conjugation chain, the polymer backbone conformation and the environment in which it is located. In real life the latter factor is rarely a strictly defined constant, rather it is a source of multiple perturbations for the conjugated backbone. In fact, the absorption spectrum of some conjugated polymers is so sensitive to the above factors and to effects of additional perturbations like temperature, mechanical strains, mechanical stress, solvents, electric fields, etc., that small changes of these may lead to chromism, a perceivable change in color of the polymer. Thus, conjugated polymers are known to exhibit the so called thermochromism, piezochromism, solvatochromism, electrochromism and pH-chromism phenomena. In very general terms the changes in color may be interpreted as arising primarily from changes in the structure of the polymer. Most often, the conjugated polymers exhibit an ability to experience thermally induced phase/structural transformations which are accompanied by visual color changes. In terms of electron spectroscopy in the visible range such thermochromism or thermochromic transitions in conjugated polymers can be illustrated, for example, by the spectra in FIG. 17. In this case, a series of exemplary optical absorption spectra for a thermochromic polydiacetylene (PDA) recorded at different temperatures is shown. The rightmost curve represents the optical absorption spectrum of the PDA at room temperature, while the leftmost one is for the same material at ca. 130° C. Those familiar with the art will recognize that such evolution of the spectra should reflect visually perceptible color changes of the material. Indeed, the material is visually navy-blue at room temperature, and the two spectra on FIG. 17 with the absorption maxima around 620 nm correspond to that state of the material. Under slow heating, the sample of this material rather abruptly is transformed into the red-colored one, and this new state is represented by the spectra having the absorption maxima around 540 nm. Heating of the material to higher temperatures leads to gradual disappearance of this absorption maximum and, instead, a broad new one centered somewhere around 450 nm appears. Visually, this latter part of the overall process looks like gradual change of color of the material from red to red-orange, then to bright orange, then to yellow-orange and, finally, to lemon-yellow. In terms of physics or materials science, however, the spectra in FIG. 17 are treated as a manifestation of thermally induced molecular structure transformations of the conjugated backbone of a PDA macromolecule. [Actually, these spectra could be treated also as an evidence for "machine-readability" of thermochromism in conjugated polymers by means of electron absorption spectroscopy.] It should be noted here that, in a number of aspects, the present invention is based on the discovery that NIR-excited Raman spectroscopy is much more precise and convenient tool for detailed analysis of conjugated polymers and structural transformations thereof compared to the RRS. See, for example, papers: "DRAFT and NIR-FT Raman—new handy tools in conjugated polymer studies."—*Proc. 1st Korea-China-Russia Symp. Synt. Metals, Jul.* 20–24, 1994, Seoul, Korea, by A. Shchegolikhin et al.; "Is NIR-FT Raman a quantitative tool for polydiacetylenes studies?"—*Synth. Met.* 85 (1997) No. 1–3, 991–992, by O. L. Lazareva et al.; "A NIR-FT Raman image of solid-state polymerization of PTS diacetylene."—*Spectrochim. Acta Part A,* 1997, 53, No.1, 67–79, by A. Shchegolikhin et al.; "Raman study of structural transitions in polyacetylene (PA) and polydiacetylenes (PDA)."—*ICSM-98 Book of Abstr.,* Jul. 12–18, 1998, Montpellier, France, WEP129, p. 159, by A. Shchegolikhin et al., the disclosures of which are incorporated herein by reference. In practical terms it infers that NIR-excited Raman spectroscopy turned out to be capable of "seeing" even minute changes in the backbone structure of conjugated polymers under different external perturbations. This finding has been advantageously exploited by the present inventors and resulted in the disclosed herein methodology permitting quantitative detection and identification of many thermochromic Raman-active taggants at different working temperatures and usage thereof for producing extremely covert molecular tags, codes and labels.

Figure 18:
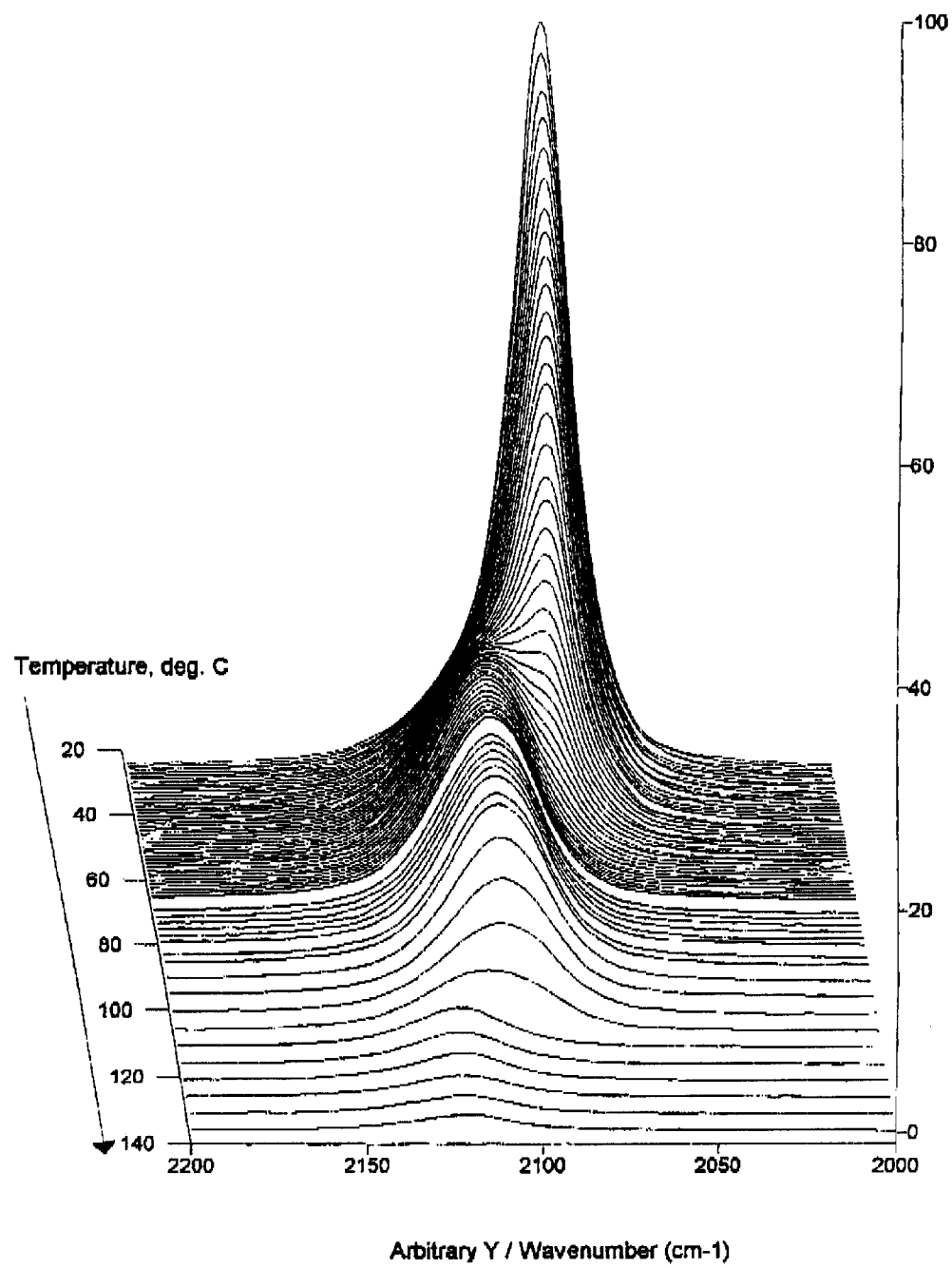
FIG. 18–Is a 3D-image of evolution of a single Raman band parameters vs. temperature during the thermochromic transition of a polydiacetylene. Note the precision in measuring of both the frequencies and the intensities of the Raman signal that becomes possible owing to employment of the near infrared laser excitation.
Figure 19:
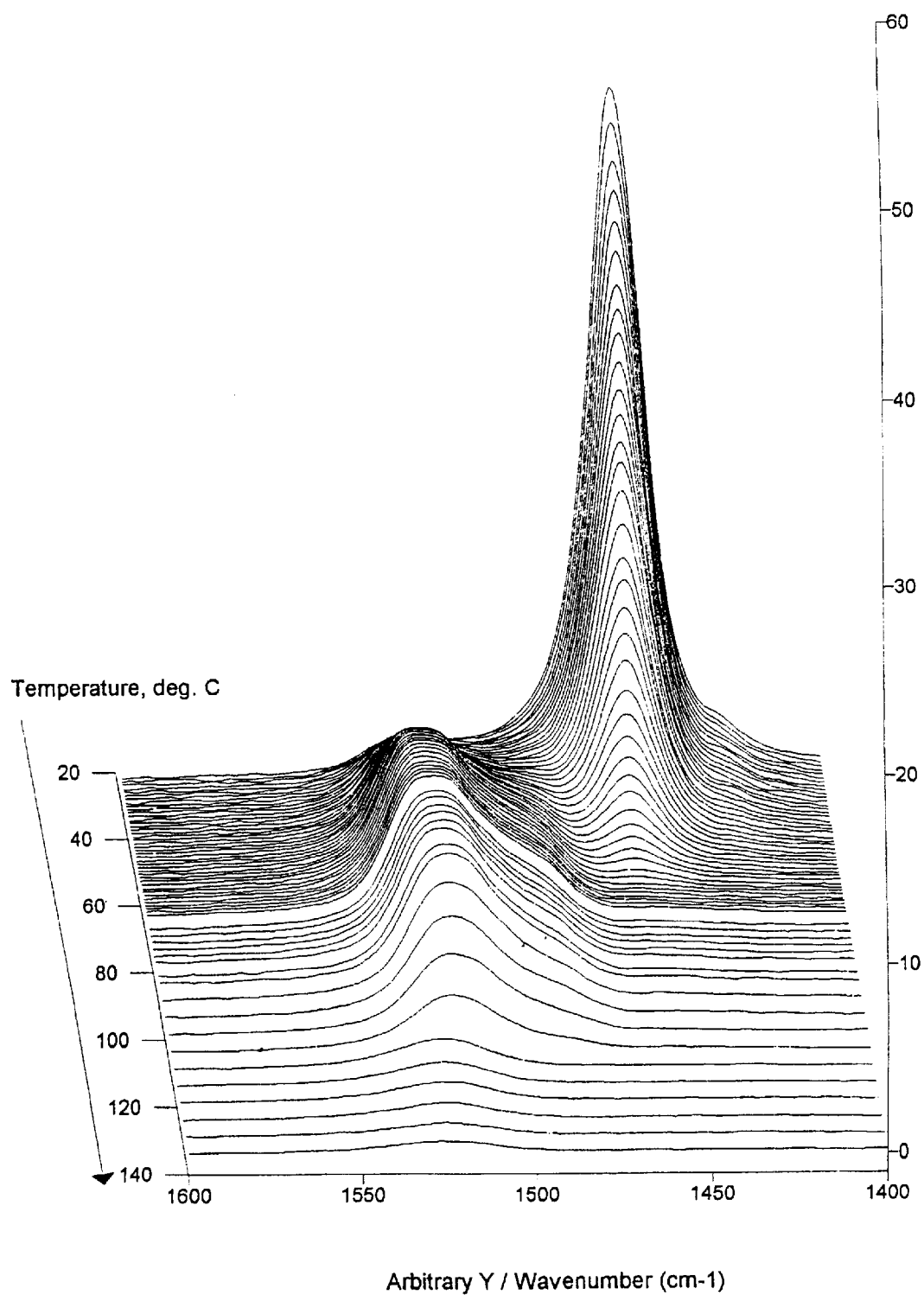
FIG. 19—Is a 3D-image of evolution of another characteristic Raman band during the thermochromic transitions of a polydiacetylene. Note the co-existence of structurally different phases within the same material at 30–60° C.
Figure 20:
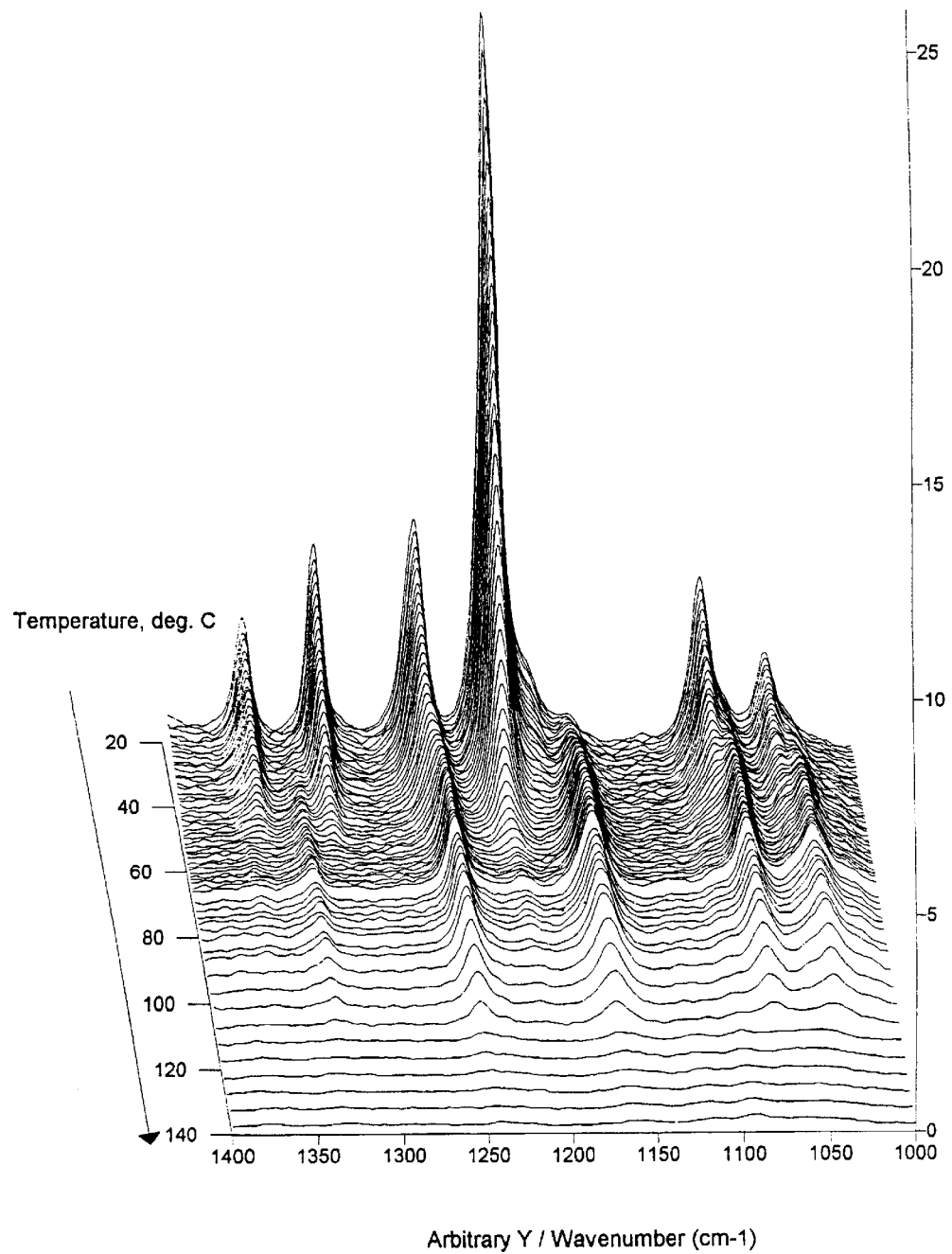
FIG. 20—Is a 3D-image of the thermochromic transition phenomenon for a polydiacetylene in a wider spectral region acquired in accordance with teaching of the invention by means of NIR-excited Raman spectroscopy. Note the overall quality of the spectra.

Additional important objects and advantages of the present invention can be better understood by those skilled in the art by reference to the accompanying figures, of which FIGS. 18, 19 and 20 each is a two dimensional projection, sometimes called a hidden line view, of a three dimensional surface which conveys the NIR-excited Raman response of the intensely colored conjugated polymer described above with reference to electron absorption spectra of FIG. 17. In FIGS. 18, 19, and 20 the oblique axis shows the temperature of the sample, ranging from 25° C. to 140° C., utilized to accomplish thermally induced structural transformations concomitant with the visually perceptible thermochromic changes for the sample of the conjugated polymer. The horizontal axis represents the Raman shift values measured in wave numbers. The vertical axis depicts the intensity of the observed Raman signals drawn to an arbitrary scale. In particular, as it may be seen with more clarity in FIGS. 18 and 19, all characteristics of the Raman spectral band, viz. the intensity, the frequency and the shape, rather dramatically vary with temperature during the thermochromic transitions. Note that the overall set of spectra in FIG. 18 is in fact a Raman imaging of only one individual and specific vibrational band from the whole (and rather rich) spectrum. This band is assigned to the so called stretching vibration of the —C≡C— molecular fragment, an inherent building block of the macromolecule backbone in polydiacetylenes (PDA) [cf. general formulae XI and XII above]. Physically, the 3D image in FIG. 18 illustrates the evolution of this particular molecular vibration under raising temperature conditions. It is obvious that, as the temperature of the material becomes higher, this highly Raman-active vibration (with a characteristic frequency around 2084 $cm^{-1}$) becomes progressively weaker. At temperatures close to 50° C. the molecular fragments of this same type (—C≡C—) vibrate already at different frequencies ranging from 2084 $cm^{-1}$ to 2110 $cm^{-1}$. At higher temperatures, almost all —C≡C— fragments vibrate with this new frequency of ca 2110 $cm^{-1}$, and the Raman-activity of these vibrations becomes progressively lower. Finally, at temperatures around 100° C., a new change in the vibration frequency is observed, this time up to 2120 $cm^{-1}$. At this point, however, the vibration is almost Raman-inactive, and more so at the higher temperatures. It is of importance that during this experiment the macromolecular PDA chains were not changed at all in terms of their chemical composition. They still have the same molecular mass and still consist of alternating —C≡C—, —C=C— and —C—C— building blocks. But, in terms of physics, these macromolecular chains have changed dramatically. This is because their electronic structure has been changed enormously and, hence, the Raman-active molecular vibrations also. Further, the 3D Raman image in FIG. 19 must more clearly illustrate that, when subjected to heating from room temperature to 140° C., the PDAs live rather complex vibrational life. Particularly, this figure evidences that, in a temperature interval, there may concomitantly exist two types of vibrationally quite specific chromophores (cf. the band with maximum at ca. 1520 $cm^{-1}$ and that with maximum close to 1450 $cm^{-1}$ in the temperature range from 30° C. up to 60° C.) which are not distinguishable chemically! In fact, both bands belong to a stretching vibration of >C=C< moiety, another building block of the PDA conjugated backbone. FIG. 20 illustrates that, in principle, a NIR-excited Raman spectrum of a thermochromic conjugated polymer, acquired in accordance with preferred embodiments of the present invention, contains a huge amount of spectral information which can be used to advantage for achieving aims of the invention. In particular, FIG. 20 shows that not only stretching vibrations of the —C≡C— and —C=C— chromophores belonging to the PDA backbone (FIGS. 18 and 19, correspondingly), but deformational vibrations of the same chromophores, e.g. those at around 1200 $cm^{-1}$ (δ>C=C<) and the two weaker bands in the vicinity of 1330–1360 $cm^{-1}$ (which may be tentatively assigned to deformational vibrations of the first methylene fragments coupled to the backbone —C=C— chromophore) are of clear analytical value. Although, in principle, almost any vibrational band present in these spectra could be assigned to particular molecular vibrations, this task is beyond the aims and scope of the present invention. And the partial analysis undertaken above with recourse to FIGS. 18–20 was solely aimed to demonstrate that NIR-excited Raman spectra of conjugated polymers obtained in accordance with the present invention are able to provide a plenty of valuable digital information that can be advantageously used for providing very high degree of security owing to employment of the NIR Raman-active compounds of the invention as efficient machine-readable taggants.

Not entering further into detailed scientific explanation of all meanings of every particular change observable in thus obtainable vibrational pictures of thermochromic and non-thermochromic conjugated polymers and other improved Raman-active compounds of the invention, it seems reasonable to emphasize here that: (i) NIR-excited Raman detection in accordance with preferred embodiments of the present invention is highly sensitive to minute structural changes experienced by conjugated polymers under external effects; (ii) NIR-excited Raman spectra of conjugated polymers acquired in accordance with preferred embodiments of the present invention provide a huge amount of spectral information relevant not only to the polymer backbone structure but to contributions of the side chain molecular fragments also; (iii) NIR-excited Raman spectra of conjugated polymers and other Raman-active materials of the invention acquired in accordance with preferred embodiments of the present invention exhibit an excellent SNR and are devoid of adverse contributions from fluorescence and thermal backgrounds; (iv) since NIR-excited Raman spectra of the Raman-active taggants of the invention are intrinsically consist of a few well resolved spectral lines, they can be used to produce unprecedently complex and covert molecular fingerprints and codes, yet readily amenable to error-free recognition by a dedicated machine.

Figure 21:
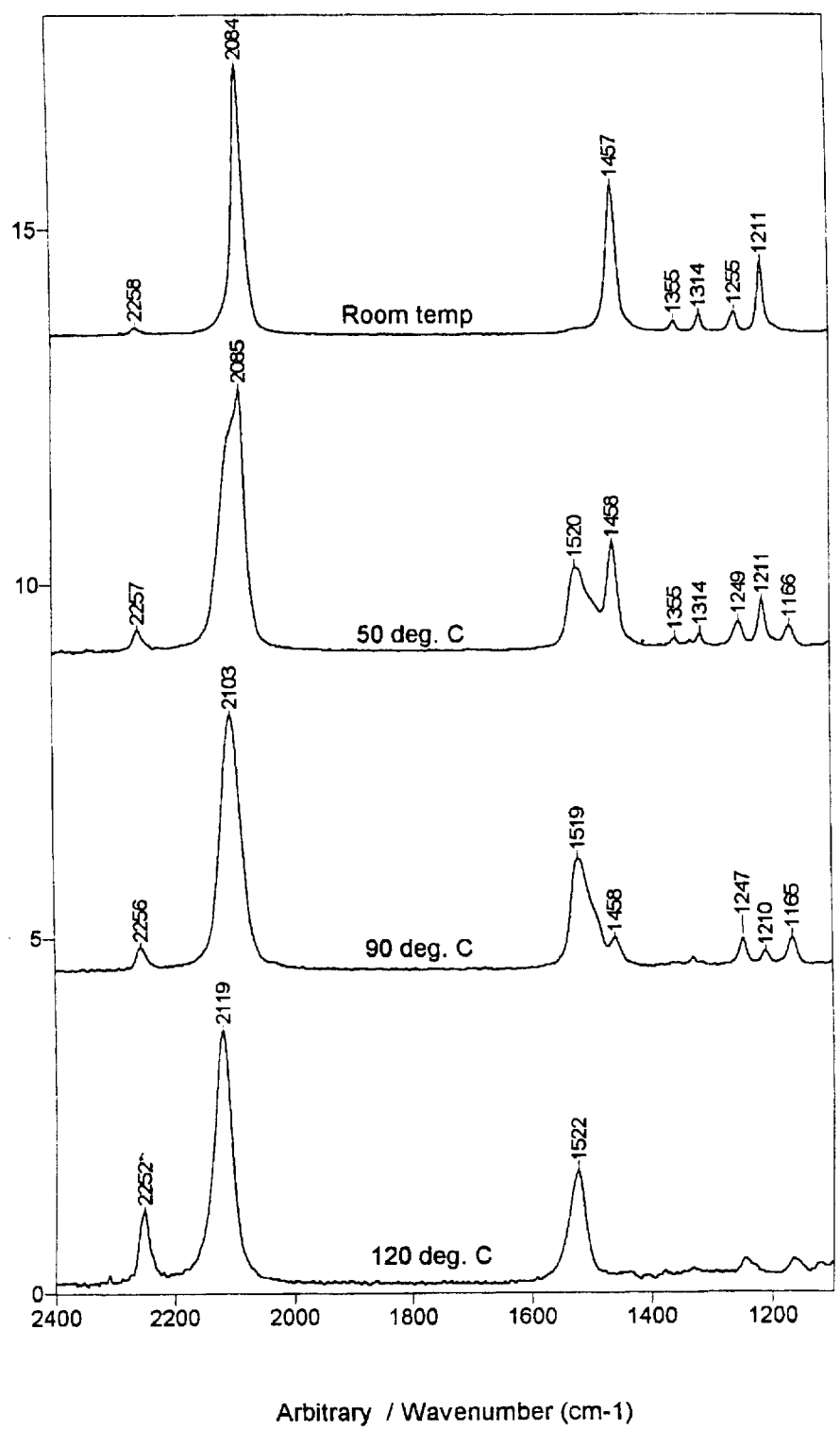
FIG. 21—Shows a series of NIR-excited Raman spectra for a thermochromic polydiacetylene obtainable in accordance with the present invention at different specified temperatures.

Yet in another embodiment, the thermochromic Raman-active taggants of the invention are employed for producing highly covert molecular codes, tags and labels which are identified by NIR Raman spectroscopy at specific predetermined temperatures selectable within a temperature interval ranging from ca. −200° C. up to ca. 200° C. The mode of practicing this embodiment can be best illustrated by way of referencing to FIG. 21. The individual NIR-excited Raman spectra, shown for clarity purposes stacked in FIG. 21, have been taken from the overall 3-D sets which were thoroughly analyzed above (cf. FIGS. 18–20). It should be remembered here that, because of absorption of the visible laser beam energy by a colored sample during RRS measurements, the sample is constantly reprocessing the "useless" absorbed photons into heat. The current temperature of the solid sample during such experiment will be dependent upon several hard to quantify factors, such as molar extinction coefficient at the laser wavelength used, physical state of the sample, its density, thickness of the layer, heat conductivity of the sample or heat conductivity and other physical and optical characteristics of a diluent matrix (if the latter is present), etc. Even heat conductivity of a substrate upon which the sample is applied can play a determining role. Thus, those familiar with the art will probably agree that it is virtually impossible to predict the actual temperature of an intensely colored sample at different moments of time in the course of the RRS spectrum acquisition procedure (provided expensive or cumbersome special measures are not undertaken to stabilize the temperature of the sample). Hence, hypothetically, if somebody will try to acquire a Raman spectrum of a thermochromic material at room temperature by means of RRS (e.g. the spectrum of the material depicted above by FIGS. 18–20), generally speaking, any one spectrum from the four depicted in FIG. 21 can be obtained. However, due to the reasons indicated above, there are infinitesimal chances to obtain by RRS the spectrum shown at the very top in FIG. 21. Rather, the spectrum corresponding to that relevant for 50° C. or 90° C. would be obtained. (Though the chances to obtain a spectrum similar to that at the very bottom might be high also—especially as a result of careless choice of the laser power or due to desire to obtain a better SNR by virtue of more scans.) It is obvious, however, that only one spectrum of the four depicted in FIG. 21 does truly represents this particular material at a specified temperature, at room temperature in this example. The other three spectra, being characteristic for specific temperatures 50° C., 90° C. and 120° C. (as well as many other spectra relevant to other intermediate temperatures from, e.g. 30° C. up to 140° C.), in fact belong to the materials which, strictly speaking, drastically differ in terms of their electronic structure from that unique and the standard thermochromic material which exists only at 25° C. Obviously, the NIR Raman spectroscopy in accordance with preferred embodiments of the present invention permits reliable identification of the thermochromic Raman-active taggants of the invention at many specified discrete temperatures. Therefore, the NIR-excited Raman spectra of the thermochromic taggants of the invention recorded at different specified beforehand temperatures, being coupled with simple visual inspection of the color of the thermochromic tag of the invention, constitute a novel and highly useful security feature in the art.

Figure 22A:
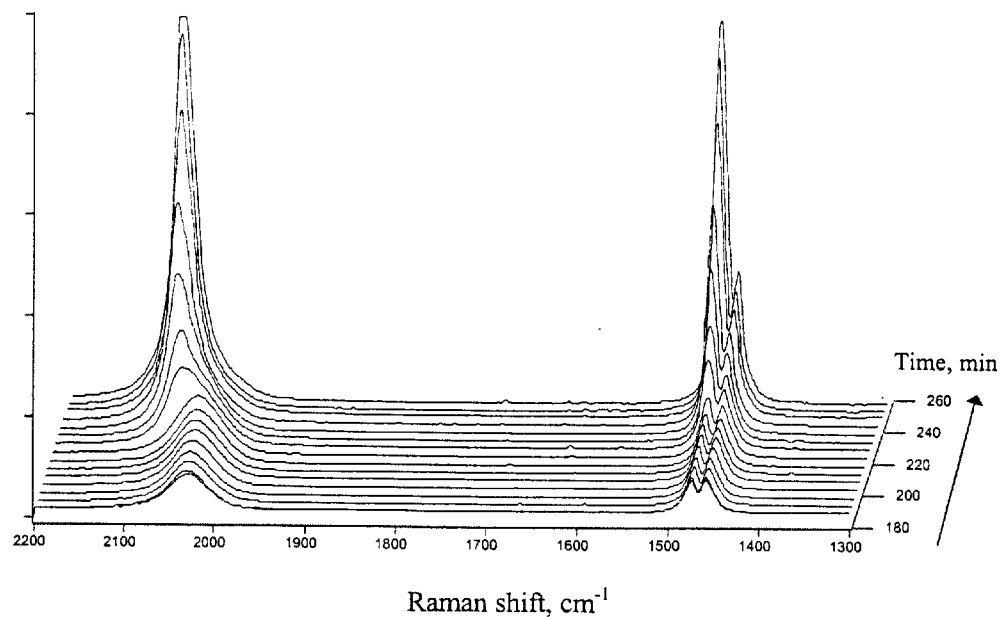
FIGS. 22(a–b)—Shows a 3D-image of evolution of the NIR-excited Raman spectra in the course of a diacetylene polymerization. Note the spectacular changes in the Raman bands parameters during the polymerization.
Figure 22B:
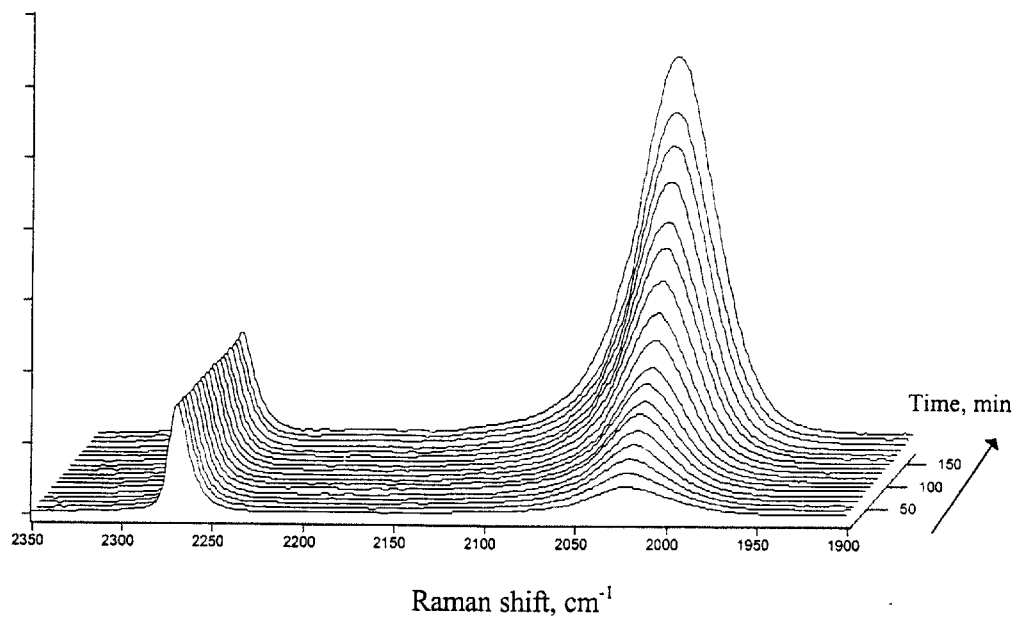

In yet another embodiment, the Raman-active taggants of the invention are employed for producing novel the so called "polymerization-depth-sensitive" or "having time dependent characteristics" molecular codes, tags and labels identifiable by NIR-excited Raman spectroscopy in accordance with the present invention. As NIR Raman spectra in FIG. 22 show, all characteristics of the Raman spectral bands of a conjugated polymer, viz. the intensity, the frequency and the shape, dramatically vary during polymerization. FIGS. 22(*a*) and 22(*b*) each is a two dimensional projection, sometimes called a hidden line view, of a three dimensional surface which conveys the NIR-excited Raman response of a conjugated polymer [poly-2,4-Hexadiyne-1,6-diol bis-p-toluene sulfonate, sub-class J of the invention in this case] during the process of its formation from the corresponding monomer. In FIG. 22 the oblique axis shows the time elapsed from the start of the solid-state polymerization reaction in minutes. The horizontal axis represents the Raman shift values measured in wave numbers. The vertical axis depicts the intensity of the observed Raman signals drawn to an arbitrary scale. The main factors influencing the NIR-Raman spectrum in such systems are the conjugation length, conformation of the backbone of the macromolecule and the concentration of the polymer in the parent, initially essentially monomeric matrix. The latter factor is directly related to the degree of conversion of the monomer into the corresponding polymer (or to the "depth" of the polymerization reaction). The present invention advantageously exploits the fact that, at different specified moments of time during the polymerization reaction, the polymerizing system has different Raman fingerprints. In terms of practicing the invention it infers that, based on one and the same taggant, many different molecular codes and labels can be produced. It should be noted that different specified depths of polymerization in such systems may be attained by thermal annealing or by photo-irradiation of the monomer during specified time intervals. Alternatively, for other Raman-active taggants of the invention such as polyenes and polyacetylenes (sub-class H), polysilanes (sub-class F), polymes (sub-class E) and poly(phenylene)ethynylenes (sub-class I), similar modification of the Raman fingerprints may be accomplished by purely chemical means, that is by means of controlled and systematical elongation of the conjugated backbone chain for one more unit. Thus, the specialists in the art will probably appreciate that the NIR-excited Raman spectra of conjugated polymers recorded at different specified depths of the polymerization reaction or at different specified lengths of the conjugated chains, constitute a novel, extremely covert and highly useful security feature in the art.

Figure 23:
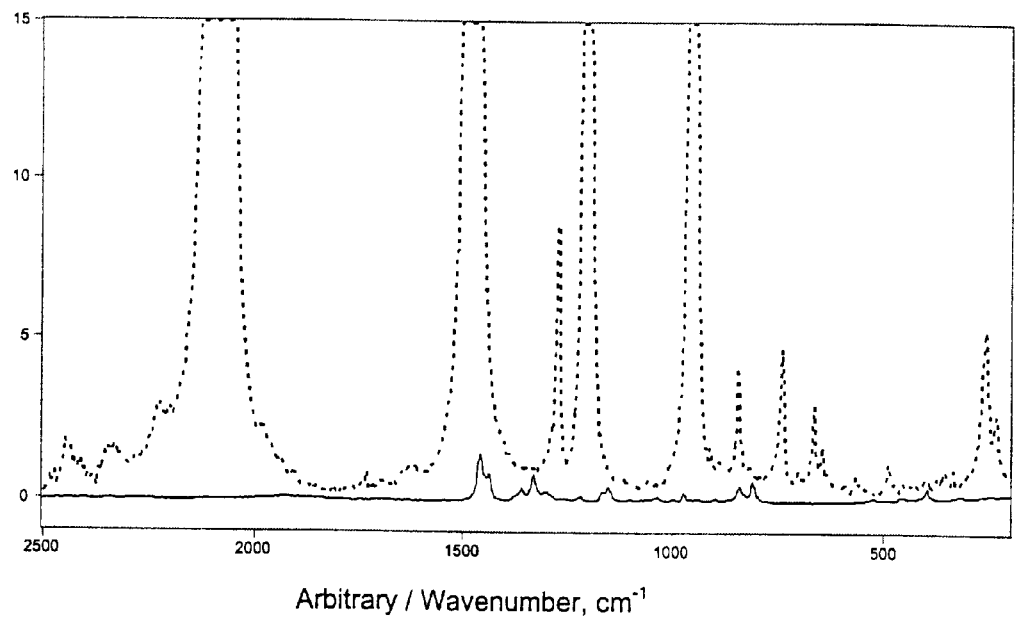
FIG. 23—Is a comparison of the NIR Raman cross-sections of a Raman-active compound of the invention (dotted line) and that of an ordinary polymer (full line)

Yet in another embodiment, the Raman-active taggants of the invention are employed for producing completely hidden from the eye molecular codes, tags and labels which, nonetheless, are readily detectable by NIR-excited Raman spectroscopy in accordance with the present invention. Generally and as a very rough approximation, all materials in terms of the present invention can be categorized for strongly Raman-active and weakly Raman-active (or Raman-inactive) ones. Some representatives from the first group has been characterized in the preceding text as Raman-active taggants suitable for producing readily Raman-detectable molecular codes, tags and labels. Remember that these materials have been judiciously designed or selected for the role owing to their special physical characteristics, making them different from many ordinary materials. Many other natural or synthetic materials, on the other hand, are moderate or only weak Raman scatterers. Namely this circumstance is advantageously used in the present embodiment of the invention. Also, many ordinary materials are opaque in the visible, but comparatively transparent in the NIR spectral region. The most important from these in frames of the present invention are paper and plastic films. Certainly, paper as well as plastics have their specific Raman spectra of some sort, and these Raman spectra may be of value e.g. in polymer science and/or in paper and polymers technology. In the present embodiment, however, it is of practical value that, at a given power of an incident NIR laser beam: (i) intensity of the NIR-excited Raman signal emitted by a Raman-active taggant (or by a molecular tag based thereon) will be considerably higher than the signal from an ordinary paper or a polymer; and (ii) although ordinary paper or plastic substrates (or cover layers) bearing (or covering) the Raman-active compound (marking composition) can be opaque in the visible, they often are actually transparent to both the exciting NIR laser wavelength and the NIR Stokes Raman photons generated. In practice it means that the Raman-active taggants (or marking compositions based thereon) may be applied so as to be completely hidden from the eye, e.g. by a sheet of paper or by a film of opaque or translucent polymer. For example, as FIG. 23 shows, an authenticating marking made of a PDA (sub-class J of the invention) on the surface of an ordinary printing paper, being covered by a pigmented sheet of ethylenepropylene copolymer (and, thus, hidden from the eye), turns out to be readily seen by the NIR-Raman spectrometer. It should be noted that the spectrum of the copolymer film (fill line in FIG. 23)) has been acquired separately by using an order of value higher laser power than that used for recording the spectrum of a polydiacetylene (dotted line in FIG. 23). Only the lower portion of the spectrum of the Raman-active tag is shown here for clarity, and both spectra are shown overlaid after normalization to equal laser excitation power. In fact, the spectra in FIG. 23 evidence that the Raman-active compounds of the invention can be 100 times more Raman-active than ordinary olefin polymers. Actually the same results are obtained when the marking is covered by a sheet of printing paper or even when the marking is hidden behind a 1-mm-thick silicon chip. Thus, specialists in the art will probably appreciate that, owing to their much lower Raman cross-section compared to the NIR-Raman-active taggants of the invention, many sheet materials traditionally employed in printing industry can be conveniently used in conjunction with the Raman-active taggants for producing invisible to the eye, but readily NIR-Raman-detectable molecular codes and labels in accordance with the present invention.

Yet in another embodiment, the Raman-active taggants of the invention are employed incorporated into matrices of inherently Raman-silent materials. Since the latter are not capable of giving an essential contribution to the resulting NIR Raman spectrum of the taggant, these may be rather freely used as a matrix, a diluent or a carrier for the Raman-active taggant (or a composition thereof). Thus, for example, the Raman-active compounds of the present invention may be compatibilized with polymers, such as polyethylene, polypropylene, polystyrene, etc., and then articles may be manufactured from thus covertly protected polymers. Alternatively, the NIR Raman-active compounds of the present invention may be used as inherent constituents of the paper. Further, the Raman-active compounds may be introduced into an article between two layers as a lamina.

Yet in another embodiment, essentially inorganic, the so called anti-Stokes, up-converting phosphors are used individually or as specified mixtures of one with another for producing covert markings, codes and labels that are readily detectable by the same Raman instrumentation which, in other embodiments, is employed for identification of organic or organoelement Raman-active compounds of the invention. In their traditional applications, these materials are excited with IR radiation to emit radiation of a higher energy in the visible region of the spectrum. Remember that in normal fluorescence the exciting radiation must have a shorter wavelength than the emitted light. This is referred to as Stoke's Law. In difference to this, the upconverting phosphors are able to absorb two or three photons of infrared light and, having combined their energies, are capable of emitting a single photon of visible light (that is, a photon of higher energy or of a shorter wavelength). Phosphors of this class usually have characteristic excitation spectra in the infrared, often coinciding with the wavelengths provided by many commercially available compact and economic NIR and IR light emitting diodes (LEDs) or diode lasers. The latter are very convenient to use as the excitation sources in order to obtain a bright (red, green, yellow or blue) glow in the visible range, in response to the excitation. Therefore, these materials are considered to have great potential for anti-counterfeiting namely due to their ability to effectively produce anti-Stokes emission. In the present embodiment of the invention, however, an employment of these materials in a more covert fashion is provided. In fact it is suggested to leave aside their upconverting (or anti-Stokes) ability and, instead, to exploit the Stokes photons generated by these materials under laser excitation. As it has been found by the present inventors, the same Raman spectrometers which, in other embodiments, are employed for identification of organic or organoelement Raman-active compounds of the invention are ideally suited also for identification of the Stokes laser induced fluorescent (LIF) fingerprints of the up-converting phosphors. Usually, fluorescence emission is highly unwanted during Raman spectra acquisition. Being several orders of magnitude more effective physical phenomenon than Raman scattering, fluorescence in most cases completely masks the much weaker Raman signals. With some upconverting phosphors, however, the Stokes LIF signal is represented by a limited number of well resolved spectral features. Spectral characteristics of interest for two exemplary up-converting phosphors, as measured in the course of typical NIR-Raman experiment, are illustrated by the spectra in FIG. 10. These spectra evidence that up-converting phosphors of different chemical structure (or of different composition) provide clearly differing LIF spectra which can be conveniently employed in accordance with aims and scope of the present invention. It should be noted that the Raman shift values indicated in FIG. 10 are counted off the 9394 $cm^{-1}$ point on the absolute wavenumbers scale, corresponding to the excitation source wavelength used in this case (Nd:YAG laser Rayleigh line, 1.064 $\mu m \equiv 9394$ $cm^{-1}$). Since frequencies of the LIF spectral bands are "insensitive" to the exact frequency of the excitation and are determined by the nature of the fluorescing compound, it is more convenient to represent them in the absolute scale. Thus, the interval of 2600–3200 $cm^{-1}$ Raman shifts in FIG. 10 corresponds to the spectral region of 6800–6200 $cm^{-1}$ in the absolute scale (that is, to the wavelengths region of 1470–1610 nm or 1.47–1.61 $\mu m$). It should be noted also that the spectra in FIG. 10 illustrate spectral behavior of two green up-converting phosphors. Red or blue upconverting phosphors will produce Stokes LIF spectra in other spectral ranges (roughly from 0.8 up to 2.5 mcm). It infers that the detector for the LIF experiment with upconverting phosphors should be chosen judiciously in order to cover the spectral range of interest. For example, the LIF spectra shown in FIG. 10 have been recorded with the aid of a Raman spectrometer equipped with an InGaAs detector. Importantly, the LIF spectra of up-converting phopsphors can be recorded in accordance with the present invention by using very low laser powers incident on the sample. Alternatively, the up-converting phosphors can be detected in accordance with the present invention in very low concentrations (or quantities). Therefore, these materials are treated as very useful ingredients of complex security codes and labels produced in accordance with the present invention. Moreover, being detected in accordance with the invention, these materials leave a wide spectral region unoccupied with any spectral features. As the specialists in the art will probably appreciate, the latter circumstance provides grounds for using the up-converting phosphors simultaneously with other organic and inorganic taggants of the invention.

Therefore, still in another alternative embodiment, these essentially inorganic, the so called anti-Stokes, up-converting phosphors are employed in conjunction with the organic and organoelement Raman-active taggants of the present invention. Obviously, such approach permits to devise a plenty of highly covert security labels, markings and codes based on the following advantageous circumstances. For example, since fluorescence is much more effective phenomenon than Raman scattering, the fluorescing substance can be used in proportionally much lower concentration than the Raman-active one (in fact, it may be trace quantities only). The latter circumstance means that it would be difficult (if at all possible) task for a wrong-doer to identify this critical component in the mixture with organic taggants when attempting to analyze and/or reverse engineer the molecular code or label. But without this fluorescing component present in infinitesimal quantities the molecular code will be incomplete for a Raman reader machine. Alternatively, in case of using the up-converting phosphors in mix with the organic taggants, there is a possibility to induce the two-photon absorption and generation of visible light under a NIR laser irradiation. Namely this may be "sold" to wrong-doers as the major security feature of the label, while the reading machine will expect to see a complete LIF/Raman spectrum containing both Raman bands from an organic taggant and LIF bands from an upconverting phosphor, and not only fluorescence from a phosphor.

Figure 24:
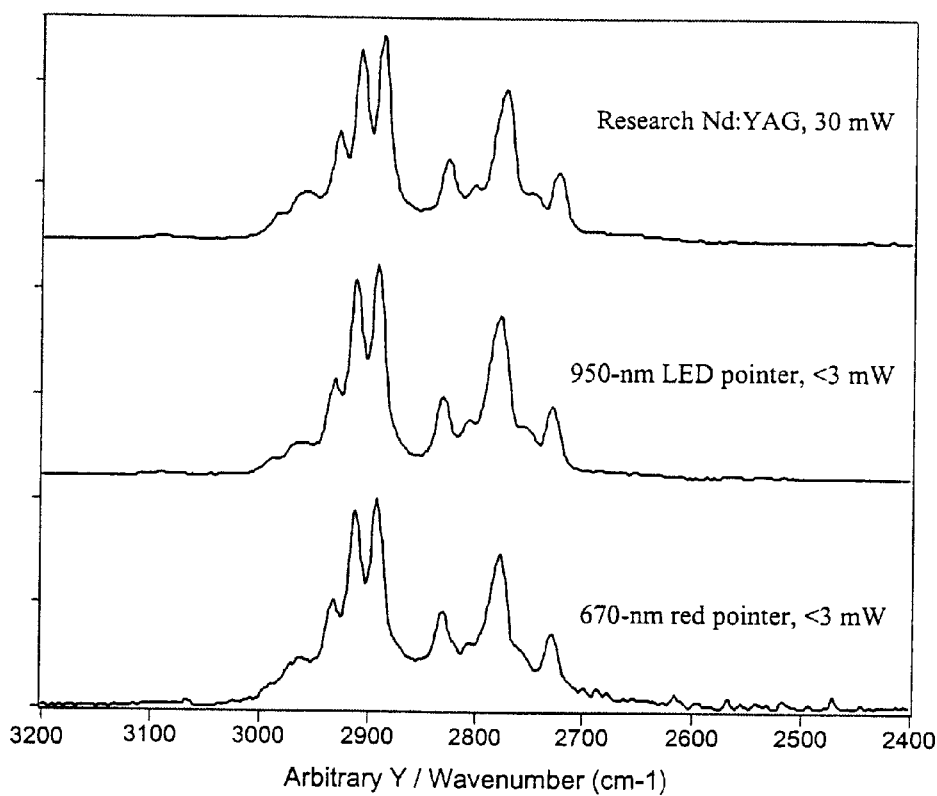
FIG. 24—Shows Stokes part of Laser Induced Fluorescence (LIF) spectra for a "green upconverting phosphor" that have been acquired with the aid of a Raman spectrometer by using three different laser excitation sources.

Yet in another embodiment, the Stokes LIF/Raman spectra can be excited in accordance with the present invention not only by NIR LEDs or NIR lasers inducing the up-conversion phenomenon and thus producing a visible glow, but also by those lasers which are not able to provide photons suitable for the two-photon absorption/up-conversion process. As it has been found by the present inventors, such lasers are still able to induce the Stokes LIF signal sufficiently intense to be detected by the Raman instrumentation in accordance with other embodiments of the invention, thus permitting identification of the up-converting phosphor used or authentication of the code based thereon. The LIF/Raman spectra in FIG. 24 evidence that the Stokes fluorescence of up-converting phosphors is rather "insensitive" to the wavelength of the excitation laser source. It may be seen that consistent LIF spectra of a phosphor can be measured by a NIR-FT Raman spectrometer despite the excitation wavelength has been varied considerably. Of importance for the purposes of the present invention is also the fact that "the quality" of the excitation line obviously has little effect on the LIF spectrum. In particular, besides a research-grade Nd:YAG laser ($TEM_{00}$, 1064 nm, 0.1 $cm^{-1}$ bandwidth), two "key-chain" laser pointers (emitting nominally at 950 and 630 nm) have been employed in this experiment. It may be seen that the two pointers (which are multimode sources having total bandwidths of several tens of nanometers and the outputs of ca. 1 mW) give actually the same and quite useful results. Strictly speaking, because of the multimode nature and their bandwith, these laser pointers could induce very much distorted and almost useless Raman spectra (if any). FIG. 24 shows, however, that these turn out to be quite sufficient to induce LIF spectra of excellent quality, provided the latter are measured with the aid of Raman instrumentation in accordance with teachings of the present invention. It should be noted also that, owing to the outstanding thermal stability of these materials, they may be used, for example, being melted with glass, ceramics and even metals without loss of their functional properties as the LIF/Raman-detectable tags. Thus, specialists will probably appreciate that the up-converting phosphors, when used in accordance with the aims and teachings of the present invention, provide novel anti-counterfeiting measures, a higher degree of security and considerably widen the applicability of the security tags in the art.

In all embodiments of the invention: (1) a Raman-active taggant of the invention is included into a marking composition; (2) this composition is then used for producing a mark which is applied to a genuine item to be protected against forgery or counterfeiting; (3) the mark is then exposed to radiation of a predetermined near infrared wavelength to produce Raman scattering spectral bands; (4) at least a portion of the Raman spectral bands are collected and processed by a Raman spectrometer to convert the same into an electrical signal; and (5) the electrical signal is processed to detect and identify, qualitatively and/or quantitatively, the taggant(s).

Any of a wide variety of suitable marking methods can be employed. Generally, an efficient Raman-active compound (or a mixture thereof hereinbelow referred to as Raman-active matter) is introduced along with other suitable ingredients, whether solid or liquid, into a marking composition, and the marking composition thus prepared is then used in any suitable imaging method. In some instances, the marking composition may consist of 100 percent of the Raman-active compound (or a Raman-active matter). The individual Raman-active compound is present in the marking composition in any amount effective for enabling detection and/or identification of a Raman spectrum of this Raman-active compound when the mark produced of the marking composition on the protected item is irradiated with near-infrared monochromatic radiation. Typically, the Raman-active matter is present in the marking composition in amounts of from about 0.1 to about 100 percent by weight, preferably from about 5 to about 100 percent by weight, and most preferably from about 50 to about 100 percent by weight, although the amount can be outside these ranges. Any individual Raman-active compound is present in the said Raman-active matter in any amount of from about 0.1 to about 99.9 percent by weight. The mark containing the Raman-active matter can be placed on the article to be protected against forgery or counterfeiting by any desired or suitable method, and may be either visible to the naked eye or substantially hidden, at least upon cursory inspection. Generally, the Raman-active matter can be included within a conventional marking material, either in the presence of a colorant or in the absence of another colorant.

In one embodiment, the Raman-active matter is used included within a powder toner composition suitable for producing images by xerographic process. Toner typically comprises a resin and a colorant. Typical toner resins include polyesters, polyamides, epoxies, polyurethanes, diolefins, vinyl resins and polymeric esterification products of a dicarboxylic acid and a diol. Optionally, if it is desired to generate images that are visible with the naked eye, the toner composition can also contain a colorant. Typically, the colorant material is a pigment, although dyes can also be employed. Specific examples of suitable dyes and pigments include carbon black, nigrosine dye, aniline blue, magnetites, and mixtures thereof, with carbon black being the most common colorant. The pigment should be present in an amount sufficient to render the toner composition highly colored to permit the formation of a clearly visible image on a carrier member. Colored toner pigments are also suitable for use with the present invention, including red, green, blue, brown, magenta, cyan, and yellow particles, as well as mixtures thereof, wherein the colored pigments are present in amounts that enable the desired color. The toner compositions of the present invention can be prepared by a number of known methods, including mechanical blending and melt blending the toner resin particles, pigment particles or colorants, and other additives followed by mechanical attrition. Other methods include those well known in the art such as spray drying, mechanical dispersion, melt dispersion, dispersion polymerization, extrusion, and suspension polymerization. The toners can be subjected to known micronization, and classifications to provide toner particles with an average volume diameter of from about 9 to about 20, and preferably from about 10 to about 15 microns. The toner and developer compositions of the present invention may be selected for use in developing images in electrostatographic imaging and systems, containing therein, for example, conventional photoreceptors, such as selenium and selenium alloys. Besides the U.S. Pat. No. 5,935,755, which has been reviewed thoroughly above, U.S. Pat. No. 5,232, 810 discloses a toner composition comprised of resin particles, pigment particles, and a charge enhancing additive comprising a fullerene or fullerenes wherein the fullerene or fullerenes are represented by C60, C70, C84, C234, C340, or mixtures thereof, but the latter document is silent about a possibility of Raman detection of the fillerenes as a security feature. The disclosures of each of the patents mentioned herein are totally incorporated by reference. Provided due regard is paid to their inherent physico-chemical characteristics, practically all compounds disclosed in the present application and categorized above as (i) essentially monomeric linear or branched organic and organoelement compounds containing, in internal or terminal positions within a molecule, essentially symmetrical molecular moieties having intrinsically high polarizabilities; (ii) essentially polymeric linear or quasi-one-dimensional, ladder-like or comb-like, highly branched or dendritic macromolecular compounds containing long sequences of essentially symmetrical unsaturated chromophores in their backbones exhibiting intrinsically high polarizabilities and/or characterized by extensive delocalization of electron density along the conjugated backbone such as, for example, polymes, polyenes, polysilylenes, polyenynes, poly(arylenevinylenes), poly(arylenevinyleneethynylenes), etc., along with allotropic forms of carbon or quasi-zero-dimensional spheroidal large carbon molecules such as, for example, fullerenes C60, C70, nanotubes and the like; and (iii) the lanthanide-ions-based inorganic up-converting phosphors, being used individually or as mixtures of one with another or as mixtures with other Raman-active compounds,—can be employed as the Raman-active matter included within a powder toner composition suitable for producing security NIR Raman-active markings, codes and labels identifiable in accordance with the present invention. Typically, in a dry powder toner material of the present invention the Raman-active compound (or a Raman-active matter) is present in an amount of from about 0.1 to about 95 percent by weight, more preferably from about 20 to about 90 percent by weight, and even more preferably from about 50 to about 90 percent by weight, although the amount can be outside these ranges.

In yet another embodiment, the Raman-active compound (or matter) is used included within a liquid composition suitable for producing images by ink-jet printing process. The so called drop-on-demand ink-jet printing systems are preferable in frames of the invention and the so called thermal ink jet, or bubble jet printing systems which produce high velocity droplets and allow very close spacing of nozzles are the most preferred. Thermal ink jet processes are well known and are described in, for example, U.S. Pat. No. 4,601,777 and U.S. Pat. No. 4,532,530, the disclosures of each of which are totally incorporated herein by reference. Known ink jet inks generally comprise a water soluble dye which is soluble in an ink vehicle such as water or a mixture comprising water and a water soluble or water miscible organic solvent. For example, U.S. Pat. No. 4,184,881 discloses an ink composition for use in ink jet printing comprising an aqueous solution of a water soluble dye and a humectant comprised of ethylene oxide adducts of at least one acetylenic diol in the absence of any glycol or glycol ether. This patent document is silent, however, about a possibility of Raman detection of the acetylenic component of the composition after printing. In addition, U.S. Pat. No. 4,337,183 discloses an aqueous printing ink composition which comprises a physical mixture of polyurethane resin, polyethylene resin, and water as the vehicle. Further, besides the U.S. Pat. No. 5,935,755 mentioning the use of ink jet printing compositions comprising squaraines as Raman-detectable components which has been reviewed thoroughly above, U.S. Pat. No. 5,114,477 discloses an ink composition which comprises an aqueous or organic liquid vehicle, and as a colorant a fullerene, or a mixture of fullerenes, but is silent concerning a possibility of Raman detection of the fullerenes as a security feature. The disclosures of each of the patents mentioned above are totally incorporated herein by reference. Provided due regard is paid to their inherent physico-chemical characteristics, practically all water- and/or organic solvent soluble compounds of those disclosed in the present application and categorized above as (i) essentially monomeric linear or branched organic and organoelement compounds containing, in internal or terminal positions within a molecule, essentially symmetrical molecular moieties having intrinsically high polarizabilities; (ii) essentially polymeric linear or quasi-one-dimensional, ladder-like or comb-like, highly branched or dendritic macromolecular compounds containing long sequences of essentially symmetrical unsaturated chromophores in their backbones exhibiting intrinsically high polarizabilities and/or characterized by extensive delocalization of electron density along the conjugated backbone such as, for example, polymes, polyenes, polysilylenes, polyenynes, poly(arylenevinylenes), poly(arylenevinylene)-ethynylenes, etc., along with comparatively new allotropic forms of carbon or quasi-zero-dimensional spheroidal large carbon molecules such as, for example, fullerenes C60, C70, nanotubes and the like, being used individually or as mixtures of one with another or as mixtures with other Raman-active compounds,—can be employed as the Raman-active compounds (or Raman-active matter) included within a liquid composition suitable for producing by ink-jet printing process security NIR Raman-active markings, codes and labels identifiable in accordance with the present invention. Ink compositions suitable for ink jet printing can be prepared by any suitable process. Typically, the inks are prepared by simple mixing of the ingredients. One process entails mixing all of the ink ingredients together and filtering the mixture to obtain an ink. Inks can be produced by preparing a conventional ink composition according to any desired process, such as by mixing the ingredients, heating if desired, and filtering, followed by adding any desired additives to the mixture and mixing at room temperature with moderate shaking until a homogeneous mixture is obtained. Typically, within a liquid composition of the present invention suitable for producing images by ink-jet printing process the Raman-active compound (or the Raman-active matter) is present in an amount of from about 0.1 to about 30 percent by weight, more preferably from about 1 to about 20 percent by weight, and even more preferably from about 5 to about 15 percent by weight, although the amount can be outside these ranges.

In yet another embodiment, the Raman-active compound (or the matter) is used included within a liquid ink composition suitable for producing markings applied onto a pervious writing surface preferably with a so called writing tool which is provided, for example, by a felt-tip pen, a plotter pen, a flow-master pen, a roller pen, a gel pen, a fountain pen, etc. It should be noted, however, that the ink composition is not restricted to any writing tool for writing. The ink composition of the invention may be prepared by any known method in the art. For example, a binder resin, and when necessary, a surfactant and a plasticizer, are added to a solvent and stirred, and then to a resultant solution is added the dyestuff and/or the NIR Raman-active compound (or matter) of the invention, and stirred for a sufficient period of time under heating if necessary. All the ingredients may be added to a solvent at the same time if desired. Any dispersing means such as a ball mill may be used in the preparation of the ink composition if necessary. The ink composition of the invention comprises 20–80 percent by weight of a solvent, not more than 30 percent by weight of a binder resin soluble in the solvent, not more than 30 percent by weight of a coloring agent (or a mixture thereof) and preferably 5–50 percent by weight of a Raman-active compound (or a mixture thereof) of the invention. Various coloring agents can be used, if desired, such as water- and/or organo-soluble dyes and pigments. No particular restriction is put on the type of the colorants, except that preferable in frames of the invention are those which do not induce autofluorescence when irradiated with a NIR laser. These colorants can be used singly or in the form of a mixture of two or more thereof. No particular restrictions is put on the types of the solvent and the binder resin also. Provided due regard is paid to their inherent physico-chemical characteristics, practically all compounds disclosed in the present application and categorized above as (i) essentially monomeric linear or branched organic and organoelement compounds containing, in internal or terminal positions within a molecule, essentially symmetrical molecular moieties having intrinsically high polarizabilities; (ii) essentially polymeric linear or quasi-one-dimensional, ladder-like or comb-like, highly branched or dendritic macromolecular compounds containing long sequences of essentially symmetrical unsaturated chromophores in their backbones exhibiting intrinsically high polarizabilities and/or characterized by extensive delocalization of electron density along the conjugated backbone such as, for example, polymes, polyenes, polysilylenes, polyenynes, poly (arylenevinylenes), poly(arylenevinyleneethynylenes), etc., along with comparatively new allotropic forms of carbon or quasi-zero-dimensional spheroidal large carbon molecules such as, for example, fullerenes C60, C70, nanotubes and the like; and (iii) the lanthanide-ions-based inorganic up-converting phosphors, being used individually or as mixtures of one with another or as mixtures with other Raman-active compounds,—can be employed as the Raman-active matter included within a liquid ink composition suitable for producing security NIR Raman-active markings, codes and labels applied onto a pervious writing surface with a so called writing tool and identifiable in accordance with the present invention. Typically, in a liquid ink composition of the present invention the Raman-active compound (or a mixture thereof) is present in an amount of from about 0.1 to about 50 percent by weight, more preferably from about 5 to about 50 percent by weight, and even more preferably from about 20 to about 50 percent by weight, although the amount can be outside these ranges.

The Raman-active compounds of the invention can also be applied onto a protection receiving member by any other printing or imaging process, such as thermal transfer printing (for example, by incorporating a Raman-active compound or a mixture thereof into a thermal transfer film), encapsulated marking material printing, impact printing (for example, by incorporating a Raman detectable component into an impact printer ribbon such as a dot matrix or typewriter ribbon), brushes, or the like.

In yet another preferred embodiment, the Raman-active compound (or the matter) is used included within printing inks compositions suitable for producing images by flexographic printing, gravure or heliogravure printing, intaglio (steel engraving) or plate printing, letterpress printing, indirect letterpress or dry offset printing, lithographic or wet offset printing, and screen printing processes. Preparation of such printing inks is well known in the art. Especially useful in frames of the invention are methods comprising a stage of embedding the Raman-active matter into a light-transparent, inert polymeric protecting composition. This embedding can be effected by incorporating the Raman-active compounds, before their blending into an ink formulation, into a polymeric composition which is then broken into lumps and subsequently micronized to a particle size of from 1 to 20 micrometers. Another method is to encapsulate the Raman-active compounds by the process of coacervation or encapsulation to form microcapsules, a method known per se, wherein the Raman-active compound is enveloped by a thin shell of an inert light-transparent polymer. These two embedding methods result in useful dyestuff compositions having the general properties of organic pigments. More specifically, in the first method, (A) a Raman-active compound of the classes (i), (ii) and (iii) of the present invention is incorporated into a thermoplastic, NIR-light-transparent polymer by melting together the two components at a temperature between 50° C. and 200° C. The temperature is selected such that the Raman-active compound is not altered or even destructed. Of course, the polymer has to be selected such that its melting point or melting range is low enough so that it will form the molten state at a temperature which does not alter the Raman-active compound. The melt so obtained is mixed thoroughly until perfect homogenization, and the Raman-active compound will be uniformly distributed in the melt as a solution or dispersion. An adequate inert solvent may be added before melting, in order to lower the liquid temperature of the mixture. Then, the mixture is allowed to cool to ambient temperature. Should a solvent have been used, it is stripped off during or after cooling. The Raman-active compound now forms a solid solution or dispersion with the polymer. The solid mass so obtained is then broken into lumps which are then micronized in a suitable equipment to a particle size in the pigment range, i.e. within 1 and 20 $\mu$m. The particulate composition, after micronization, is appropriate for an introduction into binder preparations on standard dispersion equipment such as three roller mills, high-speed dissolvers, or head mills, known in the art of manufacturing printing inks, to form liquid or pasty inks by adding the other standard ink components, for various technical applications. Preferred thermoplastic resins which fulfill above requirements for the polymer matrix are, for example, cellulose derivatives, polyamides, acrylic polymers and copolymers, polyvinylic resins, hydrocarbon resins such as polyolefines, polyesters, polycarbonates, or mixtures thereof. The micronized pigment-like, particulate solid solutions of the Raman-active compounds of the invention in the thermoplastic resin obtained by the above method are especially well suited for incorporation into liquid printing ink vehicles which are unable to dissolve or swell the thermoplastic resin of the protected Raman-active taggant. The resulting Raman-active ink constitutes an aqueous or non-aqueous dispersion of a Raman-active matter particles embedded in a thermoplastic host polymers. According to the second method, (B) encapsulation of a Raman-active compound of the invention in a NIR-transparent polymer shell, in the form of microcapsules is accomplished. The microencapsulation is performed in aprotic resins or solvents according to well known methods of microencapsulating or coacervation using gelatin or acacia gum as a wall material, or according to U.S. Pat. Nos. 4,428,978 and 4,517,141 which are incorporated herein by reference. According to U.S. Pat. No. 4,428,978, aqueous suspension containing 35 to 60% by weight of microcapsules having a size from 1 to 20 µm are prepared from polyisocyanates and hydrogen active compounds by a boundary surface polyaddition reaction. After polyaddition under shearing conditions, the suspension of the microcapsules may be dried to prepare dry microcapsules. The microcapsules, comprising the enclosed Raman-active compound, are then incorporated into printing ink vehicles in any standard dispersing equipment, usually in simple butterfly mixers or dissolvers under limited shear rates for not damaging the microcapsules. Still, by this invention there is provided (C) another simplified process for producing a suspension of microparticles or microcrystals of a Raman-active compound(s), involving forming an emulsion containing a Raman-active compound(s), binder, water, organic solvent, and surfactant. An emulsion can be prepared by using techniques described in "Encyclopedia of Emulsion Technology", P. Becher (Ed.), Marcel Dekker, New York, (1983); "Practical Emulsions", H. Bennett, J. C. Bishop Jr., and M. F. Wulfinghoff, Chemical Publishing Company, New York, 1968; and "Microemulsions: Structure and Dynamics", S. E. Frieberg and P. Bothorel, CRC Press, Boca Raton, Fla. Emulsions are usually prepared by homogenizing/emulsifying two immiscible liquids, e.g., a water immiscible solvent (e.g., toluene) with water using an emulsifying agent, such as a surfactant. We have exploited several processes of preparing emulsions/dispersions of compositions. The emulsions can be prepared by homogenizing a mixture containing the proper proportions of a solution of a Raman-active compound, a solution of a binder and an emulsifying agent at high speed and elevated temperature. Ionic and nonionic surface active agents can be used as emulsifiers. Sodium dodecyl sulfate, cetyltrimethyl ammonium chloride, ethoxylated para-octylphenol, 2-ethyl-hexyl alcohol ethoxylate, lecithin, polyethylene glycol (PEG) and PEG-dodecylether are some examples of surfactants which can be used to make the emulsion. Use of inorganic surfactant/emulsifiers, e.g., zinc oleate is also permittable. Preferred concentration of surfactant in the mixture is 0.01 to 5%, most preferred is 0.1–1.0%. A wide variety of solvents, from completely miscible, e.g., methanol to immiscible, e.g., dichloromethane and ethylacetate, in water, can be used to make the emulsion. The preferred solvents are methanol, MEK, ethylacetate and toluene. Preferred concentration can be 5–80%, most preferred concentration range is 10–30%. The emulsion can be prepared by processes, such as high speed homogenization and ultrasonication. Vigorous agitation, e.g., high speed (100 rpm to 20,000 rpm) stirring is a preferred method of making the emulsion. The preferred temperature is above room temperature to up to about 100° C. The most preferred temperature range is 40–70° C. Rapid cooling of the emulsion is very effective for obtaining micron and submicron sized crystals and particles of the Raman-active compounds of the invention. Procedures of fast cooling of emulsions are well known in the art and described, for example, in U.S. Pat. No. 5,420,000, the disclosures of which are totally incorporated herein by reference. The latter are dealing with diacetylenes and comprise cooling the emulsion and allowing the solvent and water to evaporate leaving a film. Simplified procedures extended for preparing micronized particles of different Raman-active compounds of the invention turned out to be adequate for the purposes of the present invention. In a preferred embodiment, the emulsions can be prepared at higher temperature without one or more of the following basic components for making an emulsion: (i) solvent for Raman-active compound, (ii) solvent for binder, (iii) binder, and (iv) emulsifying agent. The methods of making emulsions of the Raman-active compounds are preferred without one or more of the following basic components for making emulsion: (1) solvent for Raman-active compound and binder, (2) binder (3) emulsifying agent. The processes of making nonaqueous emulsions, and semi-aqueous emulsions are also preferred. Using one or more of the above methods, it is possible to make an emulsion of most Raman-active compounds under a variety of conditions. The preferred method of cooling the emulsion is by quenching the emulsion quickly to the desired temperature, for example, by pouring it into a cold volatile liquid, such as liquid nitrogen. If the emulsion is cooled quickly to a lower crystallization temperature, narrow distribution of the crystals is obtained. The method of quenching the emulsion by pouring it into liquid nitrogen is preferred mainly because (i) it does not require aging of the emulsion, (ii) freezing of the emulsion prevents the emulsion droplets from aglomeration, (iii) crystal size can be controlled from a fraction of a micron to several microns thick, (iv) it can be easily scaled up, (v) emulsions of a large number of Raman-active compounds can be formed in a variety of binders in both aqueous and nonaqueous systems. Specialists will recognize that there are many known in the art methods of controlling the size of the crystals of the compounds based on controlling the effects of several parameters, including (a) the nature and concentrations of the components, i.e., crystallizable solids, solvents, binders, and emulsifiers, (b) temperature and degree of homogenization, (c) rate of quenching the emulsion, (d) temperature at which the emulsions are cooled, and (e) temperature of crystal growth, and (f) the nature of an external strain.

The invention contemplates different printing inks for different printing methods, among them flexographic, gravure, intaglio, letterpress, dry offset, wet offset and screen printing. All these printing methods are well known to those familiar with the art. It is furthermore well known that the composition and most physical properties of printing inks must be adapted to the respective printing methods (cf., for example U.S. Pat. Nos. 5,591,255 and 5,997,849 disclosing thermochromic printing inks). For example, gravure printing inks have a much lower viscosity than intaglio printing inks. The different basic ink compositions are also well known to the one skilled in the art and will therefore not be described here in detail. Provided due regard is paid to their inherent physico-chemical characteristics, practically all compounds disclosed in the present application and categorized above as (i) essentially monomeric linear or branched organic and organoelement compounds containing, in internal or terminal positions within a molecule, essentially symmetrical molecular moieties having intrinsically high polarizabilities; (ii) essentially polymeric linear or quasi-one-dimensional, ladder-like or comb-like, highly branched or dendritic macromolecular compounds containing long sequences of essentially symmetrical unsaturated chromophores in their backbones exhibiting intrinsically high polarizabilities and/or characterized by extensive delocalization of electron density along the conjugated backbone such as, for example, polymes, polyenes, polysilylenes, polyenynes, poly (arylenevinylenes), poly(arylenevinyleneethynylenes), etc., along with comparatively new allotropic forms of carbon or quasi-zero-dimensional spheroidal large carbon molecules such as, for example, fullerenes C60, C70, nanotubes and the like; and (iii) the lanthanide-ions-based inorganic up-converting phosphors, being used individually or as mixtures of one with another or as mixtures with other Raman-active compounds,—can be employed as the Raman-active matter included within a printing ink composition suitable for producing security NIR Raman-active markings, codes and labels applied onto a writing surface by means of flexographic, gravure, intaglio, letterpress, dry offset, wet offset and screen printing processes and identifiable in accordance with the present invention. The Raman-active printing inks of the invention will contain one or several Raman-active compounds or LIF/Raman-active pigments in concentrations comprised between about 0.5 and about 50 percent by weight, referred to the total weight of vehicle, binder and the Raman-active compound. The inks of this invention are to be used for the printing of identification or forgery detection marks or patterns on security documents. This term comprises bank notes, checks, traveler's checks, stamps, shares, passports, labels and similar printed documents for which measures against counterfeiting are indicated. The inks of this invention are intended to be used simultaneously with conventional printing inks for the printing of security documents such as thermochromic and/or photochromic inks, and are intended to be used on the same machines by simple substitution of one of the normally used printing inks.

Any mark, pattern or image generated on a member to be protected against forgery or counterfeiting in accordance with above embodiments of the invention, and thus now bearing a Raman-active compound (or the matter), is then have to be detected or authenticated by means of NIR Raman spectrometry. In many embodiments of the invention, the detection or authentication as set forth above can be carried out by a Raman spectrometer selected from the group consisting of: dispersing spectrometers, multi-channel spectrometers, Fourier transform spectrometers, Hadamard transform spectrometers, stationary transform spectrometers, acousto-optic tunable filter spectrometers, integrated optic acousto-optic tunable filter spectrometers, fiber optic spectrometers, fiber optic array spectrometers, microscope spectrometers, imaging spectrometers, and imaging microscope spectrometers. Of course, the exact spectral characteristics of the Raman-active codes, marks and labels could be determined in a special analytical laboratory equipped with stationary instrumentation. [And, in fact, it should be done yet during design stage of a marking composition, in order to obtain the so called "external standard" that can be used then during measurements "in the field".] In an embodiment, practical authentication of members protected against forgery or counterfeiting with the Raman-active marks is accomplished by using a single stationary, high-performance Raman spectrometer equipped with a plurality of sampling subsystems. In one such design, the plurality of sampling subsystems may be connected to the Raman read-out subsystem via a fiber optic cables array. Each sampling subsystem is connected to the Raman spectrometer, housed within the operator station, via a fiber optic cables array that carries the Raman spectral signal from the Raman probe in each sampling subsystem in the booth to the Raman spectrometer in the operator station. If desired, a central light source such as one or more high-performance lasers may be collocated with the Raman spectrometer in the operator station, and the exciting light dispersed and carried through the fiber optic cables array to the individual sampling subsystems. Alternatively, a plurality of light sources may be collocated, e.g., one or more lasers each, with the sampling subsystems. Preferably, the Raman spectral signals traveling from the various sampling subsystems to the operator station are analyzed individually and sequentially.

In another preferred embodiment, however, monitoring of authenticity of the Raman-active marks, codes and labels is accomplished directly "in the field" with the aid of relatively autonomous and portable Raman system. In general terms, a direct authentication procedure "in the field" in accordance with the present invention consists of three steps. The first step involves bringing the Raman-active mark into contact with a Raman probe and exposing the mark to an exciting NIR laser light suitable for generating a Raman scattering spectrum. Second, a Raman spectroscopic technique is then used to collect the generated Raman photons, to sort these according to their energies, and focus them on a detector suitable for transforming the light signal into electronic signals. In the third and final step, the electronic signal obtained is compared against one or more reference spectra to determine the presence and/or identity of the authenticating mark. Accordingly, the Raman spectrometer hardware and components utilized during the Raman analysis procedure "in the field" may be selected from a list including, but not limited to, band-pass filter systems, filter-grating or prism-grating dispersive systems, multichannel systems, scanning multichannel systems, or multiplexing spectrometers such as Hadamard transform or Fourier transform or stationary transform systems, acousto-optic or integrated optic acousto-optic systems, imaging systems, or microprobe or microscopy systems, or fiber optic systems, etc., depending on constraints imposed by the desired parameters for the method or process or apparatus or device, including, for example, the desired sensitivity, specificity, accuracy, precision, and response time, the laser wavelengths to be used and the resulting wavebands to be monitored. In any instance, the Raman spectrometer system corresponding to aims and scope of the present invention should be composed of a radiation source, a means of transmitting the source radiation to a sample, a means of collecting the scattered radiation from the sample, a means of energy separation (or dispersion) of the scattered radiation, and a means of detecting the radiation.

In a preferred embodiment, the mark, pattern or image generated earlier on a member protected against forgery or counterfeiting in accordance with the invention, and thus now bearing a Raman-active compound (or a mixture thereof, i.e. the Raman-active matter), is authenticated in the field by employing a portable Raman spectrometry system that combines a dispersive grating spectrograph with a CCD detector, a single-mode diode laser, a fiber optic Raman probe, and a suitable computer. For development of the prototype instrument that would correspond to the aims of the present invention the following considerations have been taken into account by the inventors.

In order to generate a Raman spectrum of the Raman-active compound, the laser wavelength, in accordance with the spirit of the present invention, should be within the near-infrared region, more preferably in the wavelength range of from about 750 to about 1500 nanometers. For the purposes of the present invention, a laser is herein defined as a device which has the ability to produce monochromatic, coherent light. Of the various types of lasers that are commercially available, diode lasers are preferred because of the minimal maintenance required over their extended useful lifetimes. This advantage is very desirable in a component for mass analyzer instrumentation. Currently, diode lasers are available with high output powers, hypothetically making possible a great signal and, hence, a shorter measurement time. A concern with higher power diode lasers, however, is that they operate in what is called "multimode" regime, wherein many lasing modes are all simultaneously active. These individual modes are unstable with respect to one another and can render the device useless for precise quantitative analytical measurements. Instabilities in diode lasers may be reduced but not completely eliminated through proper control of temperature and unwanted emissions, as described, for example, in a paper entitled "Compact Raman instrumentation for process and environmental monitoring." *SPIE*, 1991, 1434, pp. 127–134, by Carraba et al. Without such control, diode lasers are unstable and are thus generally regarded as of little use for Raman spectroscopic investigations. Among their drawbacks also is that the wavelength of any diode laser device will gradually shift as the device ages. A diode laser device, though stable for short times, is characterized by long-term instabilities which produce a slow drift, resulting in reduced instrument reliability. In dispersive instruments, it is preferred to utilize a laser that has a wavelength between about 750 nm and 900 nm. Wavelengths beyond 900 nm adversely affect the detection capability of currently available multichannel detection systems (such as silicon CCDs). Further, it is highly preferred to utilize a laser which is pre-coupled to a fiber optic cable. Fiber coupled diode laser devices, referred to as pigtailed diode lasers, are commercially available, and provide several advantages over other laser sources. For example, they are already coupled to a fiber optic cable, which eliminates complex optical alignment mechanisms that can become unfocused and cause loss of signal. This simplicity allows for easy removal and replacement when necessary. Thus, in a preferred embodiment of the invention, a Raman spectrometry apparatus that includes a low-power, pigtailed, single-mode diode laser that emits monochromatic radiation at about 785 nm is employed. However, in other preferred embodiments of the invention, pigtailed single-mode diode lasers emitting in a range of 850–1400 nm, and more preferably, solid-state lasers emitting from 980 nm up to 1100 nm, are employed in combination with InGaAs or Ge-based multichannel or single-channel detection means. In the present invention, owing to the fact that the Raman-active taggants of the invention are inherently strong Raman scatterers, there is no necessity to use very high output laser powers. Besides general simplification of the system, it permits to employ more economical lower powered lasers from those commercially available.

Concerning the other important components of a Raman spectrometry system preferable in the present invention, the following should be noted. Inherent for this phenomenon large ratio of elastically to Raman scattered photons requires an efficient method of photon separation. Traditionally, this has been accomplished with double or triple spectrograph systems, constructed with two or three dispersive elements, respectively. Many new, currently available on the market radiation filtering devices can sufficiently reject the elastically scattered photons to permit the use of smaller, more efficient single dispersive element spectrograph devices (for example, holographic Bragg diffraction filters described in Carraba et al., *Appl. Spec.*, 1990, 44, pp.1558–1561). After the Raman scattered radiation has been collected and transmitted to the instrument, it is separated using a dispersive element, which is typically included along with focusing and collimating optical elements in a spectrograph. A dispersive element facilitates the separation of various energy levels of the scattered radiation from one another. Frequently, two or more dispersive elements are used to reject stray light more completely and increase SNR and resolution. However, there is a substantial advantage in using smaller, more efficient, single grating spectrographs with proper optical filtering, as described, for example, in Carraba et al., *SPIE*, 1991, 1434, p. 127–134. The detector element is highly important and must be capable of discerning extremely low levels of radiation. Traditional scanning monochromator systems have used photomultiplier tubes. Newer dispersive instruments employ array detectors such as photodiode arrays (PDA) or charge coupled devices (CCD). Array detectors consist of multiple optical elements that can simultaneously observe a region of the spectrum up to the entire Raman spectrum (0–3500 cm$^{-1}$ Raman shifts). CCD detectors are multi-dimensional and able to observe multiple Raman spectra at more than one wavelength simultaneously (cf., for example, Vess et al., *SPIE*, 1992, 1637, pp. 118–125).

Although many dispersive Raman spectrometers are currently commercially available from different manufacturers, only a few of them are of interest in terms of the present invention since, in a preferred embodiment, a portable, rugged, sufficiently sensitive, providing reasonable resolving power, and inexpensive Raman spectrometer is needed. In this context, for example, Ocean Optics Inc. (OOI) S2000 spectrometer could be used as the prototype. In particular, it is extremely compact, rugged, rather sensitive and relatively inexpensive. A standard 1200 lines/mm ruled grating optimized for 650 nm to 1200 nm spectral range can be installed in the spectrometer. A 25 $\mu$m×1000 $\mu$m entrance optical slit, being another resolution limiting element in the optical configuration of the S2000, in this particular case would provide optical resolution variable from 4 to 7 cm$^{-1}$ in the spectral region of interest. The detector is extremely important to effective functioning of the spectrometer. In order to obtain useful spectra, the detector should have sufficient number of closely spaced channels collecting light simultaneously. Two present detection systems that are commonly used for this purpose are charge coupled devices (CCD) and photodiode arrays (PDA). CCD are preferred as they have lower background noise levels and are extremely sensitive. CCD detectors are commercially available in a wide variety of shapes and sizes. Although they are constantly improved and become less expensive, CCD detectors are still remain the most expensive component of the spectrometer. Formats such as 512×512, 1024×256, 1024×1024, 2048 pixels by 512 pixels, etc are typical. Usually, such detectors must be cooled to below room temperature to minimize interfering, background noise levels. This can be accomplished by cooling with liquid nitrogen or water. Thermoelectric (Peltier) cooling becomes more and more popular recently. Some CCD devices utilize a technology referred to as multi-pin phasing (MPP) which lowers background signal levels and noise to achieve desirable performance at temperatures lowered by air cooling, but these are still expensive. Since, in a preferred embodiment, not only maximized signal and minimized noise, but also minimal instrument maintenance and low price are of importance, a properly air cooled CCD sensor was required. In the light of the above considerations and at the current state of the art, a CCD sensor "Sony ILX511" which is used in the Ocean Optics spectrometers could be a reasonable compromise. According to the manufacturers, the ILX511 is a rectangular reduction-type CCD linear image sensor designed for bar code hand scanner and optical measuring equipment use. A built-in timing generator and clock drivers ensure single 5V power supply for easy use. The sensor has 2048 pixels with a pixel size 14 μm×200 μm (14 μm pitch), ultra-high sensitivity and maximum clock frequency 2 MHz. CCD arrays such as the Sony ILX511 are charge transfer devices that have a fixed well depth (capacitor) associated with the photodetector. Signal to noise (S/N) ratio in photon noise systems is defined and indeed measured to be the root of the photons it takes to fill a well to saturation. In the ILX511 the full well is about 160,000 photons giving a SIN of 400. Traditional spectroscopic instruments usually use large well devices and 16 bit ADC's to achieve the defined S/N. According to the manufacturers, the Ocean Optics instruments use smaller well devices to do the same thing. That is, large-well devices are far less sensitive than small-well devices and thus require a longer integration times for the same output, although they achieve a good S/N because they integrate out photon noise. Small-well devices must use mathematical signal averaging to achieve the same result, but can do this in the same time period. In addition, electronics noise is reduced. Large-well devices require 16 bit ADC's in order to get the S/N level the array can achieve. Small-well devices can use inexpensive low power 12 bit ADC's to sample and achieve better than true 16-bit resolution with 256 samples (14-bit with only 16 samples). Large-well devices consume large amounts of power and can get warm. This usually results in the use of TE coolers to control temperature and reduce electronics (shot) noise. This then requires even more power, fans, etc. Small-well devices remain cool and electronic noise is reduced by signal averaging. The S2000 system consumes only 100 ma at 5 volts or 500 mW. Eight D size alkaline batteries with an 80% efficient switching regulator (12 volts to 5 volts) can operate an R2000 detector continuously for about 300 hrs or about 12 days.

In a preferred embodiment, fiber optic cables and/or complete fiber optic probes are advantageously used as a means of transmitting the source radiation to an authenticating mark and as a means of collecting the scattered radiation from the Raman-active mark. Traditional laboratory Raman instruments use a series of lenses, mirrors, and other optics to transmit and focus the source radiation to the sample. Advances in fiber optic cables, as described, for example, in *Appl. Spec.*, 1990, 44, pp. 1229–1231 by Allred et al., provide a simplified means to direct the radiation towards the sample. The simplicity, flexibility, and throughput efficiency of fiber optic cables make the prospect of remote sensing viable. However, the fused silica core of the fiber optic cable, though a weak Raman scatterer, can contribute an interfering background signal when long fiber lengths are used, as discussed in U.S. Pat. No. 5,112,127 and in *Appl. Opt.*, 1992, 36, pp. 7707–7715 Schoen et al., the disclosures of which are incorporated herein by reference. A principal technique used to overcome this problem employs optical filters positioned near the sample. These filters remove background-inducing radiation before interferences are generated. Fiber optic probes are typically used in conjunction with fiber optics cables to provide a means for transmitting radiation toward the sample and collecting the scattered radiation, as described, for example, in U.S. Pat. No. 4,573,761, the disclosures of which are totally incorporated herein by reference. Such probes may be constructed with combinations of fiber optic cables, lenses and/or mirrors. In one construction, for example, two or more optic fibers are secured closely together on the sampling end. One or more of these optic fibers is used to transmit the radiation to the sample, and one or more additional fibers is used to collect and transmit the scattered radiation towards the detector. In frames of the present invention, for example, an optimized "seven around one" fiber optic Enviva Raman probe manufactured by Visionex Inc. is preferred. A key aspect of this Raman probe is that photon manipulation occurs totally within the confines of the optical fiber. Light is not delivered to ancillary components (such as lenses, mirrors, etc.) for beam steering or filtering. This property lends itself to many advantages including high efficiency, robust architecture, rugged design, micro-sized packaging, etc. It is of importance for Raman applications that, owing to the "in-tip-filtering" technology exploited in the Enviva design, delivered (laser) light exits a fiber in a processed condition so that no external manipulation is required. Likewise, raw collected (Raman+Rayleigh) light enters a fiber and is internally processed. It should be obvious to specialists in the art that the above specific example is not intended to limit the scope of the invention described in this application.

In yet another preferred embodiment, the mark, pattern or image generated earlier on a member protected against forgery or counterfeiting in accordance with the invention, and thus now bearing a Raman-active taggant (or a mixture thereof, is authenticated "in the field" by employing a miniature waveguide Raman probe. Such waveguide can be thought of as miniaturized multiple internal reflection element (IRE) wherein the incident laser light undergoes total internal reflection at the interface between media of different refractive indices. At each internal reflection within the waveguide, a portion of the optical field, the evanescent wave, extends beyond the high-index waveguide into the adjacent low-index medium, to a depth dependent on the angle of incidence, the ratio of the two refractive indices and the laser wavelength. The ability of molecules outside the high-index waveguide, but near its surface, to interact with the energy travelling through the waveguide via this evanescent wave makes possible the phenomenon known as total internal reflection (TIR) or evanescent-wave Raman (EWR) spectroscopy. Applicability of TIR Raman spectroscopy to analysis of thin films (of a micron or sub-micron thicknesses) was hinted yet by Harrick et al., *Anal. Chem.* 45 (1973) 637, who for the first time measured TIR Raman spectra. The Raman signals they measured were, however, very weak and obscure, so that their results seemed to suggest that the method might not be promising as a practical method unless we could intensify the Raman signals. Later Iwamoto et al., *J. Chem. Phys.* 74, No. 9, 1981, pp. 4780–4790 has found that successful practical application of the TIR Raman method in the visible range crucially depends on selection of the material for the internal reflection element (IRE). It has been demonstrated that considerable improvement of S/N ratio of possibly very weak Raman signals can be achieved by using materials for the IRE that have the lowest background scattering possible. These recommendations has been taken into account by the present inventors during development of TIR Raman waveguides suitable for the purposes of the present invention. The basic configuration for the measurement of TIR Raman spectra of thin films is rather simple. The exciting NIR laser beam hits the end face of the IRE that has an appropriate end face angle, so that the refracted light is incident on the IRE/sample interface at an angle larger than the critical angle $\Theta_c$, which is given by $\sin \Theta_c = n_2/n_1$, where $n_1$ and $n_2$ ($n_1 > n_2$) are refractive indices of the IRE and the sample, respectively. The evanescent wave penetrating the sample gives rise to the Raman scattering, which is collected with the aid of an ancillary fiber optic Raman probe (e.g. such as the Visionex Enviva described above) and is transported to the spectrometer. The Raman scattering from the sample surface (in our case, from the surface of thin-layer prints and patterns produced, for example, by offset printing method using corresponding compositions comprising the Raman-active taggants of the invention) is inherently mixed with the Raman scattering which the laser beam produces during passing through the IRE itself, and it is not possible to isolate the former completely from the latter. In general, the passing length of the laser beam through the IRE is far greater than that of the evanescent wave through the sample. Therefore, even weak Raman peaks or background of the IRE can seriously interfere with measurements of supposedly rather weak Raman peaks produced by the evanescent wave from the sample surface. This requires the following properties to the IRE: (a) transparency in the NIR, (b) sufficiently larger refractive index than those of most samples, (c) absence of intrinsic Raman peaks in the frequency region above 500 $cm^{-1}$ of Raman shifts (which is most frequently used for detection of organic compounds), and (d) sufficiently low background scattering. Based on the optical restrictions (a)–(d) above, such high-refractive-index materials as Ge, Si, sapphire, diamond and KRS-5 ($Tl_2BrI$), are suitable for the NIR work. These materials can be cut and polished as prisms having trapezoidal or parallelogram cross-sections and miniature dimensions, as required for the particular application. When such small-area IRE is properly coupled to a pigtailed laser the advantage that miniaturization allows smaller amounts of sample to be detected displays. This advantage arises from the fact that, while the surface sensing area is smaller, the light experiences a larger number of reflection per unit length of the waveguide, yielding a concomitant increase in evanescent path length. Collection of the Raman light, as has been noted above, is accomplished with the aid of an "ordinary" fiber optic Raman probe, which simultaneously is responsible for filtering out the elastically scattered laser light.

Turning once again to the FIG. 12, it is worth noting that, although the Raman spectrum acquired with the portable dispersive spectrometer (FIG. 12b) is obviously inferior to that obtained with FT Raman instrument (FIG. 12a) in terms of both resolution (ca. 8 $cm^{-1}$ against the 4 $cm^{-1}$, respectively) and SNR (ca. 50 compared to ca. 100, respectively), the overall quality of the dispersive Raman spectrum is quite adequate for this spectrum to be unmistakably identified by a spectral search program. Note that, deliberately, in this particular example (demonstrating detectability of the taggants of the invention even with extremely simplified instrumentation), inexpensive diode laser having the output of only 15–20 mW, no thermal stabilization, ca. 1.0 nm bandwidth (HWHM) and exhibiting slight but measurable mode hopping during operation has been employed. Specialists in the art will probably recognize that, by virtue of optimization of the excitation source alone, the quality of the spectrum shown in FIG. 12b could be considerably improved. Of course, optimization of the other components of the system would do the same. As to the obvious redistribution of intensities of the Raman bands in the two spectra in FIG. 12, it is explained simply by different instrumental functions of the two spectrometers and, in particular, by that they are equipped with different detectors. Specifically, a silicon CCD array detector of the portable system has steeply decreasing sensitivity in the 900–1000 nm wavelength region, the latter being coincident with the Raman shifts of 1700–2700 $cm^{-1}$ in the spectra excited with 780–785-nm lasers, and, as a result, the intensity of the —C≡C— stretch Raman band around 2100 $cm^{-1}$ is cut in the bottom spectrum. Specialists in the art will probably appreciate that, despite a few obvious imperfections, the described above device can serve as a useful prototype of a fully instrumental, non-destructive Raman spectroscopic system for the detection, verification and authentication of inks, paints, toners, printing compositions as well as of marks on documents and financial instruments, thin films, plastics, and other items produced with the use of Raman-active compounds of the invention. The exemplified system is economical, portable and consists of a computer-controlled spectrometer, laser excitation source and collecting fiber optic probe. The spectrometer contains necessary signal processing electronics which sends a stream of data to the computer for analysis and correlation with, for example, a spectral library database on a PC hard disk.

Perhaps it should be noted that, in any Raman spectral measurement, the observed signal will always be a convolution of the desired (true) signal and an instrumental response. Normally, instrumental responses broaden, shift, or otherwise distort the desired signal. The methods are well known which make it possible to measure and compensate for both long-term and short-term variations and instabilities in the components of the Raman spectrometry apparatus. For example, this can be achieved by a referencing technique described in U.S. Pat. No. 5,455,673, the disclosures of which are totally incorporated herein by reference. Moreover, there are methods known in the art permitting to increase spectrum measurement accuracy by using digital signal processing instead of employment of improved optics and/or hardware reducing noise. Surprisingly, such methods of extracting information from an optical signal can be more efficient than sophisticated analog processing and are free of troubles characteristic thereof. This approach has significant advantages over optical processing. For example, though spectrometers have seen some significant advances in past years, digital processors are experiencing exponential performance gains. With enhanced performance, more complicated and sophisticated methods may be implemented. This allows for improved performance during the upcoming years and/or further miniaturization. Further, today's semiconductor-based integration technologies allow for VLSI implementation of digital processors and optical components. Moreover, an increase in accuracy of electrical digital signal processing does not necessarily imply an increase in technological difficulties of its implementation, which is typical of optical analog signal processing. A useful method of increasing the spectrum resolution is described, for example, in U.S. Pat. Nos. 5,991,023 and 6,002,479, the disclosures of which are totally incorporated herein by reference. Of course, more complex schemes of the Raman signal optimization can be used in frames of the present invention. It must be emphasized, however, that application of more complex optical or signal processing schemes are reserved by the present inventors for the case of employment, e.g., powerful and cheap but unstable multimode diode lasers. When true single-mode lasers are used in accordance with preferred embodiments of the invention, the sophisticated procedures are normally unnecessary due to inherently good quality of the NIR Raman spectra to be processed. Spectrometer calibrating procedures based, e.g., on measuring intermittently the unknown sample and a stable reference compound ("absolute standard") having a strong and well defined beforehand Raman spectrum, can also be used.

The Raman spectrum of the authenticating mark, pattern or image can be used in any desired manner. For example, software associated with the apparatus can be relatively simple and detect the presence or absence of one or more identifying peaks for a particular Raman-active taggant, subsequently giving a "yes" or "no" response to whether the taggant has been detected. Since the Raman spectrum is unique for each Raman-active taggant of the invention, it can also function as a "fingerprint" for that material. Thus, software associated with the apparatus can compare the measured spectrum from the article under authentication to a database containing the Raman spectra of several taggants and then indicate the identity of the taggant on the questioned article. Further, since mixtures of Raman-detectable components can be employed, their Raman spectra are superimposed on each other, and software associated with the apparatus can look for the unique spectrum formed from the superimposed spectra of each individual component contained in the mixture. Examples of software products for comparing Raman spectra with a library of reference taggants include those available from Sadtler Research Laboratories, Galactic Industries Corp., and the like. Alternatively, a tailor-made software package, e.g., that based on "Scientific Interactive Graphics" package available from SoftService, Moscow, Russia, may be used for performing the instrument control, signal processing, spectral search and "stop/pass" evaluation of the molecular codes employed in accordance with preferred embodiments of the invention.

The Raman-detectable mark can be employed for any desired purpose. Examples of purposes include those disclosed in, for example, U.S. Pat. No. 5,225,900 and U.S. Pat. No. 5,301,044, the disclosures of each of which are totally incorporated herein by reference.

Specific embodiments of the invention will now be described in detail. These examples are intended to be illustrative, and the invention is not limited to the materials, conditions, or process parameters set forth in these embodiments. All parts and percentages are by weight unless otherwise indicated.

EXAMPLE 1

General experimental setup I. A table-top system comprising a Perkin Ehner Corp. (Analytical Instruments, 761 Main Ave., Norwalk, Conn., 06859–0012 USA) NIR-FT Raman accessory fitted to a Perkin Elmer 1720 X FTIR spectrometer constituted the base of the first instrumental setup useful for accomplishing aims of the invention. The 1720X interferometer is furnished with a long-range KBr beam-splitter which gives a working range of between 370 and 10,000 $cm^{-1}$. A specially stabilized Spectron SL-301 c/w Nd:YAG laser emitting at 1064 nm (9394 $cm^{-1}$. $TEM_{00}$ mode) manufactured by Spectron Laser Systems Ltd. (Rugby, UK) specifically for Perkin Elmer was used, providing between 2 mW and 3.5 W at the sample with a stability of 0.1% RMS. The sample optics employed is based on a 180° back-scattering lens system (f/0.6). The laser beam is directed on to the sample via a small prism, and its diameter at the sample position is approximately 0.5 mm. The scattered radiation is focussed by a lens system to fill the 8 mm diameter Jacquinot stop of the interferometer. Three multi-layer dielectric transmission filters, one situated immediately beyond the Jacquinot stop and the other two prior to the detector, reject Rayleigh scattered radiation. An additional filter is used to eliminate the He—Ne laser line at 632.8 nm (inside the interferometer). The Raman sample box has dimensions of 24×24×35 cm, and can accommodate samples up to 13 cm high and 18 cm deep. All samples and sample accessories are mounted on an x, y, z adjustable stage within the Raman sample box. Sample holders for solids, gums, powders, films and liquids can be used which are slotted into a standard 3×2 inch infrared sample slide. In an embodiment, Raman-active compounds of the invention in powdered form were applied to a substrate by pressing the solid with spatula and removing loose material by gently blowing the area. Alternatively, a drop of solution of the compound in a low boiling solvent was applied onto a substrate with a pipette, and the solvent was permitted to evaporate. In both embodiments, the sample of a Raman-active compound (or composition) of the invention was applied onto a 2×2 cm piece of a sheet material to obtain near the center a small spot of the taggant a few square millimeters in area. Such samples were clamped into a standard infrared magnetic film holder, and the latter was inserted into the sample slide within the said sample compartment of the instrument. Alignment of the samples in the laser beam was achieved by monitoring the Raman spectrum in real time and adjusting the sample position in the x, y and z directions so that the Nd:YAG laser impinged on the treated spot. Different incident laser powers of from 5 mW to about 500 mW were used in experiments with different organic and organoelement compounds of the invention. The Raman spectrum obtained from the sample on a substrate was compared to the signal obtainable from an untreated spot on the same piece of the substrate. The filtering system allows the range of Raman shifts from 4000 to 150 $cm^{-1}$ to be scanned routinely. The detector is a 2 mm diameter semiconductor photo-diode made from InGaAs manufactured by EG&G Inc. At room temperature the maximum Raman shift recordable with this detector is 3500 $cm^{-1}$, whereas cooling the detector with liquid nitrogen reduces this to 3000 $cm^{-1}$. Both regimes were used in this work. Although resolutions of 0.5, 1, 2, 4, 16, 32 and 64 $cm^{-1}$ with two data points per resolution interval are available in both infrared and Raman mode on this system, 4 $cm^{-1}$ resolution and normal apodisation function were used standardly for all experiments relevant to this invention. Data manipulation was carried out on a PC in DOS or Windows'95 environments with the aid of PE IRDM and Galactic Industries Inc. GRAMS/386 software. All spectra are provided uncorrected for the instrument response function.

EXAMPLE 2

General experimental setup II. In another preferred embodiment of the invention, an alternative instrumental setup based on a miniature Raman spectrometer furnished with a fiber optic sampling probe was used for taking measurements directly "in the field". The complete system includes a S2000 miniature spectrometer manufactured by Ocean Optics Inc. (Dunedin, Fla. USA), an Enviva fiber optic Raman probe manufactured by Visionex Inc. (430 Tenth Street, N.W., Suite N205, Atlanta, Ga. 30318 USA) and, for example, an INF-780 single-mode AlGaAs diode laser manufactured by World Star Tech Inc.(Canada) as the main components. The S2000 spectrometer is based on a Czerny-Turner-type miniature spectrograph and has a Sony ILX511 noncooled rectangular reduction-type CCD linear image sensor as the detector. The sensor has 2048 pixels with a pixel size 14 $\mu m \times 200$ $\mu m$ (14 $\mu m$ pitch) and maximum clock frequency 2 MHz. In accordance with aims of the invention, a 1200 lines/mm ruled grating optimized for 650 nm to 1200 nm spectral range and a 25 $\mu m \times 1000$ $\mu m$ entrance optical slit have been installed. This particular setup provides optical resolution variable from 4 to 7 $cm^{-1}$ in the spectral region of interest. For the ILX511, the full well is about 160,000 photons giving a S/N of 400. The Enviva biomedical fiber optic Raman probe has a Visionex Inc. proprietary "In-The-Tip" filters on delivery and collection fibers. The fibers are all-silica (NA 0.22) in black Teflon spaghetti tubing. One 300-μm laser light delivery fiber is encircled by seven 300-μm Raman light collecting fibers. The collecting fibers have numerical aperture 0.22 at instrument end, while the distal end is realigned with proprietary Visionex Gaser light management technology. All eight optics are housed at the distal end in a stainless steel needle having length 43 mm and diameter at the tip of 1.5 mm. At the instrument end, the laser delivery fiber and the collecting fibers are separately SMA 905 terminated (the 7 collecting fibers are terminated into slit-style). The probe has overall length of 1.5 meter. A key aspect of this Raman probe is that photon manipulation occurs totally within the confines of the optical fiber. This property lends itself to many advantages including high efficiency, robust architecture and rugged design. Owing to the "in-the-tip" filtering technology exploited, delivered laser light exits a fiber in a processed condition so that no external manipulation is required. Likewise, raw collected light enters a fiber and is internally processed. The WSTI INF-780 laser was used as an external source, and the beam was inserted into the probe delivery fiber by using a 'laser to fiber' coupler with adjustable focus (>80% coupling efficiency nominally) manufactured by OZ Optics Ltd. (219 Westbrook Rd., Carp, ON Canada). Optionally, instead of the said INF-780 single-mode AlGaAs 40-mW diode laser pointer (12 VDC power supply, reverse polarity protected, 4 mm dia. collimated beam), diode lasers of other manufacturers have been used in a number of experiments. In all cases, the instrument spectral range was about 2700–200 $cm^{-1}$ of Raman shifts (785–1000 nm) when diode lasers were used as the excitation sources. A 500-kHz microprocessor-controlled Serial Port Interface A/D converter SAD500 manufactured by Ocean Optics Inc. was used to interface the S2000 spectrometer to desktop or portable PCs. The spectra were run by contacting the tip of the probe with a sample of a Raman-active compound (or composition thereof) on a substrate in situ. An integration time of 5–10 s was used in most cases. Data manipulation was carried out on a PC in Windows'95 environment with the aid of the proprietary Ocean Optics OOIBase and Galactic Industries Inc. GRAMS/386 software It should be obvious to specialists in the art that the above specific examples of hardware and software are not intended to limit the scope of the invention described in this application.

EXAMPLE 3

General experimental setup III (Co-pending application possible). In another embodiment, an optional experimental setup has been devised and used for measuring thin-film prints produced in accordance with the present invention. To enhance detectability of the marks, patterns or images generated on a carrier in accordance with the invention, and thus now bearing a Raman-active compound of the invention (or a mixture thereof), a miniature waveguide Raman probe was used in frames of the general setup described in Example 2. More powerful 785-nm pigtailed diode laser module, for example, that manufactured by BWTec Inc., was used as an external excitation source in this setup. Such pigtailed single-mode laser gives up to 500 mW at the distal fiber end, the spectral bandwidth of the laser line to be about 1.2 nm HWFM. The exciting NIR laser beam was inserted through the end face of an internal reflection element (IRE) that had an appropriate end face angle, so that the refracted light was incident on the IRE/sample interface at an angle larger than the critical angle $\Theta_c$, which is given by $\sin \Theta_c = n_2/n_1$, where $n_1$ and $n_2$ ($n_1 > n_2$) are refractive indices of the IRE and the sample, respectively. The evanescent wave penetrating the sample gave rise to the Raman scattering. The IRE's made from germanium, silicon and diamond have been tested and turned out to be suitable for detecting Raman-active compounds of the invention applied onto different substrates by offset, xerographic and ink-jet printing methods. Several IRE's from these materials were cut and polished as prisms having trapezoidal or parallelogram cross-sections and dimensions from 2×2×2 mm up to 5×5×3 mm. Usually the distal end of the laser light delivering fiber was cut and polished at the desired angle (depending on refractive index of the IRE material) and then "glued" with an anti-reflecting optical adhesive onto the end face of an IRE. In several instances, a diffraction grating made on the end face of an IRE was used to optimize the excitation light coupling. Since unfiltered silica fibers were used for transporting the laser light to the IRE, the Raman scattering from the sample surface (from the surface of thin-layer prints, in this case) was inherently mixed with the Raman scattering which the laser beam produced during passing through the delivering fiber and the IRE itself, and it was not possible to isolate the former completely from the latter. Accordingly, collection of the Raman light was accomplished with the aid of the Visionex Enviva fiber optic Raman probe described in Example 2, which was responsible for filtering out the elastically scattered laser light. Although thickness of the layers produced by different printing methods varied from 2 to 20 μm in the cases studied, additional investigations showed that only 0.3–0.6 μm layers were operative in providing the Raman signal. The small-area IRE's turned out to be more preferred in frames of the invention compared to the large-sized ones. When such small-area IRE is properly coupled to pigtailed laser, the light experiences a larger number of reflection per unit length of the waveguide, yielding a concomitant increase in evanescent path length. Using a λ/4 wavelength layer on the IRE sampling surface made of a material with a higher refractive index also was helpful for obtaining stronger Raman signals. The spectra of thin-film samples were taken in situ by pressing the IRE to the sample with the Enviva probe tip. An integration time of 10–60 s were used depending on the type of the sample studied. Data manipulation was carried out on a PC in Windows'95 environment with the aid of the proprietary Ocean Optics Inc. OOIBase and Galactic Industries Inc. GRAMS/386 software It should be obvious to specialists in the art that the above specific examples of hardware and software are not intended to limit the scope of the invention described in this application.

EXAMPLE 4

Preparation of 4-Nitrophenyl propargl ether. Procedure. To a solution of 10 g of propargyl alcohol (Merck) in 10 ml of dimethylsulfoxide 1.5 g of $K_2CO_3$ was added and the mixture kept stirring. 28 g of 4-Nitrofluorobenzene (Aldrich) was added gradually and the mixture stirred at room temperature for 3 days. It was poured into excess water slightly acidified with HCl. Thin layer chromatography (Ethylacetate/Hexane 3:7) showed two spots, one of which was identical with 4-nitrofluorobenzene. Preparative column chromatography on silica gel and removal of the eluent on a rotor evaporator gave a pale yellow solid (16 g, Yield ca. 50%) having m.p. 108–110° C. Analysis: IR (KBr): 3174 ($\equiv$C—H), 1581, 1316, 847 (Ar—$NO_2$) $cm^{-1}$. Having been applied onto a printing paper and analyzed as described in Example 1, the compound gave an intense NIR FT-Raman spectrum in some features similar, but clearly not identical, to that shown in FIG. 1(A) for 1-ethynyl-4-nitrobenzene (exemplary Compound #16 of the invention).

EXAMPLE 5

Preparation of N-(3-Iodo-2-propynyl)carbazole. Procedure: To a solution of 1.23 g (0.006 mol) of N-(2-propynyl)

carbazole in 19.2 mL of methanol 4.8 mL of water and 0.48 g of NaOH were added while stirring at 4° C. Addition of 6 mL of tetrahydrofurane (THF) to the turbid suspension resulted in a homogeneous solution. Then 1.52 g of crystalline iodine was added portion-wise. After 10 min of stirring the iodine color disappeared and the product started to separate as a dense white precipitate. Over 8 hrs of stirring at room temperature the product was filtered, washed with distilled water and air dried. 1.25 g (Yield 65%) of N-(3-Iodo-2-propynyl)carbazole has been obtained as crystals having m.p. 151–152° C. When applied onto a printing paper and analyzed according to Example 1, the compound gave an intense NIR FT-Raman spectrum in some features similar, but clearly not identical, to that shown in FIG. 1(A) for copper phenylacetylide (exemplary Compound #26 of the invention).

EXAMPLE 6

Preparation of 2,2,6,6-Tetramethyl-4-hydroxy-4(propyn-2-yl)piperidine. Procedure: To a solution of propargyl magniumbromide, which has been prepared from 2.4 g (0.1 mol) of Mg and 11.9 g of propargylbromide, 7.8 g (0.05 mol) of triacetonamine (Tambov, Russia) dissolved in 50 mL of absolute ether were dropped at −30° C. (dry ice/acetone bath) while stirring during 1 h. Then a saturated solution of $NH_4Cl$ has been added at 0° C. The precipitate was filtered, washed with ether and triturated with KOH solution. 8.39 g of crude 2,2,6,6-Tetramethyl-4-hydroxy-4(propyn-2-yl) piperidine isolated as a white powder (Yield 86%) was purified further by vacuum sublimation. This gave product with m.p. 74–75° C. Analysis, for $C_{12}H_{21}ON$ (%): Calctd. C, 73.79; H, 10.84; Found C, 73.84; H, 10.92. IR (cm$^{-1}$, KBr): 2120 (C≡C), 3310 (H—C≡), 3570 (N—H), 3400 (O—H). $^1$H-NMR (250 MHz, δ, $CDCl_3$): 1.11 s and 1.38 s (12H, $CH_3$), $CH_2$-cycle AB-spectrum: 2.05 d (2H, A-part, $J_{AB}$=13.45 Hz), 1.77 d (2H, B-part), 2.05 b, s (1H, NH), 2.11 t (1H, HC≡C, J=2.6 Hz), 2.30 d (2H, $CH_2$—C≡C, J=2.6 Hz). $^{13}$C-NMR (δ, $CD_3OD$): 29.3 and 35.4 ($CH_3$), 36.6 ($CH_2$ of propargyl), 46.4 ($CH_2$ of cycle), 51.3 (C-N), 72.3 (HC≡C), 72.5 (C—O), 81.25 (HC≡C). Having been applied onto a printing paper and analyzed as described in Example 1, the compound gave an intense NIR FT-Raman spectrum in some features similar, but clearly not identical, to that shown in FIG. 1(A) for 2,2,4,4-tetramethyl-1,2,3,4-tetrahydro-3-oxyl-9-(2-propynyl)-γ-carbolyne (exemplary Compound #20 of the invention).

EXAMPLE 7

Preparation of 1-[9-(2,2,4,4-Tetramethyl-1,2,3,4-tetrahydro-3-oxyl-γ-carbolynyl)]-hexa-2,4-diyn-6-ol. Procedure: To a mixture of 2.8 g (0.01 mol) of 2,2,4,4-tetramethyl-1,2,3,4-tetrahydro-3-oxyl-9-(2-propynyl)-γ-carbolyne (Compound #20 of the invention), 0.025 g of CuCl, 2 mL of 70% ethylamine/water solution, 0.05 g of $NH_2OH.HCl$ and 8 mL of THF a solution of 1.45 g of propargyl alcohol (Merck) in 1 mL of THF has been added drop-wise under an argon blanket during 20 min while stirring. After additional stirring for 1.5 hrs the reaction mixture was transferred into 60 mL of 1%-NaCN water solution, and the product was extracted with diethyl ether. The extract was washed with water and dried over $MgSO_4$. Purification by column chromatography (Aldrich $SiO_2$ L100/160, ethylacetate/hexane 3:7, product in the 3rd colored zone) and recrystallization from acetone/hexane gave 0.81 g (Yield 24%) of 1-[9-(2,2,4,4-Tetramethyl-1,2,3,4-tetrahydro-3-oxyl-γ-carbolynyl)] hexa-2,4-diyn-6-ol as orange crystals. Being applied onto a printing paper and analyzed as described in Example 1, the compound gave an intense NIR FT-Raman spectrum identical to that shown in FIG. 1(C, top) for the exemplary Compound #97 of the invention.

EXAMPLE 8

Preparation of 4,4$^1$-(distyryl)tolane. Procedure. A three-neck flask equipped with a reflux condenser, a stirrer, and an inlet for feeding argon was charged with p-diiodotolane (4.3 g, 10 mmol), styrene (6.8 ml, 60 mmol), palladium acetate (0.045 g), and tributylamine (4.8 ml). The reaction mixture was heated at 100° C. for 10 h. Upon cooling, the precipitated product was filtered, thoroughly washed with cold ethanol, and air dried. The product was recrystallized from Dimethylformamide (DMF) and dried in vacuo at 80° C. overnight. The yield of the product was 83%; m.p.= 308–309° C. Analysis: For $C_{45}H_{28}$, calcd.(%): C, 92.50; H, 4.82; Found (%): C, 92.41; H, 4.93. Having been applied onto a printing paper and analyzed as described in Example 2, the compound gave an intense NIR Raman spectrum in some features similar, but clearly not identical, to that shown in FIG. 1(B, top) for 4,4$^1$-bis(1-ethynylphenylglyoxalyl) tolane (exemplary Compound #79 of the invention).

EXAMPLE 9

Preparation of 1,4-bis[(4-phenylglyoxalyl) phenylethylnyl]benzene. Procedure. A three-neck flask equipped with a condenser, a stirrer, and an inlet for feeding argon was charged with p-iodo(phenylglyoxalyl)benzene (2.89 g, 10 mmol), p-diethynylbenzene (0.63 g, 5 mmol), $PdCl_2(Ph_3P)_2$ (0.07 g, 0.1 mmol), $Ph_3P$ (0.066-g, 0.25 mmol), copper monoiodide (0.01 g, 0.05 mmol), and triethylamine (60 ml). The reaction mixture was stirred at 50° C. for 5 hrs, the reaction being monitored by thin layer chromatography. Upon cooling, the precipitated product was filtered, washed with triethylamine, water, and ethanol, and dried. The product was further purified by recrystallization from DMF, and dried in vacuo at 80° C. overnight. 3.04 g (Yield 93%) of the product with m.p. 229–230° C. has been obtained. Analysis for $C_{38}H_{22}O_4$, %: Calcd. C, 84.11; H, 4.09; Found C, 83.98; H, 4.07; $^1$H NMR, ppm: 7.98 (d, 4H, I=7.1 Hz, 12H, 12'H); 7.97 (d, 4H, I=8.2 Hz, 7H, 7'H); 7.66 (m, 2H, I=7.5 Hz, 14H); 7.54 (s, 4H, 1H, 1'H); 7.51 (t, 4H, I=7.1 Hz, 13H, 13'H); $^{13}$C NMR, ppm: $C_1$(4) Found 199.62 (Calcd. 196.91); $C_2$(4) 125.60 (126.40); $C_3$(4) 132.63 (133.90); $C_4$ 128.05 (126.20); $C_5$ 130.01 (128.45); $C_6$ 128.27(127.70); $C_7$ 153.13(151.50); $C_8$ 130.24 (131.60); $C_9$ 127.61 (125.80); $C_{10}$ 131.17 (132.00); $C_{11}$ (4) 122.75 (121.50); $C_{12}$ 127.61; $C_{13}$ 131.17; $C_{14}$(4) 122.75. Having been applied onto a printing paper and analyzed as described in Example 2, the compound gave an intense NIR Raman spectrum apparently similar, but clearly not identical, to that shown in FIG. 1(I, top) for a poly(phenylethynyl) quinoxaline (exemplary Compound #134 of the invention).

EXAMPLE 10

Preparation of 4,4$^1$-Bis(phenylglyoxalyl)tolane. Procedure. A three-neck flask equipped with a reflux condenser, a stirrer, and an inlet for feeding argon and acetylene was charged with p-iodo(phenylglyoxalyl)benzene (3.36 g, 10 mmol), bis(triphenylphosphine)-palladium chloride (0.07 ml, 0.1 mmol), copper monoiodide (0.01 g, 0.05 mmol), and dry diethylamine (60 ml). A stream of acetylene and argon gases (1:1) was bubbled through the reaction mixture at a rate of 1 L/h. The reaction was carried out at room temperature for 2 hrs. The precipitated product was filtered, washed with diethylamine, and air dried. The product was further purified by passing it through a chromatography column (silica gel, benzene as eluent) and recrystallized from hot $CCl_4$/benzene 4:1 mixture. This gave 2.35 g (Yield 61%) of yellow fibrous crystals with m.p. 209–210° C. Analysis, for $C_{30}H_{18}O_4$: calcd.(%): C,81.43; H, 4.08; Found (%): C, 81.56; H, 4.10. $^1H$ NMR, ppm: 7.98 (d, 4H, I=8.3 Hz, 4H, 4'H); 7.97 (d, 4H, I=8.3 Hz, 9H,9'H); 7.66 (d, 4H, I=8.3 Hz, 3H, 3'H); 7.67 (m, 2H, I=7.2, 11H); 7.52 (t,4H, I=7.8 Hz, 10H, 10'H; $^{13}C$ NMR, ppm: $C_1(C\equiv\!-\!\!C)$ Found 92.40 (Calcd.); $C_2(4)$ 128.89 (128.50); $C_3$ 132.15 (132.50); $C_4$ 129.73 (129.30); $C_5(q)$ 130.01 (132.70); $C_6(C\!=\!O)$; $C_7(C\!=\!O)$; $C_8(q)$ 132.64 (133.00); $C_9$ 129.84 (129.70); $C_{10}$ 128.96 (128.90); $C_{11}$ 134.97 (134.70). 1.0 g of the product was dissolved along with 3.0 g of polystyrene granules in benzene. Spin-casting of the solution gave a yellowish transparent coat (25 μm) on a 2×2 cm silicon chip. Analysis of the sample from both sides (the coat faced, and the silicon substrate faced to the laser) in accordance with Example 1 gave intense NIR-FT Raman spectra apparently similar, but clearly not identical, to that shown in FIG. 1(I, bottom) for poly-(p-diethynylbenzene-m-phenylene)-ethynylene (exemplary Compound #132 of the invention).

EXAMPLE 11

Preparation of a poly(phenylethynyl)quinoxaline. Procedure. A three-neck flask equipped with a reflux condenser, a stirrer, and an inlet for feeding argon was charged with 1,4-bis[(4-phenylglyoxalyl)phenylethynyl]benzene prepared as in Example 9 (0.543 g, 1 mmol), 3,3',4,4'-tetraaminodiphenyloxide (0.23 g, 1 mmol) and m-cresol (2.5 ml). After heating at 120° C. for 7 hrs while stirring, the mixture was cooled to 20° C. and poured into methanol (150 ml). The precipitated polymer was filtered, washed with methanol, and dried at 100° C. in vacuo overnight, giving 0.7 g of fibrous solid with $T_{soft}$=260° C. Having been applied onto a printing paper and analyzed as described in Example 2, the compound gave an intense NIR Raman spectrum identical to that shown in FIG. 1(I, top) for a poly (phenylethynyl)-quinoxaline (exemplary Compound #134 of the invention).

EXAMPLE 12

Preparation of a binary mixture of Raman-active compounds. Procedure. 5.0 mL of a composition comprising about 5 parts by weight of polyacetylene nanoparticles, 15 parts by weight of poly(vinylbutyral) and 80 parts by weight of n-butanol (prepared as has been described in Vysokomolekulyarnye Soedineniya, Ser. B, 1994, 36, No. 5, pp. 881–894), was mixed in a beaker with 3.0 part by weight of a material (Institute of Chemical Physics, 4 Kossygina Str., Moscow, Russia) which is believed to be mainly fullerene C60 containing trace amounts of C70. The beaker was placed into a Bransonic laboratory ultrasonic bath, and sonicated at 30° C. for 2 hrs. An aliquot of the composition was applied onto a glass slide and spread across the surface by doctor-blading. The coating was dried under water respirator vacuum at room temperature until the constant weight. The peeled off the glass freely standing very dark blue film (about 50 μm thick) was transferred into the NIR-FT Raman sample compartment and analyzed as described in Example 1. The intense spectrum obtained at 20 mW of incident Nd:YAG laser power was a clear superposition of the spectra of the neat components shown in FIGS. 1(G) and 1(H), respectively.

EXAMPLE 13

Preparation of a Raman-active diacetylene compound. Synthesis of 5,7-dodecadiyne-1,12-diol. A 0.5 liter 3-necked flask equipped with a high-speed stirrer, dropping funnel, and an inlet for feeding oxygen gas was charged with 100 mL of methanol, 15 mL of N,N,N',N'-tetramethyl ethylenediamine (TMEDA), and 9 g of CuCl. Using the Hay method [see A. S. Hay, J. Org. Chem., 25 (1960) 1275], 5-Hexyn-1-ol (Aldrich) (75 mL) charged into a dropping funnel was oxidatively coupled by adding it dropwise to the reaction mixture over a 45 minute time period while oxygen was being bubbled into the vigorously stirred reaction media. During the addition, the temperature of the mixture rose to approximately 50° C., then subsided. Oxygen was bubbled into the reaction media for additional 8 hrs before isolation of the product. The reactor contents were transferred into 1000 mL of chilled water acidified with HCl to pH 2 to precipitate the product. The product was filtered and washed with distilled water. After air drying on a filter paper, the solid was dissolved in 200 ml of hot xylene/heptane 2:1 mixture, and the solution was refrigerated at −8° C. After filtration the precipitate was washed with chilled hexane and dried under vacuum. Yield: 65 g of 5,7-dodecadiyne-1,12-diol as a fluffy white product. Having been applied onto a printing paper and analyzed as described in Example 2, the compound gave an intense NIR Raman spectrum in some features similar, but clearly not identical, to that shown in FIG. 1(C, middle) for N,N'-bis(3,5-dinitrophenyl)-2,4-hexadiyne-1,6-diamide (exemplary Compound #109 of the invention).

EXAMPLE 14

Preparation of a UV-polymerizable Raman-active monomer. A mixture of 40 g 5,7-dodecadiyne-1,12-diol prepared as described in Example 13, 250 ml 1,2-dimethoxyethane, 1 g dibutyltin-di-2-ethylhexanoate and 15 ml triethylamine was prepared in a three-neck flask equipped with a stirrer, a dropping funnel and an inlet for argon blanking through a 'FireStone' valve, and the resulting mixture was stirred vigorously. A solution of 120 ml of 4-(butoxycarbonyl)-methyl isocyanate in 50 ml of 1,2-dimethoxyethane was added dropwise over a period of 60 min. After that, the mixture was stirred for an additional 2 hrs. Then the mixture was transferred into 1000 ml of chilled hexane. The precipitate was collected by filtration, washed with petroleum ether (b. r. 30–60° C.) and dried, giving 155 g (98% yield) of desired product, m.p. 74–75° C. Anal: IR (KBr pellet): 3330 cm$^{-1}$ (N-H stretching), 2920+2850 cm$^{-1}$ (C—H stretching), 1680 cm$^{-1}$ (C=O), 1530 cm$^{-1}$ (N-H bending), 1470 cm$^{-1}$ (C—H), 1260 cm$^{-1}$ (C—O—C) stretching. Upon exposure to light, the crystals changed to blue, indicating the compound, 5,7-dodecadiyne-1,12-diol bis(4-butoxycarbonyl)methylurethane (hereinbelow referred to as 4BCMU), was solid-state polymerizable. Having been applied onto a printing paper and analyzed as described in Example 2, the compound gave an intense NIR Raman spectrum in some features similar, but clearly not identical, to that shown, for example, in FIG. 1(C, top) for 1-[9-(2,2,4,4-Tetramethyl-1,2,3,4-tetrahydro-3-oxyl-γ-carbolynyl)]hexa-2,4-diyn-6-ol (exemplary Compound #97 of the invention).

EXAMPLE 15

Preparation of a thermochromic polymer. In a thin-film construction, sufficiently high depths of the solid-state polymerization can be achieved by irradiating diacetylenic monomers with UV-light. A 2×2 cm piece of a filter paper has been impregnated with a 5%-solution of 4BCMU (cf. Example 14) in acetone. Evaporation of the solvent at room temperature resulted in a plenty of microscopic colorless microcrystals of the monomer formed on both surfaces as well as in pores within the paper. The sample was irradiated under a laboratory bactericide UV lamp ($\lambda_{max}$=254 nm) at a distance of ca. 15 cm by turning the sample from side to side for ca.15 min in total. At the end of the irradiation procedure the sample had an intense dark-blue-black color with a bronze luster. Analysis of this sample in accordance with Example 1 at 10 mW of incident laser power gave an intense NIR-FT Raman spectrum identical to that shown in FIG. 1(J, middle) and belonging to poly[dibutyl-4,19-dioxo-5,18-dioxa-3,20-diaza-10,12-docosadiynedioate] (hereinbelow referred to as poly-4BCMU). The almost total absence of the signal at 2260 cm$^{-1}$, corresponding to vibration of the diacetylenic fragment in the monomer, evidenced for rather high depth of polymerization (conversion degree) achieved by means of UV-irradiation.

EXAMPLE 16

Thermochromism tests. Visual tests for thermochromicity of poly-4BCMU were carried on a temperature-controlled hot stage. It was noted that the dark-blue-black polymer evidenced dramatic irreversible color change to red at around 50–60° C. In the course of further heating to higher temperatures, the polymer changed to bright orange, then to orange-yellow and, finally, to lemon-yellow at about 130° C. The red color was restored back on cooling. This thermochromic cycle could be repeated many times with no apparent degradation. In addition, this material was also investigated using diffuse reflectance spectroscopy. The results are illustrated by the electron spectra shown in FIG. 17.

EXAMPLE 17

Dynamical authentication of a thermochromic mark by using general experimental setup 1. A sample of poly-4BCMU analogous to that used in Example 15 was fixed in good thermal contact on the brass end of a Spectra-Tech proportional heater by means of a thin quartz cover plate and a miniature wire spring clip. This controller/heater set is equipped with a chromel-alumel thermocouple and gives ±1° C. precision in temperature readings. The heater with the sample mounted on it was fixed onto an XYZ-stage inside the NIR-FT Raman sample compartment. Before the heating run, the position of the polymer sample has been optimized at room temperature by means of the XYZ-stage iterative movements, while in the instrument monitoring mode, to achieve a maximum intensity of the polymer $\nu$(C≡C) Raman band at 2084 cm$^{-1}$. After that, the power of the incident laser beam was fixedly set at a lowest level sufficient for satisfactory SNR (a few mW), and had not been varied till the end of the whole experiment. NIR-FTR spectra of the sample in the course of the heating run were taken successively over the measured time intervals after the step-wise incremental rises of the temperature on the heater setter (for +2° C. in this experiment). 2–10 Individual scans were coadded (0.1–1.0 min) at each given temperature. All Raman spectra are reported uncorrected for the instrumental response function. Analytical value of thermochromic polymers in frames of the invention is illustrated by thus obtained dynamic spectra sets shown in FIGS. 18, 19 and 20. In these figures, the oblique axis reads the temperature of the sample, ranging from 25° C. to 140° C., applied to the sample to accomplish thermally induced structural transformations concomitant with the visually perceptible thermochromic changes for the sample of the conjugated polymer. The horizontal axis represents the Raman shift values measured in wave numbers. The vertical axis depicts the intensity of the observed Raman signals drawn to an arbitrary scale.

EXAMPLE 18

Authentication of a thermochromic mark at different specified temperatures. Using the sample of poly-4BCMU, and the sample fixing and adjusting procedures analogous to those of Example 17, the NIR-FT Raman spectra of the thermochromic mark on paper were acquired only at discrete specified temperatures of 25° C. (room temperature), 50° C., 90° C. and 120° C. The results are illustrated by the spectra in FIG. 21. The spectra are stacked for clarity.

EXAMPLE 19

Preparation of a Raman-active diacetylene compound. Procedure. Synthesis of 2,4-hexadiyne-1,6-diol. Using a general synthetic procedure of Hay described in Example 13, 75 ml of propargyl alcohol (Merck) were oxidatively coupled to produce 2,4-hexadiyne-1,6-diol. Isolation: The reactor contents were transferred into 1000-mL rotor-evaporator flask, and processed under water aspirator vacuum until a semi-solid yellow cake formed in the flask. 500 ml of 1N hydrochloric acid was added to the cake and agitated until the cake dissolution. The acidic solution was extracted by diethyl ether (10×100 ml). The combined extracts were washed with water, and dried over MgSO$_4$. Freeding from ether on a rotor gave 60 g of crude creamy solid. Further purification by recrystallization from boiling toluene gave about 50 g (Yield 66%) of 2,4-hexadiyne-1,6-diol as slightly yellow platelets with m.p. 110–111° C. Having been applied onto a printing paper and analyzed as described in Example 2, the compound gave an intense NIR Raman spectrum in some features similar, but clearly not identical, to that shown in FIG. 1(C, bottom) for Bis-[(2,2,6,6-Tetramethyl-1-oxyl-1,2,5,6-tetrahydropiridinyl-4-)]-tetra-1,3-diyne (exemplary Compound #94 of the invention).

EXAMPLE 20

Preparation of a thermally polymerizable Raman-active diacetylene compound. Procedure. A 500 ml, three-necked, round bottom flask was fitted with a mechanical stirrer, a thermometer and a dropping funnel. To the flask was added 40.00 g (0.20+mole) of p-toluene sulfonyl chloride, 11.0 g (0.10 mole) of 2,4-hexadiyne-1,6-diol and 200 ml of THF. The reactor was immersed into ice/water cooling bath, the reaction mixture was stirred vigorously, and a solution of 16.8 g (0.30 mole) of potassium hydroxide in 40 ml of water was added drop-wise over a period of 15–20 min, the temperature being held in the range of 4–8° C. After vigorous stirring at the ice/water bath temperature for additional 1.5 hr, the reaction mixture was poured into 500 ml of ice-water. The product precipitated as fine whitish crystals which rapidly turned pink under effect of diffuse room light. The product was isolated on Shott filter under water respirator vacuum, and immediately washed on the filter with 100 ml of chilled ethanol. The yield of the product, 2,4-hexadiyne-1,6-diol bis-p-toluene sulfonate (hereinbelow referred to as PTS), was almost quantitative. Analysis: I.R. (KBr pellet, cm$^{-1}$: 3080 (Ar—H stretching), 2980+2920 (CH stretching), 1600 (phenyl C=C stretching), 1370 (S—O), 1180 (S—O), 740 (Ar—H). NIR-FT Raman: 2272 cm$^{-1}$ (diacetylenic —C≡C— stretch)

EXAMPLE 21

Raman-active mark with time dependent characteristics. Following the procedure described in Example 17, a marked by PTS piece of paper was fixed in good thermal contact on the tip of the heater. Before the thermal polymerization run, the position of the PTS monomer mark was optimized by means of the XYZ-stage iterative movements while in the instrument monitoring mode, to achieve a maximum intensity of the monomer $\nu(C{\equiv}C)$ Raman band at 2272 cm$^{-1}$. After that, the power of the incident laser beam was fixedly set at a lowest possible level (15 mW was sufficient to obtain a SNR which would quite satisfactory for recording the first spectrum in the series), and was not changed till the end of the experiment. Thermal polymerization of PTS monomer in an isothermal regime was accomplished then in situ, being started by setting 80° C. temperature and turning the temperature controller/heater on. The spectra of PTS in the course of polymerization were taken successively over the measured time intervals, and 2–10 individual scans were coadded (0.1–1.0 min). A series of spectra obtained in the course of the experiment are shown in FIGS. 22($a$) and 22($b$). Both figures are two dimensional projections, sometimes called a hidden line view, of a three dimensional surface which conveys the NIR-excited Raman response of a conjugated polymer (poly-PTS, sub-class J of the invention in this case) during the process of its formation from the corresponding monomer. In FIG. 22, the oblique axis shows the time elapsed from the start of the solid-state polymerization reaction in minutes. The horizontal axis represents the Raman shift values measured in wave numbers. The vertical axis depicts the intensity of the observed Raman signals drawn to a constant arbitrary scale. Specialists in the art will probably appreciate that such polymerization depth-dependent marks will be produced outside the sample compartment of the instrument. A NIR-Raman spectrometer will be used then for detecting the mark meeting a specified criteria such as, for example, the specified intensity ratio of 1:1 for the two Raman bands shown in FIG. 22($b$). The specified ratios, for example, 1:2, 1:2.5, 1:3, and so on, could be reserved for other individual marks useful for authentication of a number of different items.

EXAMPLE 22

Comparison of detectability of Raman-active compounds of the invention with the aid of different Raman instruments. Having been applied onto a printing paper from 5% solution of PTS monomer in acetone, the PTS mark was polymerized up to 100 percent conversion of the monomer into the polymer (hereinbelow referred to as poly-PTS) by annealing the sample at 80° C. for eight hrs in an oven. Following the procedure described in Example 1, a NIR-FT Raman spectrum of poly-PTS was acquired at incident Nd:YAG laser power of 10 mW. The spectrum was identical to that shown in FIG. 12($a$). The same poly-PTS mark on a paper was analyzed then using General experimental setup II described in Example 2. The spectrum acquired at incident power of 10 mW from AlGaAs 785-nm laser was identical to that shown in FIG. 12($b$). Both spectra are shown uncorrected for the instruments response functions.

EXAMPLE 23

Comparison with the prior art. To compare their NIR Raman-activity with that of compounds of the present invention, a number of squaraine compounds was prepared by synthetic procedures described, for example, in *Synthesis*, 1980, p. 961 by A. H. Schmidt; *Angew. Chem., Int. Ed. Engl.* 1968, 7, p. 530 (ibid. 1966, 5, p. 894) by H. E. Sprenger and W. Ziegenbein; and in *J. Org. Chem.* 1992, 57, pp. 3278–3286, by K.-Y. Law and F. C. Bailey, the disclosures of which are totally incorporated herein by reference. Both symmetric squaraines such as, e.g., 1,2-bis-[p-(dimethylamino)phenyl]cyclobutene-2,4-dione, and unsymmetrical ones such as, e.g., 1-[p-(dimethylamino) phenyl]-3-(p-methoxyphenyl)-squaraine have been prepared and analyzed using the General experimental setups I and II of the present invention. For example, NIR-FT Raman spectrum of the prior art compound in a 50:50 by weight mixture with a compound #114 (sub-class D of the present invention, see FIG. 5 and FIG. 1D) revealed that the prior art compound had lower or, at best, comparable intensity with the characteristic features of the other component of the mixture [cf. FIG. 11($a$)]. Further, a NIR-FT Raman spectrum of a 50:50 by weight mixture of the squaraine with poly-PTS (sub-class J of the present invention, see FIG. 12$a$) in fact clearly revealed only the latter component of the mixture [cf. FIG. 11($b$)]. Due to considerably lower Raman cross-section, the squaraine compound manifested itself in the 50:50 mixture with the conjugated polymer only as a minor component of the mixture. Other experiments in accordance with the General experimental setup I (cf Example 1) also showed that squaraines were inferior to other compounds of the present invention in terms of their NIR Raman activity. Finally, all attempts of the present inventors to obtain a Raman spectrum of a squaraine under 785-nm excitation, in accordance with the General experimental setups II of the invention (cf. Example 2), failed. In all cases the squaraine compound fluoresced strongly, thus preventing obtainment of any useful Raman spectrum under the 785-nm laser excitation.

EXAMPLE 24

Binary mixtures of individual Raman-active compounds. From about 5 to about 95 parts by weight of poly-PTS (sub-class J of the invention) was mixed with from about 5 to about 95 parts by weight$^{(*)}$ each of individual Raman-active compounds of the sub-classes A [p-nitrophenylacetylene, compound #16], B [bis(4,4'-phenyl-p-ethynyl)benzophenon, compound #60], D [2-cyanoacrylic acid, compound #114], E [poly-bis(p-diethynylbenzene-di-tert-butylphosphine platinum), compound #126], and I [poly(phenylethynyl)-quinoxaline, compound #134] of the invention to obtain 100 parts by weight of the mixture in total. In an embodiment, the individual compounds were mixed pair-wise in a specified proportion on a Wig-L-Bug ball mill and, in powdered form, were applied to a substrate by pressing the solid with spatula and removing loose material by gently blowing the area. In an alternative embodiment (the sub-class J compound being in the monomer form), a portion of the solid mixture was dissolved in an appropriate solvent and used further in different ways as required. For example, a drop of the solution of the binary mixture in a low boiling solvent was applied onto a substrate with a pipette, and the solvent was permitted to evaporate. Then the solid-state polymerization of the sub-class J compound was accomplished by annealing the sample in an oven at a specified temperature for a specified time, or by UV-irradiation. Subsequently, NIR-Raman spectra of the marks were taken by using the General experimental setup I, II or III of the invention. For example, having been produced by the said "through solution" application, the said Raman-active marks were analyzed by the procedure of Example 1 giving NIR-FT Raman spectra shown in FIG. 13. Note (*): The exact weight ratios are not reported here since these would constitute "trading secrets" in terms of possible practicing of the invention.

EXAMPLE 25

Complex mixtures of individual Raman-active compounds of the invention. FIG. 14 shows NIR-FT Raman spectra of the three marks that have been produced by judicious mixing of seven different individual Raman-active compounds of the invention. The three marks comprise the same seven components, but taken in different proportions. Note: The exact constituents and weight ratios are not reported here since these would constitute "trading secrets" in terms of possible practicing of the invention.

EXAMPLE 26

Writing tool using a Raman-active pigment. By the synthetic route described in *Vysokomolekulyarnye Soedineniya, Ser. A*, 40 (1998) No. 6, pp. 902–908 by Rusanov et al., disclosure of which is totally incorporated herein by reference, highly branched phenyl-ethynyl-substituted polyphenylene [compound #144 of the invention, see FIG. 8(b)] was prepared. The polymer is soluble in many organic solvents, and reveals intense black color both in the solid state and in solution. When applied from a solution, the polymer exhibits a film-forming ability. 0.1 g Of the polymer was added to 2 ml of chloroform, and intense black solution was obtained. A standard Hewlett Packard Color Pro plotter pen was disassembled and thoroughly washed with water from remnants of the ink and air dried. The porous cylindrical insert taken from the pen was brought into contact with the black solution of the polymer in a beaker and, soaked with the solution, the insert was placed back into the cylindrical pen case. The case was hermetically plugged at the upper end with a standard flat cap, and thus refilled and re-assembled pen was installed, the writing tip down, into the plotter carousel. A well-visible bright-black picture (cat.bmp file from MS Word clipart) was plotted on a British made 'Plus Fabric Bond' white A4 85 gsm plotter paper. An intense NIR Raman spectrum similar, but not identical, to that shown in FIG. 1(I, bottom) was obtained when the black image was analyzed following the procedures of Experiments 1, 2 or 3.

EXAMPLE 27

Writing tool using an invisible Raman-active ink. 0.2 g Of the compound #16 of the invention was added to 2 ml of butylacetate, and clear solution was obtained. A standard Hewlett Packard Color Pro plotter pen was disassembled and thoroughly washed with water from remnants of the ink and dried. The porous cylindrical insert taken from the pen was brought into contact with the solution of the compound in a beaker and, soaked with the solution, the insert was placed back into the cylindrical pen case. The refilled and reassembled as in Example 26 pen was installed into the plotter carousel. An actually invisible mark (cat. bmp file from MS Word clipart) was plotted on a glossy white A4 90 gsm plotter paper. An intense NIR Raman spectrum identical to that shown in FIG. 1(A, top) for 1-ethynyl-4-nitrobenzene was obtained when the invisible image was analyzed following the procedure of Experiment 1.

EXAMPLE 28

Writing tool using thermally developable Raman-active ink. 0.25 g of PTS monomer (obtained in Example 20) was dissolved in a 2 ml of acetone, and a drop of red water-soluble ink for Hewlett Packard plotter pens was added, resulting in a pink solution. The solution was rapidly filtered under water aspirator vacuum through a glass filter and brought into contact with a thoroughly washed and dried porous cylindrical insert taken from the HP plotter pen. The refilled and reassembled as in Example 26 pen was installed into the plotter carousel. A faintly red image (cat. bmp file from MS Word clipart) was plotted on an ordinary A4 80 gsm office paper. Having been irradiated under a laboratory bactericide UV lamp ($\lambda_{max}$=254 nm) at a distance of ca. 15 cm for ca. 5 min, the image attained dark-red appearance. Analysis of this image in accordance with Example 1 at 10 mW of incident laser power gave an intense NIR-FT Raman spectrum in some features similar, but not identical, to that shown in FIG. 1(J, bottom) and belonging to partly polymerized 5,7-dodecadiyne-1,12-diol bis($\beta$-bromopropionylcarbonyl)urethane (compound #146 of the invention). The simultaneous presence of the two strong bands in 2300–1900 cm$^{-1}$ spectral region, belonging to $\nu$(—C≡C—) vibrations of the monomer and the corresponding polymer, evidenced for respectively low degree of polymerization attained. Then, this sheet of paper with the partly UV-developed image was held in an oven at 80° C. for 6 hrs. Taken out of the oven image had a beautiful appearance with golden luster similar to that of the figure '100' on the US one hundred dollars bill. Analysis of this image in accordance with Example 2 at 20 mW of incident laser power gave an intense Raman spectrum identical to that shown in FIG. 12(b).

EXAMPLE 29

Preparation of new UV- and thermally polymerizable Raman-active diacetylene compounds. (a) Synthesis of $\beta$-bromopropionylcarbonyl isocyanate. A tree-neck flask equipped with a reflux condenser, a stirrer, and an inlet for feeding argon was charged with anhydrous chloroform freed from the stabilizers (170 ml), N-bromosuccinimide (NBS) (17.8 g, 0.1 mol), allyl chloride (5 ml), and benzoyl peroxide (40 mg). The mixture was refluxed under argon blanket while stirring until apparently complete dissolution of NBS (4 hrs). (b) Synthesis of 4,6-decadiyn-1,10-diol bis($\beta$-bromopropionylcarbonyl)urethane. 150 ml of the just prepared solution of $\beta$-bromopropionylcarbonyl isocyanate (containing ca. 0.06 mole of the product) were filtered under a slight excessive argon pressure into another flask charged with a solution of 4,6-decadiyne-1,10-diol (5 g, 0.03 mol) in chloroform (50 ml). The precipitate which formed in the second flask after mixing the two solutions was separated on a Shott filter, washed with chloroform, and recrystallized from formic acid. Yield: 13.5 g (86%) as fine spherulitic crystals, m.p. 220–230° C. (the product polymerized in the course of heating). The crystals rapidly attained red color under effect of diffused room light. Having been held in an oven at 100° C. for 0.5 h and then analyzed in accordance with the procedure of Example 1, the sample of 4,6-decadiyn-1,10-diol bis($\beta$-bromopropionylcarbonyl)urethane gave NIR-FT Raman spectrum identical to that shown in FIG. 1(J, bottom). In a similar fashion, 2,4-hexadiyn-1,6-diol bis($\beta$-bromopropionylcarbonyl)urethane, 3,5-octadiyn-1,8-diol bis($\beta$-bromopropionylcarbonyl)urethane, 5,7-dodecadiyn-1,12-diol bis($\beta$-bromopropionylcarbonyl)-urethane, 6,8-tetradecadiyn-1,14-diol-bis($\beta$-bromopropionylcarbonyl)urethane, 7,9-hexa-decadiyn-1,16-diol bis($\beta$-bromopropionylcarbonyl)urethane, 8,10-octadecadiyn-1,18-diol bis($\beta$-bromopropionylcarbonyl) urethane, 10,12-docosadiyn-1,22-diol bis(D-bromopropionylcarbonyl)urethane have been prepared.

EXAMPLE 30

Preparation of novel UV- and thermally polymerizable Raman-active diacetylene compounds. A 500-ml tree-neck flask equipped with a stirrer, a dropping funnel and an inlet for feeding argon was charged with anhydrous (additionally dried over 4A molecular sieves) dimethylsulfoxide (DMSO) (200 ml) and 11.0 g (0.1 mol) of 2,4-hexadiyn-1,6-diol. To the vigorously stirred mixture, a solution of p-toluenesulfonyl isocyanate (Aldrich) (40 ml, 0.22 mol) in 50 ml of dry DMSO was added drop-wise for 0.5 h. After stirring for additional 2 hrs at room temperature, the mixture was discharged into 1000 ml of chilled water. The water layer was decanted off the yellow heavy oil, and the oil was triturated with diethyl ether, giving a cake of fine crystals which rapidly attained blue color under effect of UV light. Recrystallization from hot ethanol/ethyl acetate 2:1 mixture gave 45.2 g (yield 90%) of 2,4-hexadiyn-1,6-diol p-toluenesulfonyl urethane as fine white crystals with m.p. 128–130° C. The crystals were readily polymerizable under effect of both UV-irradiation and temperature. Analysis: I.R. (KBr pellet, $cm^{-1}$: 3080 (Ar—H stretching), 2980+2920 (CH stretching), 1596 (phenyl C=C stretching), 1368 (S—O), 1184 (S—O), 742 (Ar—H). NIR-FT Raman: 2270 $cm^{-1}$ (diacetylenic monomer —C≡C— stretch), 2105 $cm^{-1}$ (polymer backbone —C≡C— stretch), 1540 $cm^{-1}$ (polymer backbone —C=C— stretch). Having been held in an oven at 85° C. for 2 hrs and then analyzed as described in Example 1, the compound gave an intense NIR Raman spectrum identical to that shown in FIG. 1(J, top). The simultaneous presence of the two Raman bands in 2300–1900 $cm^{-1}$ spectral region, one (weak) belonging to ν(—C≡C—) vibrations of the monomer and the other (strong) belonging to ν(—C≡C—) vibrations of corresponding polymer, evidenced for partial polymerization of the compound.

EXAMPLE 31

Preparation of novel UV- and thermally polymerizable Raman-active diacetylene compounds. The urethane fragments are known to be responsible for the crystal packing of diacetylenes, and frequently assure the packing which is favorable in terms of subsequent solid-state topochemical polymerization. Traditionally, however, the solid-state polymerizable diacetylenes were prepared by using a diacetylenic diol and a commercially available isocyanate. To best knowledge of the inventors, polymerizable diacetylenic monomers based on acetylenic isocyanates or diacetylenic diisocyanates have not been reported in the art. On these grounds, a novel general synthetic route to polymerizable diacetylenic monomers is disclosed here. The approach is based on use of N,N'-carbonyldidimidazole and permits preparing a vast majority of novel diacetylenes using a plenty of commercially available alcohols and amines instead of more expensive isocyanates. Procedures. (a) Synthesis of 4-(2,2,6,6-Tetramethyl-1-oxyl)piperidin-2-propincarbamate. Propargylamine (Aldrich) (0.56 g) dissolved in 2 mL of dry chloroform was added drop-wise during 5 min to a solution of N,N'-carbonyldidimidazole (CDI) (1.62 g) in 7 mL of dry chloroform at 0° C. To the reaction mixture kept 1 h at room temperature 1.72 g (0.01 mol) of 4-(2,2,6,6-tetramethyl-1-oxyl)-piperidinol (4-hydroxy-TEMPO, Aldrich) and 15 mL of dry benzene were added. The mixture was brought to the boiling and, after chloroform distilled off, was kept under reflux during 10 hrs. After benzene removal on rotor evaporator the product was purified by column chromatography (Merck $SiO_2$, 35–70 mesh, eluent chloroform/ether 4:1). Recrystallization from ether/hexane mixture gave 0.85 g (Yield 33.5%) of 4-(2,2,6,6-tetramethyl-1-oxyl)piperidin-2-propincarbamate as orange needles, mp. 115° C. Analysis for $C_{13}H_{20}N_2O_3$: Calctd. (%) C, 61.90; H, 9.74; N, 11.11; Found: C, 61.87; H, 9.81; N, 11.03. (b) Synthesis of bis-[4-(2,2,6,6-Tetramethyl-1-oxyl)piperidin]-2,4-hexadiyne-1,6-dicarbamate. A mixture of 0.506 g (0.002 mol) of 4-(2,2,6, 6-Tetramethyl-1-oxyl)piperidin-2-propin-carbamate, 1.2 g $Cu(CH_3COO)_2$, 8 mL of piperidine, 4 mL of methanol and a few crystals of CuCl has been stirred during 3 hrs. The reaction mixture was transferred into 150 mL of ice water. The precipitate formed over few minutes was separated by filtering, washed with water and dried under a water aspirator vacuum. Crystallization from acetone/water gave 0.19 g (Yield 38%) of bis-[4-(2,2,6,6-Tetramethyl-1-oxyl) piperidine]-2,4-hexadiyne-1,6-dicarbamate as fine orange crystals. Having been applied onto a printing paper and analyzed as described in Example 1, the compound gave an intense NIR FT-Raman spectrum in some features similar, but clearly not identical, to that shown in FIG. 1(C, middle) for N,N'-bis(3,5-dinitrophenyl)-2,4-hexadiyne-1,6-diamide (exemplary Compound #109 of the invention). Specialists in the art will probably recognize that a vast majority of novel polymerizable diacetylenes can be prepared by this general route.

EXAMPLE 32

Ink-Jet printing ink using a Raman-active pigment. Known inks for ink-jet printing generally comprise a dye which is soluble in an ink vehicle such as water or a mixture comprising water and a water soluble or water miscible organic solvent. Since most of the Raman-active compounds of the invention are not water-soluble, and since in thermal ink jet or bubble jet printing systems water is a necessary component, water miscible organic solvent should be used. Suitable water miscible organic solvents include ethylene glycol, propylene glycol, diethylene glycols, glycerine, dipropylene glycols, polypropylene glycols, glycerine, polyethylene glycols, amides, ethers, carboxylic acids, esters, alcohols, organosulfoxides, sulfones, dimethylsulfoxide, sulfolane, alcohol derivatives, carbitol, butyl carbitol, cellusolve, ether derivatives, amino alcohols, ketones, and other water miscible materials, as well as mixtures thereof. Usually, when mixtures of water and water miscible organic liquids are selected as the liquid vehicle, up to 25% wt of water may be used, but from about 1 wt % to about 10 wt %, preferably from about 4 wt % to about 6 wt %, is desirable. The non-water component of the liquid vehicle generally serves as a humectant which has a boiling point higher than that of water. The use of pigments or other forms of particulate matter is preferably avoided since such materials tend to clog the very small orifice of the jet printer. Preferred for producing the ink-jet printing inks are those compounds of the present invention which are easily soluble in harmless solvents. Those which contain strong chromophoric moieties can be used as direct dyes. The ink composition of the present invention can be prepared by thoroughly mixing the components to insure uniform mixing and complete dissolution of the organic-soluble Raman-active compound, and then filtering the resulting composition to remove any particulate contamination. As will be apparent to those skilled in the art, filtration of the composition after mixing the components is highly desirable in order to remove from the ink composition particulate matter, such as traces of insoluble polymer, contamination or undissolved matter, which might otherwise serve to clog or obstruct the jet of a jet printer during use. When polymerizable diacetylenes are used as Raman-active component, the composition must be filtered in conditions preventing "spontaneous" solid-state polymerization of microscopic crystals of the material. It is preferred to filter the composition of the invention to remove particulate matter having a diameter greater than 2 microns, and preferably 1 micron, to insure that obstruction of the jet of the jet printer will be avoided. For example, the following simple composition based on γ-Butyrolactone vehicle was prepared by mixing together the ingredients at room temperature, stirring to obtain a homogeneous solution, and filtering (in parts by weight):

| | |
|---|---|
| Distilled water | 6.0 |
| γ-Butyrolactone | 80.0 |
| Dipropylene glycol | 5.0 |
| 2,4-Hexadiyne-1,6-diol bis-p-toluene sulfonate (PTS) | 9.0 |

A standard Hewlett Packard Desk Jet 520 printer cartridge was thoroughly washed with distilled water and refilled with 30 ml of the composition. Surprisingly, it printed satisfactorily, and has idled on and off in the jet printer for several days without clogging. Printer startups, after long periods of idling, were immediate. A page of a text was printed on an ordinary office paper using this cartridge. Since PTS crystals attain faint pink coloration a few moments after formation under room light, almost unreadable pinkish print-out was obtained. As in Example 28, having been irradiated under a laboratory bactericide UV lamp ($\lambda_{max}$=254 nm) at a distance of ca. 15 cm for ca. 5 min, the text attained dark-red appearance making it quite readable. After the sheet of paper was held in an oven at 80° C. for 6 hrs, the text attained beautiful appearance with golden luster and was easily readable. Analysis of the areas of the page covered with the pigment in accordance with Example 1 at 10 mW of incident Nd:YAG laser power gave a NIR-FT Raman spectrum with rather poor SNR. Analysis of the imaged areas in accordance with Example 2 at 20 mW of incident 785-nm laser power gave Raman spectrum similar to that shown in FIG. 12(b), but still with inferior SNR. The best results were obtained when the measurements were run following the procedure disclosed in Example 3 (General experimental setup III).

EXAMPLE 33

Ink-jet printing ink giving a thermochromic Raman-active pigment. Following the considerations described in Example 32, a standard Hewlett Packard Desk Jet 520 printer cartridge was thoroughly washed with distilled water and refilled with 30 ml of the composition comprising (in parts by weight):

| | |
|---|---|
| Distilled water | 5.0 |
| Dipropylene glycol | 5.0 |
| Iso-Propyl alcohol | 83.0 |
| 10,12-Hexacosadiynoic acid | 7.0 |

The refilled cartridge printed satisfactorily, and has idled on and off in the jet printer for several days without clogging. A half-tone image was printed on an ordinary office paper using this cartridge. Since 10,12-Hexacosadiynoic acid crystals are clear-white upon formation, actually invisible print-out was obtained. As in Example 28, after irradiation under a laboratory bactericide UV lamp ($\lambda_{max}$=254 nm) at a distance of ca. 10 cm for ca. 20 min, the latent image developed, having beautiful blue appearance, making it perfectly readable. Importantly, the image had many shades of blue (close to the original), evidencing that true half-tone high-quality images can be produced with the ink compositions of the invention. Analysis of the areas of the page covered with the pigment in accordance with Example 1 at 100 mW of incident Nd:YAG laser power gave a NIR-FT Raman spectrum with rather poor SNR. Analysis of the imaged areas in accordance with Example 2 at 20 mW of incident 785-nm laser power gave Raman spectrum similar, but clearly not identical, to that shown in FIG. 1(J, middle), but still with inferior SNR. The best results were obtained when the measurements were run on the most dark colored areas of the image following the procedure disclosed in Example 3 (General experimental setup III). Tests for thermochromicity of poly-10,12-Hexacosadiynoic acid were carried on a temperature-controlled hot stage. It was noted that the dark-blue polymer evidenced dramatic irreversible color change to red at around 85–100° C. In the course of further heating to higher temperatures, the polymer changed to bright orange, then to orange-yellow and, finally, to lemon-yellow at about 150° C. The red color was restored back on cooling. This thermochromic cycle could be repeated many times with no apparent degradation. In addition, this material was investigated at several discrete specified temperatures using the General experimental setup III and the incident laser powers of 100 to 200 mW. This gave NIR Raman spectra similar, but not fully identical, to those shown in FIG. 21 for poly-4BCMU.

EXAMPLE 34

General method of making emulsions of readily crystallizable Raman-active materials. e.g., diacetylenes. This involves making an emulsion of a solution of a diacetylene with a solution of a surfactant, quenching the emulsion at a lower temperature to freeze the emulsion quickly and then thawing the solid emulsion at a higher temperature for growing crystals of the diacetylene. The preferred temperature and medium for quenching the emulsions is liquid nitrogen. More specifically, an emulsion of a diacetylene [2,4-hexadiyn-1,6-diol bis-(p-toluenesulfonyl)urethane] solution in, e.g., methylethylketone (MEK) in water and a surfactant (e.g., cetyltrimethyl ammonium chloride), can be prepared by high speed homogenization at 60° C. The emulsion is poured into liquid nitrogen to freeze the emulsion. The crystal size is controlled by controlling the thawing temperature. The emulsion is thawed at about –20° C. for the controlled growth of the diacetylene crystals. This method provided micron and submicron sized single crystals of the diacetylenes. The above emulsion was freeze dried under vacuum. After polymerization in the solid state (at 85° C. for 6 hrs), the powder was analyzed as described in Example 1, and the compound gave an intense NIR Raman spectrum similar, but not identical, to that shown in FIG. 1(J, top). These micron and submicron sized single crystals of the corresponding polydiacetylenes can be incorporated into various printing ink formulations. Inks and ink formulations suitable for producing images by flexographic printing, gravure or heliogravure printing, intaglio (steel engraving) or plate printing, letterpress printing, indirect letterpress or dry offset printing, lithographic or wet offset printing, and screen printing processes can be produced using the particulate matter prepared by this general approach.

EXAMPLE 35

Preparation of emulsion without any binder: Into a jacketed container of a high-speed blender were added 50 ml of water and two drops of PEG-dodecylether and mixed at low speed. To the mixture was added a solution of 4BCMU (8.0 g) in MEK (12 ml) and homogenized for two minutes at 50°

C. The white emulsion formed was poured into 200 ml of liquid nitrogen. The sample frozen at liquid nitrogen was brought to RT, and freeze dried under vacuum. This sample became UV active almost immediately. Investigation under microscope showed that the sample had globule type crystals of micron size.

EXAMPLE 36

Preparation of emulsion without using any solvent: 50 g of polyethylene glycol, molecular weight 13,000 (Fluka), was placed into a jacketed container of a laboratory high-shear rotary disk mixer. Hot water (90° C.) was circulated to melt the polyethylene glycol. 5 grams of 2,4-hexadiyn-1,6-diol bis(β-bromopropionylcarbonyl)urethane was added which dissolved in the molten polyethylene glycol. The mixture was homogenized for ten minutes at high speed (about 2000 rpm) and poured into 200 mL of liquid nitrogen. The solid was allowed to come to room temperature. 25 g of the solid emulsion was added into 50 ml of water, agitated for 2 min to dissolve polyethylene glycol, and separated on filter. The resulting paste was UV reactive, and after irradiation with a laboratory UV source ($\lambda_{max}$ 254 nm) during 1 min, the partly polymerized cherry-colored paste gave a NIR Raman spectrum similar, but clearly not identical, to that shown in FIG. 1(J) for 4,6-decadiyne-1,10-diol-bis(β-bromo-propionylcarbonyl) urethane (Compound #146 of the invention).

EXAMPLE 37

Thermochromic NIR Raman-active screen printing ink and color changes: The micronized diacetylene powder prepared in Example 35 was γ-irradiated under $^{60}$Co-source at the dose rate of 1 Mrad per hour for 24 hrs in total. The sample attained black-blue appearance with bronze luster which is characteristic for poly-4BCMU, and the powder apparently fully retained its flowability. 4 grams of the poly-4BCMU was homogenized with 5 ml of a commercially available raw screen ink (ink without pigment), CTI-XM (a water based ink of Chromatic Technologies Inc., Colorado Springs, Colo. USA). The resulting ink was dark-blue emulsion. The CTI logo was printed using the screen printing technique by squeezing the inks of this Example through a screen, and well readable dark-blue print-out was obtained. When heated with a hot air blower, the dark-blue color of poly-4BCMU changed to red color. Upon further heating to a higher temperature, the red color of poly-4BCMU became yellow, but slowly restored to red after heating was ceased. Another analogously made print-out was investigated at several specified (30, 50, 90 and 120° C.) temperatures using the temperature-controlled hot stage, the General experimental setup III and the incident laser powers of 100 to 200 mW. This gave NIR Raman spectra similar to those shown in FIG. 21 for poly-4BCMU, thus evidencing that these types of inks can be used as security inks in screen printing, e.g., documents, to establish their genuineness and authenticity.

EXAMPLE 38

NIR Raman-active offset and litho printing ink. As in Example 37, the micronized diacetylene powder prepared in Example 36 was γ-irradiated under $^{60}$Co-source at the dose rate of 1 Mrad per hour for 20 hrs in total. The sample attained a mellow-cherry color with bronze luster characteristic for poly-2,4-hexadiyn-1,6-diol bis(β-bromopropionylcarbonyl)-urethane (herein referred to as poly-HBU), and the powder fully retained its flowability. An offset and litho printing ink for the printing Raman-detectable marks was prepared by mixing the following ingredients:

|  | % |
| --- | --- |
| Poly-HBU powder | 37.0 |
| Long oil alkyd | 28.0 |
| Phenolic resin modified rosin soaked with linseed oil | 21.0 |
| Polyethylene wax (PE 130 - Hoechst) | 2 |
| Ink solvent 27/29 (Shell) | 2 |
| Cooked linseed oil | 5 |
| Titanium dioxide | 5 |

The ink, after printing and drying, had dark-purple appearance. Having been investigated using the General experimental setup III and the incident laser powers of 300 mW, this print-out gave NIR Raman spectrum similar to that shown in FIG. 1(J, middle), thus confirming that these types of inks can be used as security inks in offset printing, e.g., documents, to establish their genuineness and authenticity.

EXAMPLE 39

NIR Raman-active offset and litho printing ink. 8 Parts by weight of a commercially available material (ICP, Moscow, Russia) which is believed to be mainly fullerene C60 containing trace amounts of C70 was dissolved in 30 parts of benzene, 10 parts of toluene, 20 parts of ethanol and 50 parts of cellulose acetate propionate (Eastman) by heating and stirring the mixture at 60° C. for 30 min. The mixture was then dried at 80° C. for 20 hrs under reduced pressure until total evaporation of the solvents. The solid solution obtained was broken up and then micronized, and the finely divided particles thus obtained having a size of from 1 to 15 μm were incorporated in the following ink formulation by means of a three roller mill:

|  | % |
| --- | --- |
| Micronized cellulose acetate propionate solid containing 16 wt % of Fullerene C60 | 26.0 |
| Long oil alkyd | 35.0 |
| Phenolic resin modified rosin soaked with linseed oil | 25.0 |
| Polyethylene wax (PE 130 - Hoechst) | 2 |
| Ink solvent 27/29 (Shell) | 4 |
| Cooked linseed oil | 5 |
| Titanium dioxide | 3 |

The ink, after printing and drying, had dark-brown appearance. Having been investigated using the General experimental setup III and the incident laser powers of 200 mW, this print-out gave NIR Raman spectrum similar to that shown in FIG. 1(G), thus confirming that these types of inks can be used as security inks in offset printing, e.g., documents, to establish their genuineness and authenticity.

EXAMPLE 40

LIF\NIR Raman-active offset and litho printing ink. The procedures of Example 39 were repeated except 5 parts by weight of a commercially available upconverting phosphor (Institute of Chemical Physics, Moscow, Russia), being thoroughly micronized on a ball-mill, was mixed with 30 parts of toluene, 20 parts of ethanol and 50 parts of cellulose acetate propionate (Eastman) by heating the mixture at 80° C. for 15 min while stirring vigorously. The mixture was then dried at 100° C. for 24 hrs under reduced pressure until total evaporation of the solvents. The solid solution obtained was broken up and then micronized, and the finely divided particles thus obtained having a size of from 1 to 20 µm were incorporated in the following ink formulation by means of a three roller mill:

|  | % |
| --- | --- |
| Micronized cellulose acetate propionate solid containing 10 wt % of the upconverting phosphor | 20.0 |
| Long oil alkyd | 38.0 |
| Phenolic resin modified rosin soaked with linseed oil | 28.0 |
| Polyethylene wax (PE 130 - Hoechst) | 2 |
| Ink solvent 27/29 (Shell) | 2 |
| Cooked linseed oil | 5 |
| Titanium dioxide | 5 |

The ink, after printing and drying, had creamy-white appearance. Having been investigated using the General experimental setup I and the incident Nd:YAG laser power of 20 mW, this print-out gave LIF\NIR Raman spectrum identical to that shown in FIG. 10 (bottom). Earlier, the spectrum shown in FIG. 10 was obtained for a crystalline upconverting phosphor represented by the atomic formula $M_{(1-x)}R_xZ_3$, wherein M is yttrium, R is erbium, Z is chlorine, and x is a value in the range from 0.005 to 1.0. The observed identity of the spectra thus indicates that such inks can be used in offset printing, e.g., documents, to protect and establish their genuineness and authenticity.

EXAMPLE 41

An alternative general procedure of making NIR Raman-active offset and litho printing ink. Several exemplary formulations of NIR Raman-active inks are provided below based on the principles similar to those taught in the U.S. Pat. No. 5,591,255, the disclosures of which are totally incorporated herein by reference. As a first step, an aqueous slurry of a Raman-active compound (pigment) of the invention, containing approximately 50 wt % pigment solids, is prepared. Then the slurry is dried in an oven at 50–90° C. to achieve a solids concentration of 80%–95% by weight of the Raman-active pigment. Solid levels below 80% introduce excess water into finished ink formulations and make it difficult to properly disperse the pigment in the ink vehicle, and generally solids concentrations above 90% are preferable. Solids greater than 95% may result in strong agglomeration of the pigment particles and make dispersion difficult, however, drying to solids concentrations up to 98% has worked. The dried material is then combined with a grinding/mixing varnish formulated for the dispersion of dry pigment or presscake, which typically is high in tack and viscosity, may contain a significant proportion of alkyd resin, and have an acid value not to exceed 15. More specifically, the dried pigment slurry is added to the vehicle under mechanical agitation in an amount to achieve a weight/weight ratio of 1 part of pigment solids to 1 part of vehicle. Agitation may be provided by various types of mixers, however, the final viscosity of the mix will be quite high, and the flow properties of the dispersion may be poor, therefore, a dual axial, planetary, or turntable-type mixer is recommended. A three-roller ink mill may also be used for making the dispersion. Agitation is continued until a smooth glossy dispersion is obtained. The grind rating of the finished dispersion, as determined on a NPIRI Grind Gauge, should be a minimum of 3. This mix will be referred to below as Offset Ink Base. The acid value of the vehicle used in this ink should not exceed 40.

A particular example of combining the Offset Ink Base with other ink components to produce a Quick-Set lithographic ink. The ingredients were mixed as follows: (the acid value of the vehicles used should not exceed 15.)

| Ingredient | Weight % |
| --- | --- |
| Offset Ink Base (containing 50 wt % of the upconverting phosphor from Example 40) | 75.0 |
| Quick Set Gel Vehicle | 12.5 |
| Quick Set Free Flow vehicle | 7.5 |
| 12% Cobalt Drier | 1.0 |
| 6% Manganese Drier | 1.0 |
| Ink Oil (IBP 510° F.) | 3.0 |
| TOTAL | 100.0 |

The ink, after printing and drying, had creamy-white appearance. Having been investigated using the General experimental setup I and the incident Nd:YAG laser power of 30 mW, this print-out gave LIF\NIR Raman spectrum identical to that shown in FIG. 24 (top). Besides the research-grade Nd:YAG laser (TEM$_{00}$, 1064 nm, 0.1 cm$^{-1}$ bandwidth), two "key-chain" laser pointers (emitting nominally at 950 and 630 nm) have been employed in this experiment. The spectra provided in FIG. 24 (middle and bottom) show that the two pointers, which are multimode sources having total bandwidths of several tens of nanometers and the outputs of ca. 1 mW, give actually the same and quite useful results, thus indicating that such inks can be used in offset printing, e.g., documents, to protect and establish their genuineness and authenticity. Additionally, the print-out exhibited a bright green glow under effect of the invisible irradiation from the 950-nm LED key-chain pointer.

EXAMPLE 42

Invisible NIR Raman-active offset and litho printing ink. Following the procedures of Example 41, a colorless ink containing diphenyl(diethynylphenyl)silane (Compound #87 of the invention) was prepared. When the print-out made with this ink was analyzed using the General experimental setup III and the incident laser power of 300 mW, NIR Raman spectrum similar to that shown in FIG. 1B (middle) was obtained, indicating that inks of this type can be used in offset printing, e.g., documents, to protect and establish genuineness and authenticity thereof.

EXAMPLE 43

Black NIR Raman-active offset and litho printing ink. Following the procedures of Example 41, a black ink containing highly branched phenyl-ethynyl-substituted polyphenylene [compound #144 of the invention, see FIG. 8(b)] has been prepared. Since this compound is easily soluble in many organic compounds, it was micronized by rapid cooling of an emulsion in liquid nitrogen, and the stage of conditioning the water slurry of this pigment was omitted. When the print-out made with this ink was analyzed using the General experimental setup III and the incident laser power of 100 mW, NIR Raman spectrum similar, but not identical, to that shown in FIG. 1(I, bottom) was obtained, indicating that inks of this type can be used in offset printing, e.g., documents, to protect and establish genuineness and authenticity thereof.

EXAMPLE 44

Decorative bronze NIR Raman-active offset and litho printing ink. Using the procedures of Example 34, micronized PTS was obtained and freeze-dried under reduced pressure. Following the procedures of Example 41, except that the stage of conditioning the water slurry of the pigment was omitted and a stage of thermal polymerization of the PTS in an oven at 80° C. for 6 hrs was added, a dark-colored ink containing poly-2,4-hexadiyn-1,6-diol p-toluenesulfonate has been prepared. The ink, after printing and drying, had decorative appearance with bronze luster when viewed in reflected light. Having been analyzed using the General experimental setup III and the incident diode laser power of 300 mW, this print-out gave NIR Raman spectrum identical to that shown in FIG. 12(b), indicating that inks of this type can be used in offset printing, e.g., documents, to protect and establish genuineness and authenticity thereof.

EXAMPLE 45

Thermochromic NIR Raman-active plastic card. An aromatic polyamide-diacetylene, was prepared from 10,12-docosadiyne-1,22-dioic acid and p-phenylenediamine by a synthetic procedure similar to that described, for example, in U.S. Pat. No. 4,916,211, the disclosures of which are totally incorporated herein by reference. The aromatic polyamide-diacetylene macromonomer was isolated from the reaction as a white powder. Prior to cross-polymerization, this nylon type macromonomer was soluble, for example, in m-cresol, dimethylacetamide, and dimethylformamide, and could be cast into films from this solvent. The solubility of this material in, e.g., m-cresol indicates that cross-polymerization has not occurred to any great extent during synthesis and thus the macromonomer still behaves as a linear polyamide. This in turn suggests that materials of this kind may be processed using techniques established for other nylon polymers. 10 wt % of the aromatic polyamide-diacetylene macromonomer was successfully incorporated into a sindiotactic polypropylene, and the films were extruded at 140–160° C. under argon blanket. After thermal annealing at 90–100° C. for several hrs, the cross-polymerization of the macromonomer was accomplished by exposing the composition to UV light irradiation ($\lambda_{max}$=254 nm, laboratory bactericide lamp) for 30 minutes. After cross-polymerization, the material attained deep-blue color, and exhibited reversible thermochromic properties. In this particular case, the color change was from blue to red, and the color changes were reversible. The materials could be repeatedly cycled between room temperature and about 150° C. without any significant loss in optical characteristics. In this range the color of the material changed continuously from blue to red as it was heated from room temperature to higher temperatures, and restored back on cooling. The thermochromic changes were monitored as described in Examples 1, 2 and 3. Expectedly, the NIR Raman spectra of this particular thermochromic composition were unique among the spectra of other thermochromic and non-thermochromic materials of the invention, thus confirming the analytical potential of the methodology.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method of security marking, comprising the steps of:
   a) applying a Raman-active composition, comprising a conjugated polymer to a genuine item;
   b) illuminating the Raman-active composition with a near infrared light;
   c) measuring quantitatively an emissive spectrum of the Raman-active composition.

2. The method of claim 1 further including the step of:
   d) storing a copy of the emissive spectrum.

3. The method of claim 1, wherein step (a) further includes the step of:
   a1) selecting the Raman-active composition so that the Raman-active composition does not exhibit resonance Raman scattering when illuminated by the near infrared light.

4. The method of claim 1, wherein step (a) further includes the steps of:
   a1) selecting a plurality of Raman-active compounds to form the Raman-active composition.

5. The method of claim 4, further including the step of:
   a2) selecting each of the plurality of Raman-active compounds so that an individual emissive spectrum has a feature that does not overlap with another individual emissive spectrum of one of the plurality of Raman-active compounds.

6. The method of claim 1, wherein step (a) further includes the step of:
   a1) selecting a fluorescence-active compound as part of the Raman-active composition.

7. The method of claim 1, wherein step (b) further includes the step of:
   b1) illuminating the Raman-active composition with a Nd:YAG laser.

8. A method of security marking, comprising the steps of:
   a) applying to a genuine item a marking comprising a Raman-active composition, wherein the Raman-active composition includes a conjugated polymer when illuminated with a monochromatic near infrared light, generates a detectable Raman spectrum, thereby forming a machine-readable security mark on the genuine item;
   b) illuminating the machine-readable security mark on the genuine item with the monochromatic near infrared light; and
   c) quantitatively measuring with a spectrometer a Raman scattered light from the Raman-active composition while the machine-readable security mark is illuminated with the monochromatic near infrared light.

9. The method of claim 8, wherein the Raman scattered light is not a resonance Raman scattering.

10. The method of claim 8, wherein the machine-readable security mark on the genuine item is illuminated with the monochromatic near infrared light having a wavelength from about 750 to about 1500 nm.

11. The method of claim 8, wherein a spectrum of the Raman scattered light from the Raman-active composition is quantitatively measured with a NIR-FT Raman spectrometer.

12. The method of claim 8, wherein a spectrum of the Raman scattered light from the Raman-active composition is quantitatively measured with a portable fiber optic Raman spectrometer.

13. The method of claim 8, wherein a spectrum of the Raman scattered light from the Raman-active composition is quantitatively measured with a portable fiber optic Raman spectrometer having a waveguide evanescent probe.

14. A method of security marking, comprising the steps of:
   a) applying to a genuine item a marking comprising a fluorescence-active composition, wherein the fluorescence-active composition, when illuminated with a monochromatic near infrared light, generates a detectable emission spectrum, thereby forming a machine-readable security mark on the genuine item;

b) illuminating the machine-readable security mark on the genuine item with the monochromatic near infrared light; and c) simultaneously and quantitatively measuring with a spectrometer a composite emission spectrum of a Raman scattered light and of a laser induced fluorescence from the fluorescence-active composition while the machine-readable security mark is illuminated with the monochromatic near infrared light, wherein the fluorescence-active composition is essentially an inorganic anti-Stokes up-converting phosphor.

15. The method of claim 14, wherein the composition emission spectrum is quantitatively measured with a Raman spectrometer.

16. The method of claim 14, wherein the composition emission spectrum is quantitatively measured with an InGaSa detector.

17. The method of claim 14, wherein the composition emission spectrum is quantitatively measured with a Ge detector.

18. The method of claim 14, wherein the fluorescence-active composition contains a Raman-active compound.

19. The method of claim 18, wherein the Raman-active compound is a thermochromic polymer.

20. The method of claim 14, wherein the fluorescence-active composition comprises one or more of the compounds selected from the group consisting of: squaraines, cyanoacrylics, monomeric acetylenes, diacetylenes, polysilanes, linear polyynes, polyimines, polyazines, poly(ethynylene)arylenes, poly(ethynylene)heteroarylenes, trans-polyacetylenes, polyenes, polydiacetylenes, fullerenes and tubulenes.

21. The method of claim 14 wherein the fluorescence-active composition includes a plurality of Raman-active compounds.

* * * * *